United States Patent
Reid et al.

(10) Patent No.: US 8,404,260 B2
(45) Date of Patent: Mar. 26, 2013

(54) SYNERGISTIC PESTICIDE COMPOSITIONS

(75) Inventors: Byron L. Reid, Raleigh, NC (US);
Robert B. Baker, Cary, NC (US);
Nanggang N. Bao, Raleigh, NC (US);
Deborah A. Koufas, Clayton, NC (US);
Gerald J. Kent, Northfield, NH (US);
Peter Baur, Schondorf am Ammersee (DE)

(73) Assignee: Bayer Cropscience LP, Research Triangle Park, NC (US)

( * ) Notice: Subject to any disclaimer, the term of this patent is extended or adjusted under 35 U.S.C. 154(b) by 507 days.

(21) Appl. No.: 12/410,840

(22) Filed: Mar. 25, 2009

(65) Prior Publication Data
US 2010/0247684 A1    Sep. 30, 2010

Related U.S. Application Data

(60) Provisional application No. 61/163,206, filed on Mar. 25, 2009, provisional application No. 61/072,778, filed on Apr. 2, 2008.

(51) Int. Cl.
*A01N 25/00*    (2006.01)
*A01N 59/04*    (2006.01)

(52) U.S. Cl. .................................. 424/405; 504/101
(58) Field of Classification Search .................. 424/405, 424/725; 504/101
See application file for complete search history.

(56) References Cited

U.S. PATENT DOCUMENTS

| | | | |
|---|---|---|---|
| 5,472,712 A * | 12/1995 | Oshlack et al. | 424/480 |
| 5,798,112 A | 8/1998 | Heitz et al. | |
| 6,177,465 B1 * | 1/2001 | Tanaka | 514/535 |
| 6,352,704 B1 * | 3/2002 | Nicholson et al. | 424/407 |
| 6,500,416 B2 * | 12/2002 | Hofer et al. | 424/84 |
| 7,198,800 B1 * | 4/2007 | Ko | 424/443 |
| 7,368,123 B1 * | 5/2008 | Tabuchi et al. | 424/409 |
| 7,799,737 B2 * | 9/2010 | Rosenfeldt et al. | 504/100 |
| 2002/0137632 A1 | 9/2002 | Kelley | |
| 2002/0177526 A1* | 11/2002 | Chen et al. | 504/100 |
| 2003/0194419 A1* | 10/2003 | Sun et al. | 424/409 |
| 2006/0029632 A1* | 2/2006 | Henshaw | 424/410 |
| 2006/0166898 A1* | 7/2006 | Chen | 514/22 |
| 2007/0020304 A1 | 1/2007 | Tamarkin et al. | |
| 2007/0155797 A1 | 7/2007 | Andersch et al. | |
| 2007/0298967 A1 | 12/2007 | Kelley | |
| 2008/0146445 A1* | 6/2008 | De Kerpel et al. | 504/100 |

OTHER PUBLICATIONS

International Search Report Based on Application No. PCT/US2009/038349 Mailed May 11, 2009.
Written Opinion Based on Application No. PCT/US2009/038349 Mailed May 11, 2009.
International Preliminary Report on Patentability Based on Application No. PCT/US2009/038349 Mailed Oct. 5, 2010.

* cited by examiner

*Primary Examiner* — Patricia Leith
(74) *Attorney, Agent, or Firm* — Baker Donelson Bearman Caldwell & Berkowitz, PC

(57) ABSTRACT

The present invention relates to compositions that include a combination of one or more pesticides and one or more adjuvants.

9 Claims, 57 Drawing Sheets

SYNERGISTIC PESTICIDE COMPOSITIONS

This application claims priority to U.S. Provisional Application No. 61/163,206, filed Mar. 25, 2009 and U.S. Provisional Application No. 61/072,778, filed Apr. 2, 2008.

FIELD OF THE INVENTION

The present invention relates to compositions that include a combination of one or more pesticides and one or more adjuvants.

BACKGROUND OF THE INVENTION

Pesticides include any substance or mixture of substances used for preventing, controlling, or lessening the damage caused by a pest. A pesticide may be a chemical substance, biological agent such as a virus or bacteria, antimicrobial, or a disinfectant. Pests include insects, plant pathogens, weeds, mollusks, birds, mammals, fish, nematodes such as roundworms, and microbes.

Insecticides are a category of pesticides for the control of insects, namely ovicides or substances that kill eggs, larvicides or substances that kill larvae, or adulticides or substances that kill adult insects. Pesticides also include miticides, acaricides, mulluscides, nematicides, and other varieties of agents.

Pesticides are used for a variety of applications, including crop treatments, animal treatments, treatments for substrates such as wood or other surfaces, and treatment of home infestations. The choice of pesticide typically depends on a variety of factors, including the type of pest, the type of application, the likelihood of contact with humans or other animals, the porosity of the substrate, and the like.

In one application, namely crop protection, there is a need to eliminate or substantially reduce crop damage caused by insects, while at the same time, lessening the environmental impact caused by pesticide use.

In another application, namely insecticidal control, there is a need to provide effective insecticidal control in a home or business while avoiding concentrations of insecticides that might be harmful to humans or other animals. One such application includes protecting wood products from termite damage, with a preference for using agents that are less toxic than current common products such as copper/chrome/arsenic (CCA) applications.

For these and other reasons, it would be advantageous to provide compositions that enhance the efficacy of insecticides.

SUMMARY OF THE INVENTION

In one embodiment, the present invention provides a pesticidal composition comprising a pesticide and an adjuvant, wherein the composition provides a synergistic kill rate. In accordance with one embodiment of the present invention, the use of a free radical stabilizer is believed to change the permeability of an insect or plant cuticle to pesticides. An adjuvant of the present invention is preferably present in a sufficient amount so as to change the permeability of an insect or plant cuticle, without being limited thereby, for example through destabilization. By providing a sufficient amount of an adjuvant according to the present invention to destabilize the cuticle of an insect or plant, synergistic effects have been observed as shown infra. While certain components in pesticide formulations may be provided for the protection of the active pesticidal ingredient against photodegradation, the present invention provides an effective pesticidal composition, with embodiments that demonstrate a reduction in the amount of pesticide necessary to kill pests by up to 10% or more in a given application. Further, the present invention provides methodology for increasing the kill spectrum of a particular pesticide.

In one embodiment, the present invention provides a pesticidal composition comprising a pesticide; and an adjuvant, wherein the composition provides an observed kill rate that exceeds an expected kill rate, the expected kill rate calculated using the formula: $E=[X+Y]-[(X \times Y)/100]$, wherein E is the expected kill rate; X is efficacy expressed as % of untreated control of the pesticide; and Y is efficacy expressed as % of untreated control of the adjuvant.

In a further embodiment, the amount of adjuvant is an amount effective to increase the rate of cuticle penetration.

In a further embodiment, the amount of adjuvant is an amount effective to decrease the amount of pesticide required to achieve a certain kill rate, by at least around 10%. In a further embodiment, the amount of adjuvant is an amount effective to decrease the amount of pesticide required to achieve a certain kill rate, by at least around 20%. In a further embodiment, the amount of adjuvant is an amount effective to decrease the amount of pesticide required to achieve a certain kill rate, by at least around 30%.

In a further embodiment, the pesticide has a log P value of about <2.0. In a further embodiment, the pesticide has a log P value of between about >2.0 and about <4.0. In a further embodiment, the pesticide has a log P value of about >4.0.

In one embodiment, the pesticide is selected from one or more of abamectin, acephate, acetamiprid, acrinathrin, alanycarb, aldicarb, allethrin, alpha-cypermethrin, aluminium phosphide, amitraz, azadirachtin, azamethiphos, azinphos-ethyl, azinphos-methyl, bendiocarb, benfuracarb, bensultap, beta-cyfluthrin, beta-cypermethrin, bifenthrin, bioallethrin, bioallethrin S-cyclopentenyl isomer, bioresmethrin, bistrifluron, borax, buprofezin, butocarboxim, butoxycarboxim, cadusafos, calcium cyanide, calcium polysulfide, carbaryl, chlorantraniliprole, carbofuran, carbosulfan, cartap, chlorethoxyfos, chlorfenapyr, chlorfenvinphos, chlorfluazuron, chlormephos, chloropicrin, chlorpyrifos, chlorpyrifos-methyl, chromafenozide, clothianidin, cyantraniliprole, coumaphos, cryolite, cyanophos, cycloprothrin, cyfluthrin, cyhalothrin, cypermethrin, cyphenothrin, cyromazine, dazomet, deltamethrin, demeton-S-methyl, diafenthiuron, diazinon, dichlorvos, dicrotophos, dicyclanil, diflubenzuron, dimethoate, dimethylvinphos, dinotefuran, disulfoton, emamectin, emamectin benzoate, empenthrin, endosulfan, esfenvalerate, ethiofencarb, ethion, ethiprole, ethoprophos, ethylene dibromide, etofenprox, etoxazole, famphur, fenitrothion, fenobucarb, fenoxycarb, fenpropathrin, fenthion, fenvalerate, fipronil, flonicamid, flucycloxuron, flucythrinate, flufenoxuron, flumethrin, formetanate, formetanate hydrochloride, fosthiazate, furathiocarb, gamma-cyhalothrin, halofenozide, heptachlor, heptenophos, hexaflumuron, hydramethylnon, hydroprene, imidacloprid, imiprothrin, indoxacarb, isofenphos, isoprocarb, isopropyl O-(methoxyaminothiophosphoryl) salicylate, isoxathion, lambda-cyhalothrin, lithium perfluorooctane sulfonate, lufenuron, magnesium phosphide, malathion, mecarbam, mercurous chloride, metaflumizone, metam, metam-sodium, methamidophos, methidathion, methiocarb, methomyl, methoprene, methothrin, methoxychlor, methoxyfenozide, metofluthrin, methyl isothiocyanate, metolcarb, mevinphos, milbemectin, monocrotophos, naled, naphthalenic compounds, nicotine, nitenpyram, nithiazine, novaluron, noviflumuron, omethoate, oxamyl, oxydemeton-methyl, parathion, parathion-methyl, pentachlorophenol, pentachlorophenyl laurate, permethrin, petroleum oils, phenothrin, phorate, phosalone, phosmet, phosphamidon, phosphine, pirimicarb, pirimiphos-methyl, prallethrin, profenofos, propaphos, propetamphos, propoxur, prothiofos, pymetrozine, pyraclofos, pyrethrins, pyridalyl, pyridaben, pyridaphenthion, pyrimidifen, pyriproxyfen, quinalphos, resmethrin, rotenone, sabadilla, silafluofen, sodium cyanide, sodium pentachloro-phenoxide, spinetoram, spinosad, sulcofuron, sulcofuron-sodium, sulfluramid, sulfotep, sulfuryl fluoride, sulprofos, tau-fluvalinate, tebufenozide, tebupirimfos, teflubenzuron, tefluthrin, temephos, terbufos, tetrachlorvinphos, tetramethrin, theta-cypermethrin, thiacloprid, thiamethoxam, thiodicarb, thiofanox, thiometon, thiosultap-sodium, tolfenpyrad, tralomethrin, transfluthrin, triazamate, triazophos, trichlorfon, triblumuron, trimethacarb, vamidothion, xylylcarb, zeta-cypermethrin, zinc phosphide, beet juice, D-limonene, cedarwood oil, castor oil, cedar oil, cinnamon oil, citric acid, citronella oil, clove oil, corn oil, cottonseed oil, eugenol, garlic oil, geraniol, geranium oil, lauryl sulfate, lemon grass oil, linseed oil, malic acid, mint oil, peppermint oil, 2-phenethyl propionate (2-phenylethyl propionate), potassium sorbate, rosemary oil, sesame oil, sodium chloride, sodium lauryl sulfate, soybean oil, and thyme oil.

In still further an embodiment, the pesticide is selected from one or more of abamectin, acetamiprid, allethrin, alpha-cypermethrin, azadirachtin, bendiocarb, beta-cyfluthrin, bifenthrin, bioallethrin, bioallethrin S-cyclopentenyl isomer, bioresmethrin, borax, carbaryl, chlorantraniliprole, chlorfenapyr, chlorfluazuron, chromafenozide, clothianidin, cyantraniliprole, cryolite, cyfluthrin, cyhalothrin, cypermethrin, cyphenothrin, deltamethrin, diflubenzuron, dinotefuran, emamectin, emamectin benzoate, esfenvalerate, ethiprole, etofenprox, fenvalerate, fipronil, flonicamid, flucycloxuron, flufenoxuron, flumethrin, gamma-cyhalothrin, halofenozide, hexaflumuron, hydramethylnon, hydroprene, imidacloprid, imiprothrin, indoxacarb, lambda-cyhalothrin, lufenuron, malathion, metaflumizone, methoprene, methoxyfenozide, nitenpyram, novaluron, noviflumuron, permethrin, phenothrin, prallethrin, propoxur, pymetrozine, pyrethrins, pyriproxyfen, resmethrin, silafluofen, spinetoram, spinosad, tau-fluvalinate, tebufenozide, teflubenzuron, tefluthrin, tetramethrin, thiacloprid, thiamethoxam, transfluthrin, zeta-cypermethrin, D-limonene, cedarwood oil, castor oil, cedar oil, cinnamon oil, citric acid, citronella oil, clove oil, eugenol, garlic oil, geraniol, geranium oil, lauryl sulfate, lemon grass oil, malic acid, mint oil, peppermint oil, 2-phenethyl propionate (2-phenylethyl propionate), potassium sorbate, rosemary oil, sesame oil, sodium chloride, sodium lauryl sulfate, soybean oil, and thyme oil.

In one embodiment, the adjuvant is a free radical scavenger.

In one embodiment, the adjuvant is in an amount so as to provide negligible ability to function as a plasticizer.

In one embodiment, the adjuvant is selected from one or more dibasic esters, such as, for example sebacates, polyphenyl methanes, food grade preservatives, fatty acid esters, antioxidants, vitamins, fatty acids, surfactants, ibuprofen, tetramethylsilane, trimethylsilane, Compound A (used herein to describe a mixture of bis (1,2,2,6,6-pentamethyl-4-piperidinyl)sebacate and methyl(1,2,2,6,6-pentamethyl-4-piperidinyl)sebacate) at 1%), dimethyl sebacate, sebacic acid, sebacic acid dibenzyl esters, sebacic acid-bis-(N-succinimidyl) ester, bis(1-octyloxy-2,2,6,6-tetramethyl-4-piperidyl) sebacate, bis (2,2,6,6-tetramethyl-4-piperidyl) sebacate), 4-hydroxy-2,2,6,6-tetramethylpiperidine, 1,2,2,6,6-pentamethyl-4-piperidinol, 4-hydroxy-2,2,6,6 tetramethylpiperidin-l-oxyl, hindered amine light stabilizers, diphenyl methane, triphenyl methane (Gomberg's trityl), triphenyl methyl chloride (tritylchloride), BHA (butylated hydroxyanisole), BHT (butylated hydroxytoluene), BHQ (butylated hydroxyquinone), TBHQ (tertiary butyl dihydroxyquinone), methyl esters, including long chain fatty acid esters such as, for example, methyl oleate, methyl linoleate, methyl palmitate, ethyl esters, ethyl oleate, dibenzyl maleate, ascorbic acid, retinol, grape seed oil, rosveratrol, benzenepropanoic acid, oleic acid, linoleic acid, palmitic acid, omega-3-fatty acids, EPA, DHA, acetyl salicylic acid, salicylic acid, methyl salicylate, ibuprofen, tetramethylsilane, trimethylsilane, and a surfactant selected from Miranol or Mirataine.

In still further an embodiment, the adjuvant is the compounds identified herein as Compound A or bis(1,2,2,6,6-pentamethyl-4-piperidinyl)sebacate and methyl(1,2,2,6,6-pentamethyl-4-piperidinyl)sebacate.

In one embodiment, the composition is for treating flying pests. In one embodiment, the composition is applied to plants and further comprises a suitable carrier. In a further embodiment, the composition is applied to leaves of a plant, to soil adjacent to a plant, or directly to a plant root. In a further embodiment, the plant is a house plant, a bush, a tree, an ornamental or the plant is turf or grass. In one embodiment, the pesticide is a virucide, bactericide, fungicide, plant growth regulator, or herbicide. In one embodiment, the composition is designed for root application. In a further embodiment, the composition is designed for spray application.

In a further embodiment, the composition is applied to a substrate to treat or prevent a pest infestation. In still further an embodiment, the substrate is a wood product. In a further embodiment, the wood product is pressed wood, particle board, chip board, wafer board, plywood, wood laminated material, freshly cut timber, lumber, and paper. In one embodiment, the composition further includes at least one of a diluent, emulsifier, melting agent, organic binding agent, auxiliary solvent, processing additive, fixative, stability enhancer, dye, color pigment, siccative, corrosion inhibitor, anti-settlement agent, or anti-skinning agents. In one embodiment, the composition is applied by soaking the substrate in or with the composition, impregnating the substrate with the composition, brushing the composition onto the substrate, spraying the composition onto the substrate, or dipping the substrate into the composition.

In one embodiment, the composition targets eggs, larvae, nymphs, or adults of pests. In one embodiment, the composition targets crawling pests, ants, arachnids, bed bugs, beetles, centipedes, cockroaches, crickets, earwigs, fleas, scorpions, silverfish, spiders, termites, ticks, flying insects, flies, gnats, hornets, midges, mosquitoes, moths, wasps, plant pests, aphids, armyworms, bagworms, cutworms, mealybugs, mites, nematodes, plant bugs, psyllids, scale insects, thrips, or whiteflies. In still further an embodiment, the composition targets Hemiptera; Delphacidae such as *Laodelphax striatellus, Nilaparvata lugens, Sogatella furcifera* and the like; Deltocephalidae such as *Nephotettix cincticeps, Nephotettix virescens* and the like; Aphididae such as *Aphis gossypii, Myzus persicae* and the like; Pentatomidae such as *Nezara antennata, Riptortus clavetus, Eysarcoris lewisi, Eysarcoris parvus, Plautia stali, Halyomorpha mista* and the like; Aleyrodidae such as *Trialeurodes vaporariorum, Bemisia argentifolii* and the like; Coccidae such as *Aonidiella aurantii, Comstockaspis perniciosa, Unaspis citri, Ceroplastes rubens, Icerya purchasi* and the like; Tingidae; Psyllidae, and the like; Lepidoptera; Pyralidae such as *Chilo suppressalis, Cnaphalocrocis medinalis, Notarcha derogata, Plodia interpunctella* and the like; Noctuidae such as *Spodoptera litura, Pseudaletia separata, Thoricoplusia* spp., *Heliothis* spp., *Helicoverpa* spp. and the like; Pieridae such as *Pieris rapae* and the like; Tortricidae such as *Adoxophyes* spp., *Grapholita molesta, Cydia pomonella* and the like; Carposinidae such as *Carposina niponensis* and the like; Lyonetiidae such as *Lyonetia* spp. and the like; Lymantriidae such as *Lymantria* spp., *Euproctis* spp., and the like; Yponomeutidae such as *Plutella xylostella* and the like; Gelechiidae such as *Pectinophora gossypiella* and the like; Arctiidae such as *Hyphantria cunea* and the like; Tineidae such as *Tinea translucens, Tineola bisselliella* and the like; Diptera; Calicidae such as *Culex pipiens pallens, Culex tritaeniorhynchus, Culex quinquefasciatus* and the like; *Aedes* spp. such as *Aedes aegypti, Aedes albopictus* and the like; *Anopheles* spp. such as *Anopheles sinensis* and the like, Chironomidae; Muscidae such as *Musca domestica, Muscina stabulans* and the like; Calliphoridae; Sarcophagidae; Fanniidae; Anthomyiidae such as *Delia platura, Delia antiqua* and the like; Tephritidae; Drosophilidae; Psychodidae; Tabanidae; Simuliidae; Stomoxyidae; Agromyzidae, and the like; Coleoptera; *Diabrotica* spp. such as *Diabrotica virgifera virgifera, Diabrotica undecimpunctata howardi* and the like; Scarabaeidae such as *Anomala cuprea, Anomala rufocuprea* and the like; Curculionidae such as *Sitophilus zeamais, Lissorhoptrus oryzophilus, Callosobruchuys chienensis* and the like; Tenebrionidae such as *Tenebrio molitor, Tribolium castaneum* and the like; Chrysomelidae such as *Oulema oryzae, Aulacophora femoralis, Phyllotreta striolata, Leptinotarsa decemlineata* and the like; Anobiidae; *Epilachna* spp. such as *Epilachna vigintioctopunctata* and the like; Lyctidae; Bostrychidae; Cerambycidae; *Paederus fuscipes;* Blattodea such as *Blattella germanica, Periplaneta fuliginosa, Periplaneta americana, Periplaneta brunnea, Blatta orientalis* and the like; Thysanoptera: *Thrips palmi, Thrips tabaci, Frankliniella occidentalis, Frankliniella intonsa* and the like; Hymenoptera: Formicidae, Vespidae, bethylid wasp, Tenthredinidae such as *Athalia japonica*, and the like; Orthoptera: Gryllotalpidae, Acrididae, and the like; Aphaniptera: *Ctenocephalides felis, Ctenocephalides canis, Pulex irritans, Xenopsylla cheopis*, and the like; Anoplura: *Pediculus humanus corporis, Phthirus pubis, Haematopinus eurysternus, Dalmalinia ovis*, and the like; Isoptera: *Reticulitermes speratus, Coptotermes formosanus*, and the like; Acarina: Tetranychidae such as *Tetranychus urticae, Tetranychus kanzawai, Panonychus citri, Panonychus ulmi, Oligonychus* spp., and the like; Eriophyidae such as *Aculops pelekassi, Aculus schlechtendali*, and the like; Tarsonemidae such as *Polyphagotarsonemus latus*, and the like; Tenuipalpidae; Tuckerellidae; Ixodidae such as *Haemaphysalis longicornis, Haemaphysalis flava, Dermacentor taiwanicus, Ixodes ovatus, Ixodes persulcatus, Boophilus microplus*, and the like; Acaridae such as *Tyrophagus putrescentiae*, and the like; Epidermoptidae such as *Dermatophagoides farinae, Dermatophagoides ptrenyssnus*, and the like; Cheyletidae such as *Cheyletus eruditus, Cheyletus malaccensis, Cheyletus moorei*, and the like; Dermanyssidae; Araneae such as *Chiracanthium japonicum, Latrodectus hasseltii*, and the like; Chilopoda: *Thereuonema hilgendorfi, Scolopendra subspinipes*, and the like; Diplopoda: *Oxidus gracilis, Nedyopus tambanus*, and the like; Isopoda: *Armadillidium vulgare*, and the like; Gastropoda: *Limax marginatus, Limax flavus*, and the like; Nematoda: *Pratylenchus coffeae, Pratylenchus fallax, Heterodera glycines, Globodera rostochiensis, Meloidogyne hapla, Meloidogyne incognita*, and the like.

One embodiment of the present invention includes a method for controlling or preventing pest infestation, comprising administering a composition as herein described. In a further embodiment, the composition provides a longer residual pesticidal effect than the combined residual pesticidal effects of the pesticide and the adjuvant when each is applied individually at a same concentration. In a further embodiment, the composition is not phytotoxic but the pesticide, alone, is phytotoxic.

One embodiment of the present invention provides a method for treating or preventing a pest comprising: applying a an amount of pesticide at a locus together with an adjuvant, wherein the adjuvant is present in an amount sufficient to stabilize the formation of free radicals, wherein the amount of pesticide applied is at least about 10% less than expected. In other words, where an expected amount of pesticide is necessary to achieve an effect, the combination with an adjuvant within the present invention provides for a synergistic reduction in the amount of pesticide necessary to achieve an equivalent effect.

One embodiment of the present invention is a method for increasing a kill spectrum of a pesticide comprising: providing a pesticide at a locus together with an adjuvant, wherein the adjuvant is present in an amount sufficient to stabilize the formation of free radicals. In one embodiment, the adjuvant destabilizes the cuticle of a plant or an insect.

One embodiment of the present invention provides a pesticidal composition consisting essentially of a pesticide that is not an organophosphate and an adjuvant, wherein the composition provides a synergistic kill rate. For such embodiments, additional formulation components are believed to not materially affect the basic and novel characteristics of the invention.

One embodiment of the present invention provides a method for increasing the permeability of a pesticide to an insect or plant comprising exposing a cuticle of said insect or plant to an adjuvant wherein said adjuvant destabilizes said cuticle of said insect or plant.

One embodiment of the present invention provides a method for initiating a free radical reaction on insect or plant tissue thereby altering the permeability of biological membranes in said tissue comprising: exposing said insect or plant tissue to an adjuvant that destabilizes the cuticle of said insect or plant.

The present invention includes combinations of one or more embodiments herein disclosed.

BRIEF DESCRIPTION OF THE FIGURES

FIG. 1 is a graph illustrating the synergy of a free radical stabilizer, benzenepropanoic acid, with an insecticide, imidacloprid, against the Argentine ant, in terms of mortality (%) over time (hours). Diamonds represent imidacloprid at a 0.5% concentration, triangles represent benzenepropanoic acid at a 5% concentration, and squares represent a blend of imidacloprid at a 0.5% concentration and benzenepropanoic acid at a 5% concentration.

FIG. 2 is a graph illustrating the synergy of a free radical stabilizer, benzenepropanoic acid, with an insecticide, imidacloprid, against the German cockroach, in terms of mortality (%) over time (hours). Diamonds represent imidacloprid at a 0.5% concentration, triangles represent benzenepropanoic acid at a 1% concentration, and squares represent a blend of imidacloprid at a 0.5% concentration and benzenepropanoic acid at a 1% concentration.

FIG. 3 is a graph illustrating the synergy of a free radical stabilizer, oleic acid, with an insecticide, imidacloprid, against the German cockroach, in terms of mortality (%) over time (hours). Diamonds represent imidacloprid at a 0.5% concentration, triangles represent oleic acid at a 1% concentration, and squares represent a blend of imidacloprid at a 0.5% concentration and oleic acid at a 1% concentration.

FIG. 4 is a graph illustrating the synergy of a free radical stabilizer, oleic acid, with an insecticide, imidacloprid, against the Argentine ant, in terms of mortality (%) over time (hours). Diamonds represent imidacloprid at a 0.5% concentration, triangles represent oleic acid at a 0.1% concentration, and squares represent a blend of imidacloprid at a 0.5% concentration and oleic acid at a 0.1% concentration.

FIG. 5 is a graph illustrating the synergy of a free radical stabilizer, methyl oleate, with an insecticide, imidacloprid, against the Argentine ant, in terms of mortality (%) over time (hours). Diamonds represent imidacloprid at a 0.5% concentration, triangles represent methyl oleate at a 5% concentration, and squares represent a blend of imidacloprid at a 0.5% concentration and methyl oleate at a 5% concentration.

FIG. 6 is a graph illustrating the synergy of a free radical stabilizer, methyl oleate, with an insecticide, imidacloprid, against the German cockroach, in terms of mortality (%) over time (hours). Diamonds represent imidacloprid at a 0.5% concentration, triangles represent methyl oleate at a 1% concentration, and squares represent a blend of imidacloprid at a 0.5% concentration and methyl oleate at a 1% concentration.

FIG. 7 is a graph illustrating the synergy of a free radical stabilizer, methyl linoleate, with an insecticide, imidacloprid, against the Argentine ant, in terms of mortality (%) over time (hours). Diamonds represent imidacloprid at a 0.5% concentration, triangles represent methyl linoleate at a 1% concentration, and squares represent a blend of imidacloprid at a 0.5% concentration and methyl linoleate at a 1% concentration.

FIG. 8 is a graph illustrating the synergy of a free radical stabilizer, methyl linoleate, with an insecticide, imidacloprid, against the German cockroach, in terms of mortality (%) over time (hours). Diamonds represent imidacloprid at a 0.5% concentration, triangles represent methyl linoleate at a 1% concentration, and squares represent a blend of imidacloprid at a 0.5% concentration and methyl linoleate at a 1% concentration.

FIG. 9 is a graph illustrating the synergy of a free radical stabilizer, methyl palmitate, with an insecticide, imidacloprid, against the Argentine ant, in terms of mortality (%) over time (hours). Diamonds represent imidacloprid at a 0.5% concentration, triangles represent methyl palmitate at a 5% concentration, and squares represent a blend of imidacloprid at a 0.5% concentration and methyl palmitate at a 5% concentration.

FIG. 10 is a graph illustrating the synergy of a free radical stabilizer, methyl palmitate, with an insecticide, imidacloprid, against the German cockroach, in terms of mortality (%) over time (hours). Diamonds represent imidacloprid at a 0.5% concentration, triangles represent methyl palmitate at a 5% concentration, and squares represent a blend of imidacloprid at a 0.5% concentration and methyl palmitate at a 5% concentration.

FIG. 11 is a graph illustrating the synergy of a free radical stabilizer, butylated hydroxy anisole (BHA), with an insecticide, imidacloprid, against the Argentine ant, in terms of mortality (%) over time (hours). Diamonds represent imidacloprid at a 0.5% concentration, triangles represent BHA at a 1% concentration, and squares represent a blend of imidacloprid at a 0.5% concentration and BHA at a 1% concentration.

FIG. 12 is a graph illustrating the synergy of a free radical stabilizer, butylated hydroxy anisole (BHA), with an insecticide, imidacloprid, against the German cockroach, in terms of mortality (%) over time (hours). Diamonds represent imidacloprid at a 0.5% concentration, triangles represent BHA at a 1% concentration, and squares represent a blend of imidacloprid at a 0.5% concentration and BHA at a 1% concentration.

FIG. 13 is a graph illustrating the synergy of a free radical stabilizer, butylated hydroxy toluene (BHT), with an insecticide, imidacloprid, against the Argentine ant, in terms of mortality (%) over time (hours). Diamonds represent imidacloprid at a 0.5% concentration, triangles represent BHT at a 0.1% concentration, and squares represent a blend of imidacloprid at a 0.5% concentration and BHT at a 0.1% concentration.

FIG. 14 is a graph illustrating the synergy of a free radical stabilizer, butylated hydroxy toluene (BHT), with an insecticide, imidacloprid, against the German cockroach, in terms of mortality (%) over time (hours). Diamonds represent imidacloprid at a 0.5% concentration, triangles represent BHT at a 1% concentration, and squares represent a blend of imidacloprid at a 0.5% concentration and BHT at a 1% concentration.

FIG. 15 is a graph illustrating the synergy of a free radical stabilizer, t-butyl hydroquinone (TBHQ), with an insecticide, imidacloprid, against the German cockroach, in terms of mortality (%) over time (hours). Diamonds represent imidacloprid at a 0.5% concentration, triangles represent TBHQ at a 0.1% concentration, and squares represent a blend of imidacloprid at a 0.5% concentration and TBHQ at a 0.1% concentration.

FIG. 16 is a graph illustrating the synergy of a free radical stabilizer, t-butyl hydroquinone (TBHQ), with an insecticide, imidacloprid, against the Argentine ant, in terms of mortality (%) over time (hours). Diamonds represent imidacloprid at a 0.5% concentration, triangles represent TBHQ at a 1% concentration, and squares represent a blend of imidacloprid at a 0.5% concentration and TBHQ at a 1% concentration.

FIG. 17 is a graph illustrating the synergy of a free radical stabilizer, diphenyl methane, with an insecticide, imidacloprid, against the Argentine ant, in terms of mortality (%) over time (hours). Diamonds represent imidacloprid at a 0.5% concentration, triangles represent diphenyl methane at a 1% concentration, and squares represent a blend of imidacloprid at a 0.5% concentration and diphenyl methane at a 1% concentration.

FIG. 18 is a graph illustrating the synergy of a free radical stabilizer, diphenyl methane, with an insecticide, imidacloprid, against the German cockroach, in terms of mortality (%) over time (hours). Diamonds represent imidacloprid at a 0.5% concentration, triangles represent diphenyl methane at a 5% concentration, and squares represent a blend of imidacloprid at a 0.5% concentration and diphenyl methane at a 5% concentration.

FIG. 19 is a graph illustrating the synergy of a free radical stabilizer, trityl chloride, with an insecticide, imidacloprid, against the Argentine ant, in terms of mortality (%) over time (hours). Diamonds represent imidacloprid at a 0.5% concentration, triangles represent trityl chloride at a 1% concentration, and squares represent a blend of imidacloprid at a 0.5% concentration and trityl chloride at a 1% concentration.

FIG. 20 is a graph illustrating the synergy of a free radical stabilizer, trityl chloride, with an insecticide, imidacloprid, against the susceptible German cockroach, in terms of mortality (%) over time (hours). Diamonds represent imidacloprid at a 0.5% concentration, triangles represent trityl chloride at a 0.1% concentration, and squares represent a blend of imidacloprid at a 0.5% concentration and trityl chloride at a 0.1% concentration.

FIG. 21 is a graph illustrating the synergy of a free radical stabilizer, dibutyl sebacate, with an insecticide, imidacloprid, against the resistant German cockroach (T164 strain), in terms of mortality (%) over time (hours). Diamonds represent imidacloprid at a 0.5% concentration, triangles represent dibutyl sebacate at a 1% concentration, and squares represent a blend of imidacloprid at a 0.5% concentration and dibutyl sebacate at a 1% concentration.

FIG. 22 is a graph illustrating the synergy of a free radical stabilizer, dibutyl sebacate, with an insecticide, imidacloprid, against the Argentine ant, in terms of mortality (%) over time (hours). Diamonds represent imidacloprid at a 0.5% concentration, triangles represent dibutyl sebacate at a 0.1% concentration, and squares represent a blend of imidacloprid at a 0.5% concentration and dibutyl sebacate at a 0.1% concentration.

Figure 23:
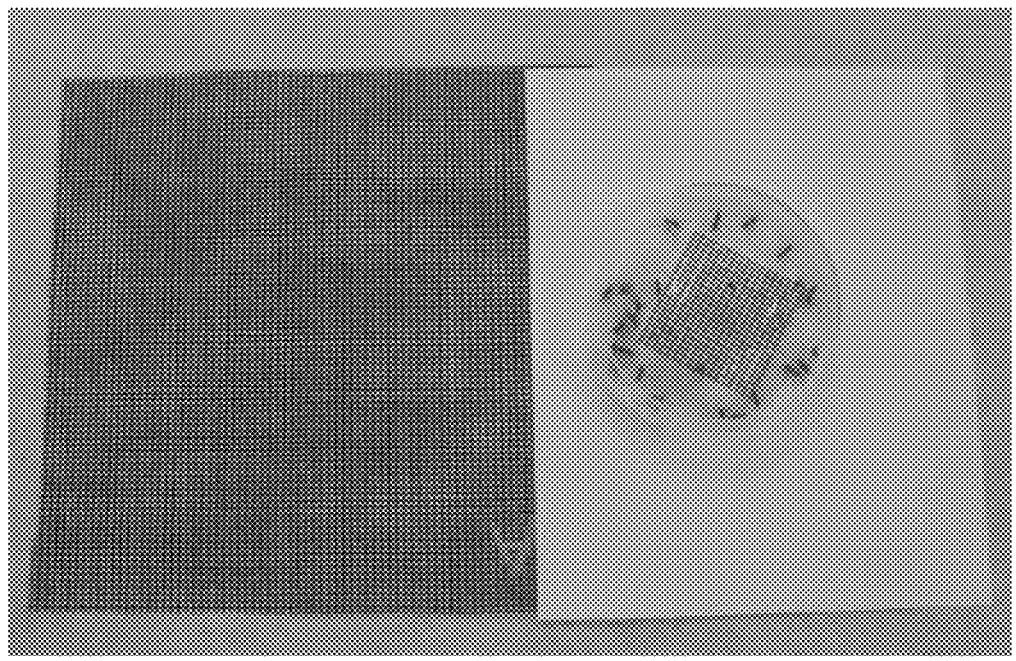
FIG. 23a is a photograph of a pre-cut fiberglass screen coated with an aqueous solution of 1% deltamethrin with and without a combination of Compound A, as used herein to describe a mixture of bis(1,2,2,6,6-pentamethyl-4-piperidinyl)sebacate and methyl(1,2,2,6,6-pentamethyl-4-piperidinyl)sebacate) at 1% and Compound B (2-(2H-Benzotriazole-2-yl)-4-methylphenyl, at 0.5%.
FIG. 23b is a photograph illustrating a petri dish that includes the screen shown in FIG. 23a, and *Aedes aegypti* mosquitos.
Figure 23:
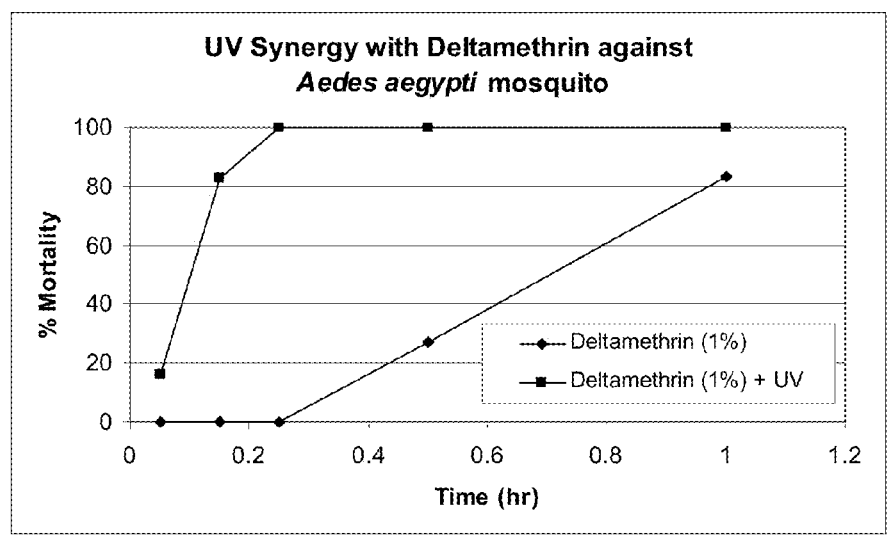

FIG. 23c is a graph illustrating the synergy of a combination of free radical stabilizers, Compound A and Compound B, with an insecticide, deltamethrin, against the *Aedes aegypti* mosquito, in terms of mortality (%) over time (hours). Diamonds represent deltamethrin at a 1% concentration, and squares represent a blend of deltamethrin at a 1% concentration and Compound A at a 1% and Compound B at a 0.5% concentration.

Figure 24:
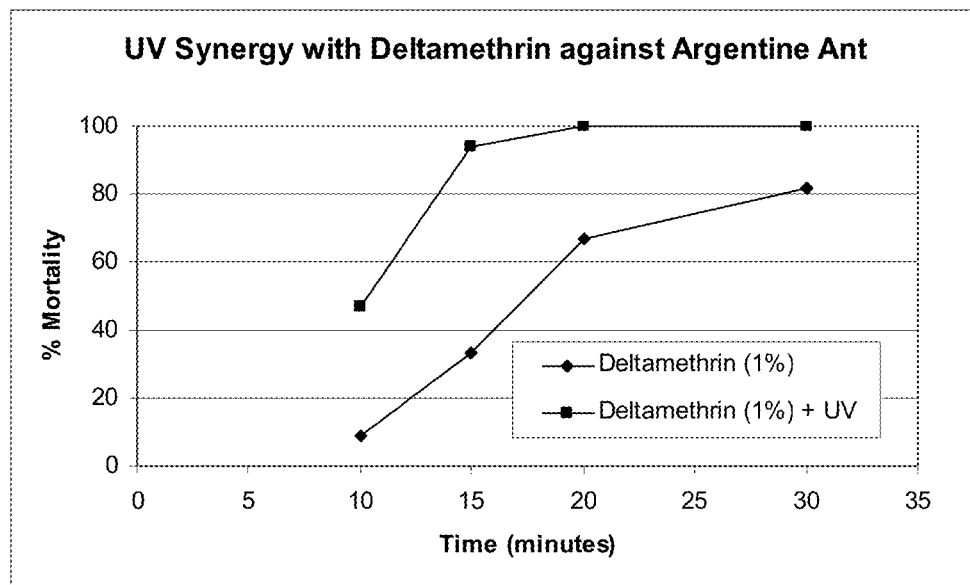

FIG. 24 is a graph illustrating the synergy of a combination of free radical stabilizers, Compound A and Compound B, with an insecticide, deltamethrin, against the Argentine ant, in terms of mortality (%) over time (minutes). Diamonds represent deltamethrin at a 1% concentration, and squares represent a blend of deltamethrin at a 1% concentration and Compound A at a 1% and Compound B at a 0.5% concentration.

Figure 25:
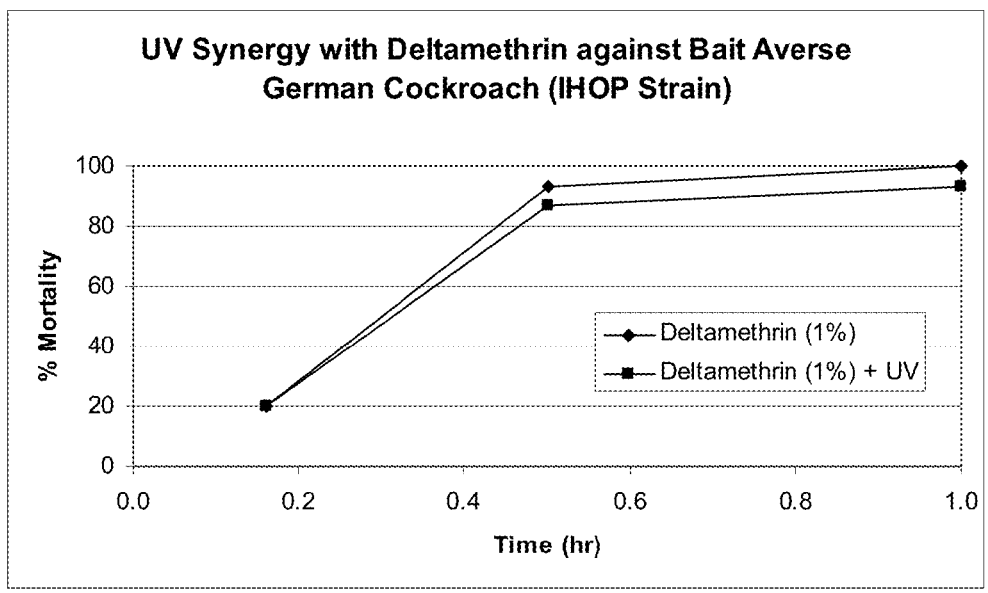

FIG. 25 is a graph illustrating the synergy of a combination of free radical stabilizers, Compound A and Compound B, with an insecticide, deltamethrin, against the bait averse German cockroach (IHOP strain), in terms of mortality (%) over time (hours). Diamonds represent deltamethrin at a 1% concentration, and squares represent a blend of deltamethrin at a 1% concentration and Compound A at a 1% and Compound B at a 0.5% concentration.

Figure 26:
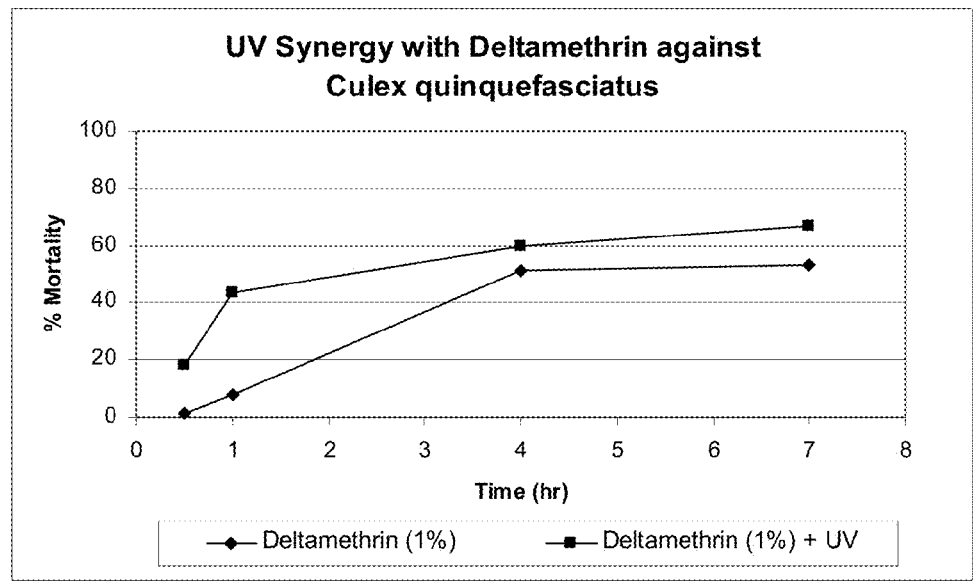

FIG. 26 is a graph illustrating the synergy of a combination of free radical stabilizers, Compound A and Compound B, with an insecticide, deltamethrin, against *Culex quinquefasciatus*, in terms of mortality (%) over time (hours). Diamonds represent deltamethrin at a 1% concentration, and squares represent a blend of deltamethrin at a 1% concentration and Compound A at a 1% and Compound B at a 0.5% concentration.

Figure 27:
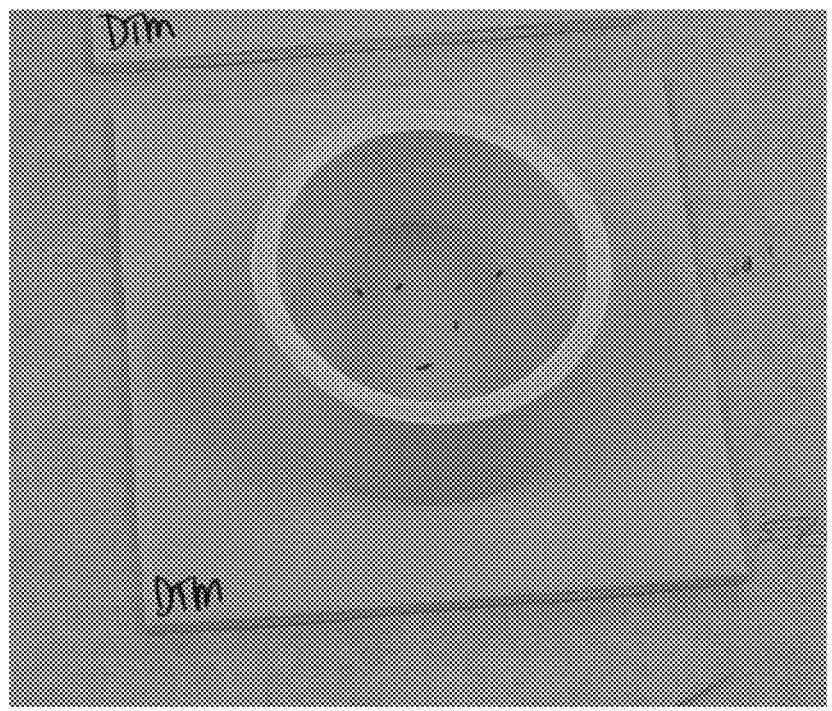
Figure 27:
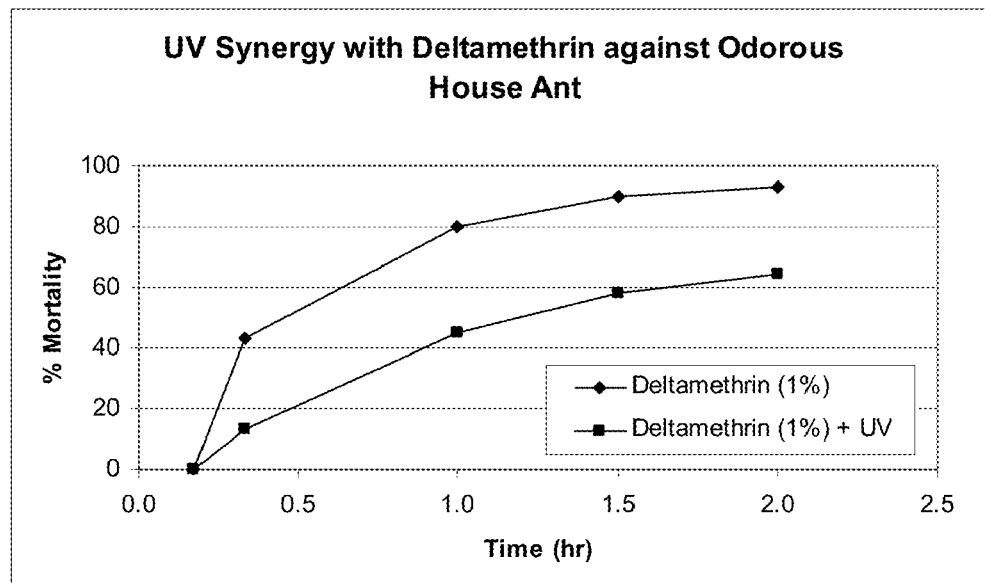

FIG. 27a is a photograph illustrating a glazed tile treated with an aqueous solution of deltamethrin at a concentration of 1% in combination with free radical stabilizers Compound A at 1% and Compound B at 0.5%. The odorous house ant, *Tapinoma sessile*, is in contact with the tile, and its escape is physically blocked, as shown in the photograph, by a column.

FIG. 27b is a graph illustrating the synergy of a combination of free radical stabilizers, Compound A and Compound B, with an insecticide, deltamethrin, against the odorous house ant, *Tapinoma sessile*, in terms of mortality (%) over time (hours). Diamonds represent deltamethrin at a 1% concentration, and squares represent a blend of deltamethrin at a 1% concentration and Compound A at a 1% and Compound B at a 0.5% concentration.

Figure 28:
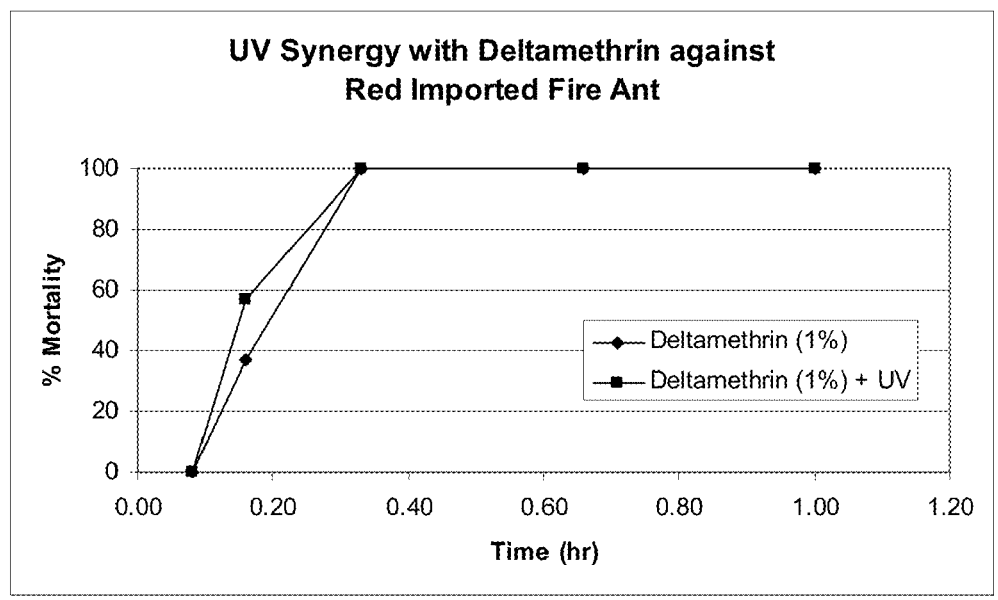

FIG. 28 is a graph illustrating the synergy of a combination of free radical stabilizers, Compound A and Compound B, with an insecticide, deltamethrin, against the red imported fire ant, in terms of mortality (%) over time (hours). Diamonds represent deltamethrin at a 1% concentration, and squares represent a blend of deltamethrin at a 1% concentration and Compound A at a 1% and Compound B at a 0.5% concentration.

Figure 29:
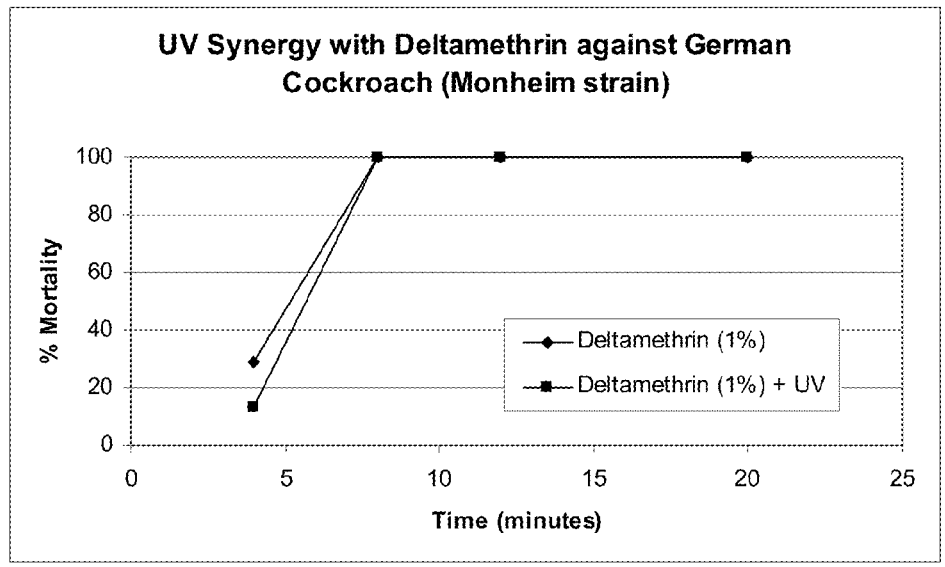

FIG. 29 is a graph illustrating the synergy of a combination of free radical stabilizers, Compound A and Compound B, with an insecticide, deltamethrin, against the German cockroach (Monheim strain), in terms of mortality (%) over time (minutes). Diamonds represent deltamethrin at a 1% concentration, and squares represent a blend of deltamethrin at a 1% concentration and Compound A at a 1% and Compound B at a 0.5% concentration.

Figure 30:
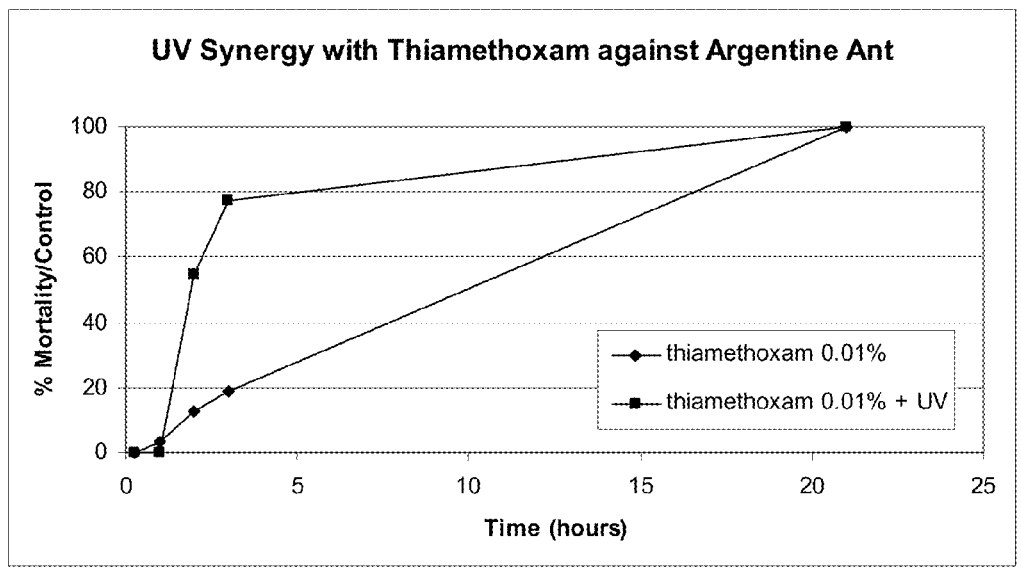

FIG. 30 is a graph illustrating the synergy of a combination of free radical stabilizers, Compound A and Compound B, with an insecticide, thiamethoxam, against the Argentine ant, in terms of mortality (%) over time (hours). Diamonds represent thiamethoxam at a 0.01% concentration, and squares represent a blend of thiamethoxam at a 0.01% concentration and Compound A at a 1% and Compound B at a 0.5% concentration.

Figure 31:
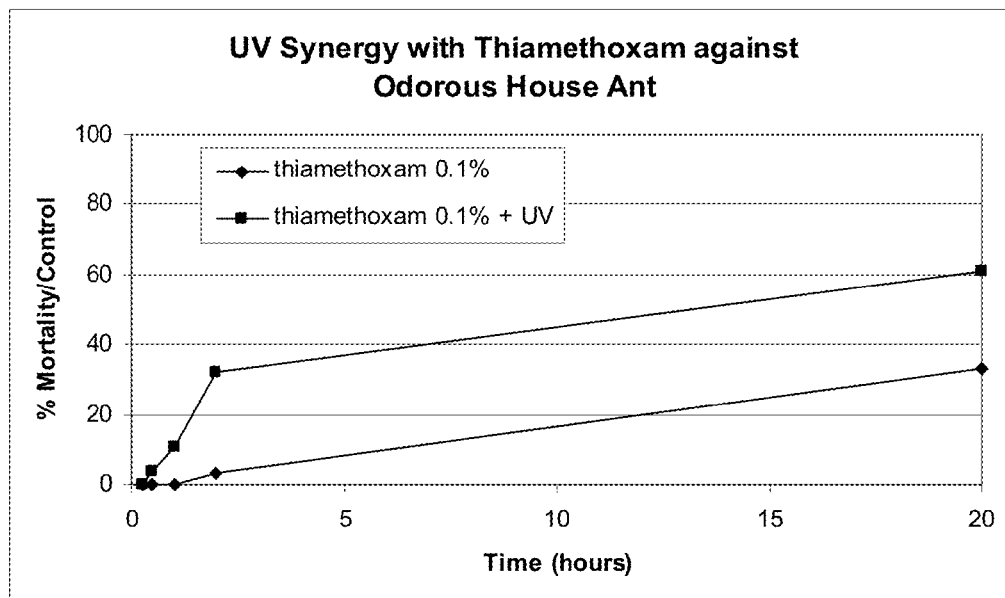

FIG. 31 is a graph illustrating the synergy of a combination of free radical stabilizers, Compound A and Compound B, with an insecticide, thiamethoxam, against the odorous house ant, in terms of mortality (%) over time (hours). Diamonds represent thiamethoxam at a 0.1% concentration, and squares represent a blend of thiamethoxam at a 0.1% concentration and Compound A at a 1% and Compound B at a 0.5% concentration.

Figure 32:
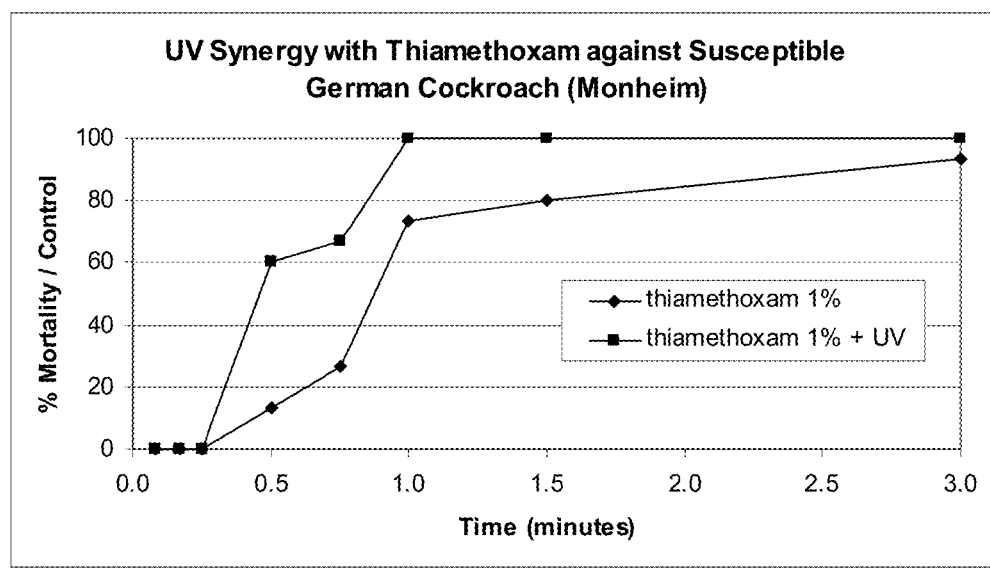

FIG. 32 is a graph illustrating the synergy of a combination of free radical stabilizers, Compound A and Compound B, with an insecticide, thiamethoxam, against the susceptible German cockroach (Monheim strain), in terms of mortality (%) over time (minutes). Diamonds represent thiamethoxam at a 1% concentration, and squares represent a blend of thiamethoxam at a 1% concentration and Compound A at a 1% and Compound B at a 0.5% concentration.

Figure 33:
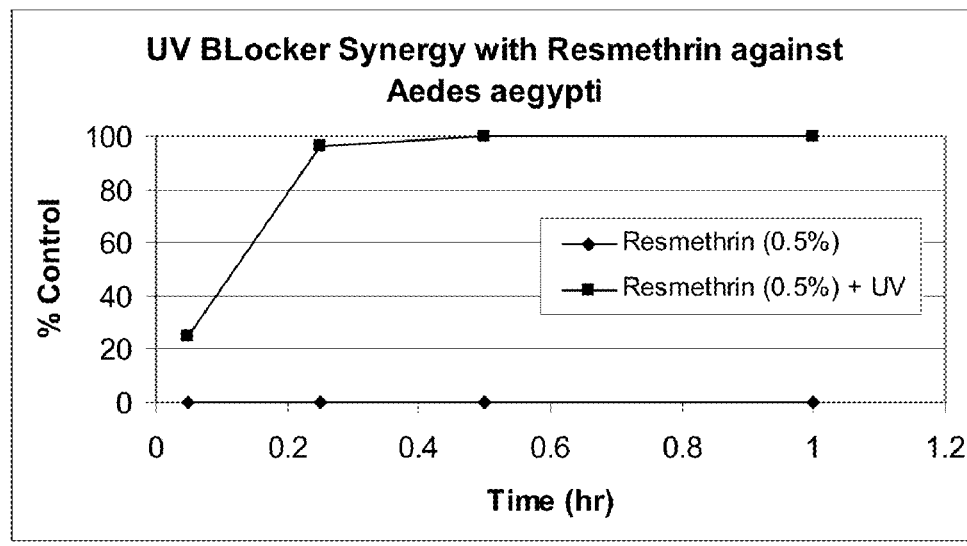

FIG. 33 is a graph illustrating the synergy of a combination of free radical stabilizers, Compound A and Compound B, with an insecticide, resmethrin, against the *Aedes aegypti* mosquito, in terms of mortality (%) over time (hours). Diamonds represent resmethrin at a 0.5% concentration, and squares represent a blend of resmethrin at a 0.5% concentration and Compound A at a 1% and Compound B at a 0.5% concentration.

Figure 34:
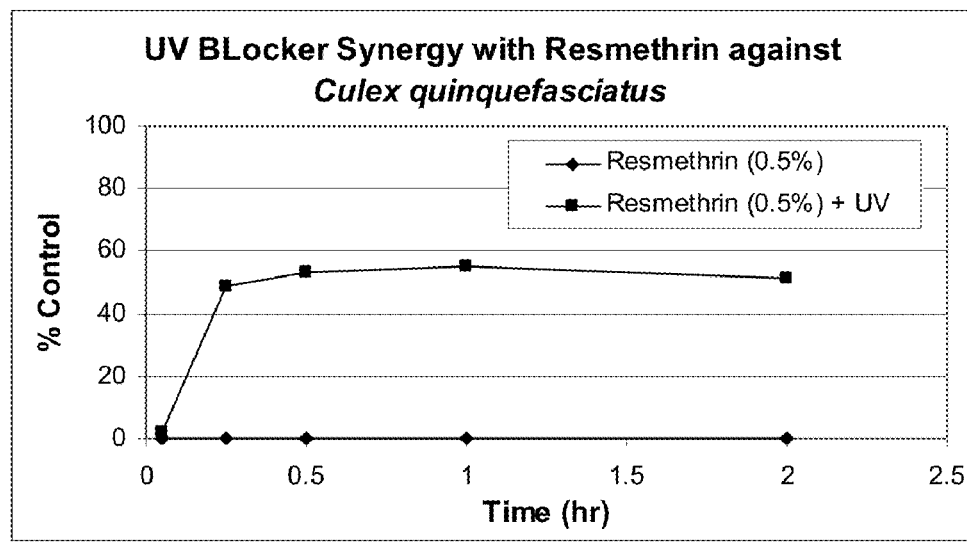

FIG. 34 is a graph illustrating the synergy of a combination of free radical stabilizers, Compound A and Compound B, with an insecticide, resmethrin, against *Culex quinquefasciatus*, in terms of control (%) over time (hours). Diamonds represent resmethrin at a 0.5% concentration, and squares represent a blend of resmethrin at a 0.5% concentration and Compound A at a 1% and Compound B at a 0.5% concentration.

Figure 35:
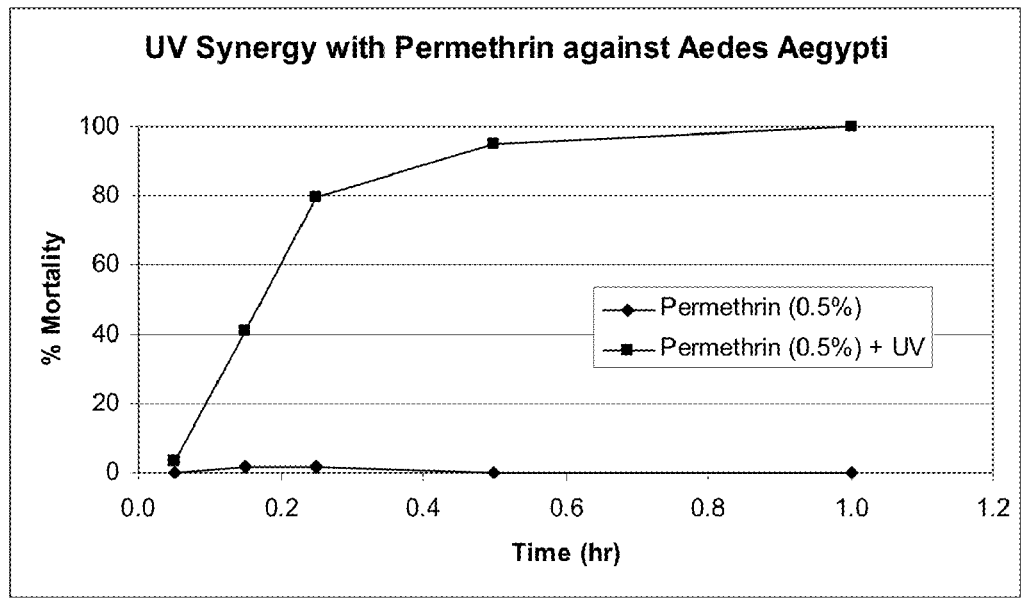

FIG. 35 is a graph illustrating the synergy of a combination of free radical stabilizers, Compound A and Compound B, with an insecticide, permethrin, against the Aedes aegypti mosquito, in terms of mortality (%) over time (hours). Diamonds represent permethrin at a 0.5% concentration, and squares represent a blend of permethrin at a 0.5% concentration and Compound A at a 1% and Compound B at a 0.5% concentration.

Figure 36:
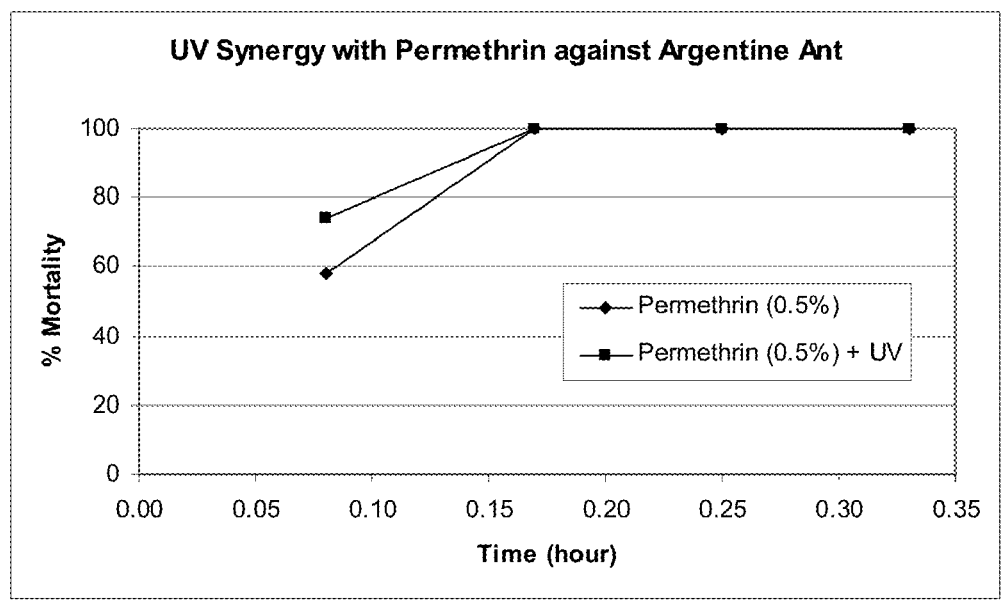

FIG. 36 is a graph illustrating the synergy of a combination of free radical stabilizers, Compound A and Compound B, with an insecticide, permethrin, against the Argentine ant, in terms of mortality (%) over time (hours). Diamonds represent permethrin at a 0.5% concentration, and squares represent a blend of permethrin at a 0.5% concentration and Compound A at a 1% and Compound B at a 0.5% concentration.

Figure 37:
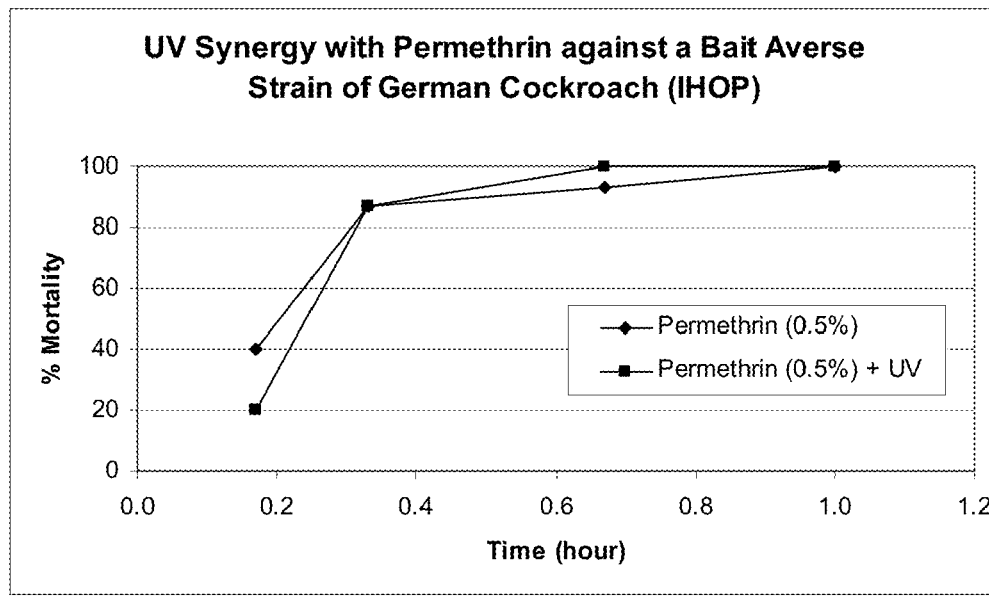

FIG. 37 is a graph illustrating the synergy of a combination of free radical stabilizers, Compound A and Compound B, with an insecticide, permethrin, against a bait averse strain of German cockroach (IHOP strain), in terms of mortality (%) over time (hours). Diamonds represent permethrin at a 0.5% concentration, and squares represent a blend of permethrin at a 0.5% concentration and Compound A at a 1% and Compound B at a 0.5% concentration.

Figure 38:
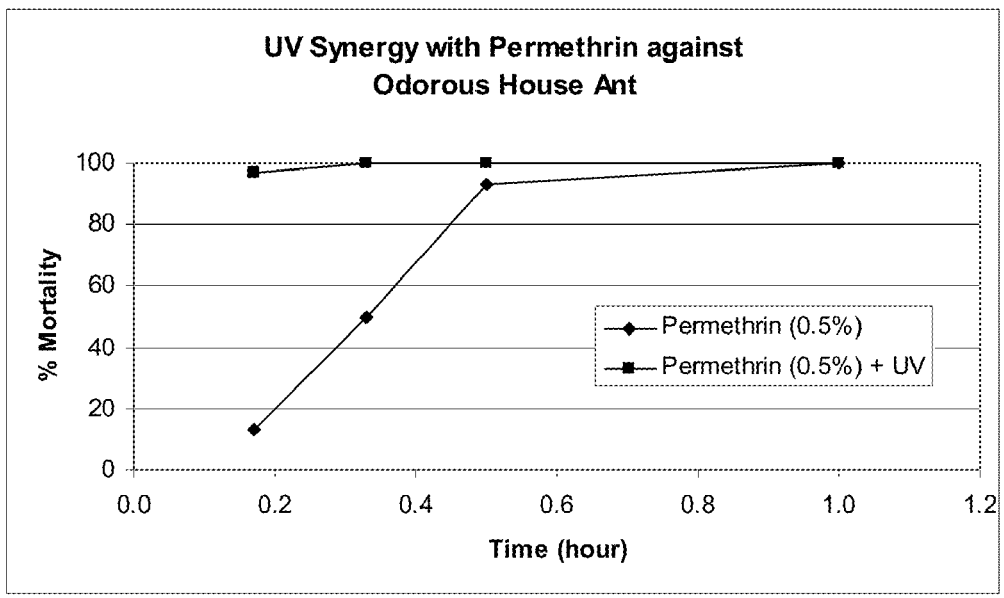

FIG. 38 is a graph illustrating the synergy of a combination of free radical stabilizers, Compound A and Compound B, with an insecticide, permethrin, against the odorous house ant, in terms of mortality (%) over time (hours). Diamonds represent permethrin at a 0.5% concentration, and squares represent a blend of permethrin at a 0.5% concentration and Compound A at a 1% and Compound B at a 0.5% concentration.

Figure 39:
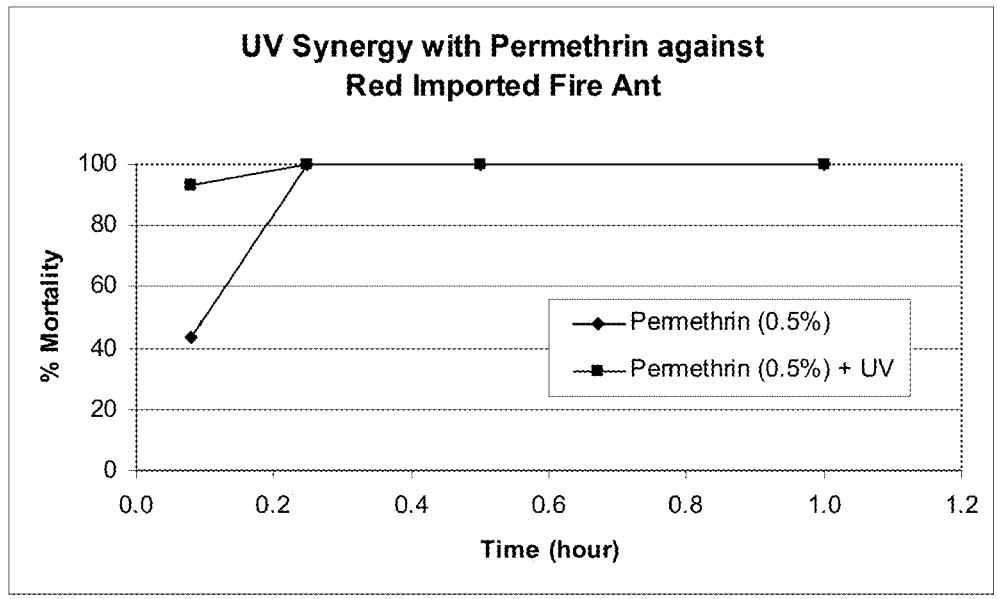

FIG. 39 is a graph illustrating the synergy of a combination of free radical stabilizers, Compound A and Compound B, with an insecticide, permethrin, against the red imported fire ant, in terms of mortality (%) over time (hours). Diamonds represent permethrin at a 0.5% concentration, and squares represent a blend of permethrin at a 0.5% concentration and Compound A at a 1% and Compound B at a 0.5% concentration.

Figure 40:
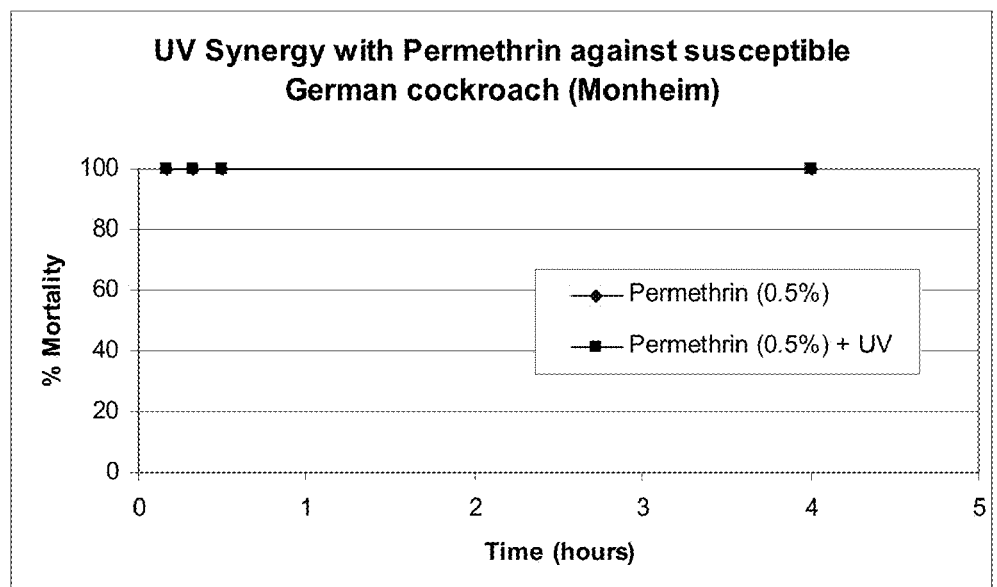

FIG. 40 is a graph illustrating the synergy of a combination of free radical stabilizers, Compound A and Compound B, with an insecticide, permethrin, against the susceptible German cockroach (Monheim strain), in terms of mortality (%) over time (hours). Diamonds represent permethrin at a 0.5% concentration, and squares represent a blend of permethrin at a 0.5% concentration and Compound A at a 1% and Compound B at a 0.5% concentration.

Figure 41:
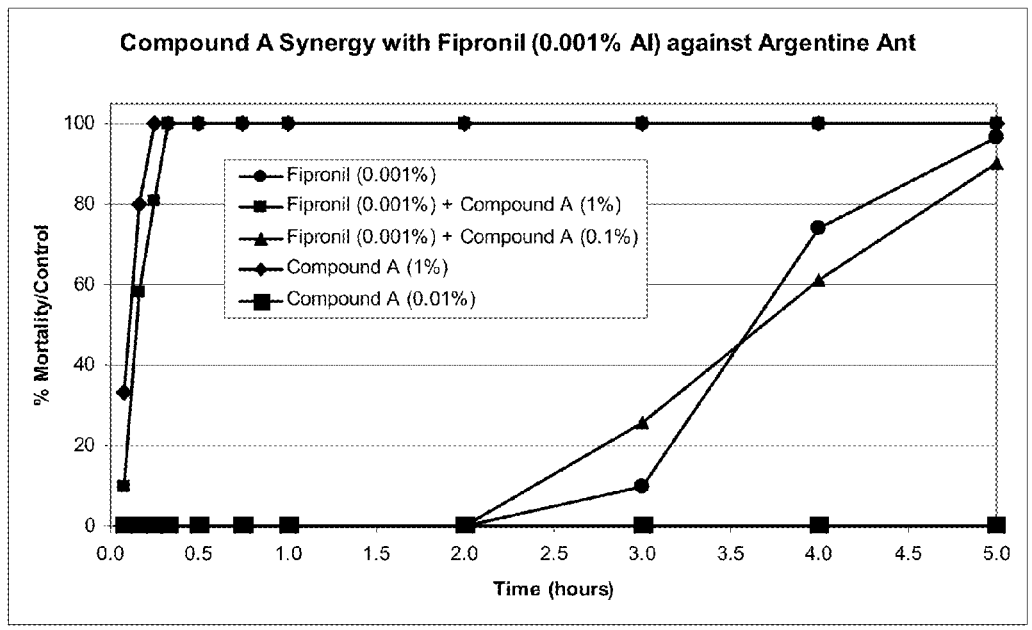

FIG. 41 is a graph illustrating the synergy of a free radical stabilizer, Compound A, with an insecticide, fipronil, against the Argentine ant, in terms of mortality/control (%) over time (hours). Diamonds represent fipronil at a 0.001% concentration, squares represent a blend of fipronil at a 0.001% concentration and Compound A at a 1%, triangles represent a blend of fipronil at a 0.001% concentration and Compound A at a 0.1% concentration, X's represent Compound A alone at a concentration of 1%, and asterisks represent Compound A alone at a concentration of 0.01%.

Figure 42:
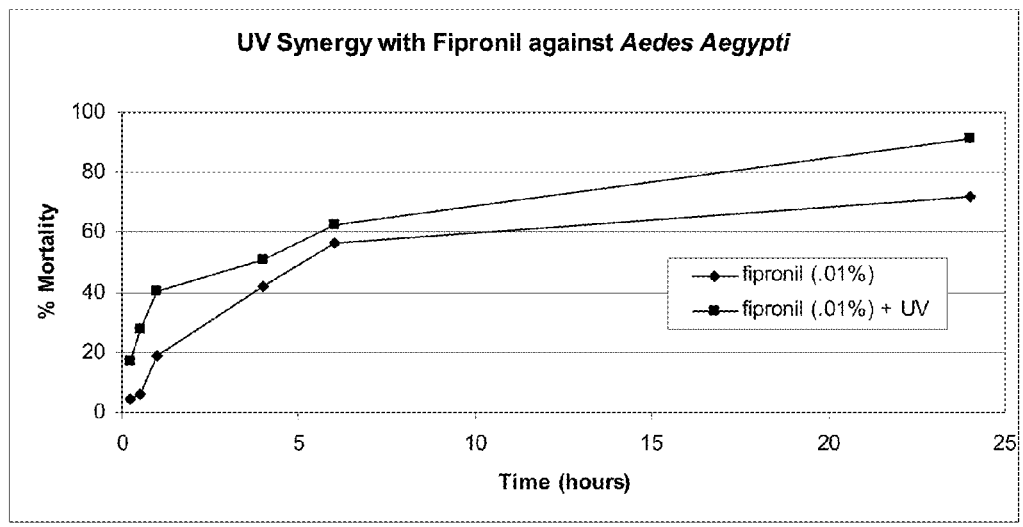

FIG. 42 is a graph illustrating the synergy of a combination of free radical stabilizers, Compound A and Compound B, with an insecticide, fipronil, against the *Aedes aegypti* mosquito, in terms of mortality (%) over time (hours). Diamonds represent fipronil at a 0.01% concentration, and squares represent a blend of fipronil at a 0.01% concentration and Compound A at a 1% and Compound B at a 0.5% concentration.

Figure 43:
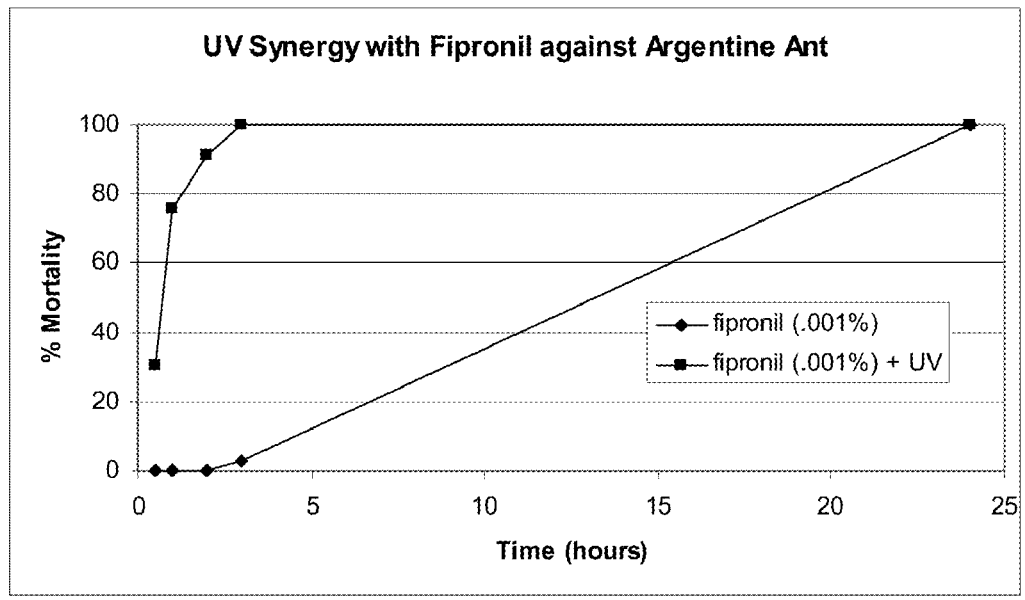

FIG. 43 is a graph illustrating the synergy of a combination of free radical stabilizers, Compound A and Compound B, with an insecticide, fipronil, the Argentine ant, in terms of mortality (%) over time (hours). Diamonds represent fipronil at a 0.001% concentration, and squares represent a blend of fipronil at a 0.001% concentration and Compound A at a 1% and Compound B at a 0.5% concentration.

Figure 44:
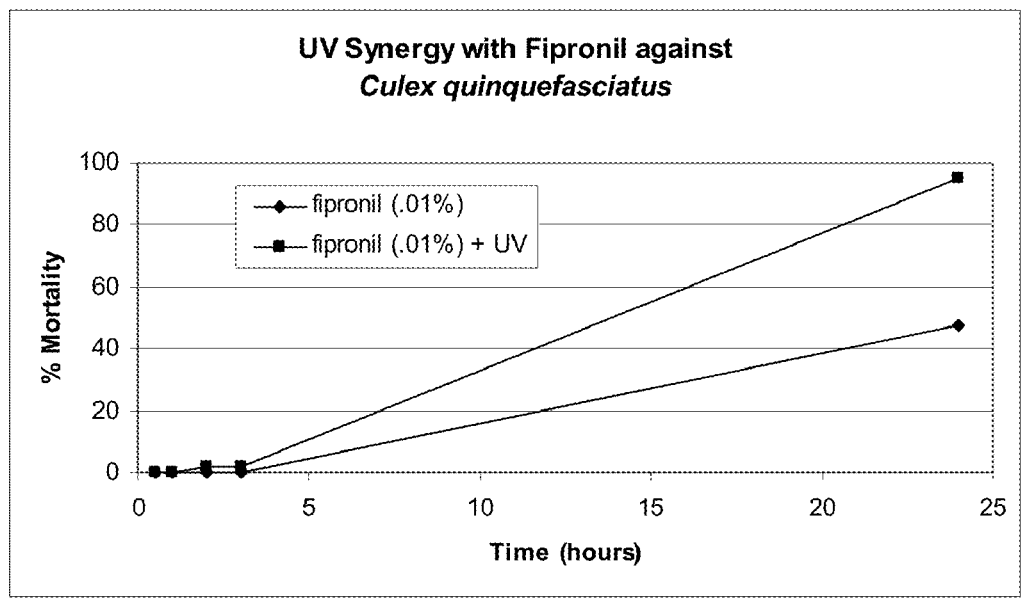

FIG. 44 is a graph illustrating the synergy of a combination of free radical stabilizers, Compound A and Compound B, with an insecticide, fipronil, against *Culex quinquefasciatus*, in terms of mortality (%) over time (hours). Diamonds represent fipronil at a 0.01% concentration, and squares represent a blend of fipronil at a 0.01% concentration and Compound A at a 1% and Compound B at a 0.5% concentration.

Figure 45:
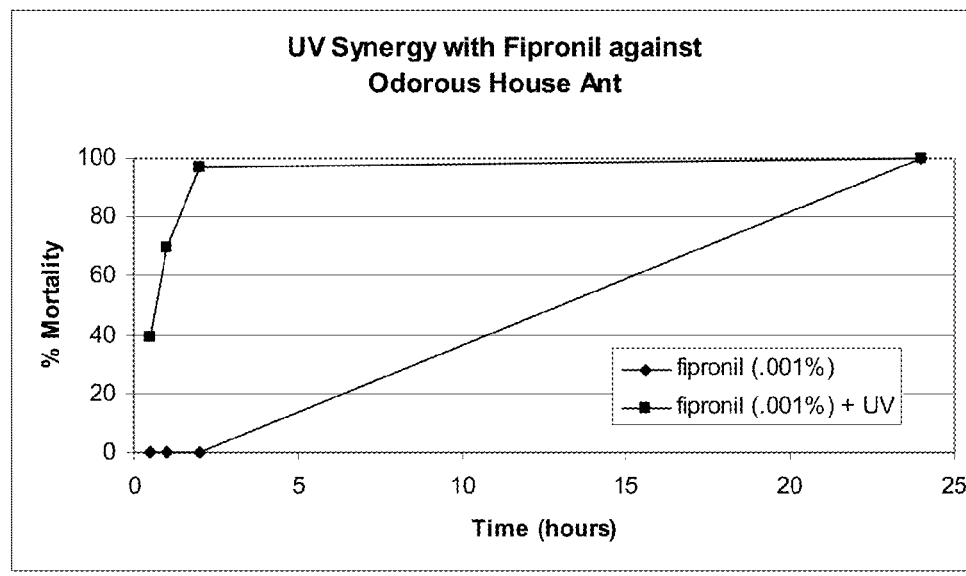

FIG. 45 is a graph illustrating the synergy of a combination of free radical stabilizers, Compound A and Compound B, with an insecticide, fipronil, against the odorous house ant, in terms of mortality (%) over time (hours). Diamonds represent fipronil at a 0.001% concentration, and squares represent a blend of fipronil at a 0.001% concentration and Compound A at a 1% and Compound B at a 0.5% concentration.

Figure 46:
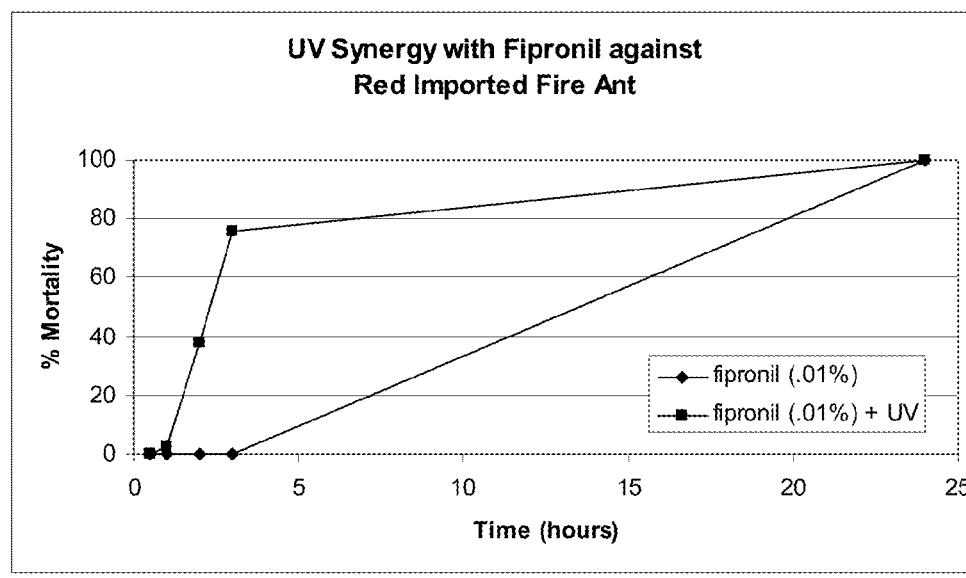

FIG. 46 is a graph illustrating the synergy of a combination of free radical stabilizers, Compound A and Compound B, with an insecticide, fipronil, against the red imported fire ant, in terms of mortality (%) over time (hours). Diamonds represent fipronil at a 0.01% concentration, and squares represent a blend of fipronil at a 0.01% concentration and Compound A at a 1% and Compound B at a 0.5% concentration.

Figure 47:
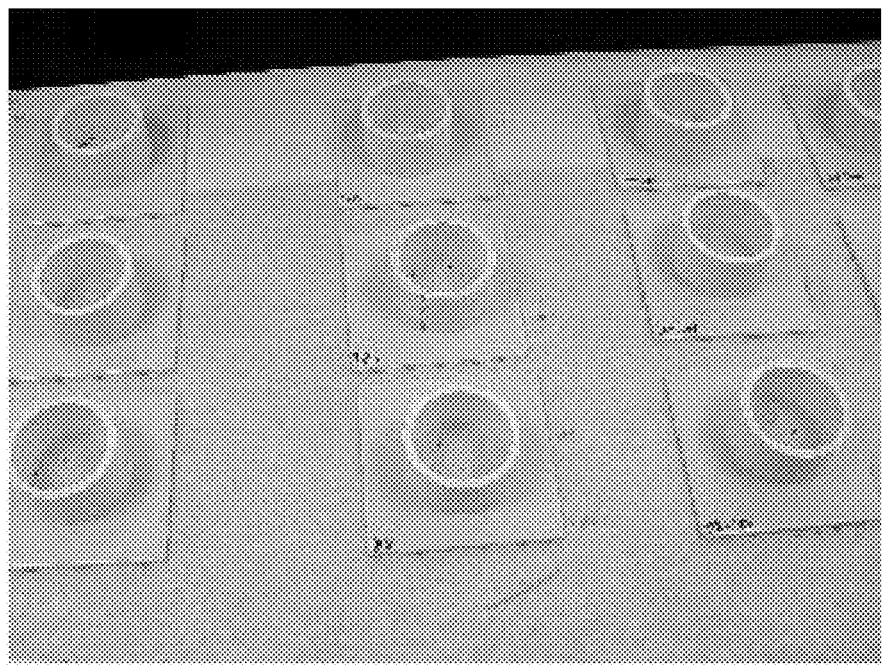

FIG. 47 is a photograph illustrating a series of glazed tiles treated with an aqueous solutions of fipronil at 0.01, 0.001 and 0.0001% active ingredient (referred to herein as "AI") were prepared with and without free radical stabilizers (a combination of Compound A at 1% and Compound B at 0.5%) in acetone. Red imported fire ants (*Solenopsis invicta*) are in contact with the tiles, and their escape is physically blocked, as shown in the photograph, by a column.

Figure 48:
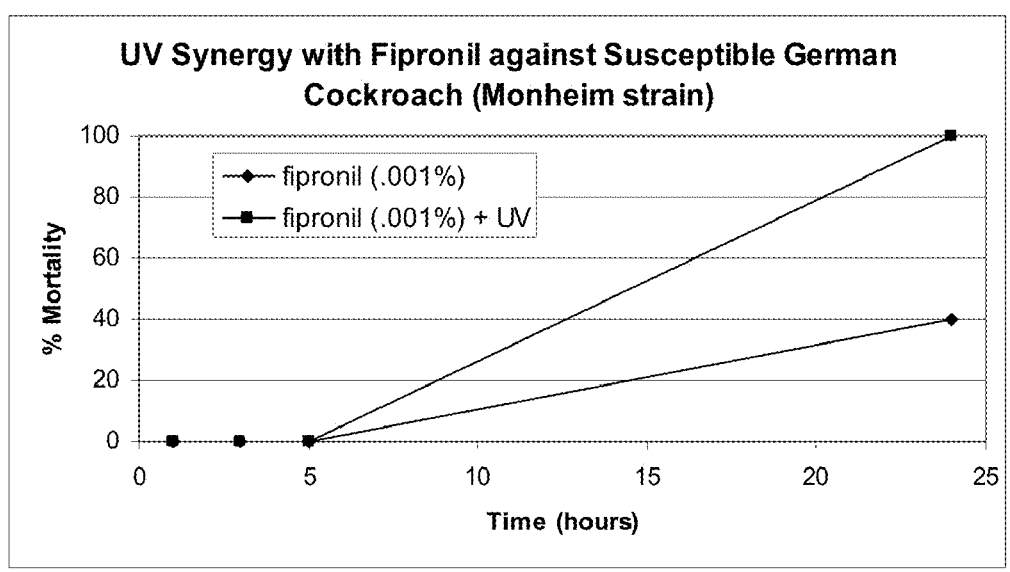

FIG. 48 is a graph illustrating the synergy of a combination of free radical stabilizers, Compound A and Compound B, with an insecticide, fipronil, against the susceptible German cockroach (Monheim strain), in terms of mortality (%) over time (hours). Diamonds represent fipronil at a 0.001% concentration, and squares represent a blend of fipronil at a 0.001% concentration and Compound A at a 1% and Compound B at a 0.5% concentration.

Figure 49:
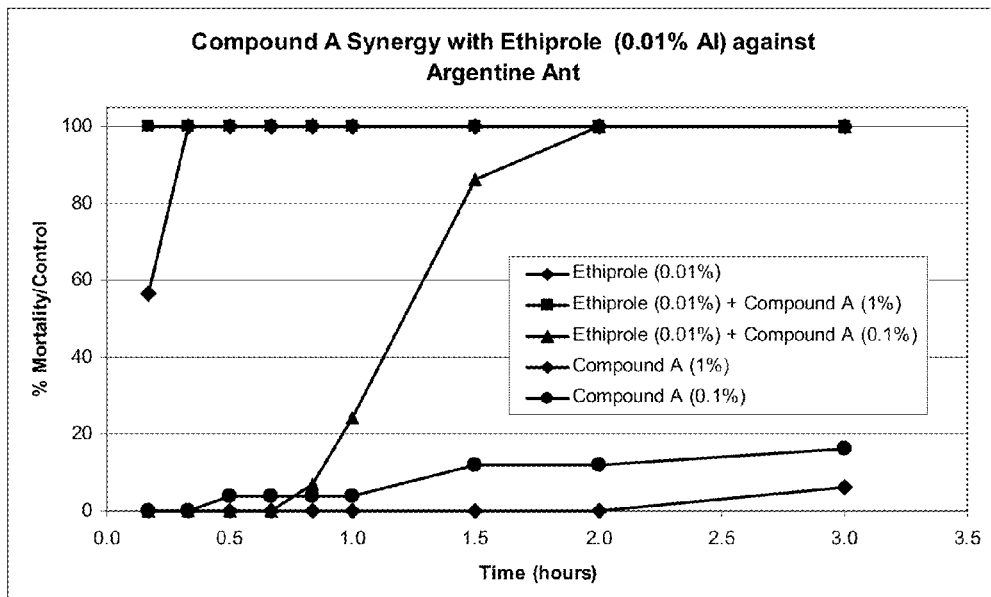

FIG. 49 is a graph illustrating the synergy of a free radical stabilizer, Compound A, with an insecticide, ethiprole, against the Argentine ant, in terms of mortality (%) over time (hours). Diamonds represent ethiprole at a 0.01% concentration, squares represent a blend of ethiprole at a 0.01% concentration and Compound A at a 1%, triangles represent a blend of ethiprole at a 0.01% concentration and Compound A at a 0.1% concentration, X's represent Compound A, alone, at a 1% concentration, and asterisks (*'s) represent Compound A, alone, at a 0.1% concentration.

Figure 50:
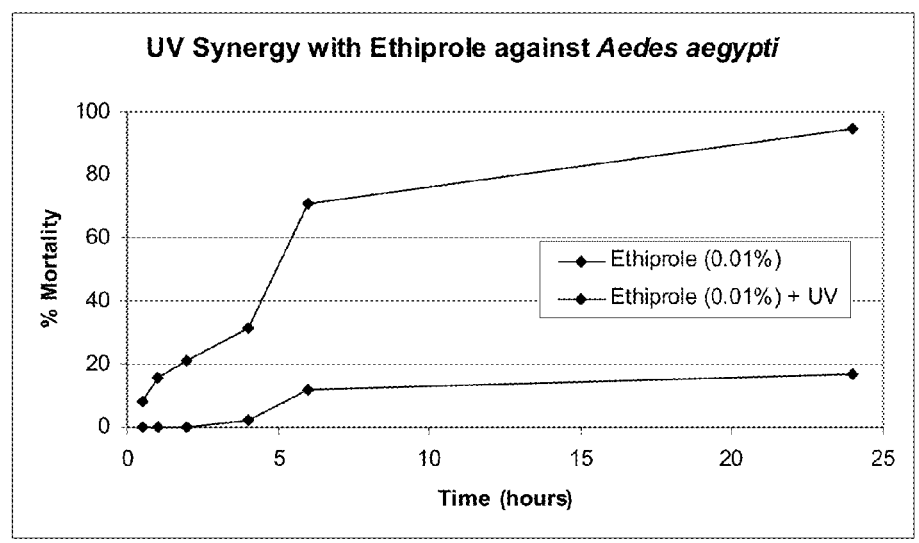

FIG. 50 is a graph illustrating the synergy of a combination of free radical stabilizers, Compound A and Compound B, with an insecticide, ethiprole, against *Aedes aegypti* mosquitos, in terms of mortality (%) over time (hours). Diamonds represent ethiprole at a 0.01% concentration, and squares represent a blend of ethiprole at a 0.01% concentration and Compound A at a 1% and Compound B at a 0.5% concentration.

Figure 51:
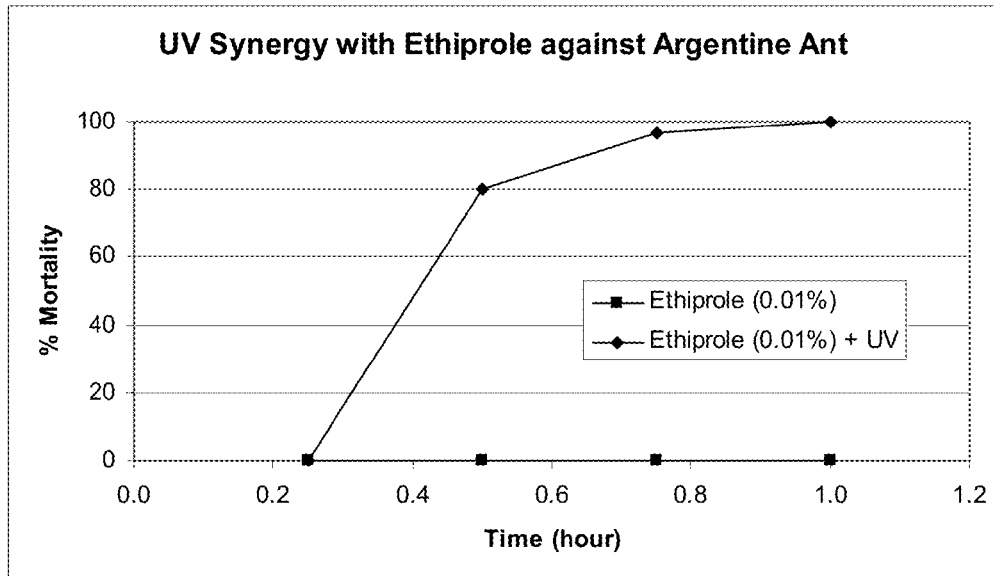

FIG. 51 is a graph illustrating the synergy of a combination of free radical stabilizers, Compound A and Compound B, with an insecticide, ethiprole, against the Argentine ant, in terms of mortality (%) over time (hours). Diamonds represent ethiprole at a 0.01% concentration, and squares represent a blend of ethiprole at a 0.01% concentration and Compound A at a 1% and Compound B at a 0.5% concentration.

Figure 52:
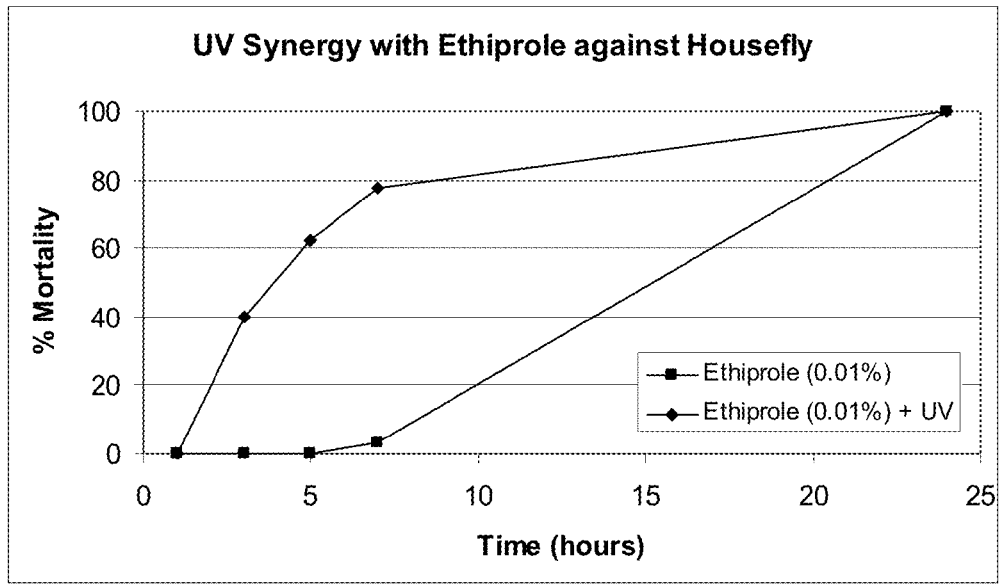

FIG. 52 is a graph illustrating the synergy of a combination of free radical stabilizers, Compound A and Compound B, with an insecticide, ethiprole, against houseflies, in terms of mortality (%) over time (hours). Diamonds represent ethiprole at a 0.01% concentration, and squares represent a blend of Ethiprole at a 0.01% concentration and Compound A at a 1% and Compound B at a 0.5% concentration.

Figure 53:
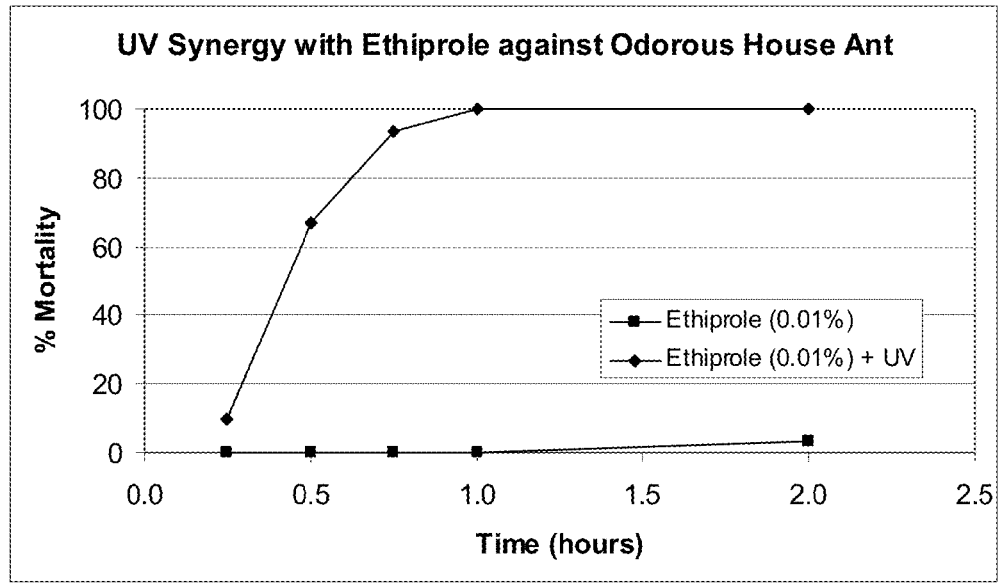

FIG. 53 is a graph illustrating the synergy of a combination of free radical stabilizers, Compound A and Compound B, with an insecticide, Ethiprole, against the odorous house ant, in terms of mortality (%) over time (hours). Diamonds represent Ethiprole at a 0.01% concentration, and squares represent a blend of Ethiprole at a 0.01% concentration and Compound A at a 1% and Compound B at a 0.5% concentration.

Figure 54:
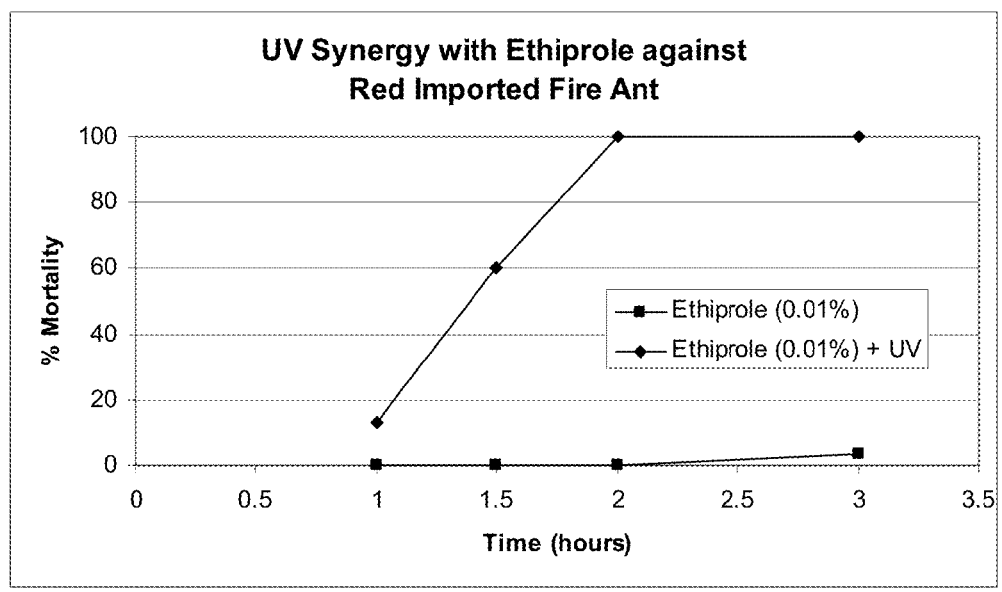

FIG. 54 is a graph illustrating the synergy of a combination of free radical stabilizers, Compound A and Compound B, with an insecticide, ethiprole, against the red imported fire ant, in terms of mortality (%) over time (hours). Diamonds represent Ethiprole at a 0.01% concentration, and squares represent a blend of Ethiprole at a 0.01% concentration and Compound A at a 1% and Compound B at a 0.5% concentration.

Figure 55:
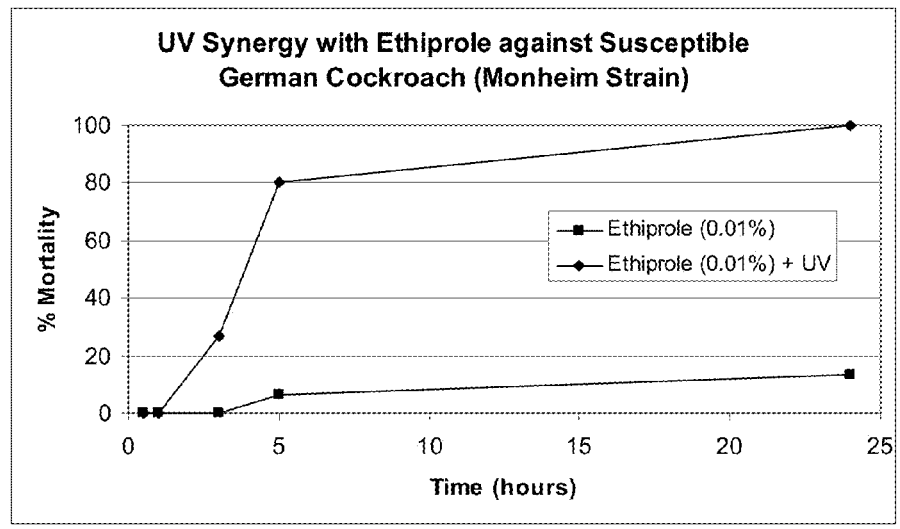

FIG. 55 is a graph illustrating the synergy of a combination of free radical stabilizers, Compound A and Compound B, with an insecticide, ethiprole, against the susceptible German cockroach (Monheim strain), in terms of mortality (%) over time (hours). Diamonds represent Ethiprole at a 0.01% concentration, and squares represent a blend of Ethiprole at a 0.01% concentration and Compound A at a 1% and Compound B at a 0.5% concentration.

Figure 56:
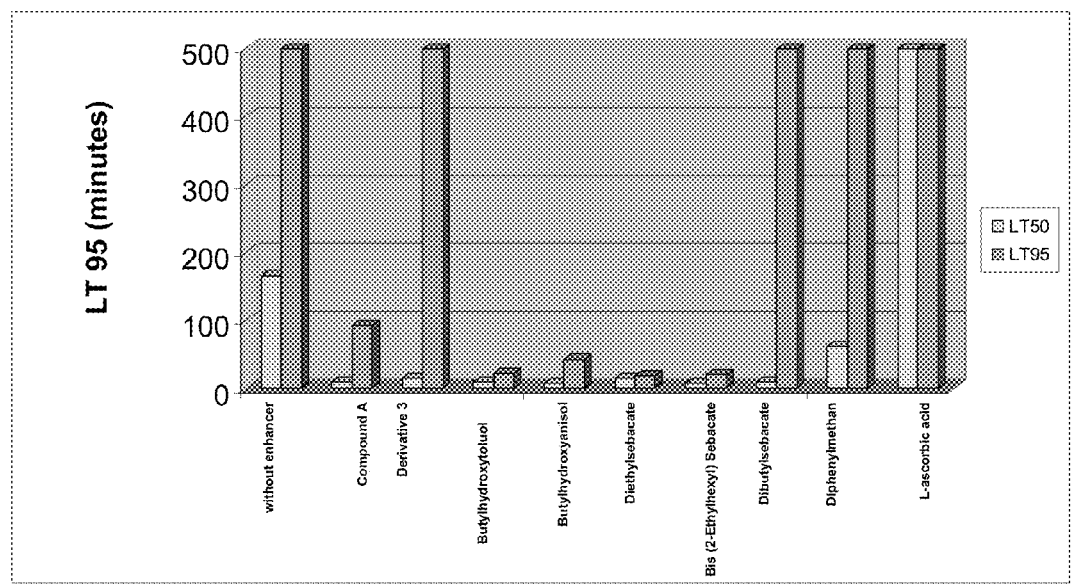

FIG. 56 is a chart illustrating the time (minutes) required for various compositions (including the insecticide bendiocarb and various adjuvants) to provide knockdown (LT50 and LT95) of *Culex quinquefasciatus* (adults, 3 days old).

Figure 57:
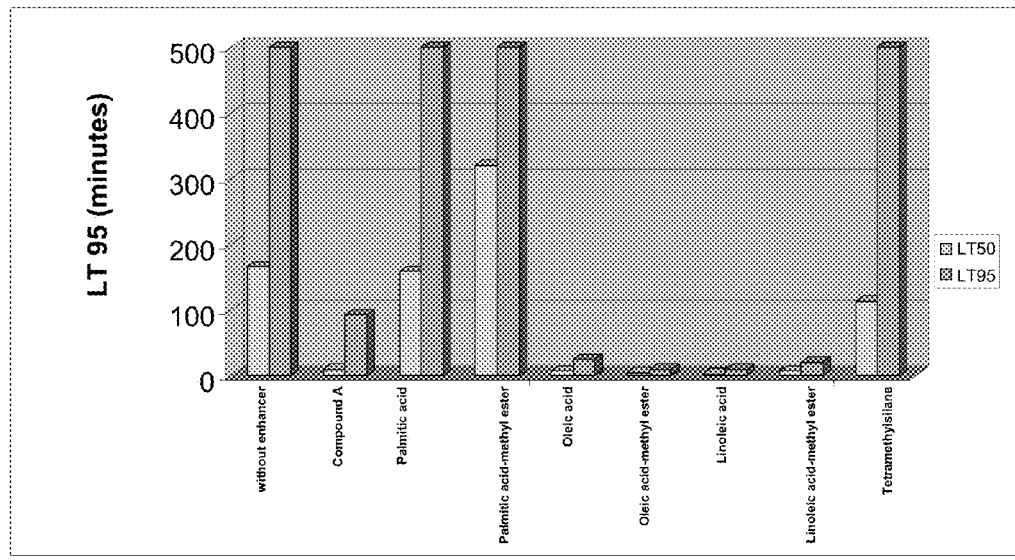

FIG. 57 is a continuation of FIG. 56 with the chart illustrating the time (minutes) required for various additional compositions (including the insecticide bendiocarb and various adjuvants) to provide knockdown (LT50 and LT95) of *Culex quinquefasciatus* (adults, 3 days old).

Figure 58:
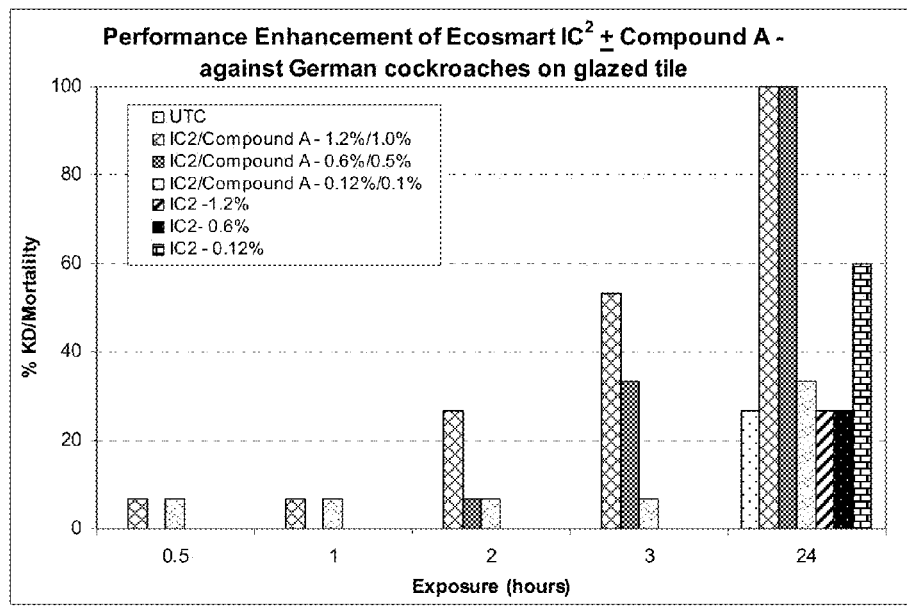

FIG. 58 is a chart illustrating the effect of a EcoSmart $IC^2$ treatments, alone or in combination with Compound A, against the German cockroach, measured in terms of mortality (%) over time (hours).

Figure 59:
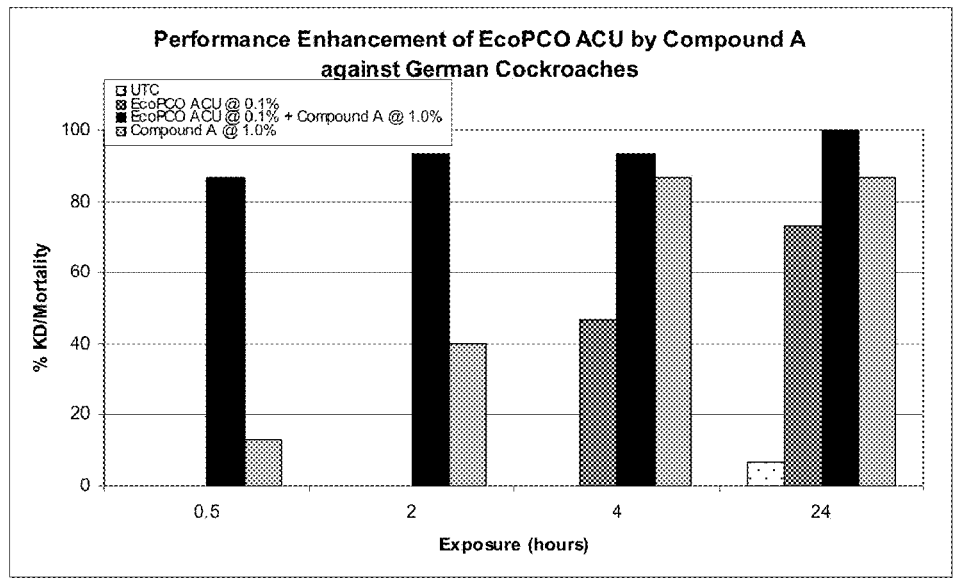

FIG. 59 is a chart illustrating the performance enhancement of Compound A against the insecticide sold under the tradename Eco PCO ACU, also described as hexa-hydroxyls, measured in terms of mortality (%) versus exposure time (hours).

Figure 60:
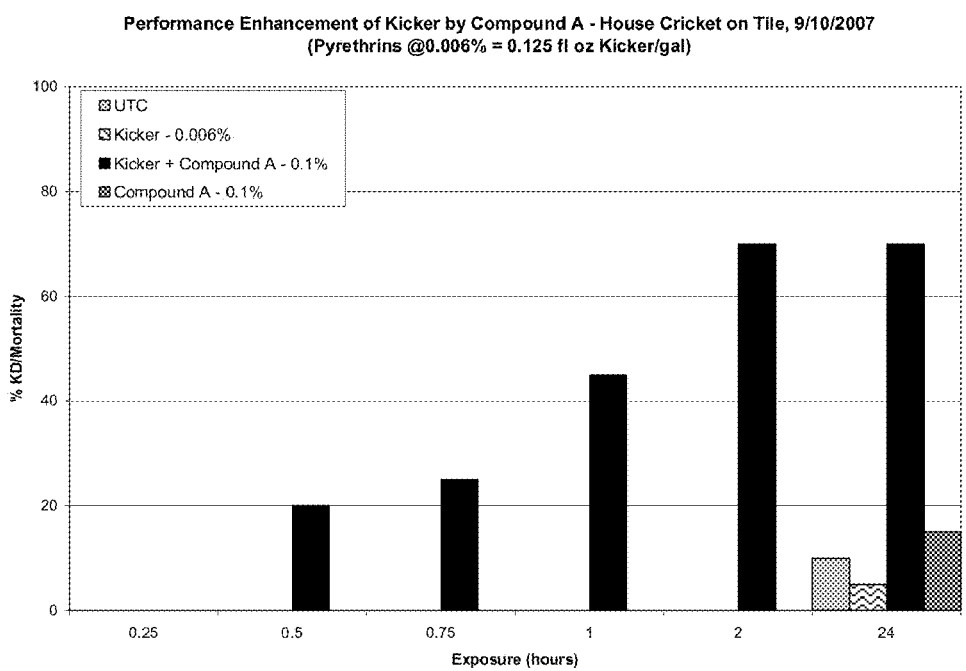

FIG. 60 is a chart illustrating the performance enhancement of Compound A on the insecticide sold under the tradename Kicker, also described as a mixture of pyrethrins and piperonyl butoxide, measured in terms of mortality (%) versus exposure time (hours).

Figure 61:
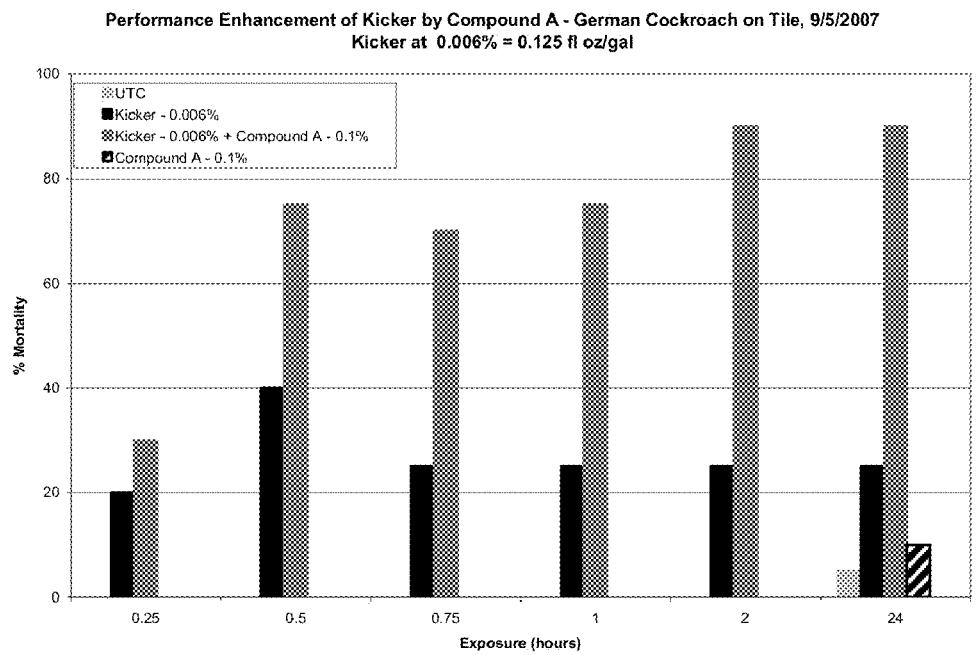

FIG. 61 is a chart illustrating the performance enhancement of Compound A in combination with the insecticide sold under the tradename Kicker, also described as a mixture of pyrethrins and piperonyl butoxide at 0.006% against German cockroaches.

Note that in the following figures, Compound A+Compound B may be alternatively referred to as "UV Block" or "BLS292".

Figure 62:
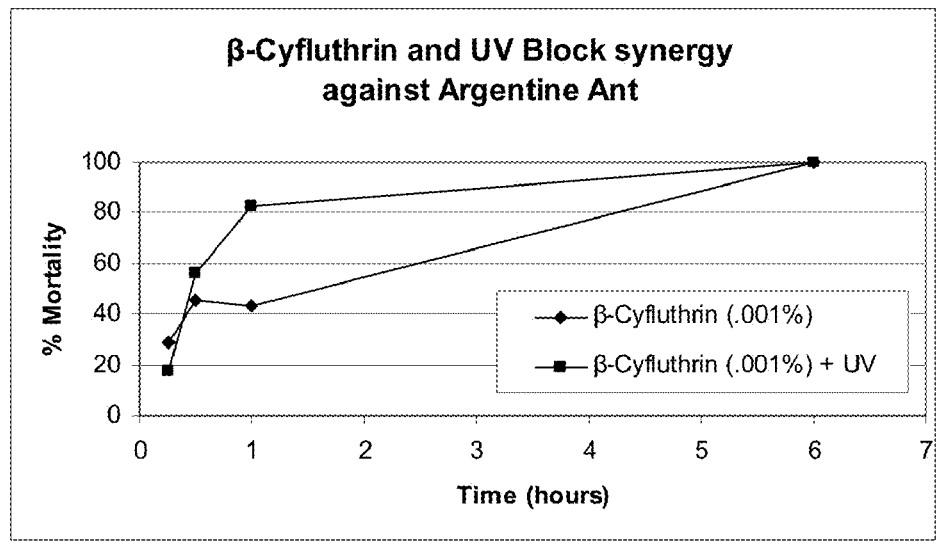

FIG. 62 is a graph illustrating the synergy of a free radical stabilizer Compound A (at a concentration of 1%) and Compound B (at a concentration of 0.5%), with the insecticide β-cyfluthrin (at a concentration of 0.001%), against the Argentine Ant, in terms of mortality (%) over time (hours).

Figure 63:
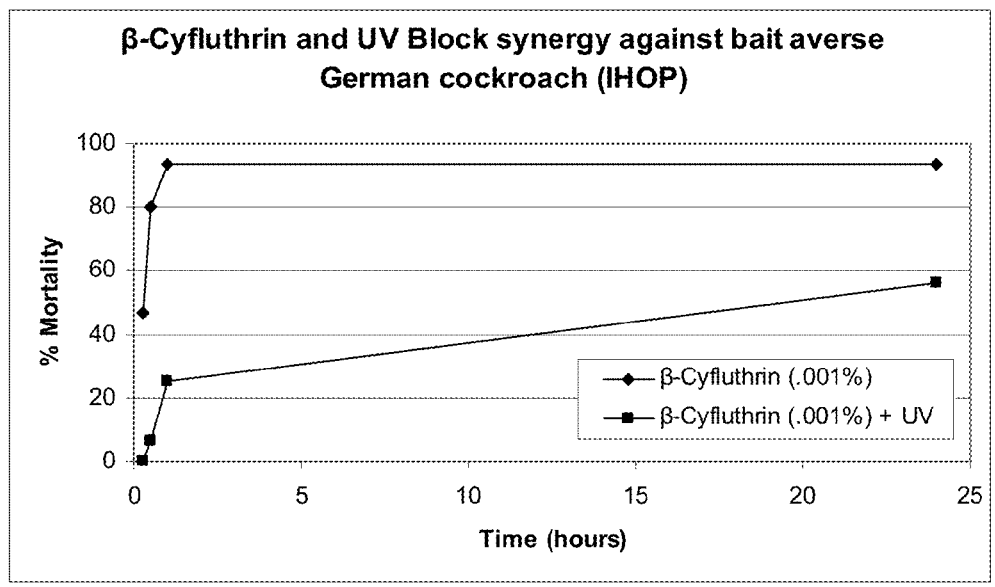

FIG. 63 is a graph illustrating the synergy of a free radical stabilizer Compound A (at a concentration of 1%) and Compound B (at a concentration of 0.5%), with the insecticide β-cyfluthrin (at a concentration of 0.001%), against the German Cockroach (IHOP), in terms of mortality (%) over time (hours).

Figure 64:
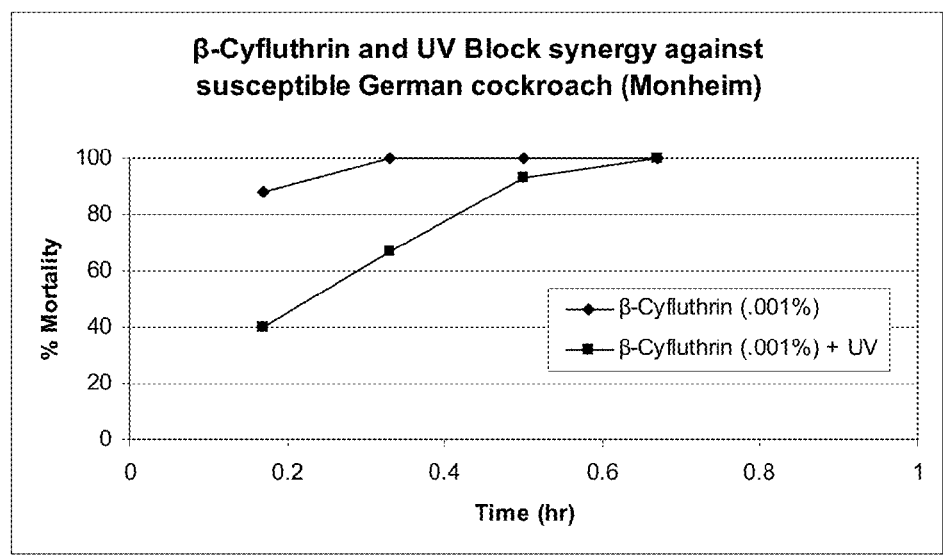

FIG. 64 is a graph illustrating the synergy of a free radical stabilizer Compound A (at a concentration of 1%) and Compound B (at a concentration of 0.5%), with the insecticide β-cyfluthrin (at a concentration of 0.001%), against the German cockroach (Monheim), in terms of mortality (%) over time (hours).

Figure 65:
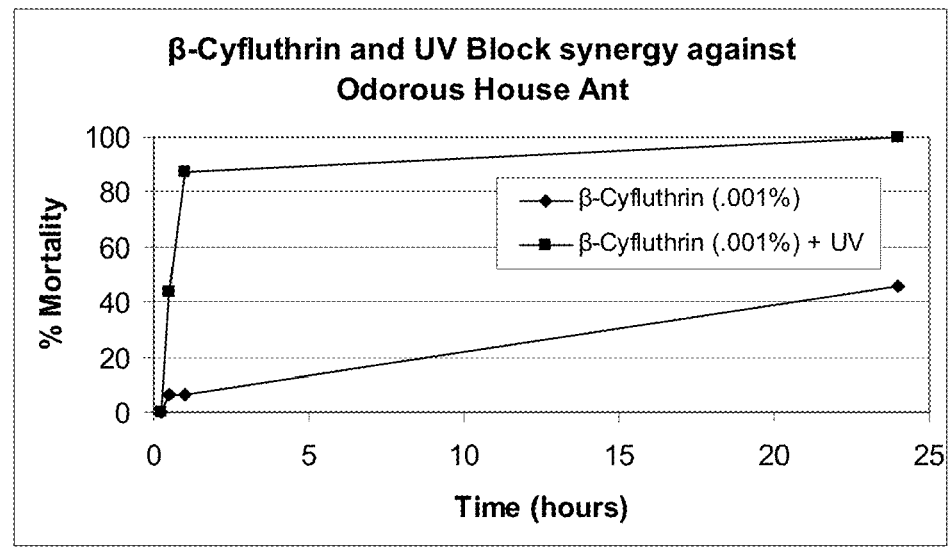

FIG. 65 is a graph illustrating the synergy of a free radical stabilizer Compound A (at a concentration of 1%) and Compound B (at a concentration of 0.5%), with the insecticide β-cyfluthrin (at a concentration of 0.001%), against the Odorous House ant, in terms of mortality (%) over time (hours).

Figure 66:
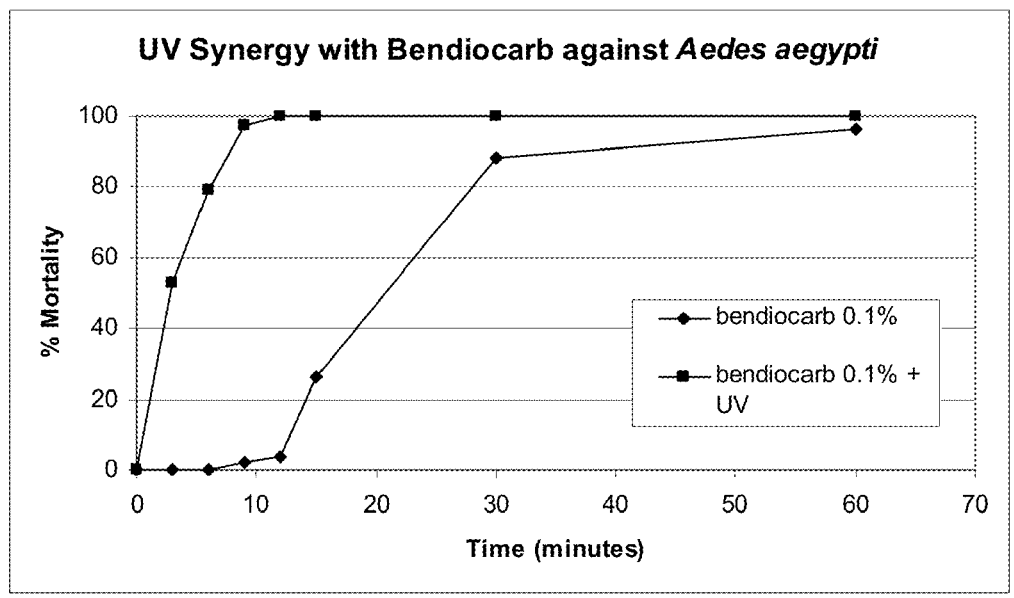

FIG. 66 is a graph illustrating the synergy of a free radical stabilizer Compound A (at a concentration of 1%) and Compound B (at a concentration of 0.5%), with the insecticide bendiocarb (at a concentration of 0.001%), against the *Aedes aegypti*, in terms of mortality (%) over time (minutes).

Figure 67:
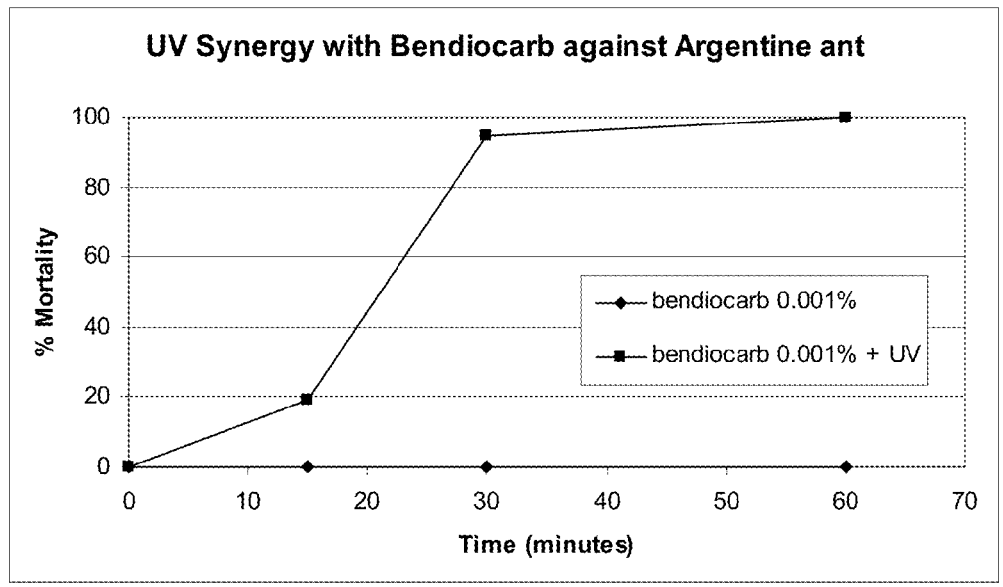

FIG. 67 is a graph illustrating the synergy of a free radical stabilizer Compound A (at a concentration of 1%) and Compound B (at a concentration of 0.5%), with the insecticide bendiocarb (at a concentration of 0.001%), against the Argentine ant, in terms of mortality (%) over time (minutes).

Figure 68:
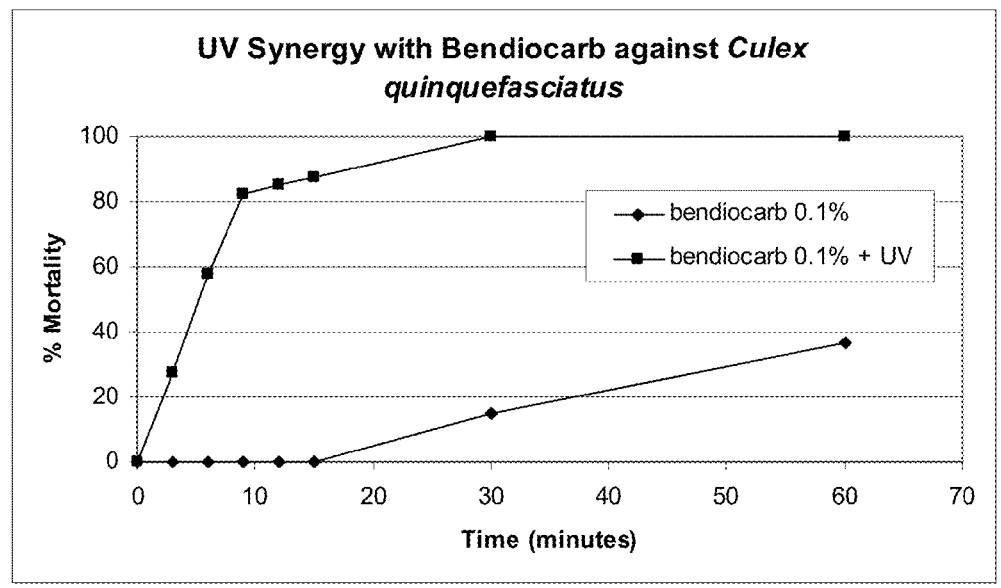

FIG. 68 is a graph illustrating the synergy of a free radical stabilizer Compound A (at a concentration of 1%) and Compound B (at a concentration of 0.5%), with the insecticide bendiocarb (at a concentration of 0.001%), against the *Culex quinquefasciatus*, in terms of mortality (%) over time.

Figure 69:
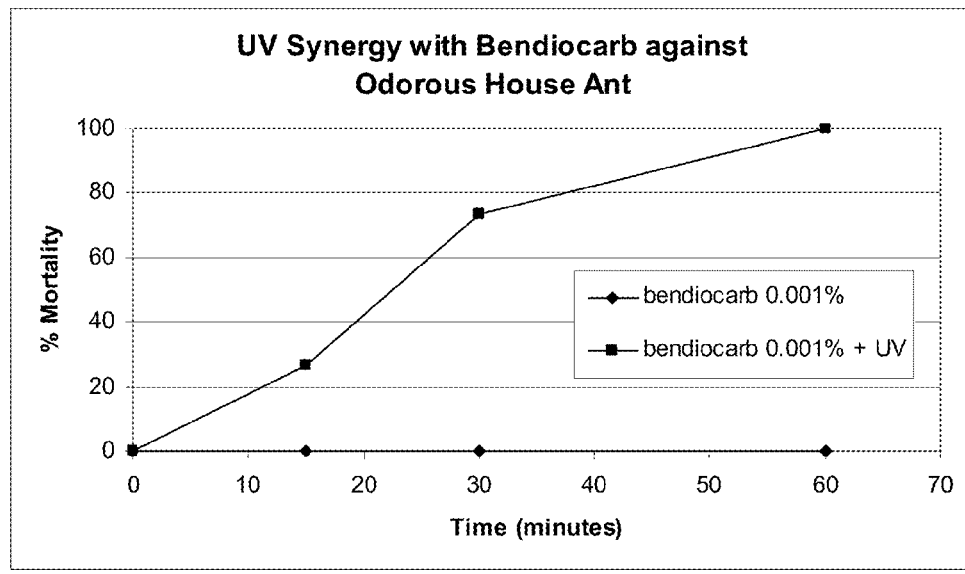

FIG. 69 is a graph illustrating the synergy of a free radical stabilizer Compound A (at a concentration of 1%) and Compound B (at a concentration of 0.5%), with the insecticide bendiocarb (at a concentration of 0.001%), against the Odorous House ant, in terms of mortality (%) over time (minutes).

Figure 70:
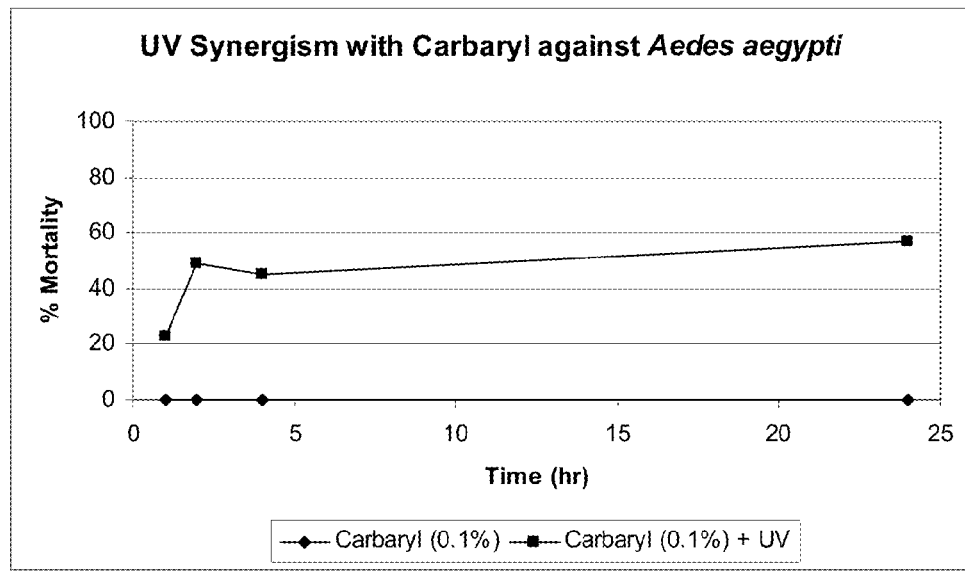

FIG. 70 is a graph illustrating the synergy of a free radical stabilizer Compound A (at a concentration of 1%) and Compound B (at a concentration of 0.5%), with the insecticide carbaryl (at a concentration of 0.1%), against *Aedes aegypti*, in terms of mortality (%) over time (hours).

Figure 71:
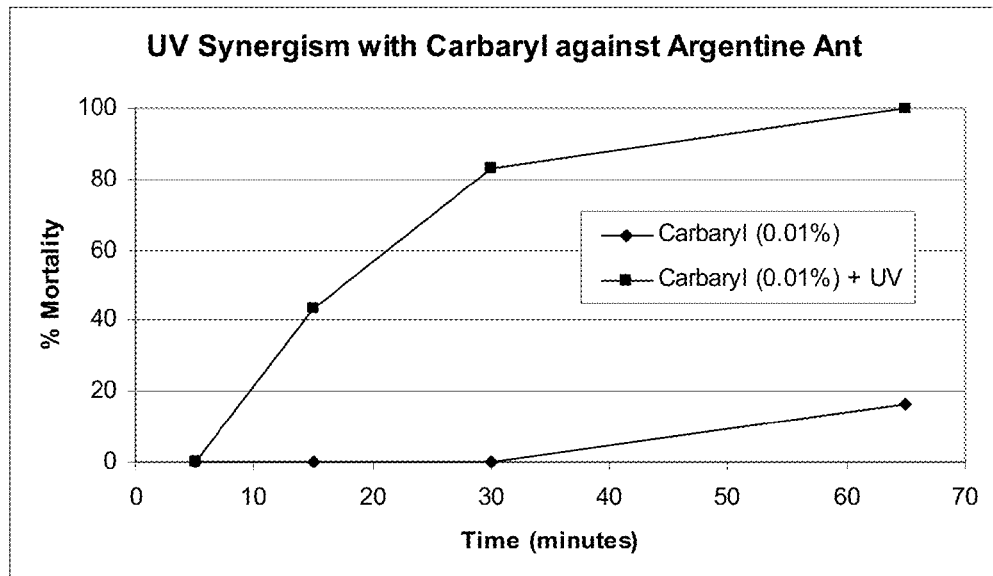

FIG. 71 is a graph illustrating the synergy of a free radical stabilizer Compound A (at a concentration of 1%) and Compound B (at a concentration of 0.5%), with the insecticide carbaryl (at a concentration of 0.1%), against the Argentine ant, in terms of mortality (%) over time (minutes).

Figure 72:
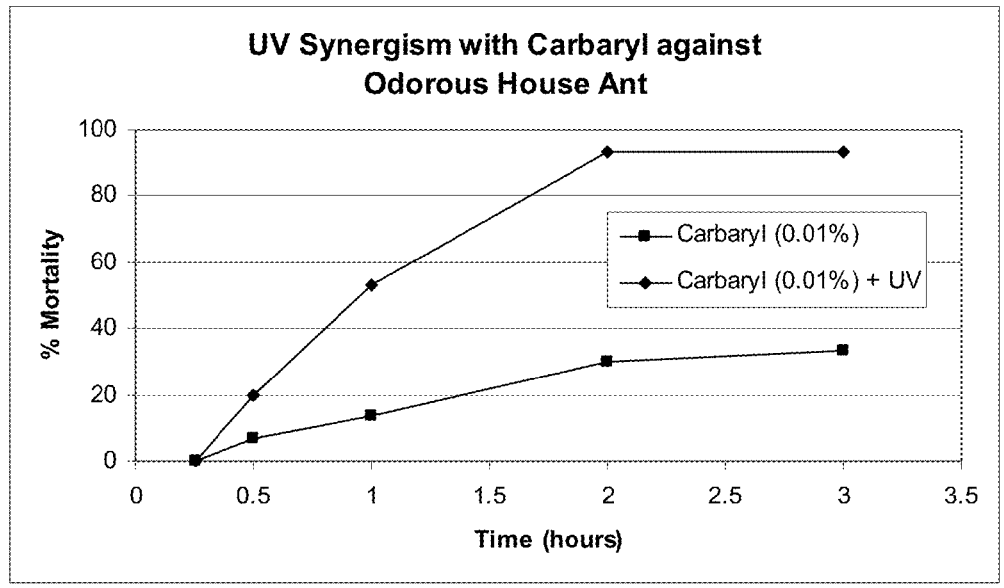

FIG. 72 is a graph illustrating the synergy of a free radical stabilizer Compound A (at a concentration of 1%) and Compound B (at a concentration of 0.5%), with the insecticide carbaryl (at a concentration of 0.1%), against the Odorous House ant, in terms of mortality (%) over time (hours).

Figure 73:
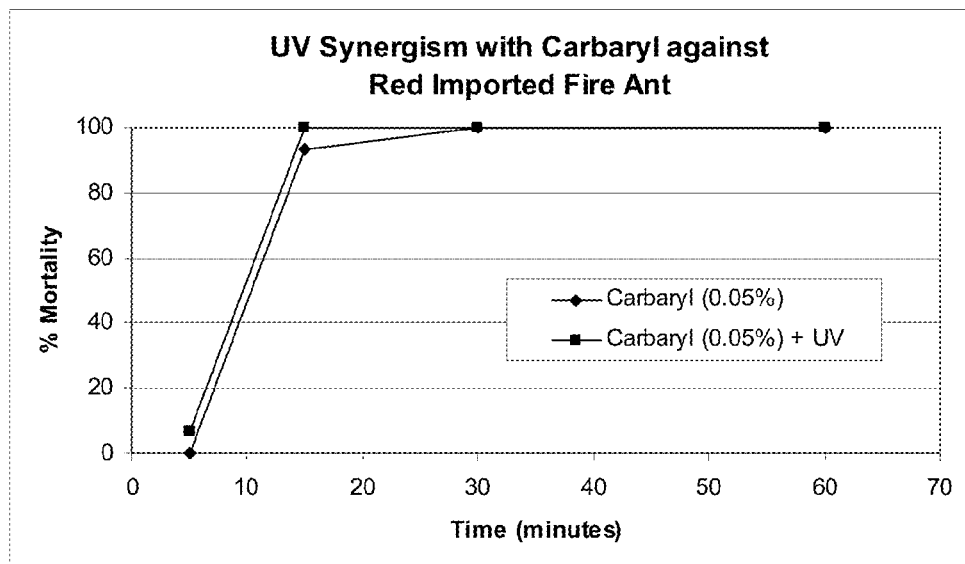

FIG. 73 is a graph illustrating the synergy of a free radical stabilizer Compound A (at a concentration of 1%) and Compound B (at a concentration of 0.5%), with the insecticide carbaryl (at a concentration of 0.1%), against the Red Imported Fire ant, in terms of mortality (%) over time (minutes).

Figure 74:
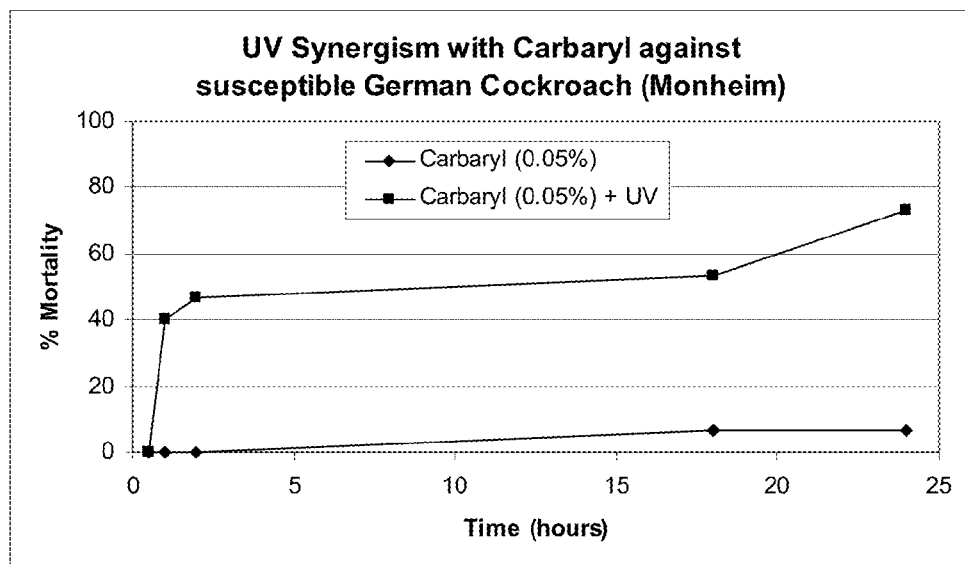

FIG. 74 is a graph illustrating the synergy of a free radical stabilizer Compound A (at a concentration of 1%) and Compound B (at a concentration of 0.5%), with the insecticide carbaryl (at a concentration of 0.5%), against the German Cockroach (Monheim), in terms of mortality (%) over time (hours).

Figure 75:
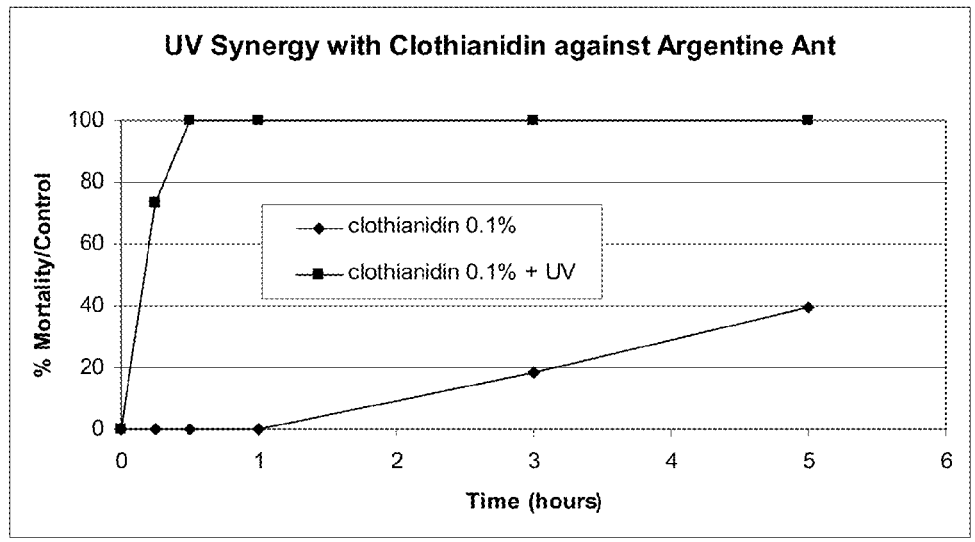

FIG. 75 is a graph illustrating the synergy of a free radical stabilizer Compound A (at a concentration of 1%) and Compound B (at a concentration of 0.5%), with the insecticide clothianidin (at a concentration of 0.1%), against the Argentine ant, in terms of mortality (%) over time (hours).

Figure 76:
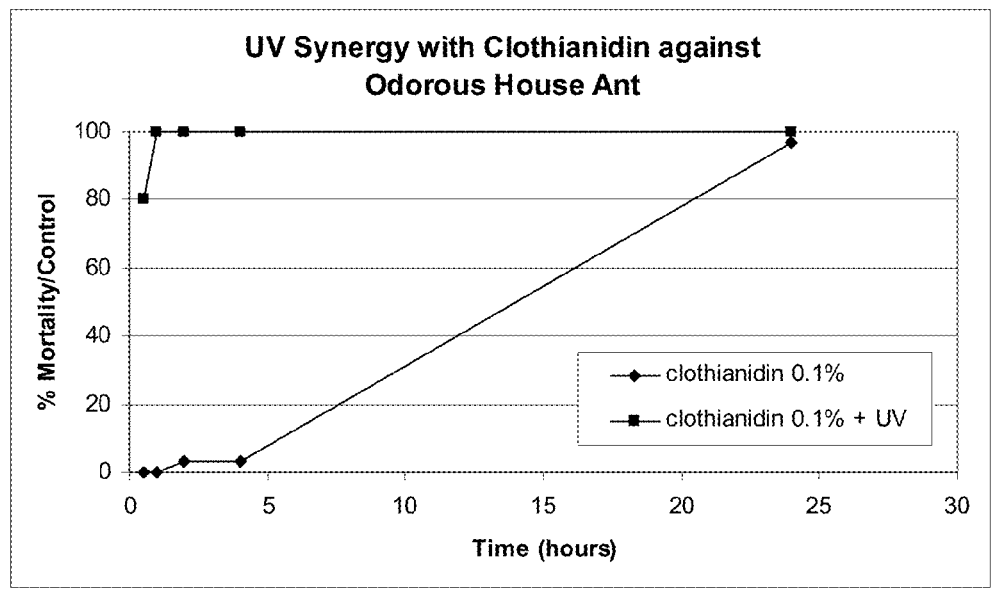

FIG. 76 is a graph illustrating the synergy of a free radical stabilizer Compound A (at a concentration of 1%) and Compound B (at a concentration of 0.5%), with the insecticide clothianidin (at a concentration of 0.1%), against the Odorous House ant, in terms of mortality (%) over time (hours).

Figure 77:
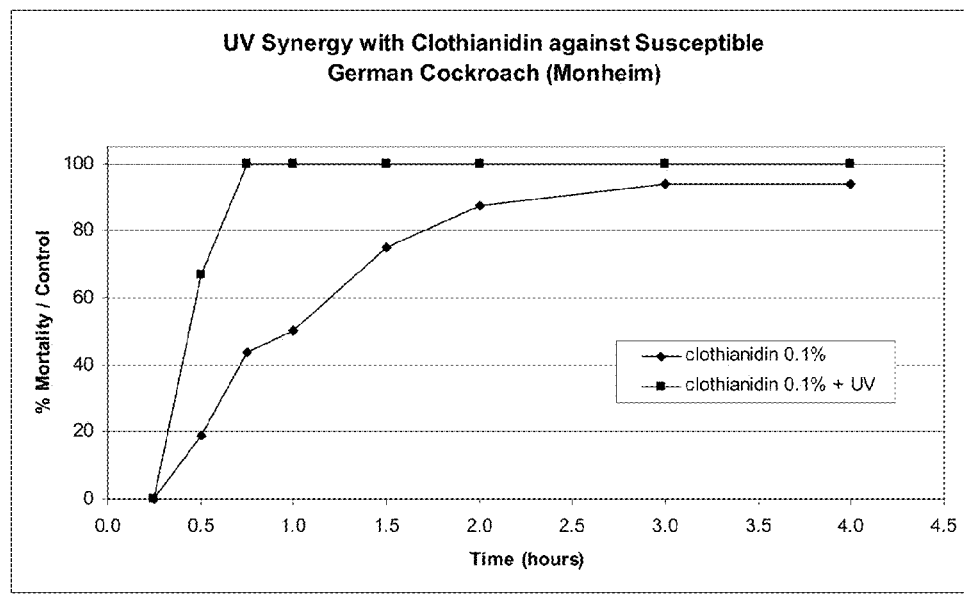

FIG. 77 is a graph illustrating the synergy of a free radical stabilizer Compound A (at a concentration of 1%) and Compound B (at a concentration of 0.5%), with the insecticide clothianidin (at a concentration of 0.1%), against the German cockroach (Monheim), in terms of mortality (%) over time (hours).

Figure 78:
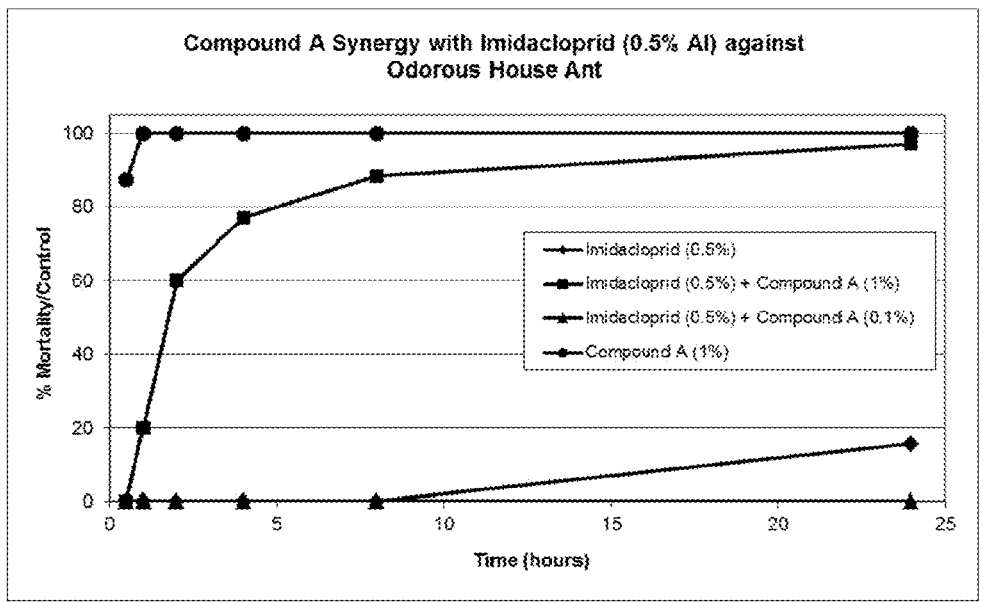

FIG. 78 is a graph illustrating the synergy of a free radical stabilizer Compound A (at a concentration of 1% or 0.1%), with the insecticide imidacloprid (at a concentration of 0.5%), against the Odorous House ant, in terms of mortality (%) over time (hours).

Figure 79:
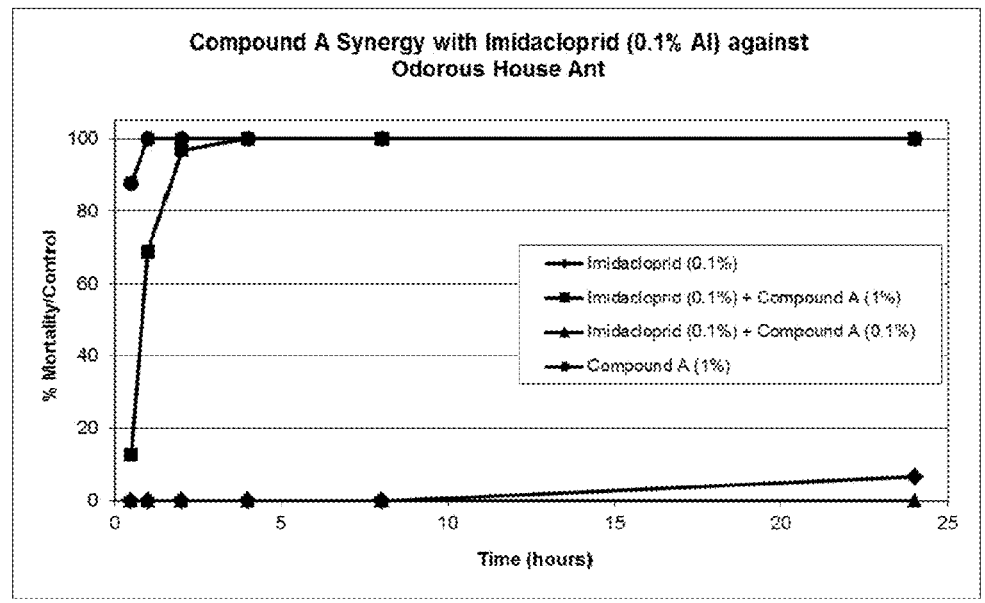

FIG. 79 is a graph illustrating the synergy of a free radical stabilizer Compound A (at a concentration of 1% or 0.1%), with the insecticide imidacloprid (at a concentration of 0.1%), against the Odorous House ant, in terms of mortality (%) over time (hours).

Figure 80:
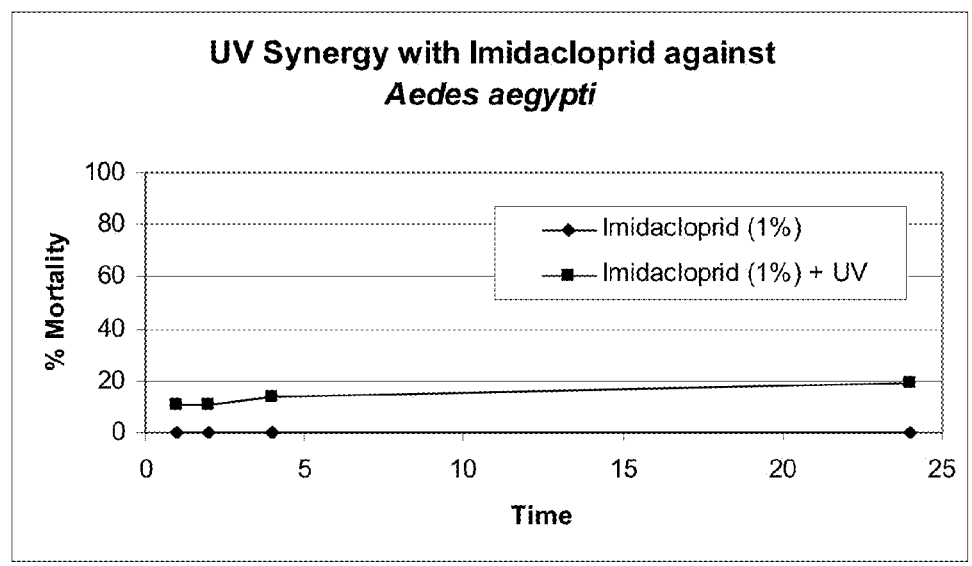

FIG. 80 is a graph illustrating the synergy of a free radical stabilizer Compound A (at a concentration of 1%) and Compound B (at a concentration of 0.5%), with the insecticide imidacloprid (at a concentration of 1%), against *Aedes aegypti*, in terms of mortality (%) over time (hours).

Figure 81:
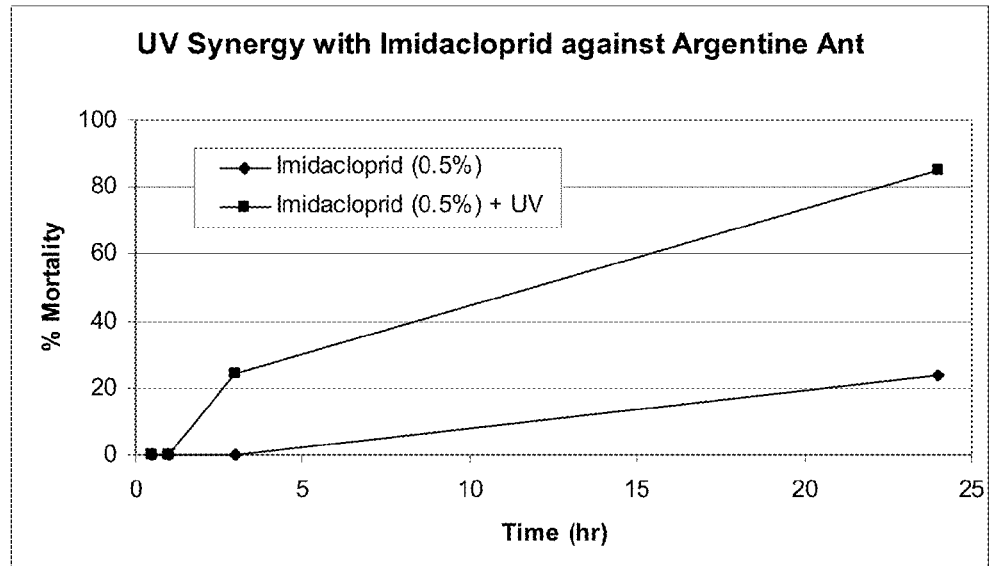

FIG. 81 is a graph illustrating the synergy of a free radical stabilizer Compound A (at a concentration of 1%) and Compound B (at a concentration of 0.5%), with the insecticide imidacloprid (at a concentration of 0.5%), against the Argentine ant, in terms of mortality (%) over time (hours).

Figure 82:
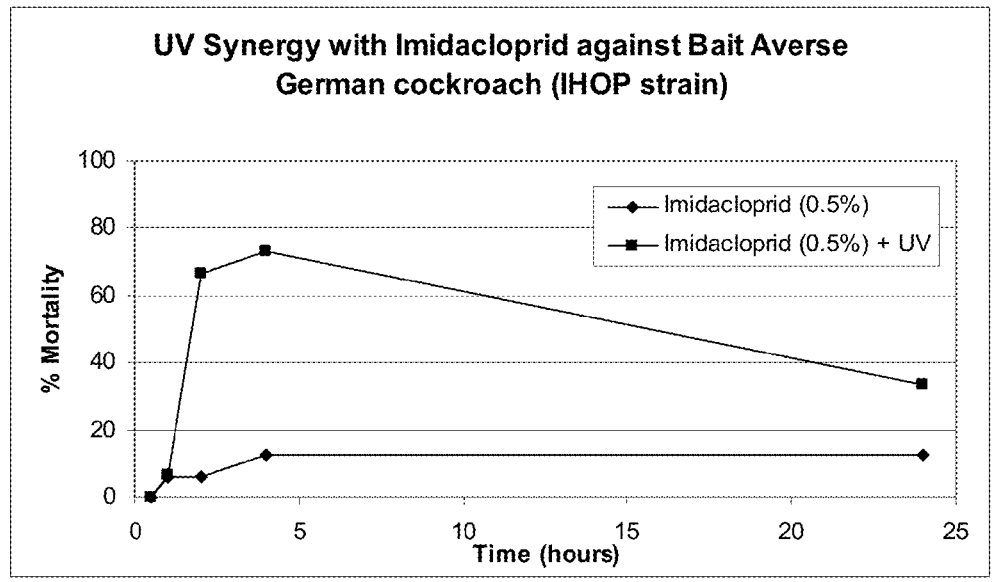

FIG. 82 is a graph illustrating the synergy of a free radical stabilizer Compound A (at a concentration of 1%) and Compound B (at a concentration of 0.5%), with the insecticide imidacloprid (at a concentration of 0.5%), against the bait adverse German cockroach, in terms of mortality (%) over time (hours).

Figure 83:
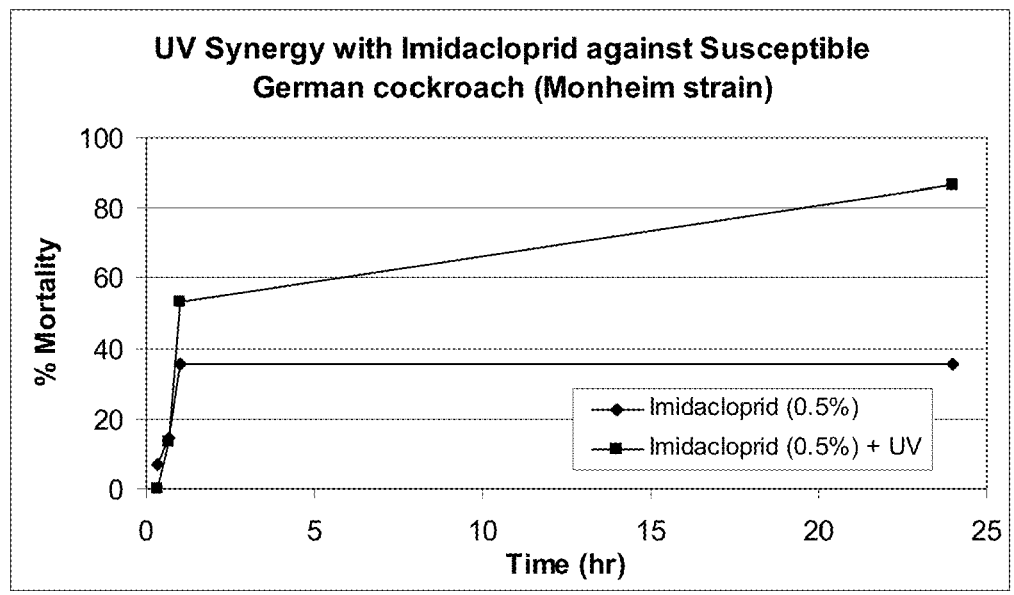

FIG. 83 is a graph illustrating the synergy of a free radical stabilizer Compound A (at a concentration of 1%) and Compound B (at a concentration of 0.5%), with the insecticide imidacloprid (at a concentration of 0.5%), against the susceptible German cockroach (Monheim strain), in terms of mortality (%) over time (hours).

Figure 84:
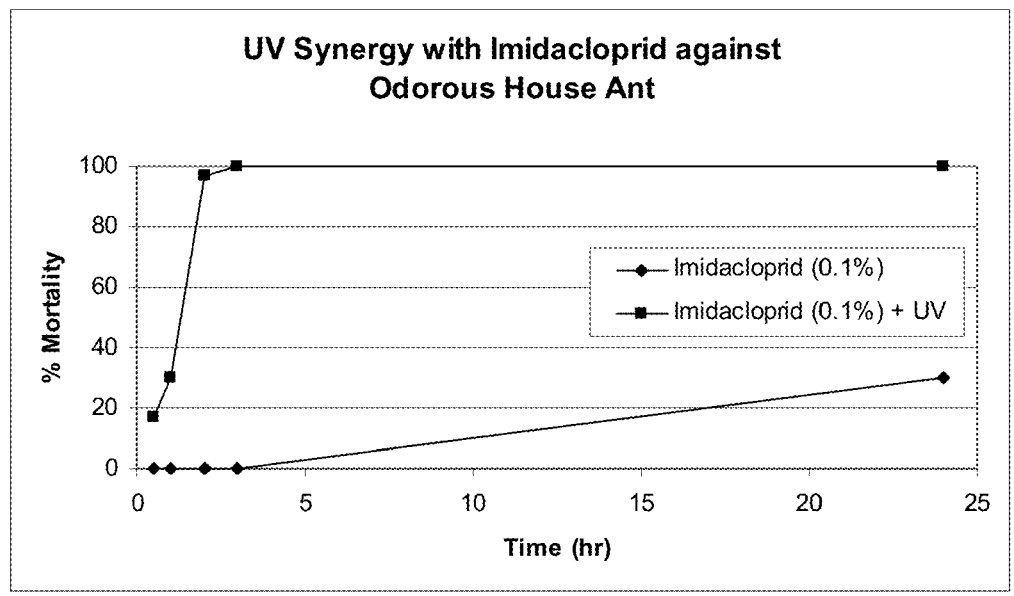

FIG. 84 is a graph illustrating the synergy of a free radical stabilizer Compound A (at a concentration of 1%) and Compound B (at a concentration of 0.5%), with the insecticide imidacloprid (at a concentration of 0.1%), against the odorous house ant, in terms of mortality (%) over time (hours).

Figure 85:
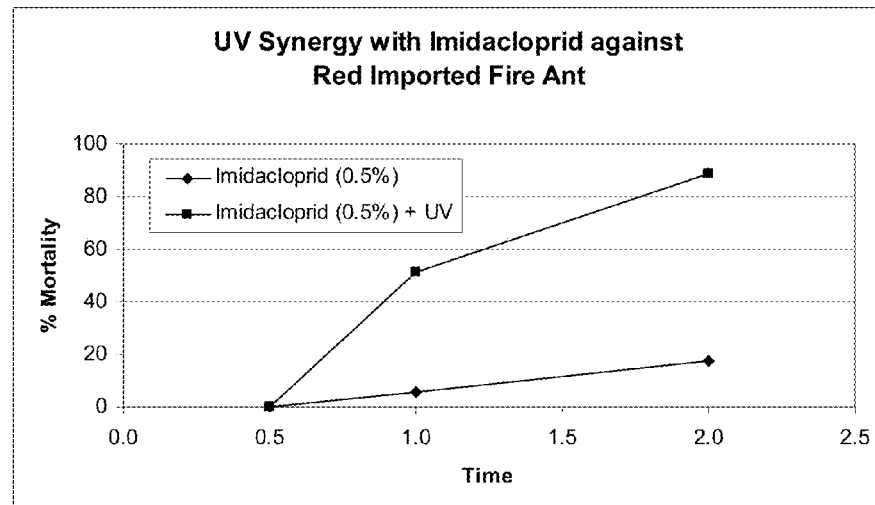

FIG. 85 is a graph illustrating the synergy of a free radical stabilizer Compound A (at a concentration of 1%) and Compound B (at a concentration of 0.5%), with the insecticide imidacloprid (at a concentration of 0.5%), against the red imported fire ant, in terms of mortality (%) over time (hours).

Figure 86:
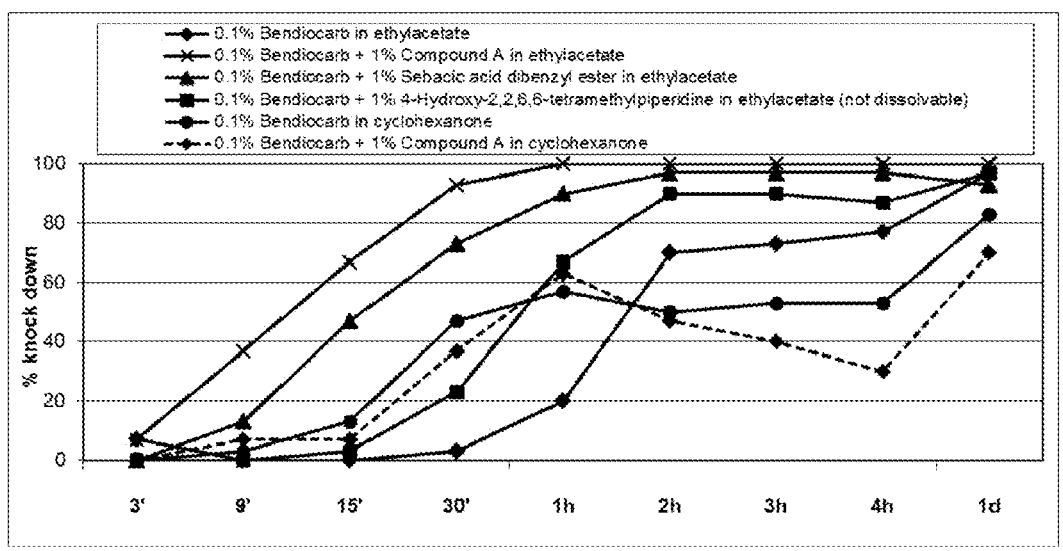

FIG. 86 is a graph illustrating the synergy of various adjuvants, with the insecticide bendiocarb (at a concentration of 0.1%), against *Culex quinquefasciatus*, in terms of percent knockdown (%) over time (minutes, hours, and days). Diamonds represent bendiocarb in combination with 1% Compound A in ethylacetate. Triangles represent bendiocarb in combination with 1% sebasic acid dibenzyl ester in ethyl acetate. Squares represent bendiocarb and 1% 4-hydroxy-2,2,6,6-tetramethylpiperidine in ethyl acetate. Light circles represent bendiocarb in cyclohexanone. Dark circles represent bendiocarb and 1% Compound A in cyclohexanone.

Figure 87:
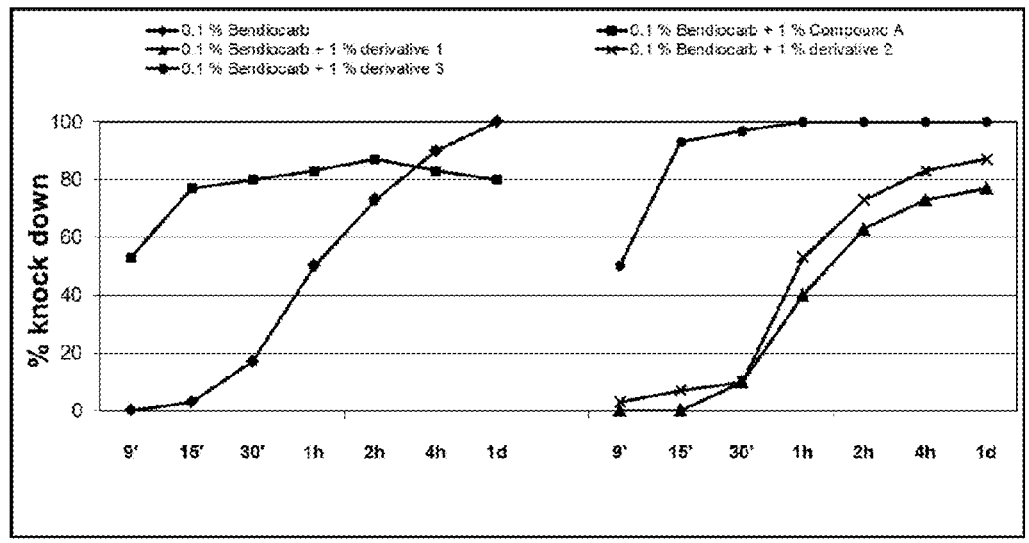
Figure 88:
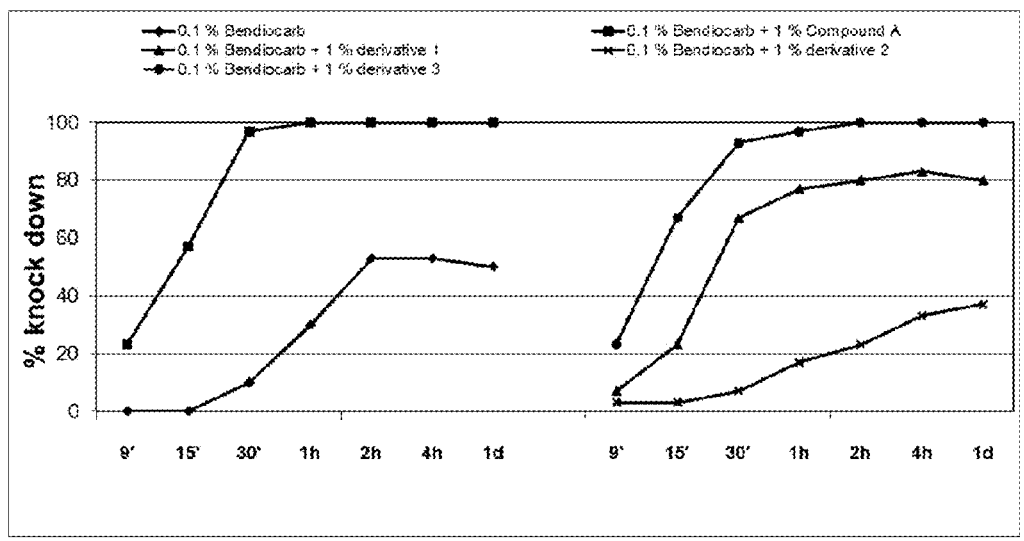

FIGS. 87 and 88 are graphs illustrating repeated analyses of the synergy of various adjuvants (each at a concentration of 1%), with the insecticide bendiocarb (at a concentration of 0.1%), against *Culex quinquefasciatus*, in terms of percent knockdown (%) over time (minutes, hours, and days). Compounds evaluated include bendiocarb, alone or in combination with Compound A, Compound 1 (diethyl sebecate), Compound 2 (sebacic acid), or Compound 3 (sebacid acid dibenzyl ester).

Figure 89:
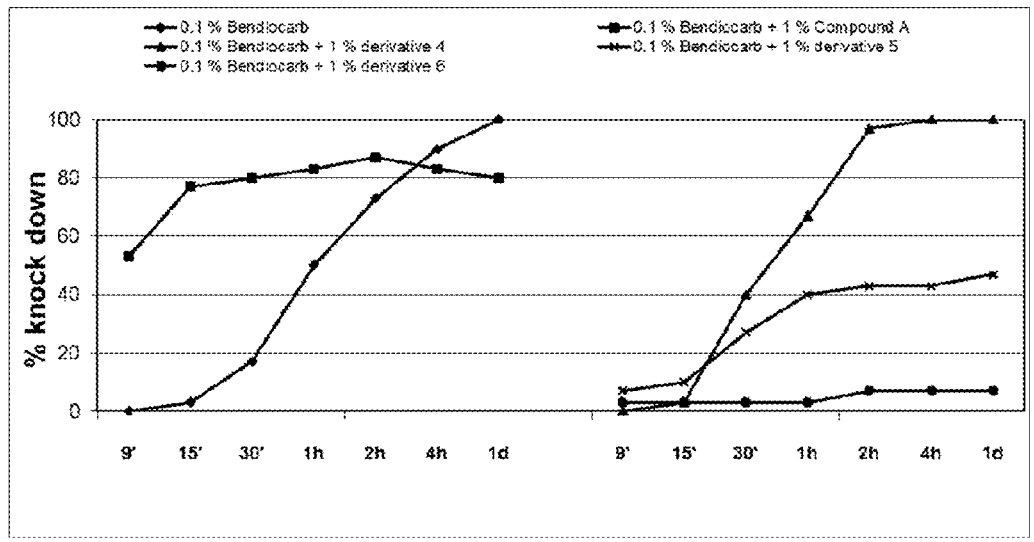
Figure 90:
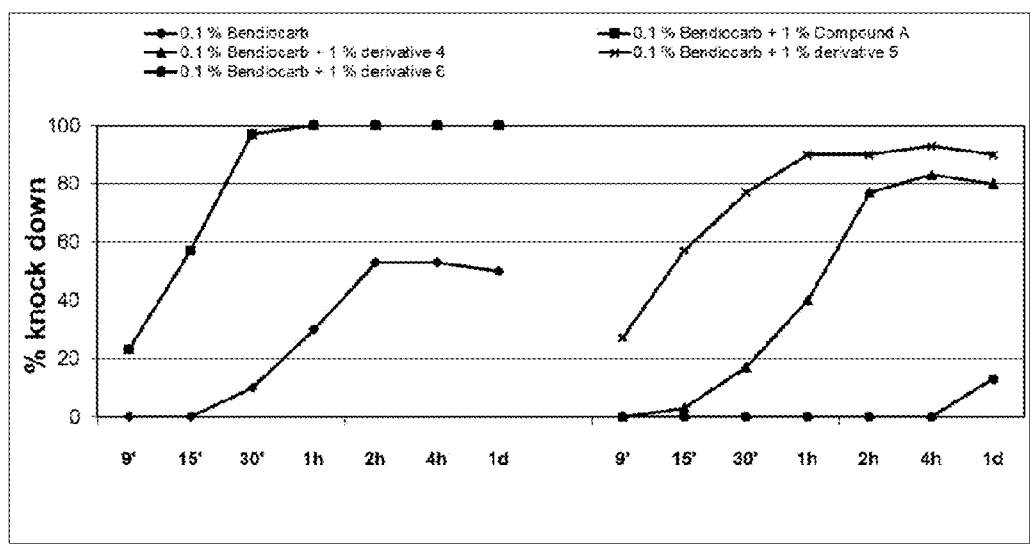

FIGS. 89 and 90 are graphs illustrating repeated analyses of the synergy of various adjuvants (each at a concentration of 1%), with the insecticide bendiocarb (at a concentration of 0.1%), against *Culex quinquefasciatus*, in terms of percent knockdown (%) over time (minutes, hours, and days). Compounds evaluated include bendiocarb, alone or in combination with Compound A, Compound 4 (sebecacid acid-bis-N-succinimidyl)ester), Compound 5 (Bis(1-octyloxy-2,2,6,6-tetramethyl-4-piperidinyl sebecate), or Compound 6 (Bis(1-2,2,6,6-tetramethyl-4-piperidinyl sebecate).

Figure 91:
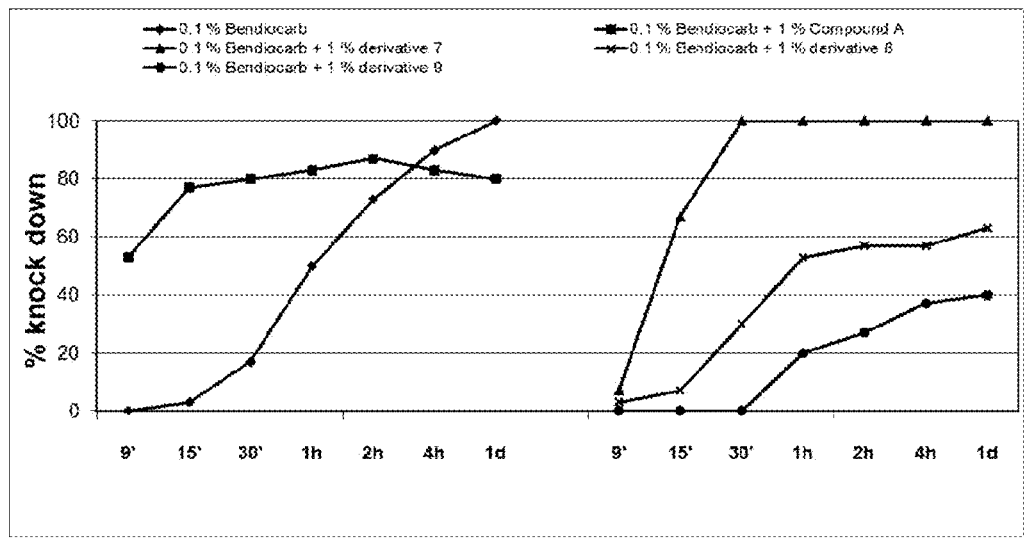
Figure 92:
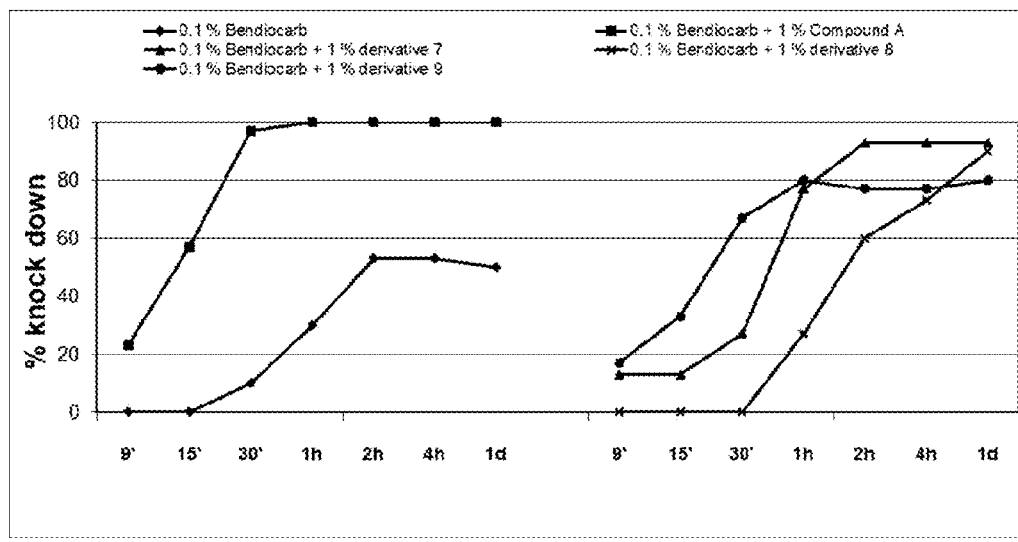

FIGS. 91 and 92 are graphs illustrating repeated analyses of the synergy of various adjuvants (each at a concentration of 1%), with the insecticide bendiocarb (at a concentration of 0.1%), against *Culex quinquefasciatus*, in terms of percent knockdown (%) over time (minutes, hours, and days). Compounds evaluated include bendiocarb, alone or in combination with Compound A, Compound 7 (4-hydroxy-2,2,6,6-tetramethyl-4-piperidine), Compound 8 (1,2,2,6,6-pentamethyl-4-piperidinol), or Compound 9 (4-hydroxy-2,2,6,6-tetramethyl-4-piperidin-1-oxyl).

Figure 93:
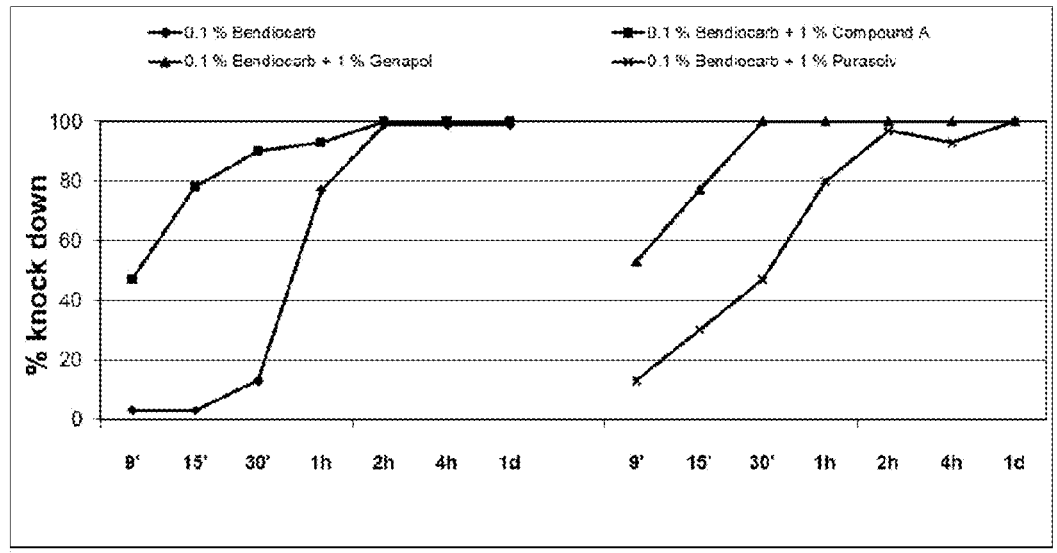
Figure 94:
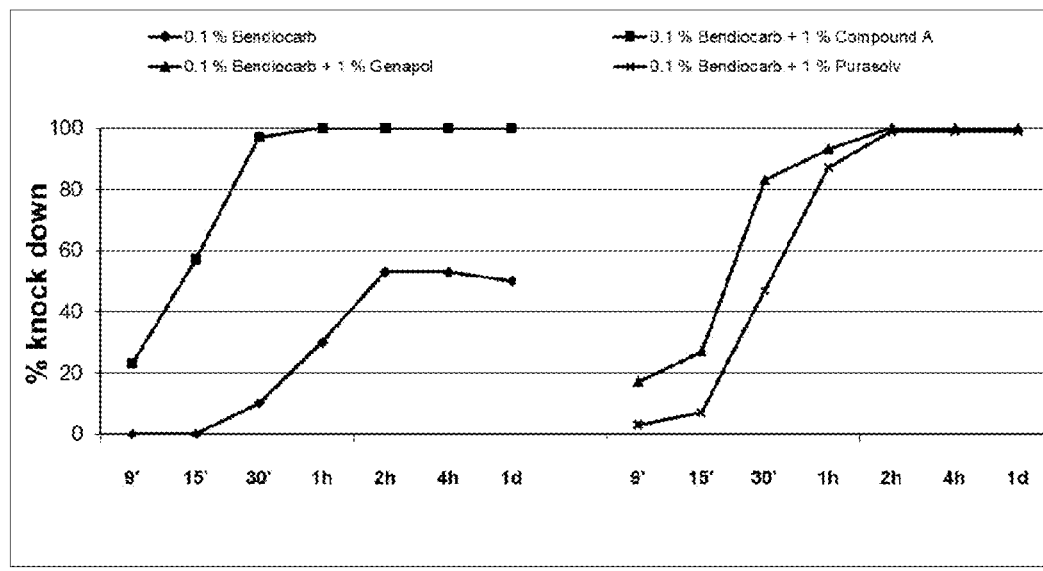

FIGS. 93 and 94 are graphs illustrating repeated analyses of the synergy of various adjuvants (each at a concentration of 1%), with the insecticide bendiocarb (at a concentration of 0.1%), against *Culex quinquefasciatus*, in terms of percent knockdown (%) over time (minutes, hours, and days). Compounds evaluated include bendiocarb, alone or in combination with Compound A, anionic and nonionic surfactants sold under the tradename Genapol®x 080, and lactate esters sold under the tradename Purasolv® EHC.

Figure 95:
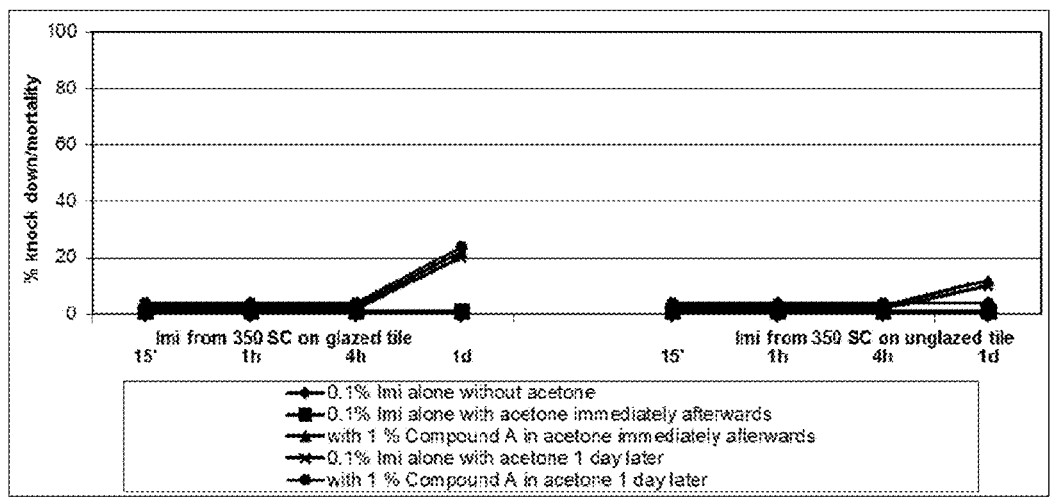

FIG. 95 is a graph illustrating the synergy of Compound A (at a concentration of 1% in acetone), with the insecticide imidacloprid 35 SC (at a concentration of 0.1%), against *Culex quinquefasciatus*, in terms of percent knockdown (%) over time (minutes, hours, and days). The graph reflects data points where the imidacloprid was applied neat (without acetone), where acetone was added immediately afterward, where Compound A in acetone was added immediately afterward, where acetone was added one day later, and where Compound A in acetone was added one day later.

Figure 96:
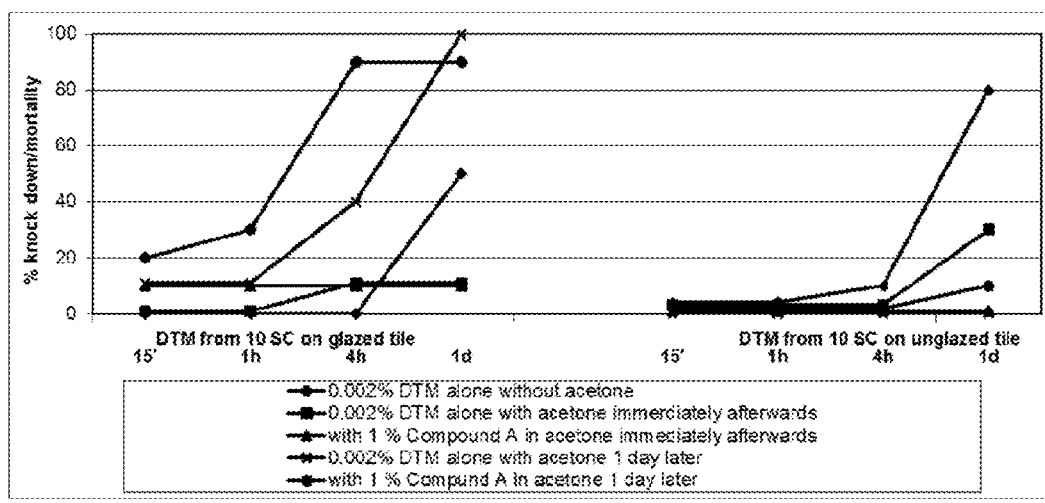

FIG. 96 is a graph illustrating the synergy of Compound A (at a concentration of 1% in acetone), with the insecticide deltamethrin 10 SC (at a concentration of 0.002%), against *Culex quinquefasciatus*, in terms of percent knockdown (%) over time (minutes, hours, and days). The graph reflects data points where the deltamethrin was applied neat (without acetone), where acetone was added immediately afterward, where Compound A in acetone was added immediately afterward, where acetone was added one day later, and where Compound A in acetone was added one day later.

Figure 97:
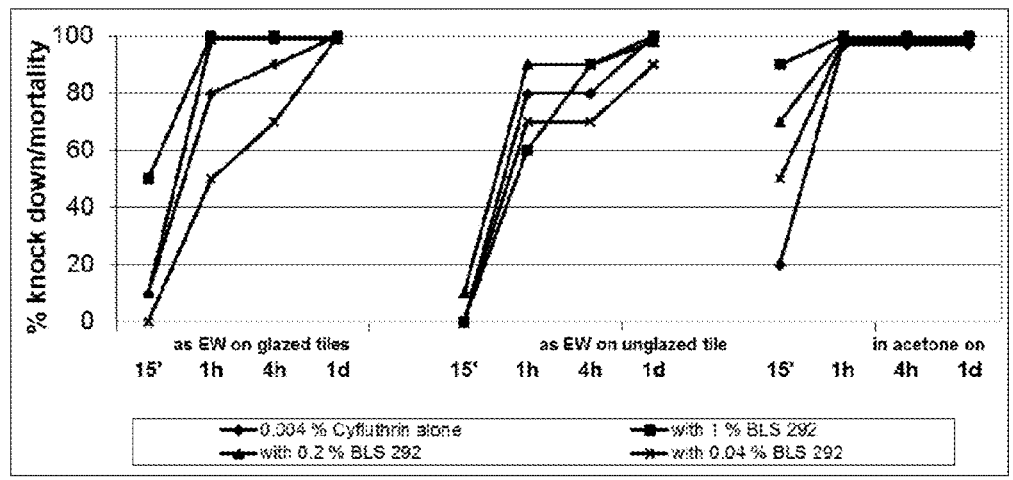

FIG. 97 is a graph illustrating the synergy of Compound A (at concentrations of 0.04, 0.02, and 1%), with the insecticide cyfluthrin (at a concentration of 0.004%), against *Musca domestica*, susceptible strain (WHO(N)), in terms of percent knockdown (%) over time (minutes, hours, and days). The graph reflects data points where the cyfluthrin was applied neat (without acetone) onto glazed tiles and unglazed tiles, and where the cyfluthrin was applied as a solution in acetone onto glazed tiles.

Figure 98:
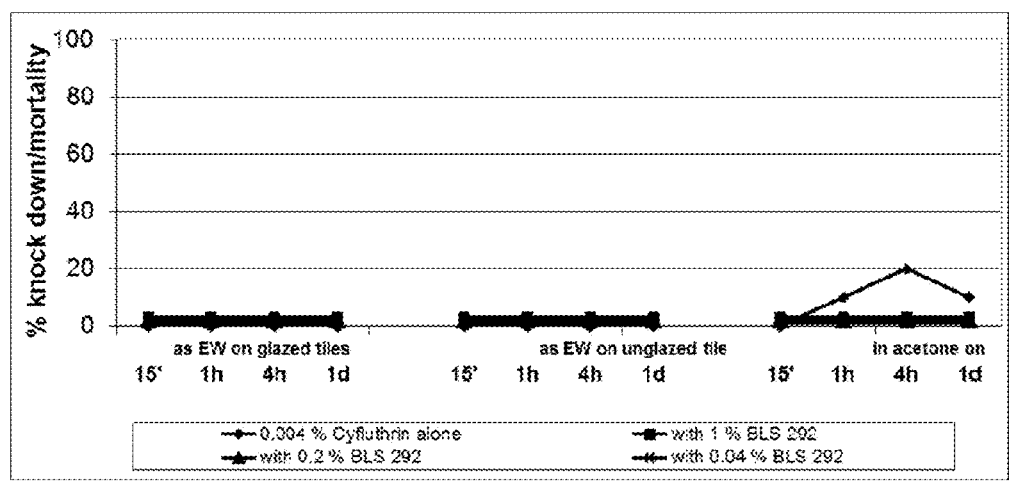

FIG. 98 is a graph illustrating the synergy of Compound A (at concentrations of 0.04, 0.02, and 1%), with the insecticide cyfluthrin (at a concentration of 0.004%), against *Musca domestica*, resistant strain (Reichswald), in terms of percent knockdown (%) over time (minutes, hours, and days). The graph reflects data points where the cyfluthrin was applied neat (without acetone) onto glazed tiles and unglazed tiles, and where the cyfluthrin was applied as a solution in acetone onto glazed tiles.

Figure 99:
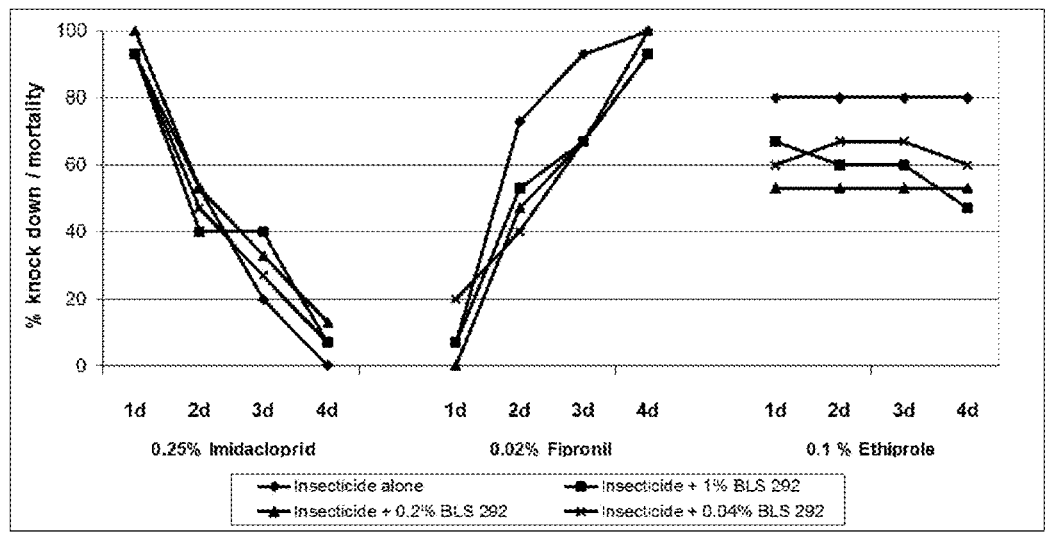

FIG. 99 is a graph illustrating the effect of imidacloprid, fipronil and ethiprole (all in an excipient such as that sold under the tradename Lutrol) with and without Compound A, against the American cockroach (*Periplaneta americana*) after oral application, measured in terms of percent knockdown (%) over time (days).

Figure 100:
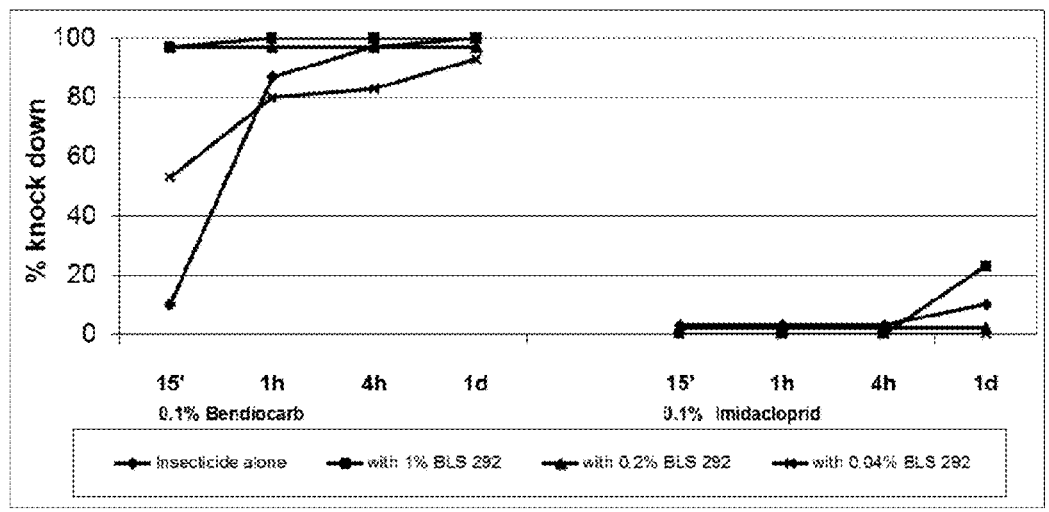

FIG. 100 is a graph illustrating the synergy of Compound A (at concentrations of 0.04, 0.2, and 1%) and bendiocarb (at a concentration of 0.1%) and imidacloprid (at a concentration of 0.1%), against *Culex quinquefasciatus*, measured in terms of percent knockdown (%) over time (days).

Figure 101:
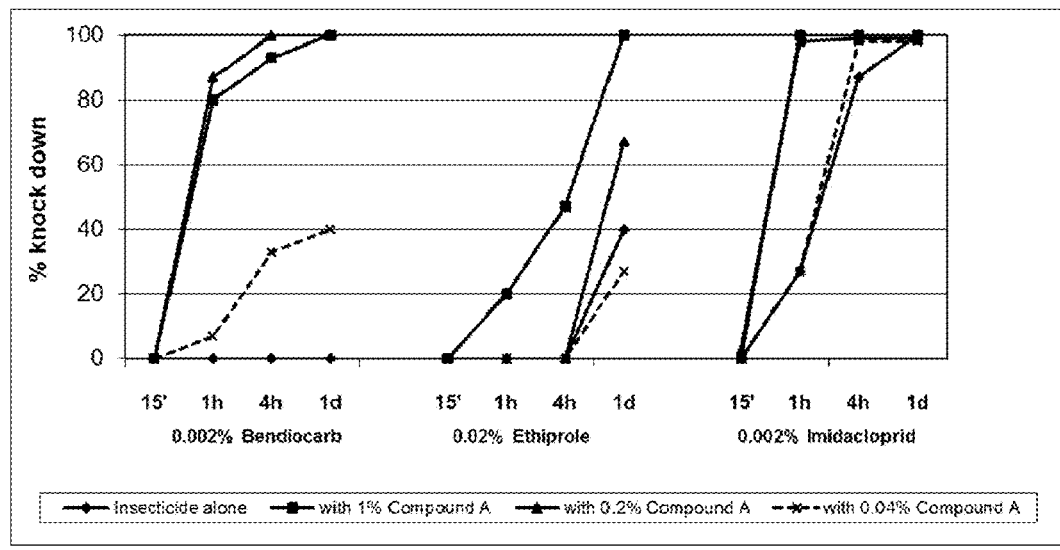

FIG. 101 is a graph illustrating the synergy of Compound A (at concentrations of 0.04, 0.2, and 1%) and bendiocarb (at a concentration of 0.002%), ethiprole (at a concentration of 0.02%), and imidacloprid (at a concentration of 0.002%), against *Cimex lectularus*, measured in terms of percent knockdown (%) over time (minutes, hours, and days).

Figure 102:
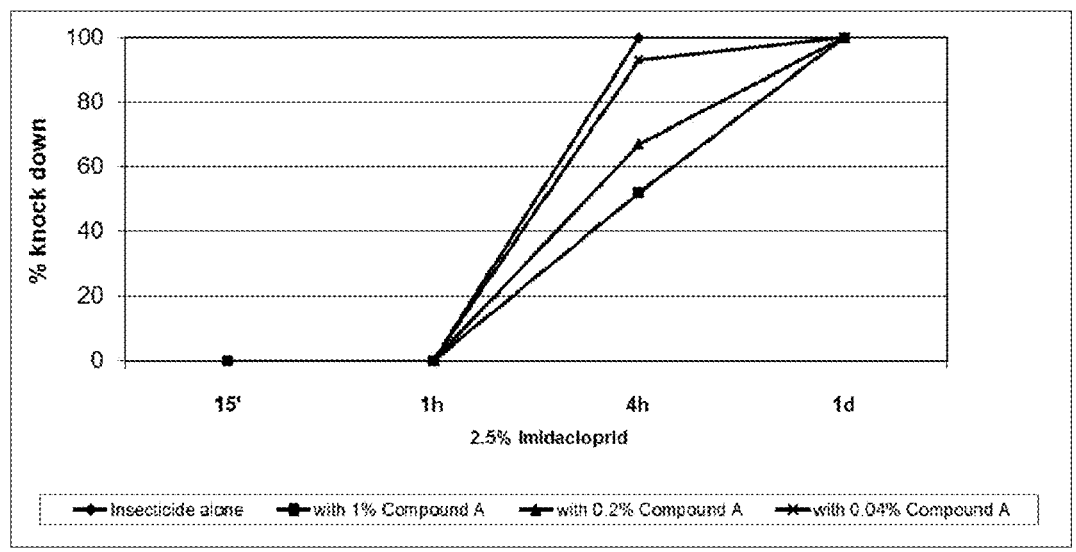

FIG. 102 is a graph illustrating the synergy of Compound A (at concentrations of 0.04, 0.2, and 1%) and imidacloprid (at a concentration of 2.5%), against *Acheta domesticus*, measured in terms of percent knockdown (%) over time (minutes, hours, and days).

Figure 103:
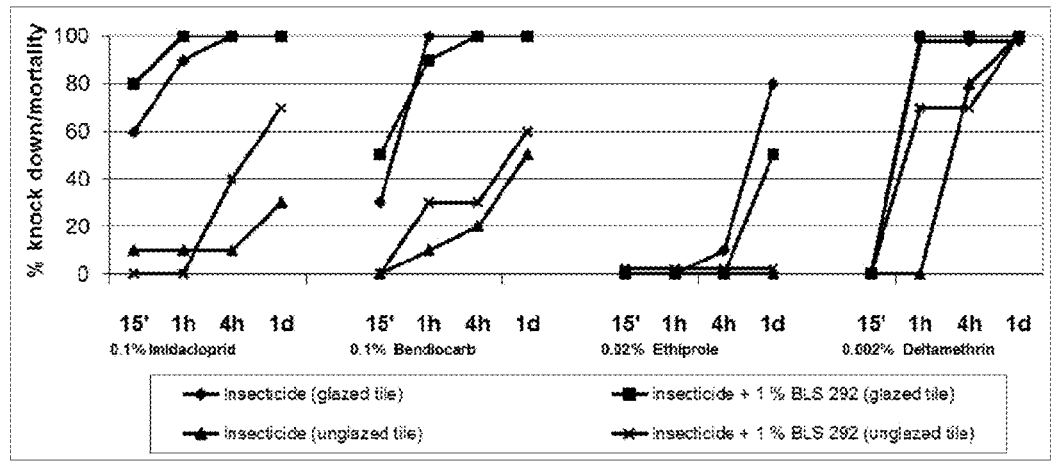

FIG. 103 is a graph illustrating the synergy of Compound A (at a concentration of 1%) and imidacloprid (at a concentration of 0.1%), bendiocarb (at a concentration of 0.1%), ethiprole (at a concentration of 0.02%), or deltamethrin (at a concentration of 0.002%) against *Culex quinquefasciatus*, on glazed and unglazed tiles, measured in terms of percent knockdown (%) over time (minutes, hours, and days).

Figure 104:
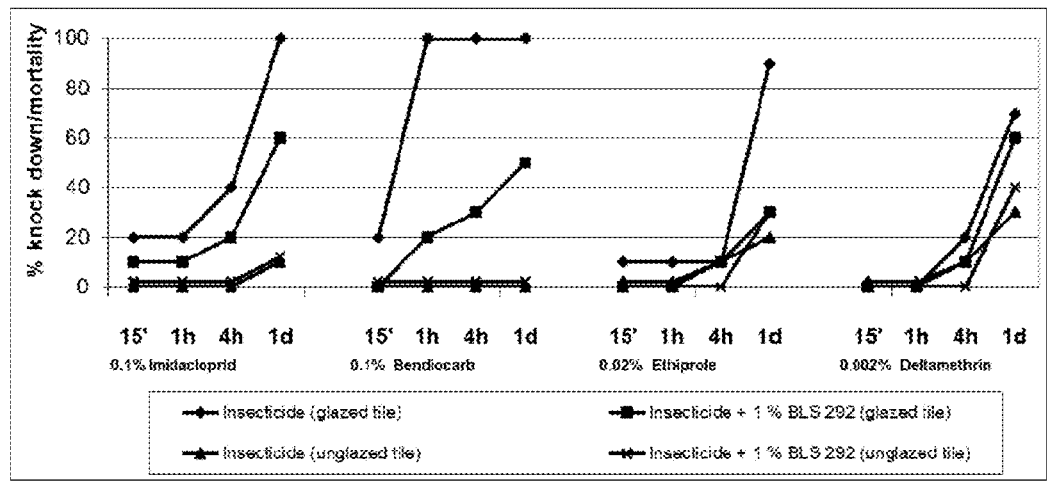

FIG. 104 is a graph illustrating the synergy of Compound A (at a concentration of 1%) and imidacloprid (at a concentration of 0.1%), bendiocarb (at a concentration of 0.1%), ethiprole (at a concentration of 0.02%), or deltamethrin (at a concentration of 0.002%) against *Musca domestica* (susceptible strain (WHO(N)), on glazed and unglazed tiles, measured in terms of percent knockdown (%) over time (minutes, hours, and days).

Figure 105:
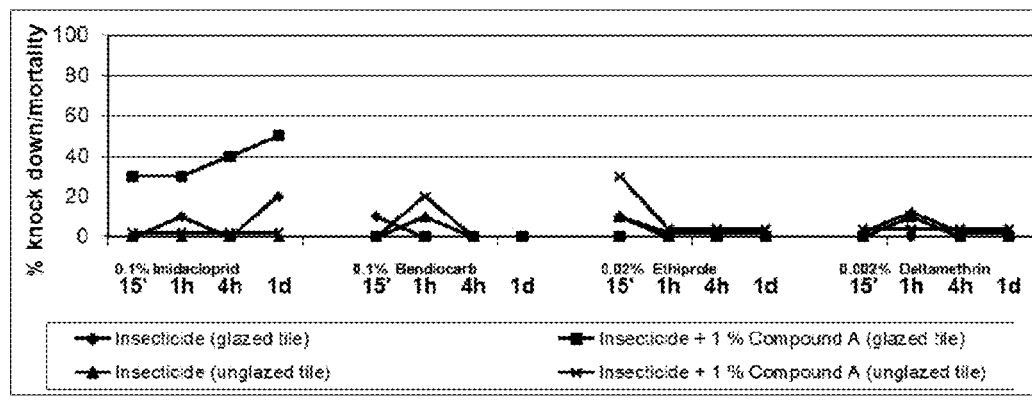

FIG. 105 is a graph illustrating the synergy of Compound A (at a concentration of 1%) and imidacloprid (at a concentration of 0.1%), bendiocarb (at a concentration of 0.1%), ethiprole (at a concentration of 0.02%), or deltamethrin (at a concentration of 0.002%), against *Musca domestica* (resistant strain (Reichswald), on glazed and unglazed tiles, measured in terms of percent knockdown (%) over time (minutes, hours, and days).

Figure 106:
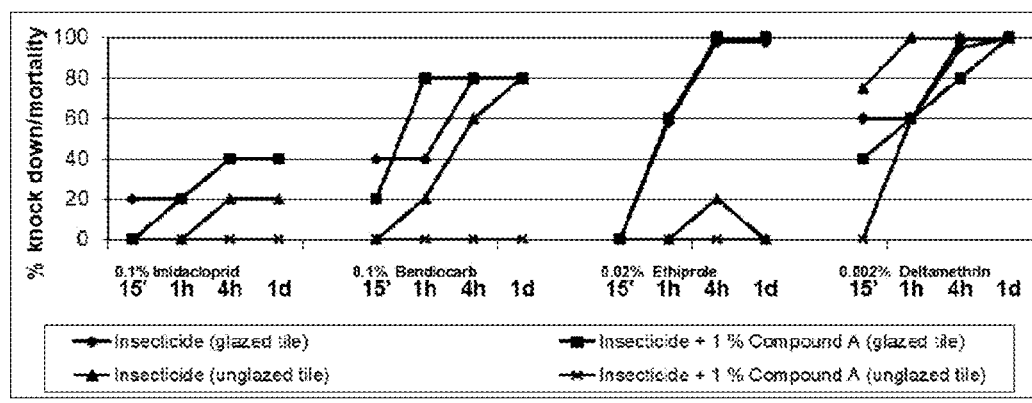

FIG. 106 is a graph illustrating the synergy of Compound A (at a concentration of 1%) and imidacloprid (at a concentration of 0.1%), bendiocarb (at a concentration of 0.1%), ethiprole (at a concentration of 0.02%), or deltamethrin (at a concentration of 0.002%) against *Blattella germanica* (susceptible), on glazed and unglazed tiles, measured in terms of percent knockdown (%) over time (minutes, hours, and days).

Figure 107:
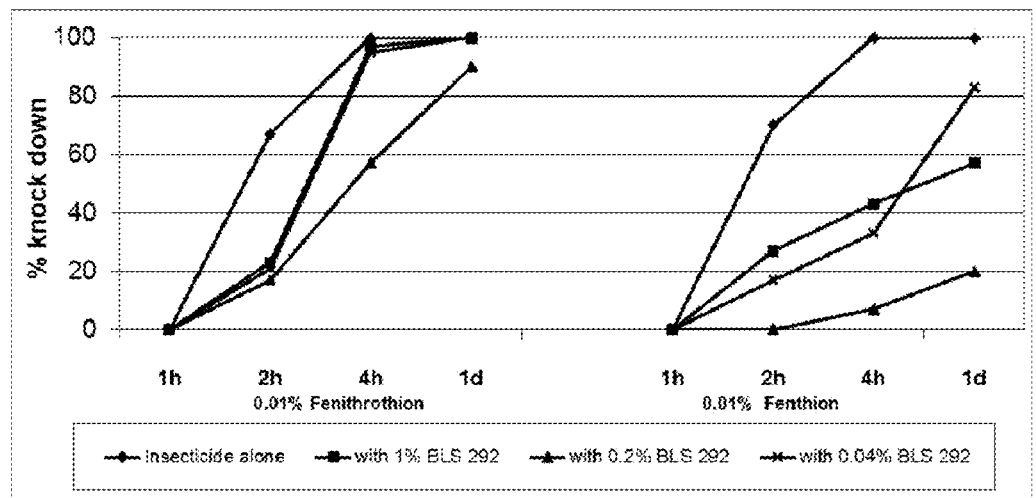

FIG. 107 is a graph illustrating the synergy of Compound A (at concentrations of 0.04, 0.2, and 1%) and fenitrothion (at a concentration of 0.01%) or fenthion (at a concentration of 0.01%), against *Culex quinquefasciatus*, measured in terms of percent knockdown (%) over time (hours, and days).

Figure 108:
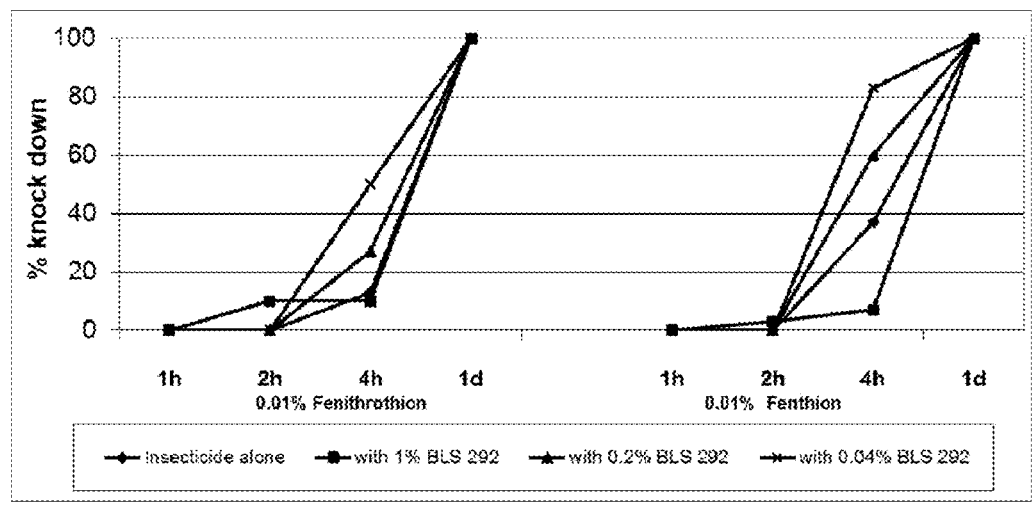

FIG. 108 is a graph illustrating the synergy of Compound A (at concentrations of 0.04, 0.2, and 1%) and fenitrothion (at a concentration of 0.01%) or fenthion (at a concentration of 0.01%), against *Cimex lectularius*, measured in terms of percent knockdown (%) over time (hours, and days).

Figure 109:
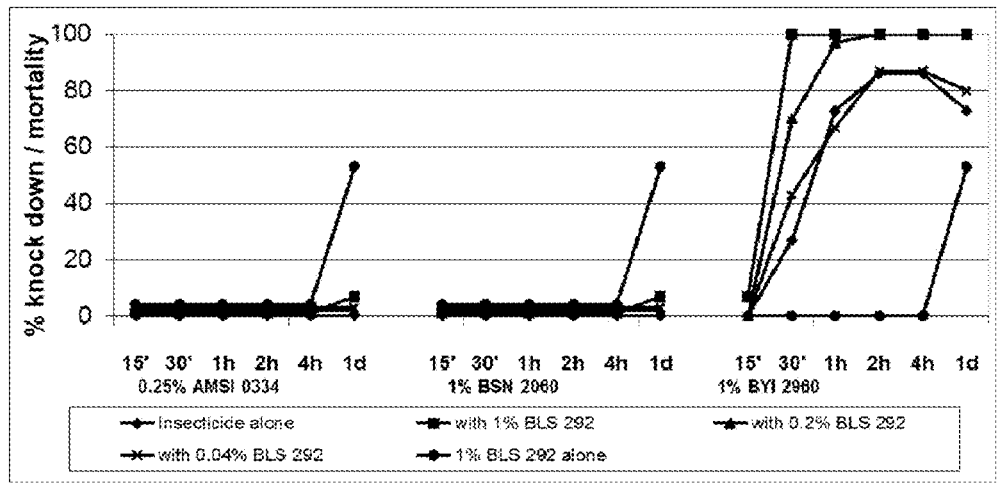

FIG. 109 is a graph illustrating the synergy of Compound A (at concentrations of 0.04, 0.2, and 1%) and a phthalic acid diamide derivative (at a concentration of 0.25%), spiromesifen (at a concentration of 1%) or a butenolide (at a concentration of 1%), against *Cimex lectularius*, measured in terms of percent knockdown (%) over time (minutes, hours, and days).

Figure 110:
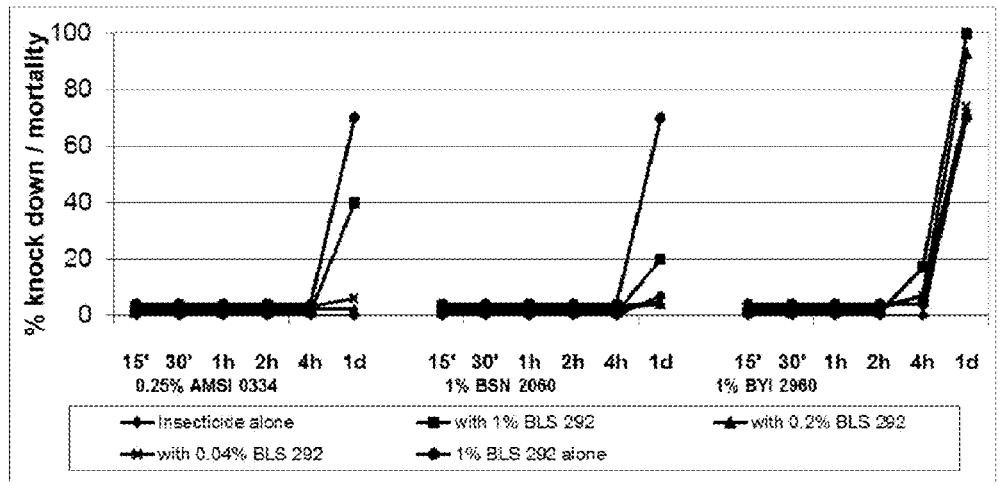

FIG. 110 is a graph illustrating the synergy of Compound A (at concentrations of 0.04, 0.2, and 1%) and a phthalic acid diamide derivative (at a concentration of 0.25%), spiromesifen (at a concentration of 1%) or a butenolide (at a concentration of 1%), against *Culex quinquefasciatus*, measured in terms of percent knockdown (%) over time (minutes, hours, and days).

Figure 111:
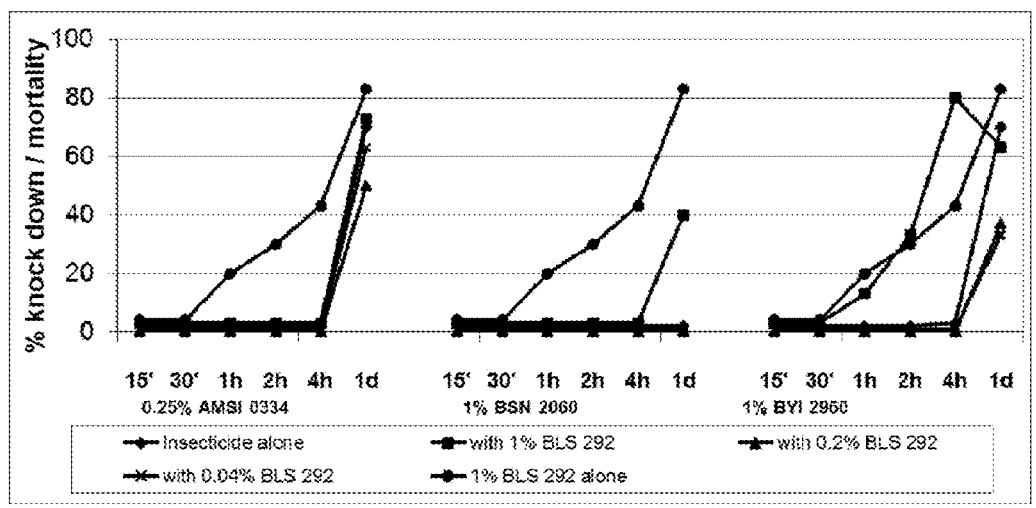

FIG. 111 is a graph illustrating the synergy of Compound A (at concentrations of 0.04, 0.2, and 1%) and a phthalic acid diamide derivative (at a concentration of 0.25%), spiromesifen (at a concentration of 1%) or a butenolide (at a concentration of 1%), against *Musca domestica* (susceptible strain), measured in terms of percent knockdown (%) over time (minutes, hours, and days).

DETAILED DESCRIPTION OF THE PREFERRED EMBODIMENTS

Pesticidal compositions, methods for their preparation, and methods for their use are described in more detail below. The present invention will be better understood with reference to the certain definitions. The fact that certain terms are defined herein, however, does not imply that those terms without specific definition are indefinite. Rather, all terms are believed to be used within the accepted meaning in the art.

Compound A, as used herein, describes a mixture of bis(1,2,2,6,6-pentamethyl-4-piperidinyl)sebacate and methyl(1,2,2,6,6-pentamethyl-4-piperidinyl)sebacate).

Compound B, as used herein, describes (2-(2H-Benzotriazole-2-yl)-4-methylphenyl. The combination Compound A+Compound B is alternatively referred to herein as "UV Block" or as "BLS292."

Throughout the present specification, the term "insect" is used in the common meaning and, more phylogenically, should be considered equivalent to the term "arthropod." Thus, as used herein the term "insect," includes chelicerates, namely spiders, mites, scorpions and related organisms characterised by the presence of chelicerae, appendages just above/in front of the mouth; myriapods, namely millipedes and centipedes and their relatives that have many body segments, each bearing one or two pairs of legs; hexapods namely insects and three small orders of insect-like animals with six thoracic legs; and crustaceans, which are primarily aquatic (a notable exception being woodlice) and are characterised by having biramous appendages.

As used herein, a free radical stabilizer is a compound that reacts with a free-radical in an electron transfer process to produce a stable free radical. Examples include hindered amine light stabilizers, such as various sebacates; polyphenyl methanes; food-grade preservatives; certain esters. Some of these free radical stabilizers are also UV absorbers, and can enhance the useful lifetime of light-sensitive compounds when they are used in an environment that is exposed to sunlight.

As used herein, a plasticizer is an additive that increases the plasticity or fluidity of the material to which it is added. A plasticizer makes or keeps such material soft or pliable.

While not wishing to be bound to a particular theory, the present inventors believe that the free radical stabilizer adjuvants of the present invention function by a direct action on the pest to be controlled, namely through the insect's cuticle, or, when applied to a plant, through the plant cuticle.

The amount of free radical stabilizer necessary to penetrate the cuticle, for example the insect cuticle, is greater than the amount typically used as a preservative.

While not wishing to be bound to a particular theory, the present inventors believe that the adjuvants of the present invention function by destabilizing the pest's, for example, insect's or plant's cuticle. Alternatively, the adjuvants of the present invention are believed to alter the permeability of the cuticle, thus, allowing for a synergistic application of pesticide. In this regard, a preferred amount of adjuvant will be that necessary to promote the free radical degradation in the cuticle. This preferential amount, however, will change depending on the pest, namely insect or plant, and also on the active ingredient employed in conjunction with the adjuvant. As will be demonstrated herein, the synergism achieved by the active ingredient and adjuvant is not predictable and, thus, the synergism associated with the compositions of the present invention is unexpected. In other words, there is no correlation between the partition coefficient of any particular active ingredient and the activity of that active ingredient with the adjuvant to achieve the synergism of the present invention.

As used herein, a "partition coefficient" is defined as the ratio of concentrations of an un-ionized compound between solutions of water and octanol. To measure the partition coefficient of ionizable solutes, the pH of the aqueous phase is adjusted such that the predominant form of the compound is un-ionized. The logarithm of the ratio of the concentrations of the un-ionized solute in the solvents is referred to herein as log P or log K ow.

As used herein, the adjuvants are described to affect the cuticle of the targeted pest. As will be appreciated by those skilled in the art, there are distinct physical and chemical differences between the cuticle of a plant pest and the cuticle of an insect pest.

In the field, there are additives which act as penetrants at the level of the cuticle, which may be referred to as accelerator additives. See, for example, Schönherr and Baur, 1994, Pesticide Science 42, 185-208. Accelerator additives penetrate from the application into the plant cuticle and thereby increase the mobility of active substances in the plant cuticle. Other additives such as polyethylene glycol, in contrast, act only in the spray covering (via the liquid phase) or act only as wetting agents, such as sodium dodecyl sulphate, for example. There is an accepted test to determine the influence of additives on the penetration properties of other substances at the level of the plant cuticle. The mobility of the test substance in the cuticle is measured with and without an additive, by way of a desorption method. The method is published in detail in the literature (Baur et al., 1997, Pesticide Science, 51, 131-152) and any deviations are within the skill of the art.

As a test substance with the function of a tracer, a selection may be made of a radiolabelled weak organic acid. Plant material may be used, such as enzymatically isolated leaf cuticles of the top face of peach leaves from outdoor trees. The cuticles may be installed in specially manufactured stainless steel diffusion cells. The tracer, in a citrate buffer at a pH of 3 in the dissolved state, may be applied to the side originally facing the inside of the leaf. This inner side readily takes up the small radioactive amount of the tracer in the undissociated acid form. Subsequently this inner side may be covered and maintained at 100% atmospheric humidity. The morphological outer side of the leaf cuticle, normally exposed to the air, may be then contacted with a buffer (pH 7), with the receptor solution, and the desorption thereby started. The penetrated acid form of the test substance is dissociated by the receptor and the desorption follows first-order kinetics. The desorption constant is proportional to the mobility of the tracer in the cuticle.

After at least 2 times for determining this constant, the desorption is then continued with a buffer which additionally includes the test additive. Depending on the property of the additive there is then sorption of the additive in the cuticle and, depending on its activity as a plasticizer for the cuticle, there is an increase in the mobility of the tracer within the cuticle. This is manifested in an increased desorption constant, and the ratio of the slopes with additive to that without additive describes the effect of the additive to act as a penetrant at the level of the cuticle. The comparison of the average effect of different additives shows their effectiveness at acting as plant cuticle plasticizers.

Free Radical Stabilization

As mentioned, in some embodiments of the present invention, the adjuvant functions as a free radical stabilizer. Certain free radical stabilizers such as, benzophenones, piperidines, or benzotriazoles, may be used in combination with pesticides for the purpose of protecting the molecular integrity of the active pesticidal compound(s) by preventing photolytic breakdown of chemical bonds in the pesticide molecules. Observers note a beneficial effect of preserving the pesticidal action for longer periods of time, either on storage or in situ following application to a locus, as compared to the pesticide presented without the mitigation of photolytic degradation afforded by the UV blockers. Thus, free radical stabilizers may prevent a free radical reaction of photolytic energy with the pesticidal compounds themselves.

The present invention is different in that it uses free radical stabilizers to initiate a free radical reaction on insect or plant tissue, thereby altering the permeability of these biological membranes. The benefits of this use are surprising in that the actions facilitate the movement of the pesticidal compound across the biological membrane and on to a physiological site of action inside the animal or plant. Therefore, in the present invention, the use of free radical stabilizers is presented in a sufficient amount to destabilize the cuticle in insects or plants. By destabilizing the cuticle, the application of a pesticide at a specific dose rate becomes unexpectedly much higher than what is observed when the cuticle is not de-stabilized. That is, based on a particular dose applied, either to a pest or to a locus, the percentage of effectiveness at reaching the physiological target site where the pesticide exerts its effects on the pest is increased when the cuticle is destabilized.

Many of the adjuvants useful in the present invention are also UV stabilizers, which can contribute to the inhibition of photodegradation of the pesticides. While protection against chemical decomposition induced by light energy can sometimes be achieved by using specific compounds, the amount needed of such chemicals to protect against decomposition is not indicative as to the amounts necessary to affect structural integrity in an insect or plant cuticle, to thereby promote greater penetration of the pesticide into the organism. Moreover, there is simply no indication that if a chemical acts as protectant to a pesticide against decomposition, that such a chemical would have any affect on how that same chemical would affect an insect or plant when administered with a pesticide. Indeed, in cases where an adjuvant is provided to reduce decomposition of a pesticide, by the time the pesticide is used in a locus and comes into contact with a plant or insect, that adjuvant may well be virtually exhausted or maybe even completely gone. As such, the adjuvant would not be capable of affecting the cuticle of the plant or insect when it is applied with a pesticide.

In the compositions of the present invention, the use of an additional attractant, namely a pheromone or a kairomone, may be contraindicated. In such circumstances, the composition of the present invention need not include an attractant in order to provide the synergistic efficacy.

The compositions of the present invention may be applied to a variety of surfaces. As mentioned above, however, the adjuvants of the present invention are provided in amounts so as to destabilize the cuticle of the targeted insect or plant. As such, when the compositions of the present invention are to be formulated into a paint composition, the formulation may be adjusted so as to provide for the UV stabilization as previously described. Preferably, the composition is not presented in a paint formulation.

The compositions of the present invention may be formulated in a variety of application forms. As is appreciated in the art, encapsulation of materials for protection from environmental elements may include UV stabilization. Similar to above, therefore, the adjuvants of the present invention are provided in amounts so as to destabilize the cuticle of the targeted insect or plant. Preferably, the compositions of the present invention are not formulated in encapsulated form with UV stabilizers.

The compositions of the present invention may be formulated with or without additional active ingredients. As one example, the composition may include an additional fungicide. In this regard, preferably such an additional component does not adversely impact the synergy of the pesticide and adjuvant. In this regard, with respect to fungicides, there is a preference for avoiding wood stain and decay fungicides.

I. Pesticides

Pesticides are defined as chemicals used to kill pests. Pesticides specifically include fungicides, herbicides, insecticides, and rodenticides. Pesticides are defined by the Federal Government in 40 CFR 152.3 as "any substance (or group of structurally similar substances if specified by the Agency) that will prevent, destroy, repel, or mitigate any pest, or that functions as a plant regulator, desiccant or defoliant withinwording the meaning of FIFRA sec. 2(a)." Several types of pesticides are described in more detail below.

A. Insecticides

An insecticide is a pesticide used against insects in all developmental forms. They include ovicides and larvicides used against the eggs and larvae of insects, respectively. Insecticides are commonly used in agriculture, medicine, industry, and for household use.

There are several classes of agricultural insecticides. Systemic insecticides are incorporated by treating plants such that insects ingest the insecticide while feeding on the plants. Contact insecticides are toxic to insects brought into direct contact with the insecticide. Contact insecticides are commonly applied by aerosol distribution and, in some examples, may remain in active form on treated surfaces for extended periods of time. Natural insecticides, such as nicotine and pyrethrum, are made by plants as defense mechanisms against insects. Inorganic insecticides are manufactured with various metal salts, including arsenates, chromium, copper, fluorine, and sulfur. Inorganic insecticides are commonly used for wood treatment, although quaternary ammonium salts and other compounds are replacing chromium and arsenates due to toxicity issues with the latter. Organic insecticides are synthetic chemicals. Most insecticides in use today are organic insecticides.

Representative insectides useful in the present invention include pyrethrum type insecticides, such as pyrethrin; pyrethroids, such as deltamethrin, permethrin, β-cyfluthrin, bifenthrin, and resmethrin; nicotinics, particularly chloronicotinyl compounds, such as acetamiprid, imidacloprid, thiamethoxam, clothianidin, acetamiprid, thiacloprid, and dinotefuran; pyrazoles such as fipronil, ethiprole, and tebufenpyrad; semicarbazones such as indoxacarb and metaflumizone, phthalic acid diamides such as flubendiamide and (S)-3-chloro-N1-{2-methyl-4-[1,2,2,2-tetrafluoro-1-(trifluoromethyl)ethyl]phenyl}-N2-(1-methyl-2-methylsulfonylethyl)phthalamide; anthranilic acid amides such as chloroanthraniliprole; organophosphates such as chlorpyrifos, malathion, and diazinon; carbamates such as bendiocarb, carbaryl, and thiodicarb; ketoenoles such as spirotetramat, spirodiclofen, and spiromesifen; phthalic acid diamides such as insecticides with an active ingredients from the anthranilic diamide class such as that sold by DuPont under the tradename Rynaxypyr (hereinafter referred to a rynaxypyr for ease of reference), and flubendiamide; IGRs such as methoprene, pyriproxifen, triflumuron, hexaflumuron, noviflumuron, fenoxycarb; and other insecticides, such as abamectin, hydramethylnon, sulfluramid, and spinosad. Representative chlorinated hydrocarbons include aldrin, chlordane, chlordecone, DDT, dieldrin, endosulfan, endrin, heptachlor, hexachlorocyclohexane, gamma-hexachlorocyclohexane, lindane, methoxychlor, mirex, pentachlorophenol, and TDE. Representative organophosphorus insecticides include acephate, azinphos-methyl, bensulide, chlorethoxyfos, chlorpyrifos, chlorpyriphos-methylm diazinon, dichlorvos (DDVP), dicrotophos, dimethoate, disulfoton, ethoprop, fenamiphos, fenitrothion, fenthion, fosthiazate, malathion, methamidophos, methidathion, methyl-parathion, mevinphos, naled, omethoate, oxydemeton-methyl, parathion, phorate, phosalone, phosmet, phostebupirim, pirimiphos-methyl, profenofos, terbufos, tetrachlorvinphos, tribufos, trichlorfon. Representative carbamates include aldicarb, carbofuran, carbaryl, methomyl, and 2-(1-methylpropyl)phenyl methylcarbamate. Representative pyrethroids include allethrin, beta-cyfluthrin, bifenthrin, cyfluthrin, deltamethrin, permethrin, resmethrin, sumithrin, tetramethrin, tralomethrin, and transfluthrin. Representative plant toxin derived insecticides include derris (rotenone), pyrethrum, neem (azadirachtin), nicotine, and caffeine.

Additional insecticides include cyclic ketoenols with insecticidal and acaricidal properties, such as those described in EP 528 156 A, WO 95/01971, EP 647 637 A, WO 96/16061, WO 96/20196, WO 96/25395, WO 96/35664, WO 97/02243, WO 97/01535, WO 97/36868, WO 97/43275, WO 98/05638, WO 98/06721, WO 99/16748, WO 99/43649, WO 99/48869, and WO 99/55673, each hereby incorporated by reference with regard to such teaching.

Certain pesticides are exempt from the requirements of the FIFRA act (40 CFR 152.25(f)). They are commonly known as minimum risk pesticides. Examples of these pesticides includes castor oil (U.S.P. or equivalent), cedar oil, cinnamon and cinnamon oil, citric acid, citronella and citronella oil, cloves and clove oil, corn gluten meal, corn oil, cottonseed oil, dried blood, eugenol, garlic and garlic oil, geraniol, geranium oil, lauryl sulfate, lemongrass oil, linseed oil, malic acid, mint and mint oil, peppermint and peppermint oil, 2-phenethyl propionate (2-phenylethyl propionate), potassium sorbate, putrescent whole egg solids, rosemary and rosemary oil, sesame (includes ground sesame plant) and sesame oil, sodium chloride (table salt), sodium lauryl sulfate, soybean oil, thyme and thyme oil, and white pepper.

Numerous heterocycles, organotin compounds, benzoylureas and pyrethroids have insecticidal and acaricidal properties, for example, see WO 93/22297, WO 93/10083, DE 2 641 343 A, EP 347 488 A, EP 210 487 A, U.S. Pat. No. 3,264,177, and EP 234 045 A, each herein incorporated by reference with regard to such teaching.

Certain bacteria, fungi, and other biological material may be active as insecticides. When these biological insecticides are inactive against other organisms, some are considered more environmentally friendly than synthetic pesticides.

Examples include, but are not limited to, *Bacillus Sphericus, Bacillus Subtilis, Bacillus cereus,* or combinations of such material.

The above-referenced exemplary insecticides may be characterized as either (i) fast acting; (ii) intermediate acting; or (iii) slow acting. As noted herein, the octanol-water partition coefficient may be used to identify the cuticular penetration of a particular active ingredient. One factor in the relative speed through which any insecticide acts is the insecticide's ability to cross the insect cuticle. A determining factor for cuticle penetration is Log K ow, also known as Log P. Log K ow (Log P) is the octanol-water partition coefficient for a neutral molecule. Log P is used hereinfurther, but, as noted above, the term is synonymous with Log K ow. As previously noted, the cuticular penetration of any particular active ingredient as against a plant cuticle is not indicative of that same active ingredient's ability to penetrate an insect cuticle. Further, as will be illustrated herein further, the base cuticular penetration for an active ingredient does not provide a direct correlation to the synergistic effect of the present invention. As such, the mechanism attributable to the synergistic effect of the adjuvant of the present invention is different from the cuticular penetration achieved by compounds by measurement of Log K ow.

The cuticular penetration of a compound is classified as "SLOW" when the compound has a Log P value of about <2.0. The cuticular penetration of a compound is classified as "FAST" when it has a Log P value of about >4.0. The cuticular penetration of a compound is classified as "INTERMEDIATE" when the Log P value is between about 2.0 and about 4.0. Log P values of representative insecticides from the various insecticide classes are shown below in Table 1.

TABLE 1

| Insecticide Class | Examples | Log P | Likelihood of Direct Insect Cuticular Penetration |
|---|---|---|---|
| pyrethrums | pyrethrin | 4.3 | Fast |
| pyrethroids | deltamethrin | 4.6 | Fast |
| | permethrin | 6.1 | Fast |
| | β-cyfluthrin | 5.9 | Fast |
| | bifenthrin | 6.0 | Fast |
| | resmethrin | 5.4 | Fast |
| chloronicotinyls | imidacloprid | 0.6 | Slow |
| | thiamethoxam | 0.1 | Slow |
| | clothianidin | 0.7 | Slow |
| | acetamiprid | 0.8 | Slow |
| | thiacloprid | 1.3 | Slow |
| | dinotefuran | 0.5 | Slow |
| pyrazoles | fipronil | 4.0 | Fast |
| | ethiprole | 2.90 | Fast |
| | tebufenpyrad | 4.9 | Fast |
| semicarbazone | indoxacarb | 4.6 | Fast |
| | metaflumizone | 5.1 | Fast |
| phthalic acid diamides | flubendiamide | 4.2 | Fast |
| organophosphates | chlorpyrifos | 5.0 | Fast |
| | malathion | 2.7 | Intermediate |
| | diazinon | 3.3 | Intermediate |
| carbamates | bendiocarb | 1.7 | Slow |
| | carbaryl | 2.8 | Intermediate |
| | thiodicarb | 1.6 | Slow |
| IGRs | methoprene | >6.0 | Fast |
| | pyriproxifen | 5.4 | Fast |
| | triflumuron | 4.9 | Fast |
| | hexaflumuron | 5.6 | Fast |
| | noviflumuron | 4.9 | Fast |
| | fenoxycarb | 4.1 | Fast |
| ketoenoles | spirodiclofen | 5.8 | Fast |
| | spiromesifen | 4.6 | Fast |
| | spirotetramate | | |

TABLE 1-continued

| Insecticide Class | Examples | Log P | Likelihood of Direct Insect Cuticular Penetration |
|---|---|---|---|
| other | abamectin | 4.4 | Fast |
| | hydramethylnon | 2.3 | Intermediate |
| | sulfluramid | >6.8 | Fast |
| | spinosad | 2.8-5.2 | Intermediate-Fast |

As noted, despite an active ingredient's chacterization for cuticular penetration, the present invention provides an unexpected synergism. As one example, an adjuvant of the present invention may allow for a decreased amount of active ingredient for an equivalent effect for an active ingredient that is already characterized as "fast." Thus, mechanistically, including physiochemically, the adjuvants of the present invention provide cuticular penetration beyond any expected level.

Certain insecticidal agents can be used to combat material destroying insects and preserve technical materials, such as wood products. They can also be used for soil treatment against termite infestation. Representative insecticidal compounds used to treat surfaces, specifically wood products, include organophosphorus insecticides such as phoxim and chloropyriphos, as well as those classified in the pyrethroid series insecticides such as permethrin, deltamethrin, cypermethrin, fenvalerate, and cyfluthrin. Additional insecticides include 1-(6-chloro-3-pyridylmethyl)-2-nitromethylene-imidazolidine, 3-(6-chloro-3-pyridylmethyl)-2-nitromethylene-thiazolidine, 1-(6-chloro-3-pyridylmethyl)-2-nitroimino-imidazolidine, 1-(6-chloro-3-pyridylmethyl)-2-nitromethylene-tetrahydropyrimidine, and 3-(6-chloro-3-pyridylmethyl)-2-nitromethylene-tetrahydro-2H-1,3-thiazine.

B. Agricultural Chemicals

Any type of agricultural chemical, pesticide, or genetic material, which results in a desired effect, may be considered a pesticide for the present invention. Thus, the active components can be herbicidal, insecticidal, bactericidal, virucidal, fungicidal, acaricidal, and the like as herein described. The active components may be genetic material to be transfected into a plant.

Plant Growth Regulators

Any compound that regulates plant growth can be included in the compositions of the invention. As used herein, the phrase "plant growth regulator" includes chemicals that are designed to affect plant growth, development, or both. They are applied for specific purposes to affect specific plant responses. Although there is much scientific information on using plant growth regulators, due to the nature of agricultural maintenance, plant growth regulation is not a predictable science. As used herein, the phrase "plant growth regulator" includes products designed to reduce or retard the growth rate of the plant, improve its color and general condition, increase plant branching for enhanced cutting production, or enhance flower initiation or synchronize flowering. As used herein the phrase "plant growth regulator" includes a turf growth regulator.

The phrase "plant growth regulator" includes: antiauxins, such as clofibric acid or 2,3,5-tri-iodobenzoic acid; auxins, such as 4-CPA (4-chlorophenoxyacetic acid), 2,4-D ((2,4-dichlorophenoxy)acetic acid), 2,4-DB (4-(2,4-dichlorophenoxy)butyric acid), 2,4-DEP (tris[2-(2,4-dichlorophenoxy)ethyl]phosphate), dichlorprop ((RS)-2-(2,4-dichlorophenoxy)propionic acid), fenoprop ((RS)-2-(2,4,5- trichlorophenoxy)propionic acid), IAA (indol-3-ylacetic acid or β-indoleacetic acid), IBA (4-indol-3-ylbutyric acid), naphthaleneacetamide, α-naphthaleneacetic acid, 1-naphthol, naphthoxyacetic acid, potassium naphthenate, sodium naphthenate, or 2,4,5-T ((2,4,5-trichlorophenoxy)acetic acid); cytokinins, such as 2iP ($N^6$-(3-methylbut-2-enyl)adenine or N-(3-methylbut-2-enyl)-1H-purin-6-amine), benzyladenine, kinetin, or zeatin; defoliants such as calcium cyanamide, dimethipin, endothal, ethephon, merphos, metoxuron, pentachlorophenol, thidiazuron, or tribufos; ethylene inhibitors, such as aviglycine or 1-methylcyclopropene; ethylene releasers such as ACC (1-aminocyclopropanecarboxylic acid), etacelasil, ethephon, or glyoxime; gibberellins such as gibberellins, gibberellin inhibitors such as trinexapac-ethyl, or gibberellic acid; growth inhibitors such as abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, or 2,3,5-tri-iodobenzoic acid; morphactins such as chlorfluren, chlorflurenol, dichlorflurenol, or flurenol; growth retardants such as chlormequat, daminozide, flurprimidol, mefluidide, paclobutrazol, tetcyclacis, or uniconazole; growth stimulators such as brassinolide, forchlorfenuron, or hymexazol; and further includes a variety of unclassified plant growth regulators such as benzofluor, buminafos, carvone, ciobutide, clofencet, cloxyfonac, cyanamide, cyclanilide, cycloheximide, cyprosulfamide, epocholeone, ethychlozate, ethylene, fenridazon, heptopargil, holosulf, inabenfide, karetazan, lead arsenate, methasulfocarb, prohexadione, pydanon, sintofen, triapenthenol, or trinexapac.

Specific embodiments of the present invention include MH (maleic hydrazide), ethephon (2-chloroethylphosphonic acid), Folex (S,S,S, tributyl phosphorothioate, Dropp (thidiazuron), Pix (mepiquat chloride), and trinexapac-ethyl (sold under tradenames Primo or Primo Maxx).

Any defoliating compound that is effective at defoliating a desired plant can be used. Specific embodiments of defoliating agents include paraquat, diquat, endothall, chlorates, ethephon, tributylyphosphorthoate, cacodylic acid and its sodium salt, MSMA, diuron, dimethipin, monocarbamide, carfentrazone, cyclanalide, and thidiazuron.

Herbicides

Any herbicide that causes the desired result can be used. Herbicides are generally broken down into broad categories, including pre-plant herbicides, burndown herbicides, and post-emergence herbicides. Those of skill in the art appreciate the appropriate use of such compounds.

There are several classes of post-emergent herbicides. These include: downwardly mobile herbicides, otherwise referred to as symplastically translocated, namely leaf to growing points such as auxin growth regulators, including phenoxy derivatives, benzoic acid derivatives, picolinic acid derivatives, amino acid inhibitors such as glyphosate, sulfosate, sulfonyl ureas, imidazolinones, sulfonanalides, pigment inhibitors, grass meristem destroyers, otherwise known as lipid biosynthesis inhibitors, such as aryloxyphenoxypropionates and cyclohexanediones, non-translocated or contact herbicides, including cell membrane destroyers, bipyridyliums, biphenyl ethers, or nitrophenyl ethers, upwardly mobile only herbicides, also known as apoplastically translocated, including photosynthetic inhibitors, such as triazines, uracils, phenylureas, or nitriles.

Examples of acid amide-based herbicides include Stam (3',4'-dichloropropionanilide, DCPA) and Alachlor (2-chloro-2',6'-diethyl-N-(methoxymethyl)-acetanilide). Examples of urea-based herbicides include DCMU (3-(3,4-dichlorophenyl)-1,1-dimethylurea) and rinuron (3-(3,4-dichlorophenyl)-1-methoxy-1-methylurea). Examples of sulfonyl urea-based herbicides include benzene sulfonamide (sold under the tradename penoxsulam), thifensulfuromethyl (methyl-3-(4-methoxy-6-methyl-1,3,5-triazin-2-ylcarbamoylsulfamoyl)-2-tanoate) and flazesulfuron (1-(4,6-dimethoxy pyrimidin-2-yl)-3-(3-trifluoromethyl-2-pyridylsulfonyl)urea). Examples of dipyridyl-based herbicides include paraquat dichloride (1,1'-dimethyl-4,4'-bipyridinium dichloride) and diquat dibromide (6,7-dihydrodipyride[1,2-a:2',1'c]-pyrazinediium dibromide). One example of a diazine-based herbicide includes bromacil (5-bromo-3-sec-butyl-6-methyluracil). Examples of S-triazine-based herbicides include gesatop (2-chloro-4,6-bis(ethylamino)-1,3,5-triazine) and simetryn (2,4-bis(ethylamino)-6-methylthio-1,3,5-triazine). An example of nitrile-based herbicides includes DBN (2,6-dichlorobenzonitrile). Examples of dinitroaniline-based herbicides include trifluralin (α,α,α-trifluoro-2,6-dinitro-N,N-dipropyl-p-toluidine). Examples of carbamate-based herbicides include thiobencarb (S-p-chlorobenzyl diethylthiocarbamate) and MCC (methyl-3,4-dichlorocarbenylate). NIP (2,4-dichlorophenyl-p-nitro-phenyl ether) is an example of diphenyl ether-based herbicides. PCP (sodium pentachlorophenoxide) is an example of a phenol-based herbicide. MDBA (3,6-dichloro-2-methoxybenzoic acid dimethylamine salt) is an example of a benzoic acid-based herbicide. Examples of phenoxy-based herbicides include 2,4-D sodium salt (sodium 2,4-dichlorophenoxyacetate), 2,4-D Esters, and mapica ([4-chloro-o-toluyl)oxy]aceto-o-chloroanilide. Examples of organic phosphorus-based herbicides include Glyphosate (N-(phosphonomethyl) glycinate, bialaphos (sodium salt of L-2-amino-4-[(hydroxy(methyl)phosphinoyl]-butylyl-alanyl-N-alanine), and glufosinate (ammonium DL-homoalanin-4-yl (methyl)phosphinate). TCA sodium salt (sodium trichloronate) is an example of an aliphatic group-based herbicides. Hydrogen peroxide is another herbicide.

In one embodiment, the herbicide used as the pesticide in the composition of the present invention is a dipyridyl-based herbicide or an organic phosphorus-based herbicides. In a further embodiment, the herbicide is an organic phosphorus-based herbicides. In a still further embodiment, the herbicide is bialaphos, glufosinate, or glyphosate.

Acaricides

Any suitable acaracide can be used. Examples of suitable acaricides include sumiito (2-tert-butyl-5-(4-tert-butylbenzylthio)-4-chloropyridazine-3-(2H)-one), acricid (2,4-dinitro-6-sec-butylphenyldimethylacrylate), chloromite (isopropyl 4,4-dichlorobenzylate), Akar (ethyl 4,4'-dichlorobenzilate), kelthane (2,2,2trichloro-1,1-bis(p-chlorophenyl)-ethanol), citrazon (benzoic 3-chloro-N-ethoxy-2,6-dimethoxybenzimidic anhydride), omite (2-(p-tert-butylphenoxy)cyclohexyl propyn-2-yl sulfite), osadan (bis[tris(2-methyl-2-phenylpropyl)tin]oxide), hexythiazox (trans-5-(4-chlorophenyl)-N-cyclohexyl-4-methyl-2-oxothiazol-idine-3-carboxamide), and amitraz (N,N-bis(2,4-xylyliminomethyl)methylamine).

Disinfectants and Antibacterial Agents

Any suitable disinfectant or antibacterial agent can be used. Examples of suitable disinfectants/antibacterial agents include quaternary ammonium salts, captan alcohols, essential oils organic acids, triazines phenols, iodine, halo and nitro phenols, isothiozolones, terpenes, acridines, esters of para-hydroxybenzoic acid, aldehydes, aromatic diamidines, biguanidines, anionic surfactants, nonionic surfactants, betaines, quinones, quinolines, derivatives of 1,3 dioxane, derivatives of imidazole, and derivatives of hexamine.

II. Adjuvants

Adjuvants useful in the present invention typically fall into the general classifications shown below in Table 2. Table 3 sets forth examples of various active ingredients (AI's) and their respective ranges along with those of the adjuvants and the ratios of AI/adjuvant that were tested.

TABLE 2

| Classification | Representative Compounds |
|---|---|
| Dibasic esters such as Sebacates | Compound A, which may also be referred to as bis (1,2,2,6,6-pentamethyl-4-piperidinyl) sebacate and methyl (1,2,2,6,6-pentamethyl-4-piperidinyl) sebacate |
| | sebacic acid dibenzyl ester |
| | Other sebecate esters known as hindered amine light stabilizers |
| | Bis-benzyl esters of carboxylic acids |
| | Bis-monosubstituted benzyl esters of dicarboxylic acids |
| | Bis-disubstituted benzyl esters of dicarboxylic acids |
| | Bis-allyl esters of dicarboxylic acids |
| | Bis-monosubstituted allyl esters of dicarboxylic acids |
| | Bis-disubstituted allyl esters of dicarboxylic acids |
| | Dibenzyl carbonate |
| | Bis-monosubstituted benzyl carbonates |
| | Bis-disubstituted benzyl carbonates |
| | Diallyl carbonate |
| | Bis-monosubstituted allyl carbonates |
| | Bis-disubstituted allyl carboantes |
| Polyphenyl methanes | diphenyl methane |
| | triphenyl methane (Gomberg's trityl) |
| | triphenyl methyl chloride (tritylchloride) |
| Food grade preservatives | BHA, butylated hydroxyanisole |
| | BHT, butylated hydroxytoluene |
| | BHQ, butylated hydroxyquinone |
| | TBHQ, tertiary butyl dihydroxyquinone |
| | Propyl gallate |
| Esters | Methyl oleate |
| | Methyl linoleate |
| | Methyl palmitate |
| | Ethyl oleate |
| | Dibenzyl maleate |
| | Methyl, ethyl, allyl, and benzyl esters of linoleic acid |
| | Gamma-linolenic acid |
| Antioxidants/vitamins | Ascorbic acid |
| | Retinol |
| | Vitamin A |

TABLE 2-continued

| Classification | Representative Compounds |
|---|---|
| | Vitamin C |
| | Vitamin E |
| | Beta Carotene |
| | Glutathione |
| | Melatonion |
| | Ubiquinones |
| | Uric Acid |
| | Flavenoids (e.g., leucocyanidin, catechin, epicatechin, kaempferol, rutin, quercitin) |
| Acids | benzenepropanoic acid |
| | Oleic |
| | Linoleic |
| | Palmitic |
| | Cinnamic Acid |
| | Alpha linolenic acid |
| | Gamma-linolenic acid |
| Omega 3 acids | EPA |
| | DHA |
| | All-cis-7,10,13-hexadecatrienoic acid |
| | ALA |
| | STD |
| | ETE |
| | ETA |
| | DPA |
| Additional Free Radical Stabilizers | Ibuprofen |
| | Acetyl salicylic acid |
| | Salicylic acid |
| | Methyl salicylate |
| | Tetramethylsilane |
| | Trimethylsilane |
| | N,N'-di-2-butyl-1,4-phenylenediamine |
| | 2,5-di-tert-butyl hydroquinine |
| | 2,4dimethyl-6-tert-butyl phenol |
| | Carprofen |
| | Naproxen |
| | Ketoprofen |
| | Allyl benzyl ether |
| | 2,4,6-Trihydroxyacetophenone |
| | 2,4,6-Trihydroxybenzaldehyde |
| | 3,4,5-Trihydroxy benzamide |
| | Resveratrol |
| | Benzotriazole |
| Surfactants | Miranol types |
| | Mirataine types |

Surprisingly, in some embodiments, the activity of the compositions of the present invention considerably exceeds the additive activity of the individual components, namely there is synergism.

TABLE 3

| Insecticide Class | AI Examples | AI amount | Adjuvant | Adjuvant amount | AI/Adj Ratio |
|---|---|---|---|---|---|
| pyrethrums | pyrethrins | 0.003 g/m² | sebacates | 0.005-0.512 g/m² | 1:1.7-1:167 |
| | | 0.006 g/m² | | 0.006-0.512 g/m² | 1:1-1:83 |
| | | 0.012 g/m² | | 0.512 g/m² | 1:42 |
| | | 0.003 g/m² | acids | 0.051-0.512 g/m² | 1:17-1:167 |
| pyrethroids | deltamethrin | 0.00032% | sebacates | 1.00% | 1:3125 |
| | | 0.0006 g/m² | | 0.62 g/m² | 1:1000 |
| | | 0.012 g/m² | | | 1:52 |
| | | 0.48 g/m² | | 0.48 g/m² | 1:1 |
| | | 0.62 g/m² | | 0.62 g/m² | 1:1 |
| | permethrin | 0.24 g/m² | sebacates | 0.48 g/m² | 1:2 |
| | | 0.31 g/m² | | 0.62 g/m² | 1:2 |
| | | 0.48 g/m² | | 0.48 g/m² | 1:1 |
| | | 0.60 g/m² | | | 1.2:1 |
| | resmethrin | 0.31 g/m² | sebacates | 0.62 g/m² | 1:2 |
| | | 0.62 g/m² | | | 1:1 |
| chloronicotinyls | imidacloprid | 0.31 g/m² | acids | 0.06-3.11 g/m² | 5:1-1:10 |
| | | | esters | 0.06-3.11 g/m² | 5:1-1:10 |
| | | | preservatives | 0.06-3.11 g/m² | 5:1-1:10 |
| | | | polyphenyl | 0.06-3.11 g/m² | 5:1-1:2 |

TABLE 3-continued

| Insecticide Class | AI Examples | AI amount | Adjuvant | Adjuvant amount | AI/Adj Ratio |
|---|---|---|---|---|---|
| | | | methanes | | |
| | | 0.006 g/m$^2$ | sebacates | 3.75 g/m$^2$ | 1:625 |
| | | 0.062-0.62 g/m$^2$ | | 0.06-3.11 g/m$^2$ | 5:1-1:10 |
| | | 0.002 g/m$^2$ | sebacates | 0.022 g/m$^2$ | 10:1 |
| | | | | 0.004 g/m$^2$ | 5:1 |
| | | | | 0.011 g/m$^2$ | 2:1 |
| | thiamethoxam | 0.006 g/m$^2$ | sebacates | 0.62 g/m$^2$ | 1:100 |
| | | 0.062 g/m$^2$ | | | 1:10 |
| | | 0.62 g/m$^2$ | | | 1:1 |
| | clothianidin | 0.062 g/m$^2$ | sebacates | 0.62 g/m$^2$ | 1:10 |
| | | 0.31 g/m$^2$ | | | 1:2 |
| | | 0.62 g/m$^2$ | | | 1:1 |
| pyrazoles | fipronil | 0.00006 g/m$^2$ | sebacates | 0.0062-0.62 g/m$^2$ | 1:100-1:10000 |
| | | 0.00062 g/m$^2$ | | | 1:10-1:1000 |
| | | 0.0062 g/m$^2$ | | | 1:1-1:100 |
| | ethiprole | 0.0062 g/m$^2$ | sebacates | 0.0062-0.62 g/m$^2$ | 1:1-1:100 |
| | | 0.062 g/m$^2$ | | | 1:10 |
| | | 0.62 g/m$^2$ | | | 1:1 |
| carbamates | bendiocarb | 0.0512 g/m$^2$ | acids esters preservatives sebacates | 0.512 g/m$^2$ | 1:10 |
| | | 0.0006/0.062 g/m$^2$ | sebacates | 0.62 g/m$^2$ | 1:10-1:1000 |
| | carbaryl | 0.0062-0.062 g/m$^2$ | sebacates | 0.62 g/m$^2$ | 1:10-1:100 |
| Botanical oils | Rosemary + peppermint oils | 0.007-0.75 g/m$^2$ | sebacates | 0.006-0.62 g/m$^2$ | 1:1 |
| | peanut oil | 0.062 g/m$^2$ | | 0.62 g/m$^2$ | 1:10 |

In one embodiment, the activity of the composition of the present invention provides a hastened effect compared to the pesticide, alone.

In one embodiment, the compositions allows for a lesser amount of pesticide needed to result in an equivalent effect. As will be demonstrated herein, the amount of adjuvant is an amount effective to decrease the amount of active ingredient required to achieve a comparable kill rate by at least around 10%, at least around 20%, or at least around 30% or more.

In still another embodiment, the residual activity of the composition of the present invention exceeds the total of the residual activity of the individual components.

As discussed herein, the pesticide component may also comprise one or more fungicidally, acaricidally, or insecticidally active components, which also may be admixed.

The weight ratios of the components of the composition may be varied within a relatively wide range.

In general, the combinations according to the invention include a pesticide and an adjuvant, wherein the composition provides a synergistic kill rate. In one embodiment, the pesticide is present in a parts ratio as compared to adjuvant in an amount of about 0.01 part of pesticide to up to about 100 parts of adjuvant. In another embodiment, the pesticide is an insecticide and is present in a parts ratio compared to adjuvant in an amount of about 0.01 parts insecticide to up to 100 parts of adjuvant. Without implicit limitation, specific embodiments include 0.01:1, 0.1:1, 1:1, 1:5, 1:10, 1:20, 1:50, and 1:100.

The formulations generally comprise between about 0.001% and about 80% by weight of a pesticide component and between about 0.00005% and about 80% by weight of an adjuvant component; and more specifically between about 0.01% and about 70% by weight of the pesticide component and between about 0.0005% and about 70% by weight of the adjuvant component. Furthermore, certain embodiments comprise between about 0.05% and about 60% of the pesticide component and between about 0.0025% and about 60% of the adjuvant component. Still further, certain embodiments comprise between about 0.1% and about 50% of the pesticide component and between about 0.005% and about 50% of the adjuvant component.

Thus, active ingredients may be used in varying amounts, including as little as about 0.001%. As hereinabove described, the ratio of pesticide:adjuvant provides a synergistic kill rate and will vary from about 0.01:1 to about 1:100.

III. Other Formulation Components

The formulations can also include additional components.

The compositions of the present invention can be formulated as solutions, emulsions, wettable powders, suspensions, powders, dusts, pastes, soluble powders, granules, suspension-emulsion concentrates, natural and synthetic materials impregnated with pesticide, and microencapsulations in polymeric materials.

These formulations are produced using known techniques in the art. One example includes mixing the components with extenders, that is, liquid solvents and/or solid carriers, optionally with the use of surfactants, that is, emulsifiers and/or dispersants, and/or foam formers. If the extender used is water, it is also possible, for example, to use organic solvents as cosolvents. The following are examples of liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethyl-formamide and dimethyl sulphoxide, or else water.

Solid carriers include, for example, ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

The compositions may include one or more colorants, such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The compositions may be composed of mixtures of pesticides, such as insecticides, attractants, sterilants, bactericides, acaricides, nematicides, fungicides, growth-regulating substances, or herbicides. The insecticides include, for example, phosphates, carbamates, carboxylates, chlorinated hydrocarbons, phenylureas and substances produced by microorganisms. Mixtures with other known active compounds such as herbicides or with fertilizers and growth regulators are also possible.

A suitable solvent or diluent is an organochemical solvent or solvent mixture or an oily or oil-type organochemical solvent or solvent mixture of low volatility or a polar organochemical solvent or solvent mixture or water and, if appropriate, an emulsifier or wetter.

Organochemical solvents which are preferably employed are oily or oil-type solvents with an evaporation number of above 35 and a flash point of above 30° C., preferably above 45° C. Such oily and oil-type solvents which are in soluble in water and of low volatility and which are used are suitable mineral oils or their aromatic fractions or mineral-oil-containing solvent mixtures, preferably white spirit, petroleum and/or alkylbenzene. Representative solvents include acetone, chloroform, ethanol, ethyl acetate, n-hexane, methanol, methylene chloride, toluene, and xylene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of terpentine, and the like are advantageously used.

In one embodiment, the solvent may be a liquid aliphatic hydrocarbons with a boiling range of about 180° C. to about 210° C., high-boiling mixtures of aromatic and aliphatic hydrocarbons with a boiling range of about 180° C. to about 220° C., spindle oil, or monochloronaphthalene, such as α-monochloronaphthalene.

The organic oily or oil-type solvents of low volatility and with an evaporation number of above 35 and a flash point of above 30° C., prefer ably above 45° C., can be replaced in part by organochemical solvents of high or medium volatility, provided that the solvent mixture also has an evaporation number of above 35 and a flash point of above 30° C., preferably above 45° C., and that the mixture is soluble or emulsifiable in this solvent mixture.

In one embodiment, some of the organochemical solvent or solvent mixture is replaced by an aliphatic polar organochemical solvent or solvent mixture. Aliphatic organochemical solvents which contain hydroxyl or ester or ether groups may be used, such as, for example, glycol ethers, esters, or the like.

Organochemical binders used for the purposes of the present invention are the synthetic resins or binding drying oils which are known in the art and which can be diluted in water or dissolved or dispersed or emulsified in the organochemical solvents employed, in particular binders comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable or drying oils or physically drying binders based on a natural or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil.

Some or all of the abovementioned binder can be replaced by a fixative (mixture) or plasticizer (mixture). These additives are intended to prevent volatilization of the active compounds, and also crystallization or precipitation.

The plasticizers, for use as a plasticizer and not as an adjuvant as herein described, are from the chemical classes of the phthalic esters, such as dibutyl phthalate, dioctyl phthalate or benzyl butyl phthalate, phosphoric esters such as tributyl phosphate, adipic esters such as di-(2-ethylhexyl)-adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

In addition to the pesticides, other agents can benefit from the enhanced penetration into the plant or insect cuticle. Examples include transfection agents and DNA desired to be transfected into the plant, wood treatment chemicals, and disinfectants and antibacterial agents.

There are numerous known transfection agents, any of which can be used in the compositions described herein. The transfection agents are used in combination with genetic material to be transfected into a cell, and optionally, an appropriate vector, for example, an adenoviral vector. The genetic material can be any genetic material capable of effecting a desired alteration in the plant genetic code, and can be in the form of a plasmid. The genetic material is preferably DNA.

Any wood treatment chemical capable of inhibiting destruction of wood by termites, fungus, mold and the like can be used. Examples of suitable wood treatment chemicals include CCA, polyethylene glycol, fungicides, termiticides, and known fungicides.

The compositions of the present invention may include one or more attractant. Attractants are inert ingredients that entice a pest, such as an insect to approach the bait, to touch the bait, to consume the bait, and/or to return to the bait. Inert ingredients that are able to achieve these goals belong to the group of food attractants and non-food attractants.

The following may be mentioned by way of example as food attractants: water, cereal powders such as wheat powder, maize powder, malts, powder, rice powder, rice bran and the like, starches such as potato starch, maize starch, and the like, sugars such as sucrose, maltose, arabinose, galactose, lactose, sorbitose, glucose, fructose, sorbitol, corn syrup, maple syrup, coca cola syrup, invert sugars (Invertix), molasses, honey and the like, and glycerol and the like. Proteins such as meat, meat extracts, meat flavours and milk powder, fish meal, fish extracts or fish flavour, sea food, sea food extracts or sea food flavour, yeast, yeast extract and yeast, flavour and the like. Fruits such as apple, apricot, banana, blackberry, cherry, currant, gooseberry, grapefruit, raspberry, strawberry (pure, syrup or extract). Fats and oils such as vegetable oils from e.g. corn, olive, caraway, peanut, sesame oil, soy bean, sunflower, animal derived fats and fish derived oils and the like. These baiting substances can be used alone or as a mixture of two or more in any ratio.

The following may be mentioned by way of example as non-food attractants: alcohols such as benzyl alcohol, butanol, decanol, ethanol, glycerin, hexanol and isobutanol; pheromones such as (Z)-9-Tricosene (also known as muscalure), a product referred to under the trade name LEJ 179, which is a mixture of n-butyric acid, muscalure, and at least one fatty acid component. Attractants which further may be mentioned by way of example are fatty acids such as caprylic acid, caproic acid, capric acid, lauric acid, oleic acid and the like, higher alcohols such as octyl alcohol, dodecyl alcohol, oleyl alcohol and the like, and natural and artificial flavours such as onion flavour, milk flavour, butter flavour, cheese flavour, and the like. These attractants can be used alone or as a mixture of two or more in any ratio. Preferred non-food attractants are alcohol, pheromones, and flavours.

IV. Pests that can be Treated

The compositions of the present invention are suitable for controlling pests, preferably arthropods, nematodes, and arachnids, in particular insects and arachnids found in agriculture, in animal health, in forests, in the protection of stored products, in homes and businesses, in materials, and in the hygiene sector.

The compositions of the present invention are believed to be active against normally sensitive and resistant species, and against all or individual developmental stages. The present invention is useful against the following pests: from the order of the Isopoda, for example, *Oniscus asellus, Armadillidium vulgare, Porcellio scaber;* from the order of the Diplopoda, for example, *Blaniulus guttulatus;* from the order of the Chilopoda, for example, *Geophilus carpophagus, Scutigera* spp.; from the order of the Symphyla, for example, *Scutigerella immaculate;* from the order of the Thysanura, for example, *Lepisma saccharina;* from the order of the Collembola, for example, *Onychiurus armatus;* from the order of the Orthoptera, for example, *Acheta domesticus, Gryllotalpa* spp., *Locusta migratoria migratorioides, Melanoplus* spp., *Schistocerca gregaria;* from the order of the Blattaria, for example, *Blatta orientalis, Periplaneta americana, Leucophaea maderae, Blattella germanica;* from the order of the Dernaptera, for example, *Forficula auricularia;* from the order of the Isoptera, for example, *Reticulitermes* spp.; from the order of the Phthiraptera, for example, *Pediculus humanus corporis, Haematopinus* spp., *Linognathus* spp., *Trichodectes* spp., *Damalinia* spp.; from the order of the Thysanoptera, for example, *Hercinothrips femoralis, Thrips tabaci, Thrips palmi, Frankliniella occidentalis;* from the order of the Heteroptera, for example, *Eurygaster* spp., *Dysdercus intermedius, Piesma quadrata, Cimex lectularius, Rhodnius prolixus, Triatoma* spp.; from the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.; from the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp.; *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dernestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus;* from the order of the Hymenoptera, for example, *Diprion* spp., *Hoplocampa* spp., *Lasius* spp., *Monomorium pharaonis, Vespa* spp.; from the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.; from the order of the Siphonaptera, for example, *Xenopsylla cheopis, Ceratophyllus* spp.; and from the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

Plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

When treating a building for pest infestation, particularly by treating non-porous surfaces within or around the building, representative pests include: from the order of the Scorpionidea, for example, *Buthus occitanus.* From the order of the Acarina, for example, *Argas persicus, Argas reflexus,*

*Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae;* from the order of the Araneae, for example, Avicullariidae; Araneidae; from the order of the Opiliones, for example, *Pseudoscorpiones chelifer, Pseudoscorpiones cheiridium, Opiliones phalangium;* from the order of the Isopoda, for example, *Oniscus asellus, Porcellio scaber;* from the order of the Diplopoda, for example, *Blaniulus guttulatus, Polydesmus* spp. From the order of the Chilopoda, for example, *Geophilus* spp.; from the order of the Zygentoma, for example, *Ctenolepisma* spp., *Lepisma saccharina, Lepismodes inquilinus;* from the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.* From the order of the Saltatoria, for example, *Acheta domesticus;* from the order of the Dermaptera, for example, *Forficula auricularia;* from the order of the Isoptera, for example, *Kalotermes* spp., *Reticulitermes* spp.; from the order of the Psocoptera, for example, *Lepinatus* spp., *Liposcelis* spp.; from the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum;* from the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa;* from the order of the Lepidoptera, for example, *Achroia grisella, Galleria mellonella, Plodia interpunctella, Tinea cloacella, Tinea pellionella, Tineola bisselliella;* from the order of the Siphonaptera, for example, *Ctenocephalides canis, Ctenocephalides fells, Pulex irritans, Tunga penetrans, Xenopsylla cheopis;* from the order of the Hymenoptera, for example, *Camponotus herculeanus, Lasius fuliginosus, Lasius niger, Lasius umbratus, Monomorium pharaonis, Paravespula* spp., *Tetramorium caespitum;* from the order of the Anoplura, for example, *Pediculus humanus capitis, Pediculus humanus corporis, Phthirus pubis;* and from the order of the Heteroptera, for example, *Cimex hemipterus, Cimex lectularius, Rhodinus prolixus, Triatoma infestans.*

The compositions described herein are not only active against plant pests, hygiene pests, stored-product pests, and household pests, but also, in the veterinary medicine sector, against animal parasites, including ectoparasites, such as hard ticks, soft ticks, mange mites, harvest mites, flies, including stinging and licking, parasitizing fly larvae, lice, hair lice, bird lice, and fleas. These parasites include: from the order of the Anoplurida, for example, *Haematopinus* spp., *Linognathus* spp., *Pediculus* spp., *Phtirus* spp., *Solenopotes* spp.; from the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.; from the order of the Siphonapterida, for example, *Pulex* spp., *Ctenocephalides* spp., *Xenopsylla* spp., *Ceratophyllus* spp.; from the order of the Heteropterida, for example, *Cimex* spp., *Triatoma* spp., *Rhodnius* spp., *Panstrongylus* spp.; from the order of the Blattarida, for example, *Blatta orientalis, Periplaneta americana, Blattela germanica, Supella* spp.; from the subclass of the Acaria (Acarida) and the order of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.; and from the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The compositions described herein are also suitable for controlling arthropods which attack agricultural livestock such as, for example, cattle, sheep, goats, horses, pigs, donkeys, camels, buffaloes, rabbits, chickens, turkeys, ducks, geese, honeybees, other domestic animals such as, for example, dogs, cats, birds, fish, hamsters, guinea pigs, rats, and mice. By controlling these arthropods, cases of death and reductions in productivity, including for meat, milk, wool, hides, eggs, honey, and the like, could be diminished, so that more economical and simpler animal husbandry is possible by the use of the active compound combinations according to the invention.

When used for cattle, poultry, domestic animals and the like, the active compound combinations can be applied as formulations (for example powders, emulsions, flowables) comprising the active compounds, either directly or after dilution, or they may be used as a chemical dip.

Moreover, the compositions described herein show a potent insecticidal action against insects which destroy industrial materials. The following insects may be mentioned by way of example and with preference, but not by way of limitation: Beetles such as *Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus;* Dermapterans such as *Sirex juvencus, Urocerus gigas, Urocerus gigas taignus, Urocerus augur;* Termites such as *Kalotermes flavicollis, Cryptoternes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* and Bristle-tails such as *Lepisma saccharine.* Particularly, representative insects to be combated or controlled by the compositions described herein include Order Isoptera, Mastotermitidae, Kalotermitidae such as *Kalotermes* spp., *Cryptotermes* spp. etc., Termopsidae such as *Zootermopsis* spp. etc., Rhinotermitidae such as *Reticulitermes* spp. *Heterotermes* spp., *Coptotermes* spp. etc., Termitidae such as *Amitermes* spp., *Nasutitermes* spp., *Acanthotermes* spp., *Mikrotermes* spp. etc., Order Coleoptera, Lyctidae such as *Lyctus brunneus* etc., Bostrychidae such as *Bostrychus capucinus, Dinoderus minutus* etc., Anobiidae such as *Anobium punctatum, Xyletinus peltatus, Xestobium rufovillosum, Ptilinus pectinicomis* etc., Cerambycidae such as *Hylotrupes bajulus, Hesperophanus cinereus, Stromatium fulvum, Chlorophorus pilosus* etc., Oedemeridae, Serropulpidae, Curculionidae, Seolytida, Platypodidae, Order Hymenoptera, Siricidae such as *Sirex* spp., *Urocerus* spp., or Formicidae such as *Camponotus* spp.

In the above Isopterous insects, especially, there may be mentioned as examples of termites in Japan: *Deucotermes speratus, Coptotermes formosanus, Glyptotermes fucus, Glyptotermes satsumensis, Glyptotermes nakajimai, Glyptotermes Kodamai, Incisitermes minor, Neotermes koshunensis, Cryptotermes domesticus, Hodotermopsis japonica, Reticulitermes miyatakei, Odontotermes formosanus, Nasutitermes takasagoensis, Capritermes nitobei*, and the like.

V. Application of Pesticide/Adjuvant Combinations

The combinations of pesticides and adjuvants described herein can be administered in a similar manner to how pesticides are commonly administered, to plants, to locations where insects are likely to be found, and in aerosol applications.

As one example, traps are well known in the art for controlling pest populations. They typically include a chemical that attracts a desired insect, for example, a pheremone or other insect attractant, and also typically include an pesticide. Traps are well known for use in controlling populations of burrowing insects, flying insects, or crawling insects, for example, roaches, ants, Japanese beetles, termites, mosquitoes, and many other insects. The traps may further include a permeabilizer to enhance the ability of the insecticide to control the insects.

VI. Use of the Compositions to Treat a Crop Locus

According to the invention, it is possible to treat all plants and parts of plants. Plants are to be understood here as meaning all plants and plant populations such as desired and undesired wild plants or crop plants, including naturally occurring crop plants. Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The compositions can be used as aerosols, pressureless spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The plants and parts of plants can be treated with the compositions directly or by action on their environment, habitat or storage area according to customary treatment methods, for example by dipping, spraying, evaporating, atomizing, broadcasting, brushing-on and, immersion, spraying, evaporation, fogging, scattering, painting on and, in the case of propagation material, in particular in the case of seeds, furthermore by one- or multi-layer coating. A particularly preferred method of application is to apply the compositions to the roots, either directly or though administration to the soil. In this manner, uptake of the active agricultural chemicals is significantly faster than if no free radical stabilizers and/or plasticizers are used.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants, and plant cultivars obtained by genetic engineering, if appropriate in combination with conventional methods, and parts thereof are treated.

The treatment results in synergistic effects: namely one or more of (i) enabling one to use reduced application rates; (ii) widening of the activity spectrum; (iii) an increase in the activity of the substances and compositions which can be used; (iv) better plant growth; (v) increased tolerance to high or low temperatures; (vi) increased tolerance to drought or to water or soil salt content; (vii) increased flowering performance; (viii) easier harvesting; (ix) accelerated maturation; (x) higher harvest yields; (xi) better quality; (xii) higher nutritional value of the harvested products; (xiii) better storage stability; and (xiv) better processability of the harvested products. Also, the active compounds in the compositions can show increased residual activity.

Exemplary crop plants include cereals (wheat, rice), maize, soya beans, potatoes, cotton, tobacco, oilseed rape, and also fruit plants (apples, pears, citrus fruits, and grapes), and particular emphasis is given to maize, soya beans, potatoes, cotton, tobacco, and oilseed rape.

VII. Use of the Compositions for Pest Infestation

The active compound combinations are also suitable for controlling pests, in particular insects, arachnids and mites, which are found in enclosed spaces such as, for example, dwellings, factory halls, offices, vehicle cabins, and the like. They can be employed in domestic insecticide products for controlling these pests. They are active against sensitive and resistant species and against all developmental stages.

The compositions can be used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

Ideally, the compositions are applied to non-porous surfaces, so that the active compounds remain present at the surface. The compositions are extremely effective against insects that drag portions of their bodies along a surface, in particular, crawling insects.

In one embodiment, the compositions are applied to non-porous tile (i.e., glazed tile). As shown in various working examples below, the compositions typically show enhanced efficacy when applied to glazed versus unglazed tiles.

The compositions can also be used in spray applications, or applied to screens or other places where flying insects are prone to land, in order to provide effective control of flying insects. The components of a conventional aerosol spray formulation can be used with the combinations of active agents and adjuvants described herein.

The material which is to be protected from insect attack is very especially preferably wood and timber products. Wood and timber products which can be protected by the composition according to the invention, or mixtures comprising it, are to be understood as meaning, for example: Construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes. The compound combinations can be applied to the materials by spraying, dipping, or other means.

The above-mentioned formulations can be prepared in a manner known to those of skill in the art, for example, by mixing a pesticide with an effective amount of an adjuvant, along with at least one solvent or diluent, emulsifier, dispersant, binder, or fixative, water repellant, if desired, desiccants, and, if desired colorants and pigments and other processing auxiliaries.

Particularly effective timber protection is achieved by industrial-scale impregnating processes, for example the vacuum, double-vacuum or pressure processes.

In one embodiment, the invention relates to the use of combinations of pesticidal compounds and adjuvants to combat insects, for example, termites, that are known to destroy technical materials, such as wood. In some embodiments, depending on the pesticidal compounds, or the addition of other compounds, the technical materials can be protected not only against insects, but also against fungi, bacteria, and algae. In some embodiments, the compositions are also useful for treating soil to protect technical materials against termite infestations.

Different pests are known to infest technical materials, so that due to serious damage is caused. This produces undesirable effects on the living environment and cultural assets principally made of these materials have posed a social problem, urgently requiring effective controlling of the pests. Termites are known as important examples of these pests.

The active compounds can be prepared into the customary formulations, such as solutions, emulsions, suspensions, powders, foams, pastes, granules, aerosols, natural and synthetic materials impregnated with active compounds, and micro-capsules.

These formulations may be produced in a known manner, for example, by mixing the active compounds with extenders, that is to say liquid or liquefied gaseous or solid diluents or carriers, optionally with the use of surface-active agents, that is to say emulsifying agents, dispersing agents, and/or foam-forming agents. In the case of using water as an extender, organic solvents can, for example, also be used as auxiliary solvents.

As liquid diluents or carriers can be mentioned, for example, aromatic hydrocarbons, such as xylene, toluene and alkyl naphthalenes, chlorinated aromatic or chlorinated aliphatic hydrocarbons, such as chlorobenzenes, chloroethylenes and methylene chloride, aliphatic or alicyclic hydrocarbons, such as cyclohexane or paraffins, for example, mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulfoxide, as well as water.

By liquefied gaseous diluents or carriers are meant liquids which are gaseous at normal temperature and under normal pressure, for example, aerosol propellants, such as halogenated hydrocarbons as well as butane, propane, nitrogen and carbon dioxide.

As solid diluents there may be used ground natural minerals, such as kaolins, clays, talc, chalk, quartz, attapulgite, montmorillonite or diatomaceus earth, and ground synthetic minerals, such as highly-dispersed silicic acid, alumina and silicates.

As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used nonionic and ionic emulsifiers, such as polyoxyethylene-fatty acid esters, polyoxyethylene-fatty alcohol ethers, for example, alkylaryl polyglycol ethers, alkylsulfonates, alkylsulfates, arylsulfonates as well as albumin hydrolysis products. Dispersing agents include, for example, lignin sulfite waste liquors and methyl cellulose.

Adhesives such as carboxymethyl cellulose and natural and synthetic polymers, (such as gum arabic, polyvinyl alcohol and polyvinyl acetate) can be used in the formulations in the form of powders, granules or emulsifiable concentrations.

It is possible to use colorants such as inorganic pigments, for example, iron oxide, titanium oxide and Prussian Blue, and organic dyestuffs, such as alizarin dyestuffs, azo dyestuffs or metal phthalo-cyanine dyestuffs, and trace elements, such as salts of iron, manganese, boron, copper, cobalt, molybdenum and zinc.

In order to protect the above-mentioned materials against fungi, bacteria and algae, they can be treated with compositions may further contain at least one biological active fungicide, bactericide, or algizide.

Exemplary fungicides include compounds and biological substances, including trihalosulfenyl-Compounds such as N-dichlorofluoromethylthio-N',N'-dimethyl-N-phenyl-sulfuric acid diamide (Dichlofluanide), N-dichlorofluoromethylthio-N',N'-dimethyl-N-p-toluylsulphamide (Tolylfluanide), N-trichloromethylthiophthalimide (Folpet), N-dichlorofluoromethylthiophthalimide (Fluorfolpet), and the like, iodine-compounds such as 3-iodo-2-propynyl-butyl-carbamate (IPBC), 3-iodo-2-propynyl-hexylcarbamate, 3-iodo-2-propynyl-cyclohexylcarbamate, 3-iodo-2-propynyl-phenylcarbamate, diiodmethyl-p-tolylsulphone (Amical 48), and the like, phenols such as ortho-phenylphenol, tribromophenol, tetrachlorophenol, pentachlorophenol, and the like, azole-compounds such as 1-(4-chlorophenoxy)-3,3-dimethyl-1-(1H-1,2,4 triazol-1-yl)-2-butanone (Triadimefon), beta-(4-chlorophenoxy)-alpha-(1,1 dimethyl-ethyl)-1H-1,2,4 triazole-1-ethanol (Triadimenol), +/−alpha[2-(4-chlorophenyl)ethyl]-alpha-(1,1-dimethylethyl)-1H-1,2,4-triazole-1-ethanol (Tebuconazole), 1-[2(2,4-dichlorophenyl) 4-propyl-1,3-dioxolan-2-ylmethyl]-1H-1,2,4-triazole (Propiconazol), 1-[2(2,4-dichlorophenyl)-1,3-dioxolan-2-yl-methyl]-1H-1,2,4-triazole (Azaconazol), (RS)-2(2,4-dichlorophenyl)-1-(1H-1,2,4 triazol-2-yl)-2-ol (Hexaconazol), 1-N-propyl-N-[2-(2,4,6-trichlorophenoxy)ethyl]carbamoylimidazol (Prochloraz), and the like, tin compounds such as tributyl tin octoate, tributyl tin oleate, bistributyl tin oxide, tributyl tin naphthenate, tributyl tin phosphate, tributyl tin benzoate, and the like, thiocyanate Compounds such as methylenebisthiocyanate (MBT), 2-thiocyanomethylthiobenzothiazole (TCMTB), and the like, quarternary ammonium compounds such as benzyl-dimethyl-tetradecylammoniumchloride, benzyl-dimethyl-dodecylammoniumchloride, and the like; Benzimidazole compounds such as 2-(2'-Furyl)-1H-benzimidazole (Fuberidazole), Methylbenzimidazol-2-yl-carbamate (BCM), 2-(41-thiazolyl)benzimidazole (Thiabendazole), Methyl(1-butylcarbamoyl)-2-benzimidazole carbamate (Benomyl), Isothiazolinone compounds such as N-Methylisothiazolin-3-one, 5-Chloro-N-methylisothiazolin-3-one, 4,5-Dichloro-N-octylisothiazolin-3-one, N-Octyl-isothiazolin-3-one, Morpholine compounds such as C14-C11-4-Alkyl-2,6-dimethylmorpholine (Tridemorph), Pyridine compounds such as 1-Hydroxy-2-pyridine-thione and Sodium Iron, Manganese or Zinc-Salt thereof, Tetrachloro-4-methyl sulphonyl pyridine, N-Cyclohexyldiaziniumdioxy compounds such as Tris-(N-cyclohexyldiaziniumdioxy)aluminium, Bis-(N-cyclohexyldiaziniumdioxy) copper, Naphthenate compounds such as zinc naphthenate, Quinoline compounds such as the copper salt of 8-hydroxyquinoline, Nitriles such as 1,2,3,5-Tetrachloro-4,6-cyanobenzene, Boric compounds such as boric acid, borax, borates, Ureas such as N'(3,4-dichlorophenyl)-N,N-dimethylurea, Furane derivatives such as Furmecyclox.

These fungicidally-effective substances are added to the composition to protect against wood-discoloring fungi such as Ascomycetes (*Caratocystis minor*), Deuteromycetes (*As-*

*pergillus niger, Aureobasidium pullulans, Dactyleum fusarioides, Penicillium Variabile, Sclerophoma pithyophila, Scopularia phycomyces, Trichoderma viride, Trichoderma liguorum*), Zygomycetes (*Mucor spinosus*), and/or wood-destroying fungi such as Ascomycets (*Chetomium albaarenulum, Chaetonium globosum, Humicola grisea, Petriella setifera, Trichurus spiralis*), Basidiomycetes (*Coniophera puteana, Coriolus versicolor, Donbiopora expansa, Glenospora graphii, Gloeophyllum abietinum, Gloeophyllum adoratum, Gloeophyllum protactum, Gloeophyllum trabeum, Gloeophyllum sepiarium, Lentinus cyathioformes, Lentinus edodes, Lentinus lepideus, Lentinus squavrolosus, Paxillus panuoides, Pleurofus ostreatus, Poria placenta, Poria monticola, Poria vaillantii, Poria vaporia, Serpula himantoides, Serpula lacrymans, Tyromyces palustris*), and Deuteromycetes (*Cladosporium herbarum*).

Generally the compositions also will include at least one additional diluent, emulsifier, melting agent, organic binding agent, auxiliary solvents, processing additives, fixatives, plasticizers, UV-stabilizers or stability enhancers, dyes (water soluble, water insoluble), color pigments, siccatives, corrosion inhibitors, antisettlement agents, additional insecticides (such as insecticidal carbamates, organophosphorus compounds, halogenated hydrocarbons, pyrethroides etc.), anti-skinning agents and the like. The above-mentioned additional ingredients and their use are described, for example, in EP 370 665 A, DE 3 531 257 A, DE 3 414 244 A.

The compositions can be provided as ready for use products or as concentrates, which have to be diluted prior to use.

The compositions can be applied by means of brushing, spraying, dipping, double vacuum and the like as known in the art. The compositions can be prepared by any technique known in the art.

The present invention will be better understood with reference to the following non-limiting examples.

EXAMPLES

As will be appreciated by those skilled in the art, the following examples are representative of the present invention. All formulations herein described may be further optimized, as all such further development should be considered within the scope of the present invention.

The pesticidal action of the compositions described herein can be seen from the examples which follow. While the individual active compounds may show weaknesses in their action as an individual agent, the combination shows a synergistic action, namely that which exceeds a simple sum of actions.

Given that many of the adjuvants, preferably free radical stabilizers, have no pesticidal properties of their own, any increase in activity of the pesticide when combined with the free radical stabilizer is due to synergy with the free radical stabilizer.

The action for a combination of two compounds can be calculated as follows, using the formula of S. R. Colby, Weeds 15 (1967), 20-22, herein incorporated by reference:

$$E = X + Y - (X \text{ times } Y)/100$$

where

X is efficacy, expressed as % of the untreated control, when employing a first compound at an application rate of mg/ha or in a concentration of m ppm, Y is efficacy, expressed as % of the untreated control, when employing a second compound at an application rate of m g/ha or in a concentration of m ppm, and E is efficacy, expressed as % of the untreated control, when employing a combination of the first and second compounds at application rates of m and n g/ha or in a concentration of m and n ppm.

If the actual pesticidal kill rate exceeds the calculated value, the action of the combination is synergistic.

In this case, the actually observed insecticidal kill rate should exceed the value calculated using the above formula for the expected insecticidal kill rate (E).

In this test, for example, the following compositions including a combination of pesticide and adjuvant as described herein exhibit a synergistically enhanced activity compared to the active compounds applied individually.

The examples that follow demonstrate the use of various adjuvants, some of which are free radical stabilizers and some of which are UV absorbers, or both, including various organic acids, esters, preservatives (BHA, BHT), polyphenyl methanes, and sebacates such as Compound A, which may also be referred to as bis(1,2,2,6,6-pentamethyl-4-piperidinyl)sebacate and methyl(1,2,2,6,6-pentamethyl-4-piperidinyl)sebacate, with insecticides such as imidacloprid, deltamethrin, thiamethoxam, resmethrin, permethrin, fipronil, Ethiprole, bendiocarb, various cyfluthrins, and pyrethrins and pyrethroids, against insects and arachnids such as the bait averse/resistant German cockroach (T-164 Strain), the susceptible German cockroach (Monheim Strain), the Argentine ant, the odorous house ant, the red imported fire ant (RIFA), the *Aedes aegypti* Mosquito, the *Culex quinquefasciatus* mosquito, and various spiders.

In the examples that follow, one or more standard methodology was used. One of these standard methods is described below.

Determination of the Efficacy of Formulations on Surfaces

The surfaces were treated as follows:

A flat fan nozzle (type SS 8003-E) in a spray cabin was moved automatically over a defined area where the solutions were sprayed very evenly onto the surfaces. The formulation was mixed with water to give a concentration which corresponded to the desired quantity of a.i./m². A defined quantity of this solution was sprayed onto the area (nominal 350 liter/ha=0.77 ml per surface).

All surfaces were provided with talcum-coated glass rings (diameter 9.5 cm, height 5.5 cm) one day later.

The test insects were anesthetized with $CO_2$, 20 individuals were placed onto the treated surfaces and the glass ring was covered with wire gauze ring.

Knock down was determined after 15 and 30', 1, 2, 4 and 6 hours, mortality after 1 day exposure.

Each test consisted of at least one replicate and any additional replicates are noted.

Example 1

Evaluation of the Synergy of Organic Acids with Imidacloprid Against the Argentine Ant The objective of this study was to investigate the synergistic effect of imidacloprid in combination with organic acids on efficacy against the Argentine ant, *Linepithema humile*.

MATERIALS AND METHODS: Solutions of imidacloprid at 0.5% active ingredient (hereinafter "AI") were prepared with and without benzenepropanoic acid (benzenepropanoic acid) @0.1, 1.0 and 5.0% in acetone. Treatments were applied using a micropipette to dispense 1 ml of test solution evenly on a 6"×6" glazed tile. Actual coverage was about 5"×5" (or 161 cm²) for easy handling. Treatments were allowed to dry overnight. Ten Argentine ant workers were placed within a fluon or talc-coated PVC ring (φ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

RESULTS: A summary of imidacloprid/benzenepropanoic acid synergy study against the Argentine ant is shown, Table 4 and FIG. 1

| Treatment | Rate (g/m$^2$) | Average % Knockdown & Mortality after | | | | |
|---|---|---|---|---|---|---|
| | | 30 min | 1 hr | 3 hr | 7 hr | 24 hr |
| UTC | 0 | 0 | 0 | 0 | 0 | 0 |
| imidacloprid (0.5%) | 0.31 | 0 | 0 | 0 | 0 | 20 |
| imidacloprid (0.5%) + benzenepropanoic acid (5%) | 0.31 + 3.11 | 0 | 7 | 70 | 97 | 100 |
| imidacloprid (0.5%) + benzenepropanoic acid (1%) | 0.31 + 0.62 | 0 | 0 | 0 | 3 | 27 |
| imidacloprid (0.5%) + benzenepropanoic acid (0.1%) | 0.31 + 0.06 | 0 | 0 | 0 | 3 | 7 |
| Benzenepropanoic acid (5%) | 0 + 3.11 | 0 | 0 | 0 | 7 | 7 |
| Benzenepropanoic acid (1%) | 0 + 0.62 | 0 | 0 | 0 | 0 | 3 |
| Benzenepropanoic acid (0.1%) | 0 + 0.06 | 0 | 0 | 0 | 0 | 0 |

Figure 1:
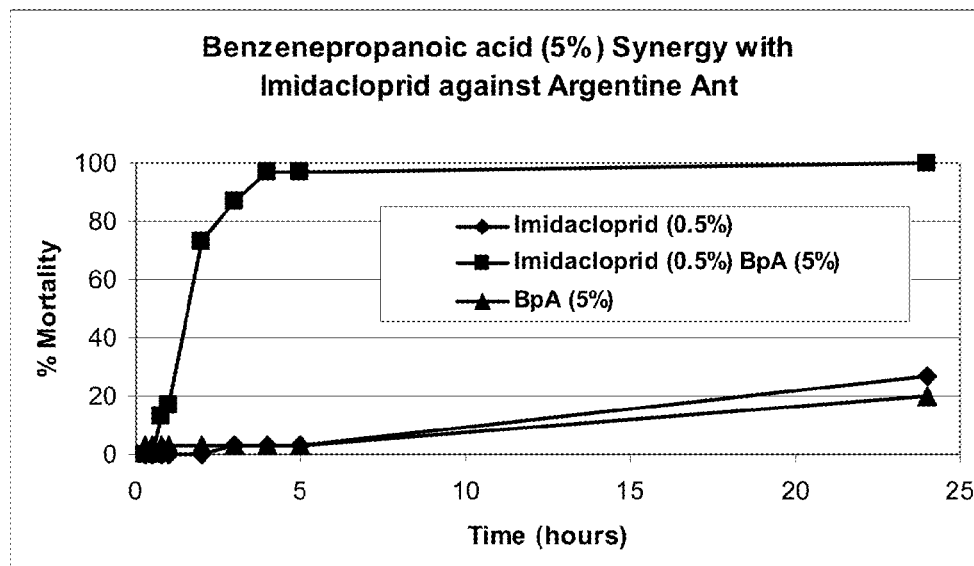

SUMMARY: A synergistic effect Was seen with the two high rates (1 & 5%) of benzenepropanoic acid with imidacloprid against the Argentine ants. Benzenepropanoic acid alone at all rates tested was not toxic to the Argentine ants. The results are illustrated in FIG. 1, both imidacloprid and the free radical stabilizer benzenepropanoic acid showed a relatively low mortality against the Argentine ant at a concentration of 5%, whereas the combination of the two showed relatively high mortality.

Example 2

Evaluation of the Synergy of Organic Acids with Imidacloprid Against Bait Averse/Resistant German Cockroach (T-164 Strain)

The objective of this study was to investigate the synergistic effect of imidacloprid in combination with organic acids on efficacy against bait averse/resistant German cockroach (T-164 strain).

MATERIALS AND METHODS: Solutions of imidacloprid at 0.5% AI were prepared with and without benzenepropanoic acid (benzenepropanoic acid) @0.1, 1.0 and 5.0% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five male German cockroaches were placed within a Fluon-coated PVC ring ($\phi$7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

Figure 2:
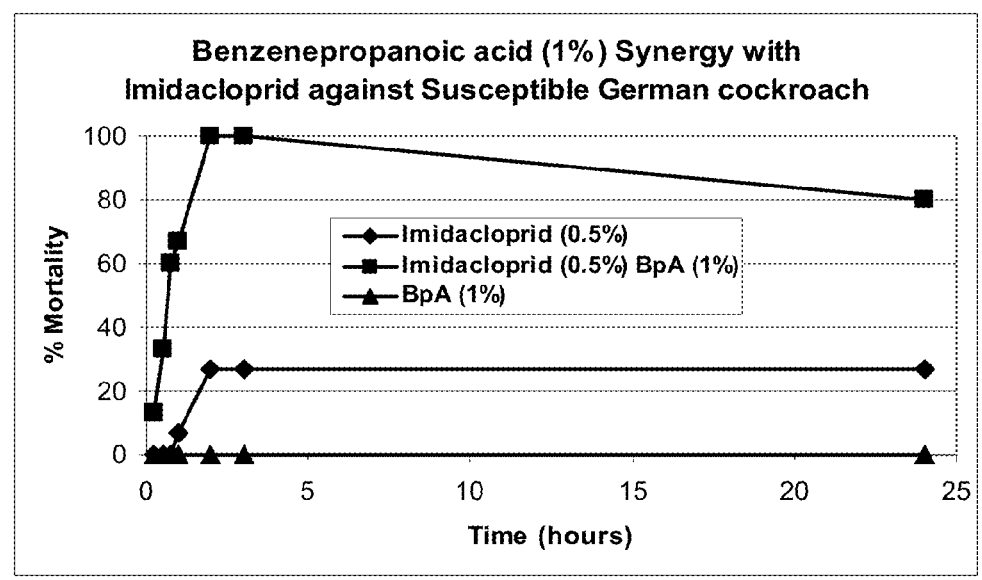

RESULTS: Table 5 and FIG. 2: Summary of imidacloprid/benzenepropanoic acid synergy study against German cockroach (T-164 strain)

| Treatment | Rate (g/m$^2$) | Average % Knockdown & Mortality after | | | | |
|---|---|---|---|---|---|---|
| | | 15 min | 30 min | 1 hr | 2 hr | 24 hr |
| UTC | 0 | 0 | 0 | 0 | 0 | 0 |
| imidacloprid (0.5%) | 0.31 | 0 | 0 | 7 | 27 | 27 |
| imidacloprid (0.5%) + benzenepropanoic acid (5%) | 0.31 + 3.11 | 93 | 100 | 100 | 100 | 100 |
| imidacloprid (0.5%) + benzenepropanoic acid (1%) | 0.31 + 0.62 | 13 | 33 | 67 | 100 | 80 |
| imidacloprid (0.5%) + benzenepropanoic acid (0.1%) | 0.31 + 0.06 | 7 | 7 | 33 | 47 | 33 |
| benzenepropanoic acid (5%) | 0 + 3.11 | 0 | 0 | 0 | 0 | 20 |
| benzenepropanoic acid (1%) | 0 + 0.62 | 0 | 0 | 0 | 0 | 0 |
| benzenepropanoic acid (0.1%) | 0 + 0.06 | 0 | 0 | 0 | 0 | 13 |

SUMMARY: A synergistic effect was seen with the three rates of benzenepropanoic acid with imidacloprid against German cockroaches (T-164 strain). Some recovery was observed at 24 hours. Benzenepropanoic acid alone was slightly to not toxic to the German cockroach.

Example 3

Evaluation of the Synergy of Organic Acids with Imidacloprid Against Bait Averse/Resistant German Cockroach (T-164 Strain)

The objective of this study was to investigate the synergistic effect of imidacloprid in combination with organic acids on efficacy against bait averse/resistant German cockroach (T-164 strain).

MATERIALS AND METHODS: Solutions of imidacloprid at 0.5% AI were prepared with and without Oleic acid @0.1, 1.0 and 5.0% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five male German cockroaches were placed within a Fluon-coated PVC ring ($\phi$7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

Figure 3:
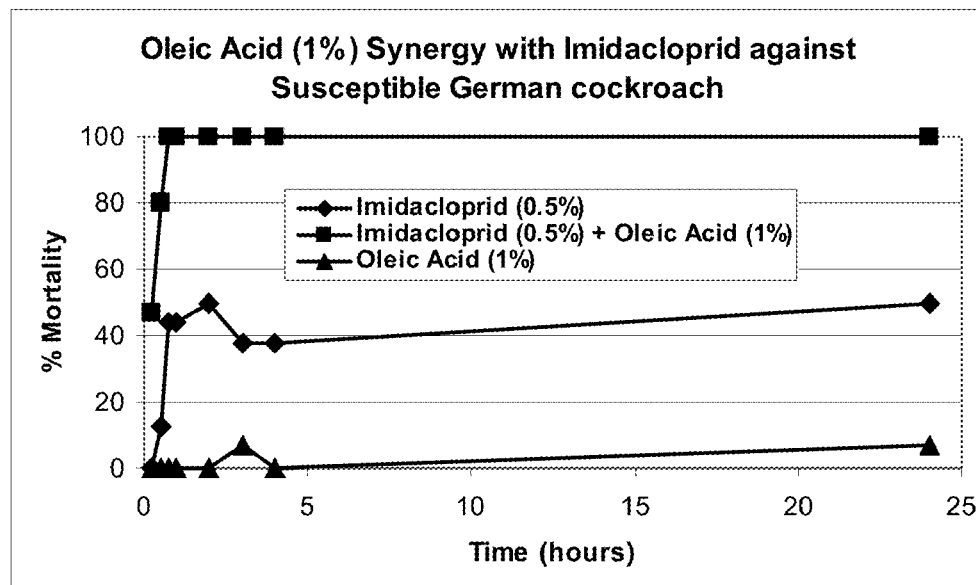

RESULTS: Table 6 and FIG. 3: Summary of imidacloprid/Oleic acid synergy study against German cockroach (T-164 strain)

| Treatment | Rate (g/m$^2$) | Average % Knockdown & Mortality after | | | | |
| --- | --- | --- | --- | --- | --- | --- |
| | | 15 min | 30 min | 1 hr | 2 hr | 24 hr |
| UTC | 0 | 0 | 0 | 0 | 0 | 0 |
| imidacloprid (0.5%) | 0.31 | 0 | 13 | 44 | 50 | 50 |
| imidacloprid (0.5%) + Oleic Acid (5%) | 0.31+3.11 | 88 | 100 | 100 | 100 | 100 |
| imidacloprid (0.5%) + Oleic Acid (1%) | 0.31+0.62 | 47 | 80 | 100 | 100 | 100 |
| imidacloprid (0.5%) + Oleic Acid (0.1%) | 0.31+0.06 | 7 | 7 | 13 | 27 | 67 |
| Oleic Acid (5%) | 0 +3.11 | 0 | 0 | 44 | 94 | 94 |
| Oleic Acid (1%) | 0 +0.62 | 0 | 0 | 0 | 0 | 7 |
| Oleic Acid (0.1%) | 0 +0.06 | 0 | 0 | 0 | 0 | 0 |

SUMMARY: A synergistic effect was seen with the three rates of Oleic acid with imidacloprid against German cockroaches (T-164 strain). Oleic acid alone was toxic to German cockroaches at the high rate (5%), but not toxic at the two low rates.

Example 4

Evaluation of the Synergy of Organic Acids with Imidacloprid Against the Argentine Ant The objective of this study was to investigate the synergistic effect of imidacloprid in combination with organic acids on efficacy against the Argentine ant, *Linepithema humile*.

MATERIALS AND METHODS: Solutions of imidacloprid at 0.5% AI were prepared with and without Oleic acid @0.1, 1.0, and 5.0% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Ten Argentine ant workers were placed within a fluon or talc-coated PVC ring ($\phi$7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

Figure 4:
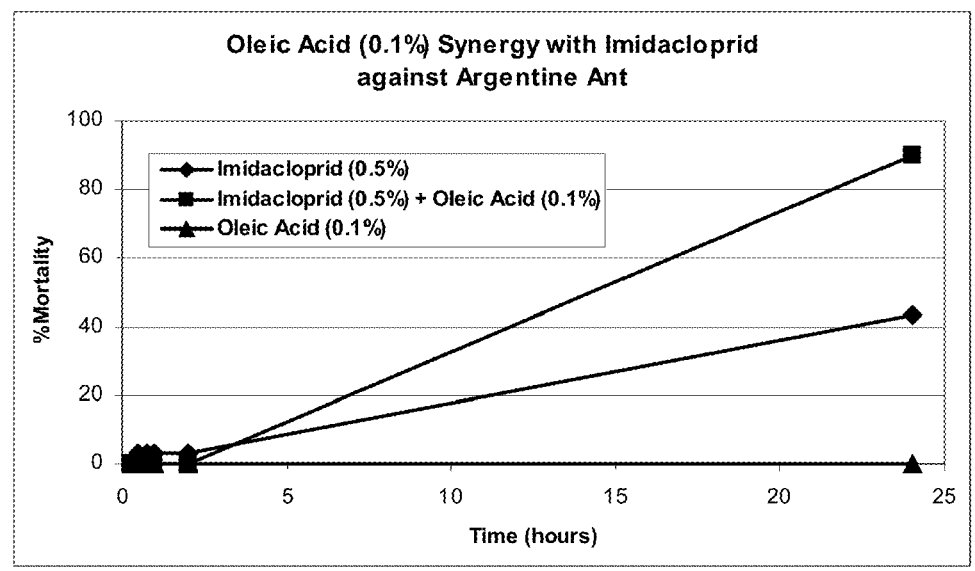

RESULTS: Table 7 and FIG. 4: Summary of imidacloprid/Oleic acid synergy study against the Argentine ant:

| Treatment | Rate (g/m²) | Average % Knockdown & Mortality after | | | | |
|---|---|---|---|---|---|---|
| | | 30 min | 1 hr | 3 hr | 7 hr | 24 hr |
| UTC | 0 | 0 | 0 | 0 | 0 | 0 |
| imidacloprid (0.5%) | 0.31 | 0 | 3 | 3 | 3 | 43 |
| imidacloprid (0.5%) + Oleic acid (5%) | 0.31 + 3.11 | 100 | 100 | 100 | 100 | 100 |
| imidacloprid (0.5%) + Oleic acid (1%) | 0.31 + 0.62 | 50 | 93 | 100 | 100 | 100 |
| imidacloprid (0.5%) + Oleic acid (0.1%) | 0.31 + 0.06 | 0 | 0 | 0 | 0 | 90 |
| Oleic acid (5%) | 0 + 3.11 | 93 | 100 | 100 | 100 | 100 |
| Oleic acid (1%) | 0 + 0.62 | 14 | 50 | 82 | 100 | 100 |
| Oleic acid (0.1%) | 0 + 0.06 | 0 | 0 | 0 | 0 | 0 |

SUMMARY: A synergistic effect was seen with the three rates of Oleic acid with imidacloprid against the Argentine ants. Oleic acid alone at the high rates (1 & 5%) was toxic to the Argentine ants, but not at the low rate (0.1%).

Example 5

Evaluation of the Synergy of Esters with Imidacloprid Against the Argentine Ant

The objective of this study was to investigate the synergistic effect of imidacloprid in combination with esters on efficacy against the Argentine ant, *Linepithema humile*.

MATERIALS AND METHODS:

Solutions of imidacloprid at 0.5% AI were prepared with and without methyl oleate @0.1, 1.0 and 5.0% in acetone. Treatments were applied using a micropipette to dispense 1 ml of test solution evenly on a 6"×6" glazed tile. Actual coverage was about 5"×5" (or 161 cm²) for easy handling. Treatments were allowed to dry overnight. Ten Argentine ant workers were placed within a fluon or talc-coated PVC ring (φ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

SUMMARY: A synergistic effect was seen with the three rates of methyl oleate with imidacloprid tested against the Argentine ants. Methyl oleate alone was toxic to the Argentine ants.

Example 6

Evaluation of the Synergy of Esters with Imidacloprid Against Bait Averse/Resistant German Cockroach (T-164 Strain)

The objective of this study was to investigate the synergistic effect of imidacloprid in combination with esters on efficacy against bait averse/resistant German cockroach (T-164 strain).

MATERIALS AND METHODS: Solutions of imidacloprid at 0.5% AI were prepared with and without methyl oleate @0.1, 1.0 and 5.0% in acetone. Treatments were applied using a micropipette to dispense 1 ml of test solution evenly on a 6"×6" glazed tile. Actual coverage was about 5"×5" (or 161 cm²) for easy handling. Treatments were allowed to dry overnight. Five male German cockroaches were placed within a Fluon-coated PVC ring (φ7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

Figure 5:
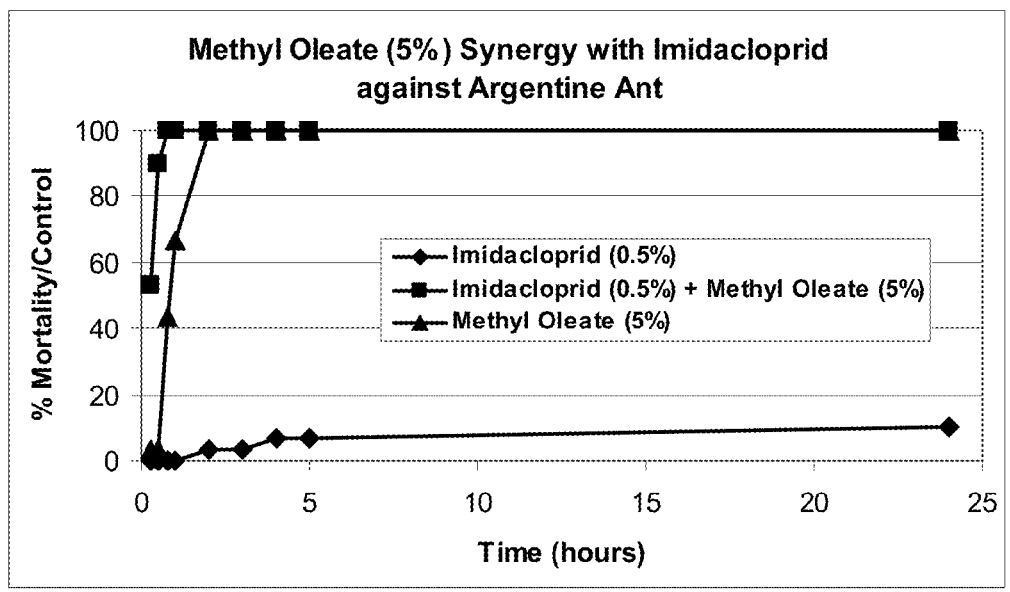

RESULTS: Table 8 and FIG 5: Summary of imidacloprid/Methyl Oleate synergy study against the Argentine ant:

| Treatment | Rate (g/m²) | Average % Knockdown & Mortality after | | | | |
|---|---|---|---|---|---|---|
| | | 15 min | 30 min | 1 hr | 4 hr | 24 hr |
| UTC | 0 | 0 | 0 | 0 | 0 | 3 |
| imidacloprid (0.5%) | 0.31 | 0 | 0 | 0 | 7 | 10 |
| imidacloprid (0.5%) + Methyl Oleate (5%) | 0.31 + 3.11 | 53 | 90 | 100 | 100 | 100 |
| imidacloprid (0.5%) + Methyl Oleate (1%) | 0.31 + 0.62 | 0 | 0 | 0 | 17 | 43 |
| imidacloprid (0.5%) + Methyl Oleate (0.1%) | 0.31 + 0.06 | 0 | 0 | 0 | 13 | 47 |
| Methyl Oleate (5%) | 0 + 3.11 | 3 | 3 | 67 | 100 | 100 |
| Methyl Oleate (1%) | 0 + 0.62 | 0 | 3 | 3 | 55 | 65 |
| Methyl Oleate (0.1%) | 0 + 0.06 | 0 | 0 | 0 | 13 | 13 |

Figure 6:
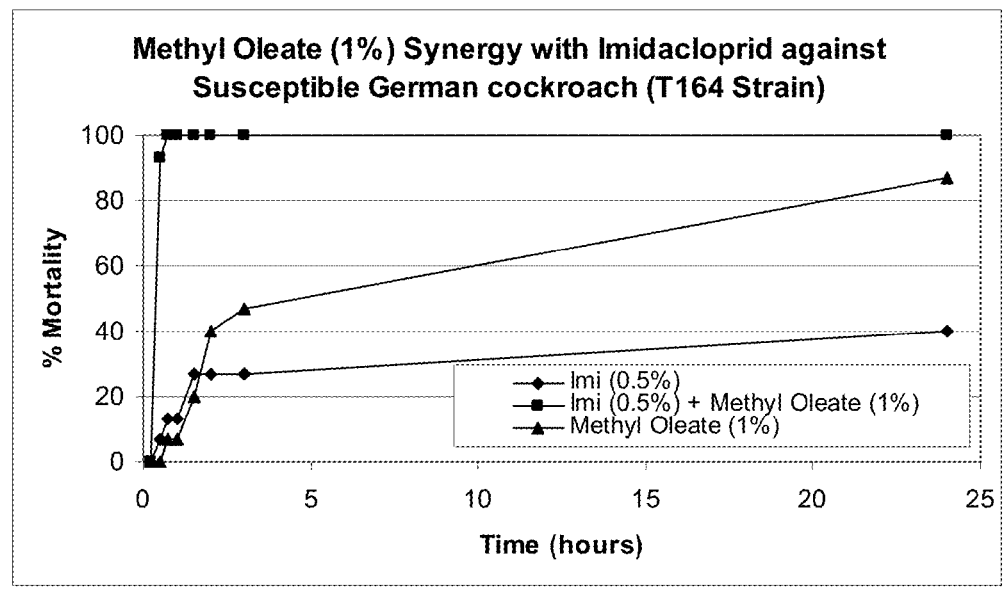

RESULTS: Table 9 and FIG 6: Summary of imidacloprid/Methyl Oleate synergy study against German cockroach (T-164 strain)

| Treatment | Rate (g/m$^2$) | Average % Knockdown & Mortality after | | | | |
|---|---|---|---|---|---|---|
| | | 15 min | 30 min | 1 hr | 2 hr | 24 hr |
| UTC | 0 | 0 | 0 | 0 | 0 | 0 |
| imidacloprid (0.5%) | 0.31 | 0 | 7 | 13 | 27 | 40 |
| imidacloprid (0.5%) + Methyl Oleate (5%) | 0.31 + 3.11 | 88 | 100 | 100 | 100 | 100 |
| imidacloprid (0.5%) + Methyl Oleate (1%) | 0.31 + 0.62 | 0 | 93 | 100 | 100 | 100 |
| imidacloprid (0.5%) + Methyl Oleate (0.1%) | 0.31 + 0.06 | 0 | 20 | 47 | 60 | 73 |
| Methyl Oleate (5%) | 0 + 3.11 | 7 | 13 | 87 | 100 | 100 |
| Methyl Oleate (1%) | 0 + 0.62 | 0 | 0 | 7 | 40 | 87 |
| Methyl Oleate (0.1%) | 0 + 0.06 | 0 | 0 | 0 | 7 | 13 |

SUMMARY: A synergistic effect was seen with the three rates of methyl oleate with imidacloprid against the insecticide-resistant German cockroaches (T-164 strain). Methyl oleate at the higher rates (1 & 5%) showed delayed toxic effect to the German cockroach.

Example 7

Evaluation of Synergy of Esters with Imidacloprid Against the Argentine Ant

The objective of this study was to investigate the synergistic effect of imidacloprid in combination with esters on efficacy against the Argentine ant, *Linepithema humile*.

MATERIALS AND METHODS: Solutions of imidacloprid at 0.5% AI were prepared with and without methyl linoleate @0.1, 1.0 and 5.0% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Ten Argentine ant workers were placed within a fluon or talc-coated PVC ring (ϕ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

SUMMARY: A synergistic effect was seen with the two high rates (1 & 5%) of methyl linoleate with imidacloprid against the Argentine ants. Methyl linoleate alone at high rates (1 & 5%) was toxic to the Argentine ants.

Example 8

Evaluation of the Synergy of Esters with Imidacloprid Against Bait Averse/Resistant German Cockroach (T-164 Strain)

The objective of this study was to investigate the synergistic effect of imidacloprid in combination with esters on efficacy against bait averse/resistant German cockroach (T-164 strain).

Figure 7:
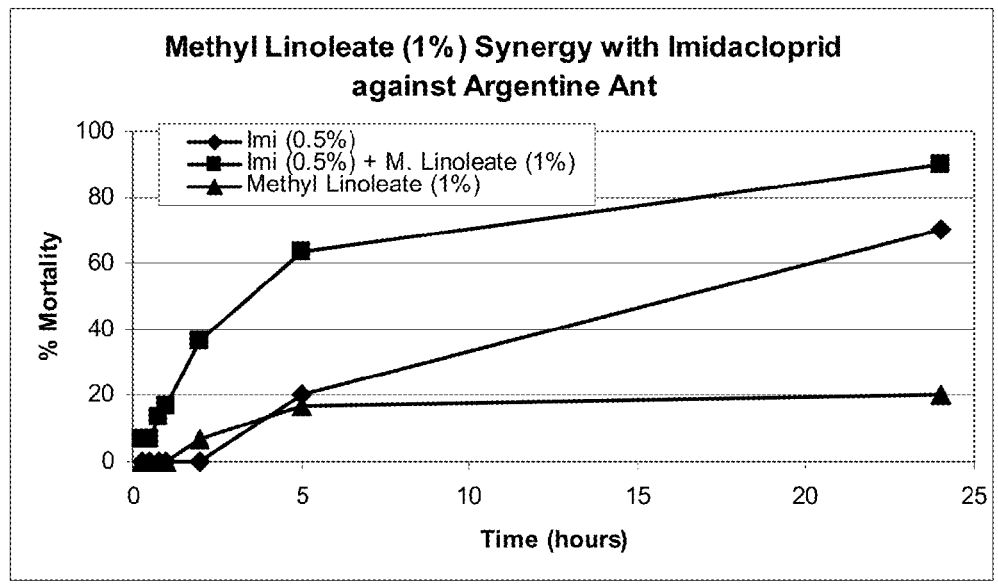

MATERIALS AND METHODS: Solutions of imidacloprid at 0.5% AI were prepared with and without methyl linoleate @0.1, 1.0 and 5.0% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five male German cockroaches were placed within a Fluon-coated PVC ring (ϕ7.6 cm×H 5.1 cm) under continuous exposure. A small vial cap filled with a cotton ball soaked in water was added as a drinking source after 3 hours. Treatments were replicated a minimum of three RESULTS: Table 10 and FIG 7: Summary of imidacloprid/Methyl Linoleate synergy study against the Argentine ant:

| Treatment | Rate (g/m$^2$) | Average % Knockdown & Mortality after | | | | |
|---|---|---|---|---|---|---|
| | | 15 min | 30 min | 1 hr | 4 hr | 24 hr |
| UTC | 0 | 0 | 0 | 0 | 0 | 3 |
| imidacloprid (0.5%) | 0.31 | 0 | 0 | 0 | 0 | 70 |
| imidacloprid (0.5%) + Methyl Linoleate (5%) | 0.31 + 3.11 | 43 | 77 | 97 | 100 | 100 |
| imidacloprid (0.5%) + Methyl Linoleate (1%) | 0.31 + 0.62 | 7 | 7 | 17 | 37 | 90 |
| imidacloprid (0.5%) + Methyl Linoleate (0.1%) | 0.31 + 0.06 | 3 | 3 | 3 | 3 | 63 |
| Methyl Linoleate (5%) | 0 + 3.11 | 7 | 7 | 20 | 67 | 97 |
| Methyl Linoleate (1%) | 0 + 0.62 | 0 | 0 | 0 | 7 | 20 |
| Methyl Linoleate (0.1%) | 0 + 0.06 | 0 | 0 | 0 | 0 | 3 | times. Evaluations for knockdown/mortality were made at various intervals and at 24 hours after exposure.

Figure 8:
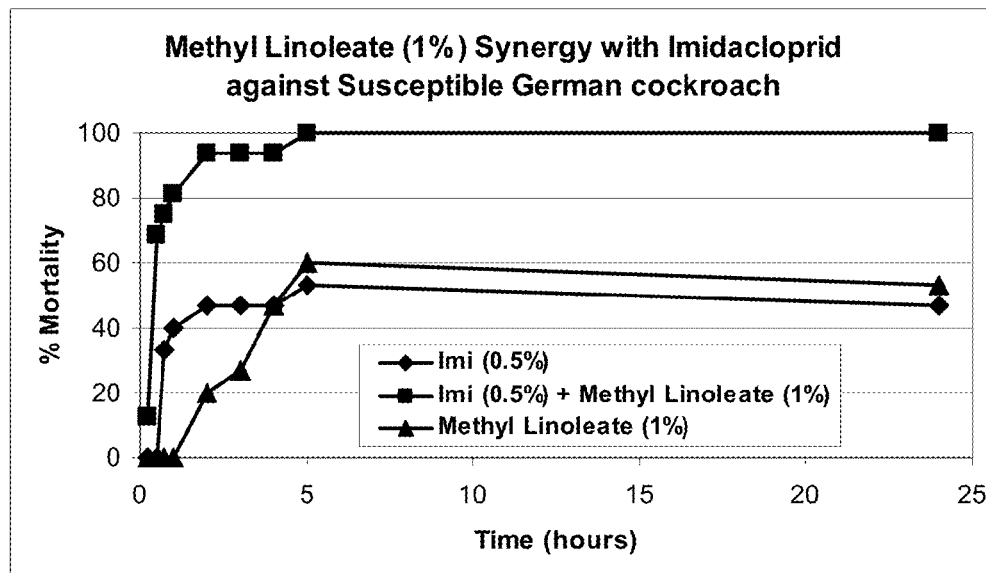

RESULTS: Table 11 and FIG 8: Summary of imidacloprid/Methyl Linoleate synergy study against German cockroach (T-164 strain)

| Treatment | Rate (g/m$^2$) | Average % Knockdown & Mortality after | | | | |
|---|---|---|---|---|---|---|
| | | 15 min | 30 min | 1 hr | 2 hr | 24 hr |
| UTC | 0 | 0 | 0 | 0 | 0 | 20 |
| imidacloprid (0.5%) | 0.31 | 0 | 0 | 40 | 47 | 47 |
| imidacloprid (0.5%) + Methyl Linoleate (5%) | 0.31 + 3.11 | 67 | 100 | 100 | 100 | 100 |
| imidacloprid (0.5%) + Methyl Linoleate (1%) | 0.31 + 0.62 | 13 | 69 | 81 | 94 | 100 |
| imidacloprid (0.5%) + Methyl Linoleate (0.1%) | 0.31 + 0.06 | 0 | 20 | 47 | 53 | 80 |
| Methyl Linoleate (5%) | 0 + 3.11 | 0 | 20 | 60 | 100 | 100 |
| Methyl Linoleate (1%) | 0 + 0.62 | 0 | 0 | 0 | 20 | 53 |
| Methyl Linoleate (0.1%) | 0 + 0.06 | 0 | 0 | 0 | 0 | 20 |

SUMMARY: A synergistic effect was seen with the three rates of methyl linoleate with imidacloprid against German cockroaches (T-164 strain). Methyl linoleate alone was toxic to the German cockroach.

Example 9

Evaluation of the Synergy of Esters with Imidacloprid Against the Argentine Ant The objective of this study was to investigate the synergistic effect of imidacloprid in combination with esters on efficacy against the Argentine ant, *Linepithema humile*.

MATERIALS AND METHODS:

Solutions of imidacloprid at 0.5% AI were prepared with and without methyl palmitate @0.1, 1.0 and 5.0% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Ten Argentine ant workers were placed within a fluon or talc-coated PVC ring (ϕ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

SUMMARY: A synergistic effect was seen with the two high rates (1 & 5%) of methyl palmitate with imidacloprid against the Argentine ants. Methyl palmitate alone at all rates tested was not toxic to the Argentine ants.

Example 10

Evaluation of the Synergy of Esters with Imidacloprid Against Bait Averse/Resistant German Cockroach (T-164 Strain)

The objective of this study was to investigate the synergistic effect of imidacloprid in combination with esters on efficacy against bait averse/resistant German cockroach (T-164 strain).

MATERIALS AND METHODS: Solutions of imidacloprid at 0.5% AI were prepared with and without methyl palmitate @0.1, 1.0 and 5.0% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five male German cockroaches were placed within a Fluon-coated PVC ring (ϕ7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

Figure 9:
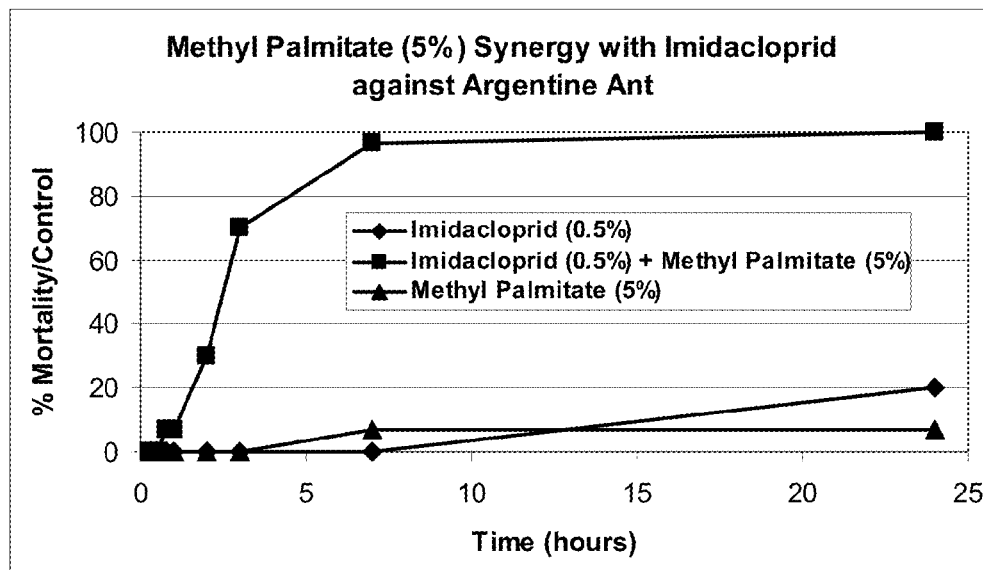

RESULTS: Table 12 and FIG 9: Summary of imidacloprid/Methyl Palmitate synergy study against the Argentine ant:

| Treatment | Rate (g/m$^2$) | Average % Knockdown & Mortality after | | | | |
|---|---|---|---|---|---|---|
| | | 30 min | 1 hr | 3 hr | 7 hr | 24 hr |
| UTC | 0 | 0 | 0 | 0 | 0 | 0 |
| imidacloprid (0.5%) | 0.31 | 0 | 0 | 0 | 0 | 20 |
| imidacloprid (0.5%) + Methyl Palmitate (5%) | 0.31 + 3.11 | 0 | 7 | 70 | 97 | 100 |
| imidacloprid (0.5%) + Methyl Palmitate (1%) | 0.31 + 0.62 | 0 | 0 | 0 | 3 | 27 |
| imidacloprid (0.5%) + Methyl Palmitate (0.1%) | 0.31 + 0.06 | 0 | 0 | 0 | 3 | 7 |
| Methyl Palmitate (5%) | 0 + 3.11 | 0 | 0 | 0 | 7 | 7 |
| Methyl Palmitate (1%) | 0 + 0.62 | 0 | 0 | 0 | 0 | 3 |
| Methyl Palmitate (0.1%) | 0 + 0.06 | 0 | 0 | 0 | 0 | 0 |

Figure 10:
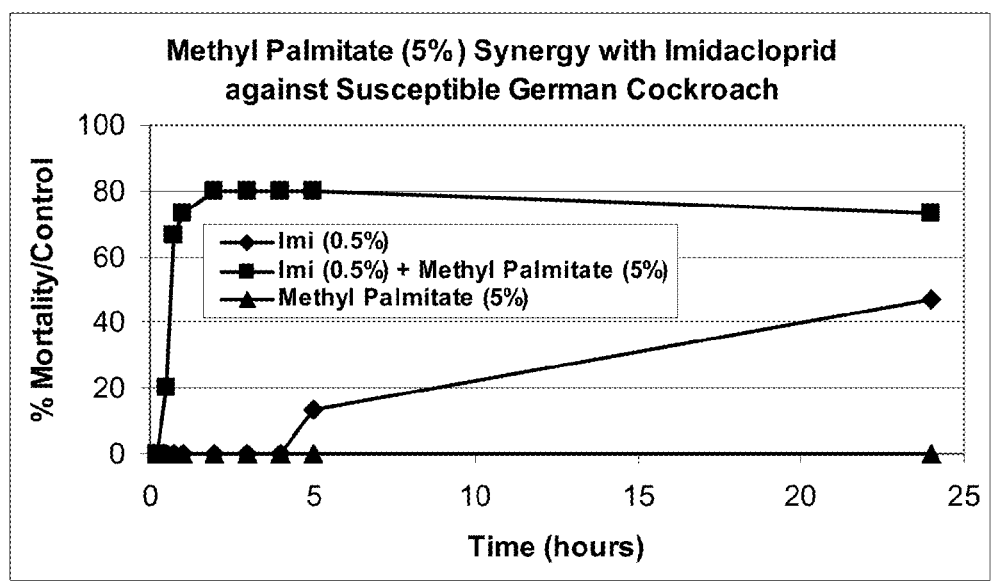

RESULTS: Table 13 and FIG 10: Summary of imidacloprid/Methyl Palmitate synergy study against German cockroach (T-164 strain)

| Treatment | Rate (g/m²) | \multicolumn{5}{c}{Average % Knockdown & Mortality after} |
|---|---|---|---|---|---|---|
| | | 30 min | 1 hr | 2 hr | 4 hr | 24 hr |
| UTC | 0 | 0 | 0 | 0 | 0 | 0 |
| imidacloprid (0.5%) | 0.31 | 0 | 0 | 0 | 0 | 47 |
| imidacloprid (0.5%) + Methyl Palmitate (5%) | 0.31 + 3.11 | 20 | 73 | 80 | 80 | 73 |
| imidacloprid (0.5%) + Methyl Palmitate (1%) | 0.31 + 0.62 | 0 | 40 | 40 | 40 | 47 |
| imidacloprid (0.5%) + Methyl Palmitate (0.1%) | 0.31 + 0.06 | 0 | 0 | 0 | 27 | 60 |
| Methyl Palmitate (5%) | 0 + 3.11 | 0 | 0 | 0 | 0 | 0 |
| Methyl Palmitate (1%) | 0 + 0.62 | 0 | 0 | 0 | 0 | 0 |
| Methyl Palmitate (0.1%) | 0 + 0.06 | 0 | 0 | 0 | 0 | 0 |

SUMMARY: A synergistic effect was seen with the three rates of methyl palmitate with imidacloprid against German cockroaches (T-164 strain). Methyl palmitate alone was not toxic to the German cockroach.

Example 11

Evaluation of the Synergy of Preservatives with Imidacloprid Against the Argentine Ant The objective of this study was to investigate the synergistic effect of imidacloprid in combination with common food preservatives on efficacy against the Argentine ant, *Linepithema humile*.

MATERIALS AND METHODS: Solutions of imidacloprid at 0.5% AI were prepared with and without butylated hydroxyanisole (BHA) @0.1, 1.0 and 5.0% in acetone. Treatments were applied using a micropipette to dispense 1 ml of test solution evenly on a 6"×6" glazed tile. Actual coverage was about 5"×5" (or 161 cm²) for easy handling. Treatments were allowed to dry overnight. Ten Argentine ant workers were placed within a fluon or talc-coated PVC ring (φ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

SUMMARY: No synergistic effect was seen with the three rates of BHA with imidacloprid tested against the Argentine ants. BHA alone showed delayed toxicity to the Argentine ants. Due to the unusual high mortality in UTC, the trial will be repeated.

Example 12

Evaluation of the Synergy of Preservatives with Imidacloprid Against Bait Averse/Resistant German Cockroach (T-164 Strain)

The objective of this study was to investigate the synergistic effect of imidacloprid in combination with common food preservatives on efficacy against bait averse/resistant German cockroach (T-164 strain).

MATERIALS AND METHODS: Solutions of imidacloprid at 0.5% AI were prepared with and without butylated hydroxyanisole (BHA) @0.1, 1.0 and 5.0% in acetone. Treatments were applied using a micropipette to dispense 1 ml of test solution evenly on a 6"×6" glazed tile. Actual coverage was about 5"×5" (or 161 cm²) for easy handling. Treatments were allowed to dry overnight. Five male German cockroaches were placed within a Fluon-coated PVC ring (φ7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

Figure 11:
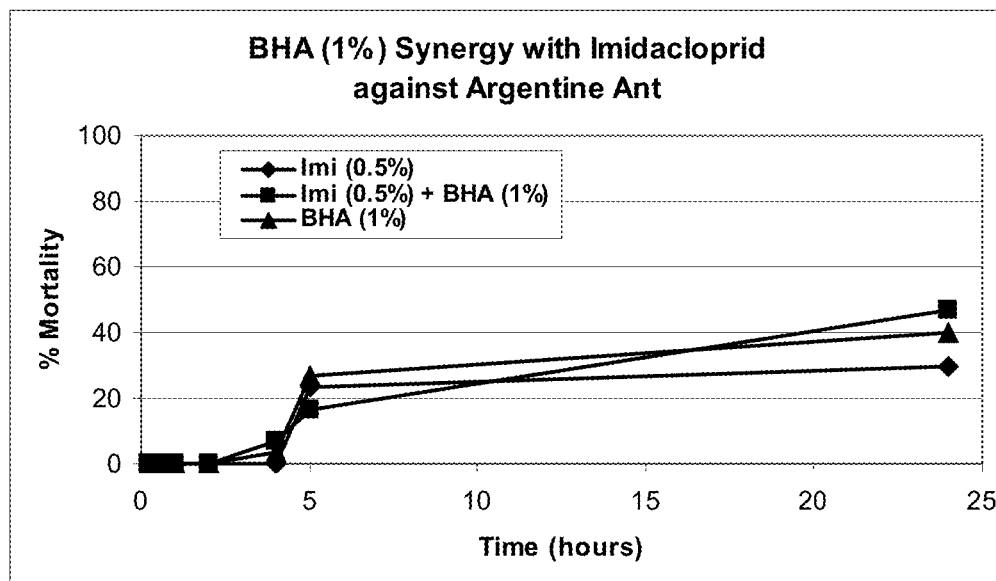

RESULTS: Table 14 and FIG 11: Summary of imidacloprid/BHA synergy study against the Argentine ant:

| Treatment | Rate (g/m²) | \multicolumn{5}{c}{Average % Knockdown & Mortality after} |
|---|---|---|---|---|---|---|
| | | 30 min | 1 hr | 2 hr | 4 hr | 24 hr |
| UTC | 0 | 0 | 0 | 0 | 0 | 63 |
| imidacloprid (0.5%) | 0.31 | 0 | 0 | 0 | 0 | 30 |
| imidacloprid (0.5%) + BHA (5%) | 0.31 + 3.11 | 0 | 0 | 0 | 12 | 64 |
| imidacloprid (0.5%) + BHA (1%) | 0.31 + 0.62 | 0 | 0 | 0 | 7 | 47 |
| imidacloprid (0.5%) + BHA (0.1%) | 0.31 + 0.06 | 0 | 0 | 0 | 10 | 52 |
| Butylated hydroxyanisole (BHA) (5%) | 0 + 3.11 | 0 | 0 | 0 | 19 | 74 |
| Butylated hydroxyanisole (BHA) (1%) | 0 + 0.62 | 0 | 0 | 0 | 3 | 40 |
| Butylated hydroxyanisole (BHA) (0.1%) | 0 + 0.06 | 0 | 0 | 0 | 10 | 37 |

Figure 12:
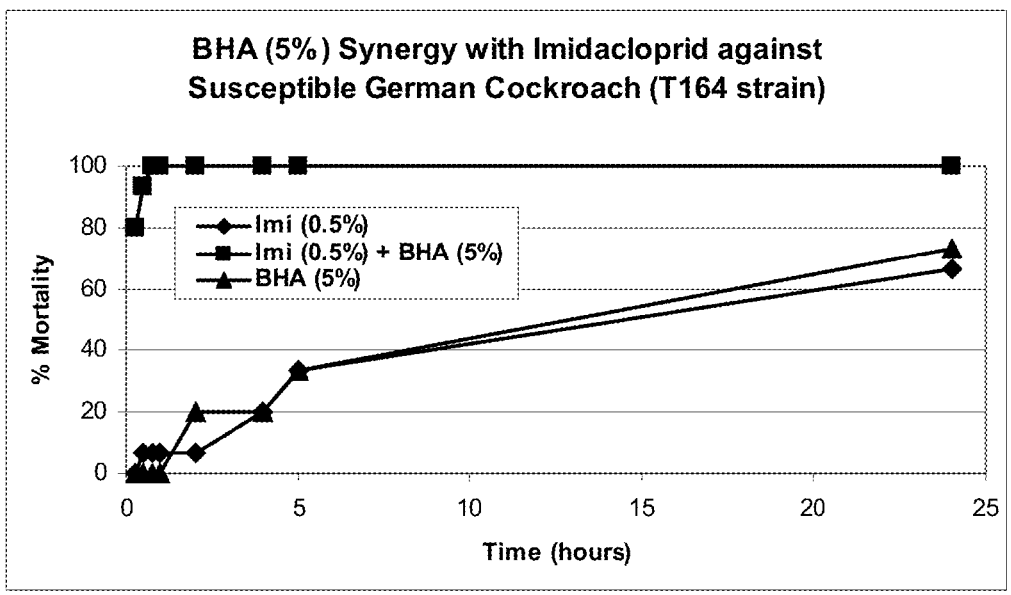

RESULTS: Table 15 and FIG. 12: Summary of imidacloprid/BHA synergy study against German cockroach (T-164 strain)

| Treatment | Rate (g/m²) | Average % Knockdown & Mortality after | | | | |
|---|---|---|---|---|---|---|
| | | 30 min | 1 hr | 2 hr | 4 hr | 24 hr |
| UTC | 0 | 0 | 0 | 0 | 0 | 0 |
| imidacloprid (0.5%) | 0.31 | 7 | 7 | 7 | 20 | 67 |
| imidacloprid (0.5%) + BHA (5%) | 0.31 + 3.11 | 93 | 100 | 100 | 100 | 100 |
| imidacloprid (0.5%) + BHA (1%) | 0.31 + 0.62 | 0 | 13 | 20 | 20 | 40 |
| imidacloprid (0.5%) + BHA (0.1%) | 0.31 + 0.06 | 0 | 7 | 13 | 20 | 40 |
| Butylated hydroxyanisole (BHA) (5%) | 0 + 3.11 | 0 | 0 | 20 | 20 | 73 |
| Butylated hydroxyanisole (BHA) (1%) | 0 + 0.62 | 0 | 0 | 0 | 0 | 0 |
| Butylated hydroxyanisole (BHA) (0.1%) | 0 + 0.06 | 0 | 0 | 0 | 0 | 20 |

SUMMARY: A synergistic effect was seen with the high rate (5%) of BHA with imidacloprid against German cockroaches (T-164 strain). BHA at the high rate (5%) was toxic to the German cockroach, but not at its lower rates (1.0 and 0.1%) tested.

Example 13

Evaluation of the Synergy of Preservatives with Imidacloprid Against the Argentine Ant The objective of this study was to investigate the synergistic effect of imidacloprid in combination with common food preservatives on efficacy against the Argentine ant, *Linepithema humile*.

MATERIALS AND METHODS: Solutions of imidacloprid at 0.5% AI were prepared with and without butylated hydroxytoluene (BHT) @0.1, 1.0 and 5.0% in acetone. Treatments were applied using a micropipette to dispense 1 ml of test solution evenly on a 6"×6" glazed tile. Actual coverage was about 5"×5" (or 161 cm²) for easy handling. Treatments were allowed to dry overnight. Ten Argentine ant workers were placed within a fluon or talc-coated PVC ring (ϕ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

Figure 13:
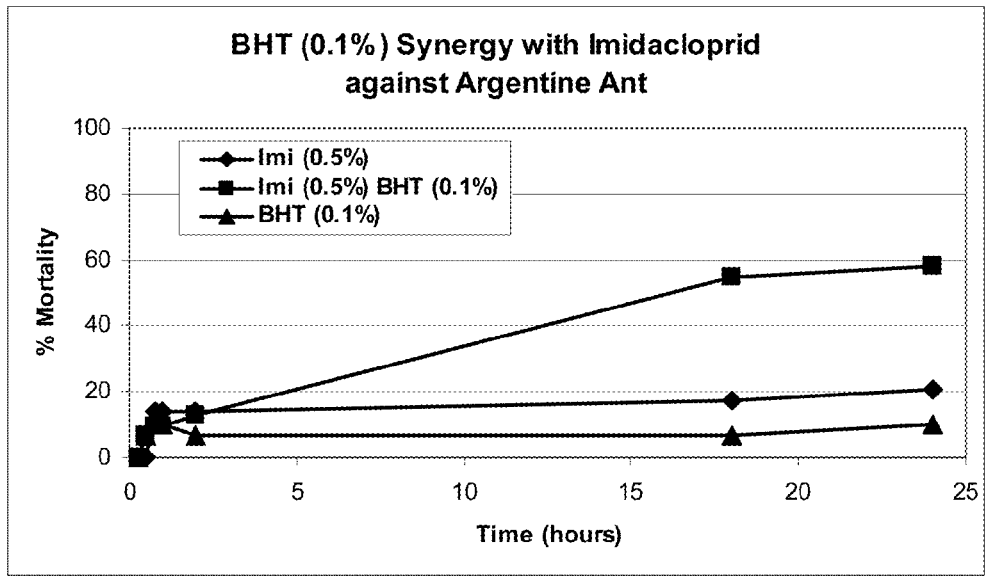

RESULTS: Table 16 and FIG. 13: Summary of imidacloprid/BHT synergy study against the Argentine ant:

| Treatment | Rate (g/m²) | Average % Knockdown & Mortality after | | | | |
|---|---|---|---|---|---|---|
| | | 30 min | 1 hr | 2 hr | 18 hr | 24 hr |
| UTC | 0 | 0 | 0 | 0 | 0 | 0 |
| imidacloprid (0.5%) | 0.31 | 0 | 14 | 14 | 17 | 21 |
| imidacloprid (0.5%) + BHT (5%) | 0.31 + 3.11 | 13 | 17 | 20 | 90 | 100 |
| imidacloprid (0.5%) + BHT (1%) | 0.31 + 0.62 | 11 | 11 | 14 | 29 | 39 |
| imidacloprid (0.5%) + BHT (0.1%) | 0.31 + 0.06 | 7 | 10 | 13 | 55 | 58 |
| Butylated hydroxytoluene (BHT) (5%) | 0 + 3.11 | 7 | 7 | 7 | 79 | 83 |
| Butylated hydroxytoluene (BHT) (1%) | 0 + 0.62 | 3 | 3 | 3 | 3 | 3 |
| Butylated hydroxytoluene (BHT) (0.1%) | 0 + 0.06 | 7 | 10 | 7 | 7 | 10 |

SUMMARY: A synergistic effect was seen with the three rates of BHT with imidacloprid tested against the Argentine ants. BHT alone was toxic to the Argentine ants.

Example 14

Evaluation of the Synergy of Preservatives with Imidacloprid Against Bait Averse/Resistant German Cockroach (T-164 Strain)

The objective of this study was to investigate the synergistic effect of imidacloprid in combination with common food preservatives on efficacy against bait averse/resistant German cockroach (T-164 strain).

MATERIALS AND METHODS: Solutions of imidacloprid at 0.5% AI were prepared with and without butylated hydroxytoluene (BHT) @0.1, 1.0 and 5.0% in acetone. Treatments were applied using a micropipette to dispense 1 ml of test solution evenly on a 6"×6" glazed tile. Actual coverage was about 5"×5" (or 161 cm²) for easy handling. Treatments were allowed to dry overnight. Five male German cockroaches were placed within a Fluon-coated PVC ring (ϕ7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

Figure 14:
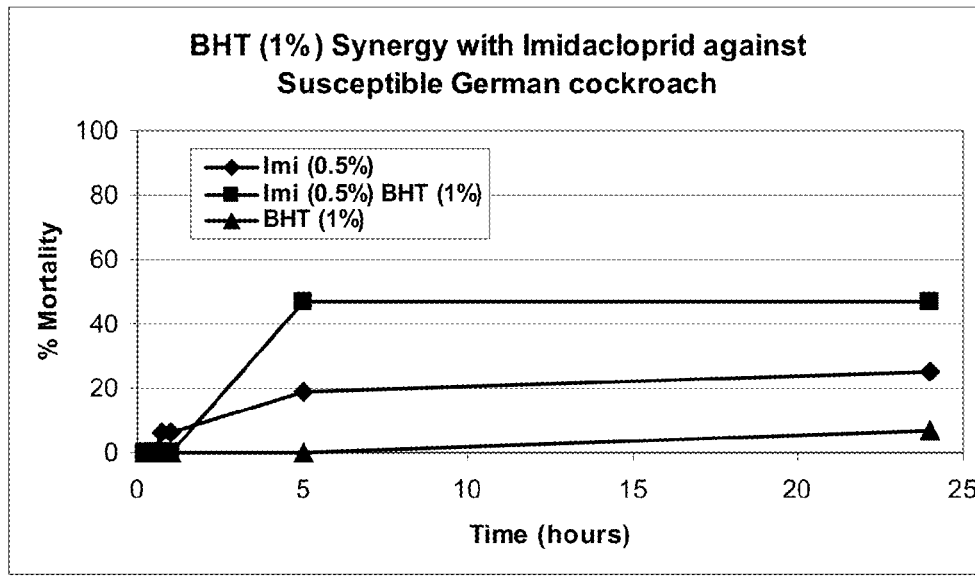

RESULTS: Table 17 and FIG. 14: Summary of imidacloprid/BHT synergy study against German cockroach (T-164 strain)

| Treatment | Rate (g/m$^2$) | Average % Knockdown & Mortality after | | | |
|---|---|---|---|---|---|
| | | 30 min | 1 hr | 5 hr | 24 hr |
| UTC | 0 | 0 | 0 | 0 | 0 |
| imidacloprid (0.5%) | 0.31 | 0 | 6 | 19 | 25 |
| imidacloprid (0.5%) + BHT (5%) | 0.31 + 3.11 | 0 | 0 | 0 | 0 |
| imidacloprid (0.5%) + BHT (1%) | 0.31 + 0.62 | 0 | 0 | 47 | 47 |
| imidacloprid (0.5%) + BHT (0.1%) | 0.31 + 0.06 | 0 | 13 | 27 | 27 |
| Butylated hydroxytoluene (BHT) (5%) | 0 + 3.11 | 0 | 0 | 0 | 7 |
| Butylated hydroxytoluene (BHT) (1%) | 0 + 0.62 | 0 | 0 | 0 | 7 |
| Butylated hydroxytoluene (BHT) (0.1%) | 0 + 0.06 | 0 | 0 | 0 | 0 |

SUMMARY: Synergistic effect was seen with the lower rates (1 & 0.1%) of BHT with imidacloprid against German cockroaches (T-164 strain). BHT at the high rate (5%) showed antagonistic effect. All BHT rates tested were not toxic to the German cockroach strain.

Example 15

Evaluation of the Synergy of Preservatives with Imidacloprid Against Bait Averse/Resistant German Cockroach (T-164 Strain)

The objective of this study was to investigate the synergistic effect of imidacloprid in combination with common food preservatives on efficacy against bait averse/resistant German cockroach (T-164 strain).

MATERIALS AND METHODS: Solutions of imidacloprid at 0.5% AI were prepared with and without tertiary butyl dihydroxyquinone (TBHQ) @0.1, 1.0 and 5.0% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five male German cockroaches were placed within a Fluon-coated PVC ring (φ7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

Figure 15:
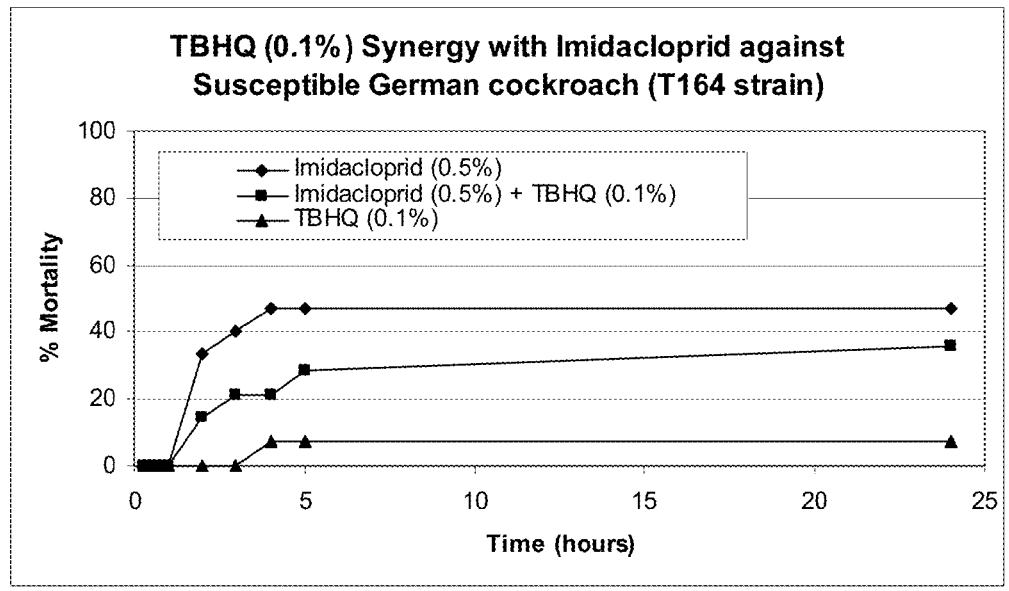

RESULTS: Table 18 and FIG. 15: Summary of imidacloprid/TBHQ synergy study against German cockroach (T-164 strain)

| Treatment | Rate (g/m$^2$) | Average % Knockdown & Mortality after | | | | |
|---|---|---|---|---|---|---|
| | | 30 min | 1 hr | 2 hr | 4 hr | 24 hr |
| UTC | 0 | 0 | 0 | 0 | 0 | 0 |
| imidacloprid (0.5%) | 0.31 | 0 | 0 | 33 | 47 | 47 |
| imidacloprid (0.5%) + TBHQ (5%) | 0.31 + 3.11 | 0 | 7 | 7 | 13 | 20 |
| imidacloprid (0.5%) + TBHQ (1%) | 0.31 + 0.62 | 0 | 0 | 7 | 13 | 27 |
| imidacloprid (0.5%) + TBHQ (0.1%) | 0.31 + 0.06 | 0 | 0 | 14 | 21 | 36 |
| TBHQ (5%) | 0 + 3.11 | 0 | 7 | 7 | 7 | 47 |
| TBHQ (1%) | 0 + 0.62 | 0 | 0 | 0 | 0 | 40 |
| TBHQ (0.1%) | 0 + 0.06 | 0 | 0 | 0 | 7 | 7 |

SUMMARY: Synergistic effect was seen with the three rates of TBHQ with imidacloprid against German cockroaches (T-164 strain). TBHQ at the higher rates (1 & 5%) showed delayed toxic effect to the German cockroach.

Example 16

Evaluation of the Synergy of Preservatives with Imidacloprid Against the Argentine Ant The objective of this study was to investigate the synergistic effect of imidacloprid in combination with common food preservatives on efficacy against the Argentine ant, *Linepithema humile*.

MATERIALS AND METHODS: Solutions of imidacloprid at 0.5% AI were prepared with and without tertiary butyl dihydroxyquinone (TBHQ) @0.1, 1.0 and 5.0% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Ten Argentine ant workers were placed within a fluon or talc-coated PVC ring ($\phi$7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

Figure 16:
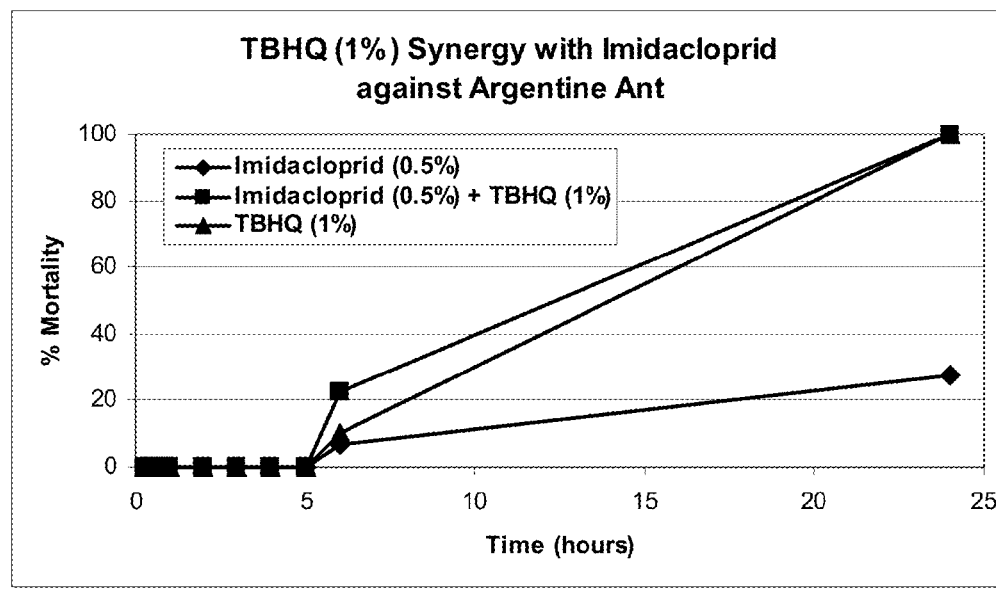

RESULTS: Table 19 and FIG. 16: Summary of imidacloprid/TBHQ synergy study against the Argentine ant:

| Treatment | Rate (g/m$^2$) | Average % Knockdown & Mortality after | | | | |
|---|---|---|---|---|---|---|
| | | 30 min | 1 hr | 4 hr | 6 hr | 24 hr |
| UTC | 0 | 0 | 0 | 0 | 0 | 0 |
| imidacloprid (0.5%) | 0.31 | 0 | 0 | 0 | 7 | 28 |
| imidacloprid (0.5%) + TBHQ (5%) | 0.31 + 3.11 | 0 | 0 | 0 | 22 | 100 |
| imidacloprid (0.5%) + TBHQ (1%) | 0.31 + 0.62 | 0 | 0 | 0 | 23 | 100 |
| imidacloprid (0.5%) + TBHQ (0.1%) | 0.31 + 0.06 | 0 | 0 | 0 | 0 | 38 |
| TBHQ (5%) | 0 + 3.11 | 0 | 0 | 10 | 23 | 100 |
| TBHQ (1%) | 0 + 0.62 | 0 | 0 | 0 | 10 | 100 |
| TBHQ (0.1%) | 0 + 0.06 | 0 | 0 | 0 | 7 | 11 |

SUMMARY: A synergistic effect was seen with the two high rates (1 & 5%) of TBHQ with imidacloprid tested against the Argentine ants. However, the effect may be directly contributed by the toxic effect of TBHQ to the Argentine ants.

Example 17

Evaluation of Synergy of Polyphenyl Methanes with Imidacloprid Against the Argentine Ant The objective of this study was to investigate the synergistic effect of imidacloprid in combination with polyphenyl methanes on efficacy against the Argentine ant, *Linepithema humile*.

MATERIALS AND METHODS: Solutions of imidacloprid at 0.5% AI were prepared with and without diphenyl methane @0.1, 1.0 and 5.0% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Ten Argentine ant workers were placed within a fluon or talc-coated PVC ring ($\phi$7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

Figure 17:
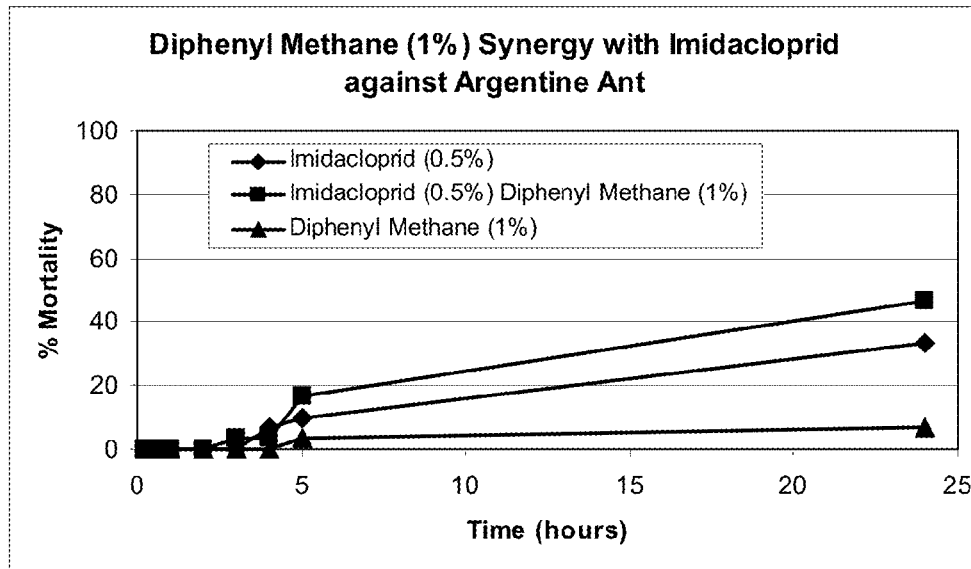

RESULTS: Table 20 and FIG. 17: Summary of imidacloprid/Diphenyl methane synergy study against the Argentine ant:

| Treatment | Rate (g/m$^2$) | Average % Knockdown & Mortality after | | | | |
|---|---|---|---|---|---|---|
| | | 30 min | 1 hr | 2 hr | 4 hr | 24 hr |
| UTC | 0 | 0 | 0 | 0 | 3 | 33 |
| imidacloprid (0.5%) | 0.31 | 0 | 0 | 0 | 7 | 33 |
| imidacloprid (0.5%) + DPM (5%) | 0.31 + 3.11 | 0 | 0 | 0 | 13 | 33 |

RESULTS: Table 20 and FIG. 17: Summary of imidacloprid/Diphenyl methane synergy study against the Argentine ant:

| Treatment | Rate (g/m$^2$) | Average % Knockdown & Mortality after | | | | |
|---|---|---|---|---|---|---|
| | | 30 min | 1 hr | 2 hr | 4 hr | 24 hr |
| imidacloprid (0.5%) + DPM (1%) | 0.31 + 0.62 | 0 | 0 | 0 | 3 | 47 |
| imidacloprid (0.5%) + DPM (0.1%) | 0.31 + 0.06 | 0 | 0 | 0 | 17 | 53 |
| Diphenyl methane (DPM) (5%) | 0 + 3.11 | 0 | 0 | 0 | 0 | 7 |
| Diphenyl methane (DPM) (1%) | 0 + 0.62 | 0 | 0 | 0 | 0 | 7 |
| Diphenyl methane (DPM) (0.1%) | 0 + 0.06 | 0 | 0 | 0 | 13 | 27 |

SUMMARY: No synergistic effect was seen with the three rates of diphenyl methane with imidacloprid tested against the Argentine ants. Diphenyl methane alone was not toxic to the Argentine ants.

Example 18

Evaluation of the Synergy of Polyphenyl Methanes with Imidacloprid Against Bait Averse/Resistant German Cockroach (T-164 Strain)

The objective of this study was to investigate the synergistic effect of imidacloprid in combination with polyphenyl methanes on efficacy against bait averse/resistant German cockroach (T-164 strain).

MATERIALS AND METHODS: Solutions of imidacloprid at 0.5% AI were prepared with and without diphenyl methane (DPM) @0.1, 1.0 and 5.0% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five male German cockroaches were placed within a Fluon-coated PVC ring (φ7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

SUMMARY: No synergistic effect was seen with all rates of diphenyl methane with imidacloprid against German cockroaches (T-164 strain). Diphenyl methane alone was not toxic to German cockroaches.

Example 19

Evaluation of the Synergy of Polyphenyl Methanes with Imidacloprid Against the Argentine Ant The objective of this study was to investigate the synergistic effect of imidacloprid in combination with polyphenyl methanes on efficacy against the Argentine ant, *Linepithema humile*.

MATERIALS AND METHODS: Solutions of imidacloprid at 0.5% AI were prepared with and without tritylchloride @0.1, 1.0 and 5.0% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Ten Argentine ant workers were placed within a fluon or talc-coated PVC ring (φ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

Figure 18:
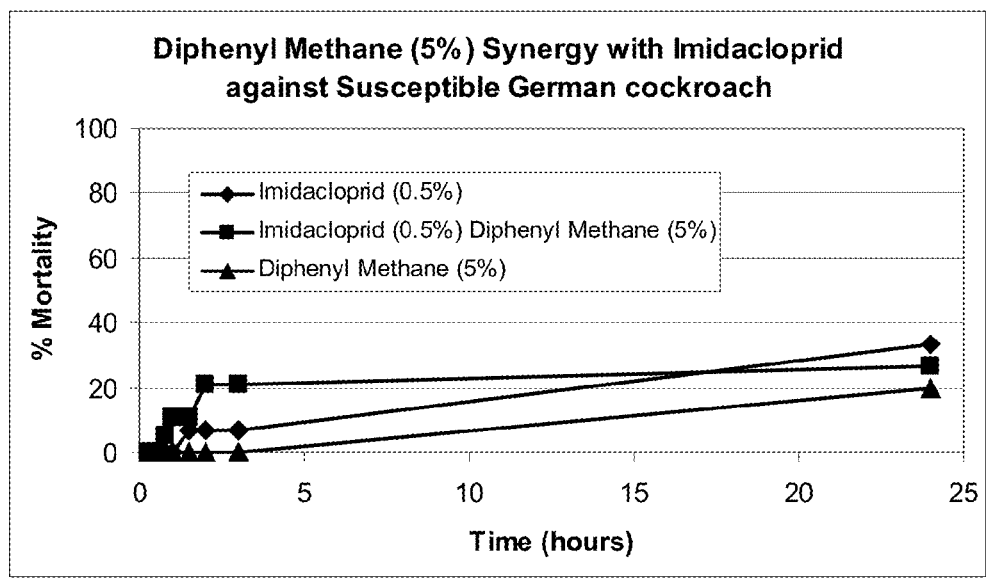

RESULTS: Table 21 and FIG. 18: Summary of imidacloprid/Diphenyl methane synergy study against German cockroach (T-164 strain)

| Treatment | Rate (g/m$^2$) | Average % Knockdown & Mortality after | | | | |
|---|---|---|---|---|---|---|
| | | 30 min | 1 hr | 2 hr | 3 hr | 24 hr |
| UTC | 0 | 0 | 0 | 0 | 0 | 6 |
| imidacloprid (0.5%) | 0.31 | 0 | 0 | 7 | 7 | 33 |
| imidacloprid (0.5%) + DPM (5%) | 0.31 + 3.11 | 0 | 11 | 21 | 21 | 26 |
| imidacloprid (0.5%) + DPM (1%) | 0.31 + 0.62 | 0 | 0 | 0 | 7 | 33 |
| imidacloprid (0.5%) + DPM (0.1%) | 0.31 + 0.06 | 0 | 0 | 0 | 0 | 27 |
| Diphenyl methane (DPM) (5%) | 0 + 3.11 | 0 | 0 | 0 | 0 | 20 |
| Diphenyl methane (DPM) (1%) | 0 + 0.62 | 0 | 0 | 0 | 0 | 6 |
| Diphenyl methane (DPM) (0.1%) | 0 + 0.06 | 0 | 0 | 0 | 0 | 8 |

Figure 19:
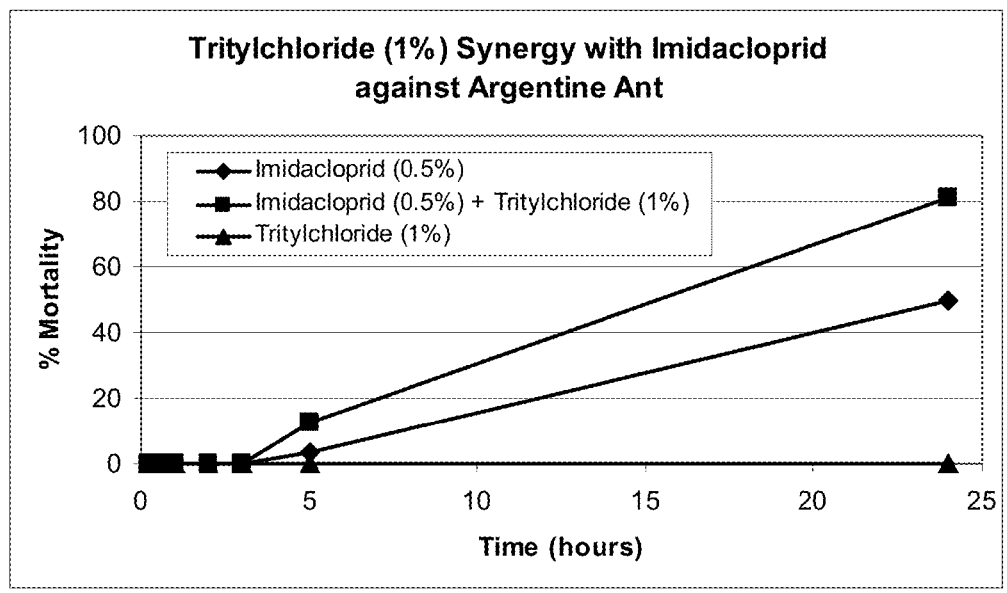

RESULTS: Table 22 and FIG. 19: Summary of imidacloprid/tritylchloride synergy study against the Argentine ant:

| Treatment | Rate (g/m²) | Average % Knockdown & Mortality after | | | | |
|---|---|---|---|---|---|---|
| | | 30 min | 1 hr | 2 hr | 5 hr | 24 hr |
| UTC | 0 | 0 | 0 | 0 | 0 | 10 |
| imidacloprid (0.5%) | 0.31 | 0 | 0 | 0 | 4 | 50 |
| imidacloprid (0.5%) + Tritylchloride (5%) | 0.31 + 3.11 | 0 | 0 | 0 | 0 | 24 |
| imidacloprid (0.5%) + Tritylchloride (1%) | 0.31 + 0.62 | 0 | 0 | 0 | 13 | 81 |
| imidacloprid (0.5%) + Tritylchloride (0.1%) | 0.31 + 0.06 | 0 | 0 | 0 | 7 | 72 |
| Tritylchloride (5%) | 0 + 3.11 | 0 | 0 | 0 | 0 | 0 |
| Tritylchloride (1%) | 0 + 0.62 | 0 | 0 | 0 | 0 | 0 |
| Tritylchloride (0.1%) | 0 + 0.06 | 0 | 0 | 0 | 0 | 7 |

SUMMARY: A synergistic effect was seen with the two lower rates of tritylchloride with imidacloprid tested against the Argentine ants. Tritylchloride alone was not toxic to the Argentine ants.

Example 20

Evaluation of Synergy of Polyphenyl Methanes with Imidacloprid Against Bait Averse/Resistant German Cockroach (T-164 Strain)

The objective of this study was to investigate the synergistic effect of imidacloprid in combination with polyphenyl methanes on efficacy against bait averse/resistant German cockroach (T-164 strain).

MATERIALS AND METHODS: Solutions of imidacloprid at 0.5% AI were prepared with and without tritylchloride @0.1, 1.0 and 5.0% in acetone. Treatments were applied using a micropipette to dispense 1 ml of test solution evenly on a 6"×6" glazed tile. Actual coverage was about 5"×5" (or 161 cm²) for easy handling. Treatments were allowed to dry overnight. Five male German cockroaches were placed within a Fluon-coated PVC ring (ϕ7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

Figure 20:
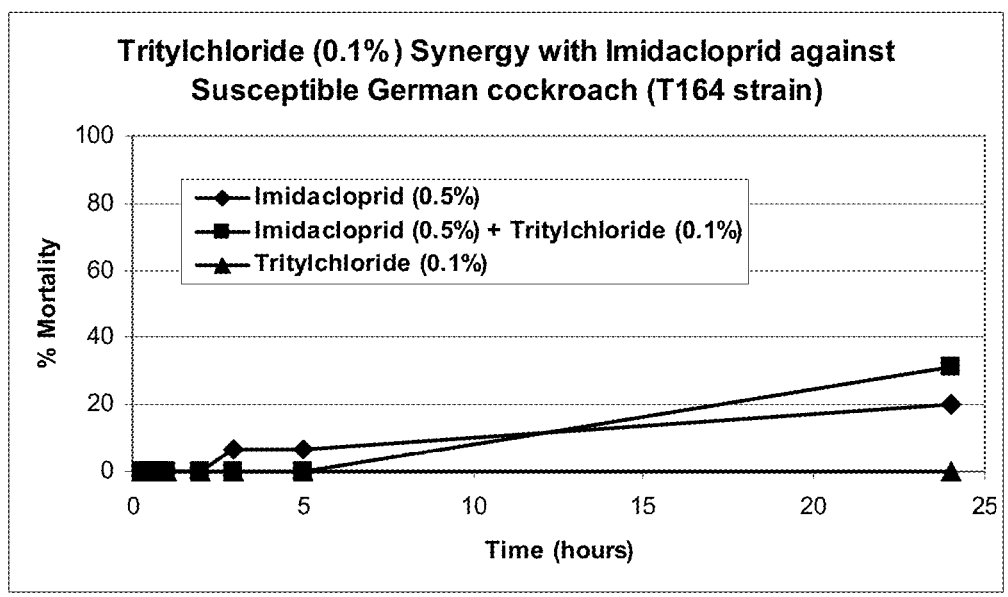

RESULTS: Table 23 and FIG. 20: Summary of imidacloprid/Tritylchloride synergy study against German cockroach (T-164 strain)

| Treatment | Rate (g/m²) | Average % Knockdown & Mortality after | | | | |
|---|---|---|---|---|---|---|
| | | 30 min | 1 hr | 2 hr | 3 hr | 24 hr |
| UTC | 0 | 0 | 0 | 0 | 0 | 0 |
| imidacloprid (0.5%) | 0.31 | 0 | 0 | 0 | 7 | 20 |
| imidacloprid (0.5%) + Tritylchloride (5%) | 0.31 + 3.11 | 0 | 0 | 0 | 0 | 0 |
| imidacloprid (0.5%) + Tritylchloride (1%) | 0.31 + 0.62 | 0 | 0 | 0 | 0 | 19 |
| imidacloprid (0.5%) + Tritylchloride (0.1%) | 0.31 + 0.06 | 0 | 0 | 0 | 0 | 31 |
| Tritylchloride (5%) | 0 + 3.11 | 0 | 0 | 0 | 0 | 0 |
| Tritylchloride (1%) | 0 + 0.62 | 0 | 0 | 0 | 0 | 0 |
| Tritylchloride (0.1%) | 0 + 0.06 | 0 | 0 | 0 | 0 | 0 |

SUMMARY: No synergistic effect was seen with all rates of trityichloride with imidacloprid against the insecticide-resistant German cockroaches (T-164 strain). Tritylchloride alone was not toxic to the resistant German cockroach strain.

Example 21

Evaluation of the Synergy of Sebacates with Imidacloprid Against Bait Averse/Resistant German Cockroach (T-164 Strain)

The objective of this study was to investigate the synergistic effect of imidacloprid in combination with sebacates on efficacy against bait averse/resistant German cockroach (T-164 strain).

MATERIALS AND METHODS: Solutions of imidacloprid at 0.5% AI were prepared with and without dibutyl sebacate (DBS) @0.1, 1.0 and 5.0% in acetone. Treatments were applied using a micropipette to dispense 1 ml of test solution evenly on a 6"×6" glazed tile. Actual coverage was about 5"×5" (or 161 cm²) for easy handling. Treatments were allowed to dry overnight. Five male German cockroaches were placed within a Fluon-coated PVC ring (ϕ7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

Figure 21:
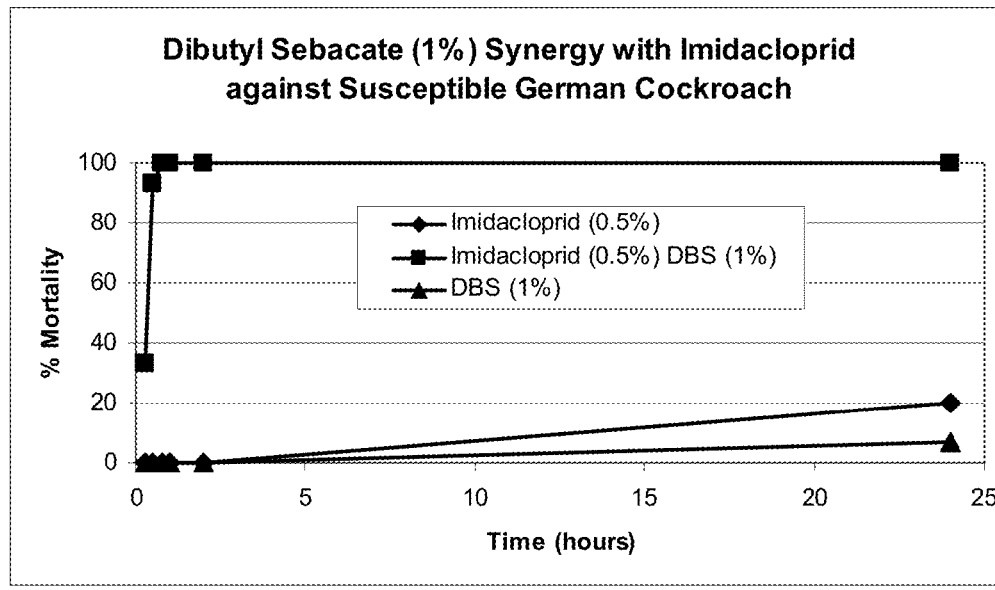

RESULTS: Table 24 and FIG. 21: Summary of
imidacloprid/Dibutyl Sebacate synergy
study against German cockroach (T-164 strain)

| Treatment | Rate (g/m²) | Average % Knockdown & Mortality after | | | | |
|---|---|---|---|---|---|---|
| | | 30 min | 45 min | 1 hr | 2 hr | 24 hr |
| UTC | 0 | 0 | 0 | 0 | 0 | 0 |
| imidacloprid (0.5%) | 0.31 | 0 | 0 | 0 | 0 | 20 |
| imidacloprid (0.5%) + DBS (5%) | 0.31 + 3.11 | 100 | 100 | 100 | 100 | 100 |
| imidacloprid (0.5%) + DBS (1%) | 0.31 + 0.62 | 93 | 100 | 100 | 100 | 100 |
| imidacloprid (0.5%) + DBS (0.1%) | 0.31 + 0.06 | 21 | 43 | 57 | 57 | 43 |
| DBS (5%) | 0 + 3.11 | 0 | 0 | 6 | 13 | 100 |
| DBS (1%) | 0 + 0.62 | 0 | 0 | 0 | 0 | 7 |
| DBS (0.1%) | 0 + 0.06 | 0 | 0 | 0 | 0 | 0 |

SUMMARY: A synergistic effect was seen with all rates of DBS with imidacloprid against the German cockroaches (T-164 strain). Some recovery was observed at the lowest rate of DBS @ 0.1% with imidacloprid at 24 hours. DBS alone was not toxic to German cockroaches, except at its highest rate (5%) tested.

Example 22

Evaluation of the Synergy of Sebacates with Imidacloprid Against the Argentine Ant The objective of this study was to investigate the synergistic effect of imidacloprid in combination with sebacates on efficacy against the Argentine ant, *Linepithema humile*.

MATERIALS AND METHODS: Solutions of imidacloprid at 0.5% AI were prepared with and without dibutyl sebacate (DBS) @0.1, 1.0 and 5.0% in acetone. Treatments were applied using a micropipette to dispense 1 ml of test solution evenly on a 6"×6" glazed tile. Actual coverage was about 5"×5" (or 161 cm²) for easy handling. Treatments were allowed to dry overnight. Ten Argentine ant workers were placed within a fluon or talc-coated PVC ring (ϕ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

Figure 22:
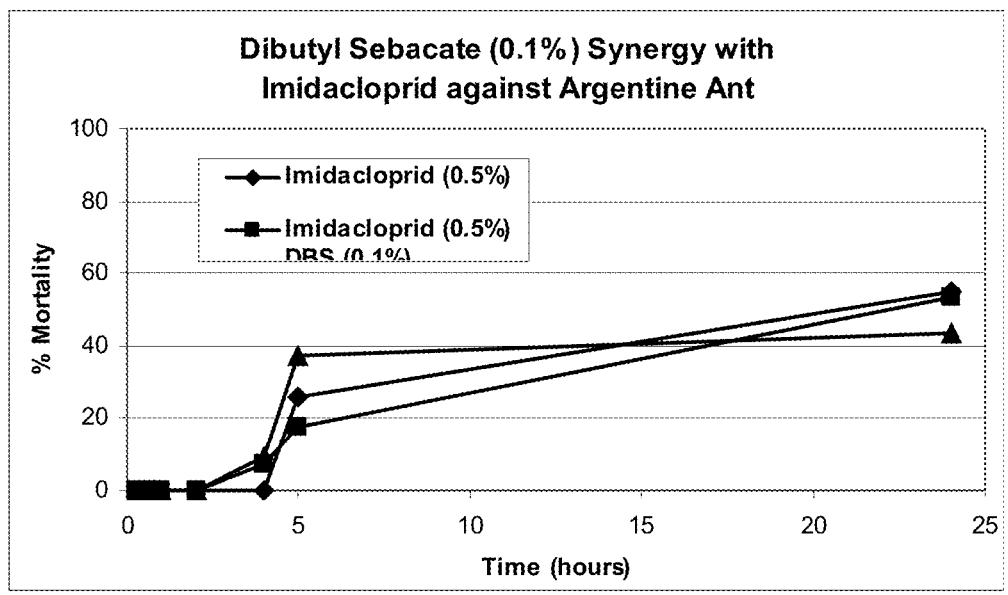

RESULTS: Table 25 and FIG. 22: Summary of
imidacloprid/Dibutyl Sebacate synergy
study against the Argentine ant:

| Treatment | Rate (g/m²) | Average % Knockdown & Mortality after | | | | |
|---|---|---|---|---|---|---|
| | | 30 min | 1 hr | 2 hr | 4 hr | 24 hr |
| UTC | 0 | 0 | 0 | 0 | 3 | 26 |
| imidacloprid (0.5%) | 0.31 | 0 | 0 | 0 | 0 | 55 |
| imidacloprid (0.5%) + DBS (5%) | 0.31 + 3.11 | 100 | 100 | 100 | 100 | 100 |
| imidacloprid (0.5%) + DBS (1%) | 0.31 + 0.62 | 0 | 0 | 0 | 47 | 81 |
| imidacloprid (0.5%) + DBS (0.1%) | 0.31 + 0.06 | 0 | 0 | 0 | 7 | 54 |
| DBS (5%) | 0 + 3.11 | 53 | 100 | 100 | 100 | 100 |
| DBS (1%) | 0 + 0.62 | 0 | 0 | 0 | 77 | 100 |
| DBS (0.1%) | 0 + 0.06 | 0 | 0 | 0 | 9 | 44 |

SUMMARY: No synergistic effect was seen with the three rates of DBS with imidacloprid tested against the Argentine ants. DBS alone was toxic to the Argentine ants, and the lower rates (0.1 & 1.0%) of DBS showed delayed toxicity.

Example 23

Evaluation of the Synergy of Combination of Compound A & Compound B with Deltamethrin Against *Aedes aegypti* Mosquito The objective of this study was to investigate the synergistic effect of deltamethrin in combination with the adjuvant on efficacy against *Aedes aegypti* mosquito.

MATERIALS AND METHODS: Aqueous solutions of 1% deltamethrin with and without an adjuvant composition, which is sold under the tradename Suspend® SC. The adjuvant is a combination of Compound A at 1% and Compound B at 0.5%. Pre-cut fiberglass screen (5"×5", or 161.3 cm²) were dipped in each treatment solution and excessive solution was allowed to drain completely (see FIG. 23a). Weight of the solution coated on the screen was then determined. The treated screen was then allowed to air-dry overnight. USDA Petri Dish Method was used as initial screening protocol (see FIG. 23b). Twenty, 4-6 day old female *Aedes aegypti* were exposed to treated window screen for 3 minutes and then moved onto a clean untreated white paper index card. Treatments were replicated a minimum of three times. Mosquito knockdown was evaluated at 3 minute intervals for the first 15 minutes and then at 5 minute intervals for the remainder of an hour. A small cotton ball with sucrose solution was added on the screen top of the Petri dish as a drinking source. Mortality was evaluated at 24 hours after exposure.

RESULTS: Table 26 and FIGS. 23a, 23b, and 23c:
Summary of deltamethrin/adjuvant
synergy study against *Aedes aegypti* mosquito

| Treatment | Rate (g/m²) | Average % Knockdown & Mortality after | | | | | |
|---|---|---|---|---|---|---|---|
| | | 3 min | 9 min | 15 min | 30 min | 60 min | 24 hr |
| UTC | 0 | 0 | 0 | 0 | 0 | 0 | 0 |
| deltamethrin (1%) | 0.48 | 0 | 0 | 0 | 27 | 84 | 100 |
| deltamethrin (1%) + adjuvant | 0.48 | 16 | 83 | 100 | 100 | 100 | 100 |
| adjuvant | 0 | 0 | 0 | 0 | 1 | 3 | 10 |

SUMMARY: Synergy between deltamethrin and adjuvant was observed at 3 minutes after exposure against *A. aegypti*. Deltamethrin in combination with adjuvant provides 100% mosquito knockdown within 15 minutes after exposure. Deltamethrin alone provides good knockdown with 100% mortality at 24 hours after exposure.

Example 24

Evaluation of the Synergy of Combination of Compound A & Compound B with Deltamethrin Against Argentine Ant

The objective of this study was to investigate the synergistic effect of deltamethrin in combination with the adjuvant on efficacy against Argentine ant, *Linepithema humile*.

MATERIALS AND METHODS: Aqueous solutions of deltamethrin at 1% AI were formulated with and without adjuvant. The adjuvant is a combination of Compound A at 1% and Compound B at 0.5%. Treatments were applied using a micropipette to dispense 1 ml of test solution on 6"×6" glazed tile. Actual coverage was about 5"×5" (or 161 cm$^2$) for easy handling. Treatments were allowed to dry overnight. Ten Argentine ant workers were placed within a fluon or talc-coated PVC ring ($\phi$7.6 cm×H 5.1 cm) under continuous exposure. Treatments were replicated a minimum of three times. Evaluations for ant knockdown/mortality were made at various intervals for 30 minutes after exposure.

RESULTS: Table 27 and FIG. 24: Summary of deltamethrin/adjuvant synergy study against Argentine ant

| Treatment | Rate (g/m$^2$) | Average % Mortality after | | | |
|---|---|---|---|---|---|
| | | 10 min | 15 min | 20 min | 30 min |
| UTC | | 0 | 0 | 0 | 0 |
| deltamethrin (1%) | 0.62 | 9 | 33 | 67 | 82 |
| deltamethrin (1%) + adjuvant | 0.62 | 47 | 94 | 100 | 100 |
| adjuvant | | 0 | 0 | 22 | 56 |

SUMMARY: A synergistic response was observed for deltamethrin and adjuvant against Argentine ant, the evaluations were terminated at 30 minutes. High mortality in the adjuvant treatment may be due to the sticky nature of the adjuvant ingredients on glazed tile. deltamethrin was formulated in water instead of acetone to treat the tiles. As a result, when the adjuvant composition dried, a sticky residue was present on the surface of the glazed tile, causing some of the ants to get stuck and die.

Example 25

Evaluation of the Synergy of Combination of Compound A & Compound B Synergy Deltamethrin Against Bait Averse/Resistant German Cockroach (IHOP strain)

The objective of this study was to investigate the synergistic effect of deltamethrin in combination with adjuvant on efficacy against bait averse/resistant German cockroach (IHOP strain), *Blattella germanica*.

MATERIALS AND METHODS: Aqueous solutions of deltamethrin at 1% AI were prepared with and without adjuvant. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm$^2$) for easy handling. Treatments were allowed to dry overnight.

Five male German cockroaches were placed within a Fluon-coated PVC ring ($\phi$7.6 cm×H 5.1 cm) under continuous exposure. A small vial cap filled with a cotton ball soaked in water was added as drinking source after 3 hours. Treatments were replicated a minimum of three times. Evaluations for cockroach knockdown/mortality were made at various intervals for 1 hour and at 24 hours after exposure.

RESULTS: Table 28 and FIG. 25: Summary of deltamethrin/adjuvant synergy study against bait averse German cockroach (IHOP strain)

| Treatment | Rate (g/m$^2$) | Average % Mortality after | | | |
|---|---|---|---|---|---|
| | | 10 min | 30 min | 60 min | 24 hr |
| UTC | | 0 | 0 | 0 | 0 |
| deltamethrin (1%) | 0.62 | 20 | 93 | 100 | 100 |
| deltamethrin (1%) + adjuvant | 0.62 | 20 | 87 | 93 | 100 |
| adjuvant | | 0 | 0 | 0 | 0 |

SUMMARY: Synergy between deltamethrin at 1% AI and adjuvant was not seen against bait averse/resistant German cockroaches (IHOP). A lower rate of deltamethrin in combination with adjuvant may produce a positive response.

Example 26

**Evaluation of the Synergy of Combination of Compound A & Compound B with Deltamethrin Against *Culex quinquefasciatus* Mosquito**

The objective of this study was to investigate the synergistic effect of deltamethrin in combination with adjuvant on efficacy against *Culex quinquefasciatus* mosquito.

MATERIALS AND METHODS: Aqueous solutions of 1% deltamethrin with and without adjuvant were prepared using product sold under the tradename Suspend® SC. The adjuvant is a combination of Compound A at 1% and Compound B at 0.5%. Pre-cut fiberglass screen (5"×5", or 161.3 cm$^2$) were dipped in each treatment solution and excessive solution was allowed to drain completely. Weight of the solution coated on the screen was then determined. The treated screen was then allowed to air-dry overnight. USDA Petri Dish Method was used as initial screening protocol. Twenty, 4-6 day old female *Culex quinquefasciatus* were exposed to treated window screen for 3 minutes and then moved onto a clean untreated white paper index card. Treatments were replicated a minimum of three times. Mosquito knockdown was evaluated at 3 minute intervals for the first 15 minutes and then at 5 minute intervals for the remainder of an hour. A small cotton ball soaked in sucrose solution was added on the screen top of the petri-dish as a drinking source. Mortality was evaluated at 24 hours after exposure.

RESULTS: Table 29 and FIG. 26: Summary of deltamethrin/adjuvant synergy study against *Culex quinquefasciatus* mosquito

| Treatment | Rate (g/m$^2$) | Average % Knockdown & Mortality after | | | | | |
|---|---|---|---|---|---|---|---|
| | | 15 min | 30 min | 45 min | 60 min | 4 hr | 24 hr |
| UTC | 0 | 0 | 0 | 0 | 0 | 0 | 0 |
| deltamethrin (1%) | 0.48 | 0 | 2 | 3 | 8 | 52 | 86 |

-continued

RESULTS: Table 29 and FIG. 26: Summary of deltamethrin/adjuvant synergy study against *Culex quinquefasciatus* mosquito

| Treatment | Rate (g/m²) | Average % Knockdown & Mortality after | | | | | |
|---|---|---|---|---|---|---|---|
| | | 15 min | 30 min | 45 min | 60 min | 4 hr | 24 hr |
| deltamethrin (1%) + adjuvant | 0.48 | 2 | 18 | 28 | 43 | 60 | 90 |
| adjuvant | | 0 | 0 | 0 | 0 | 0 | 0 |

SUMMARY: Synergy between deltamethrin and adjuvant was seen with *Culex*. Deltamethrin in combination with adjuvant increased speed of knockdown of *Culex* compared to deltamethrin alone with overall mortality being similar at 24 hours.

Example 27

Evaluation of the Synergy of Combination of Compound A & Compound B with Deltamethrin Against Odorous House Ant The objective of this study was to investigate the synergistic effect of deltamethrin in combination with adjuvant on efficacy against *Tapinoma sessile*, Odorous House ant.

MATERIALS AND METHODS: Aqueous solutions of deltamethrin at 1% AI were formulated with and without adjuvant. The adjuvant is a combination of Compound A at 1% and Compound B at 0.5%. Treatments were applied using a micropipette to dispense 1 ml of test solution on 6"×6" glazed tile (FIG. 27a). Actual coverage was about 5"×5" (or 161 cm²) for easy handling. Treatments were allowed to dry overnight. Ten Odorous House ant workers were placed within a fluon or talc-coated PVC ring (φ7.6 cm×H 5.1 cm) under continuous exposure. Treatments were replicated minimum three times. Evaluations for ant knockdown/mortality were made at various intervals for 2 hours after exposure.

RESULTS: Table 30 and FIGS. 27a and 27b: Summary of deltamethrin/adjuvant synergy study against Odorous House ant

| Treatment | Rate (g/m²) | Average % Mortality after | | | |
|---|---|---|---|---|---|
| | | 20 min | 60 min | 90 min | 2 hr |
| UTC | | 0 | 0 | 0 | 0 |
| deltamethrin (1%) | 0.62 | 43 | 80 | 90 | 93 |
| deltamethrin (1%) + adjuvant | 0.62 | 13 | 45 | 58 | 65 |
| adjuvant | | 10 | 21 | 25 | 27 |

SUMMARY: Evaluations were terminated after 2 hours due to the lack of synergy between deltamethrin and adjuvant against Odorous House ants.

Example 28

Evaluation of Synergy of Combination of Compound A & Compound B with Deltamethrin Against Red Imported Fire Ant (RIFA)

The objective of this study was to investigate the synergistic effect of deltamethrin in combination with adjuvant on efficacy against Red Imported Fire ant (RIFA), *Solenopsis invicta*.

MATERIALS AND METHODS: Aqueous solutions of deltamethrin at 1% AI were formulated with and without adjuvant. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm²) for easy handling. Treatments were allowed to dry overnight. Ten Red Imported Fire ant workers were placed within a fluon or talc-coated PVC ring (φ7.6 cm×H 5.1 cm) under continuous exposure. Treatments were replicated minimum three times. Evaluations for ant knockdown/mortality were made at various intervals for 60 minutes after exposure.

RESULTS: Table 31 and FIG. 28: Summary of deltamethrin/adjuvant synergy study against RIFA

| Treatment | Rate (g/m²) | Average % Mortality after | | | |
|---|---|---|---|---|---|
| | | 10 min | 20 min | 40 min | 60 min |
| UTC | | 0 | 0 | 0 | 0 |
| deltamethrin (1%) | 0.62 | 37 | 100 | 100 | 100 |
| deltamethrin (1%) + adjuvant | 0.62 | 57 | 100 | 100 | 100 |
| adjuvant | | 0 | 0 | 0 | 0 |

SUMMARY: Synergy was not seen with deltamethrin at 1% AI and adjuvant against RIFA. It is believed that a lower rate of deltamethrin in combination with adjuvant will produce a positive response.

Example 29

Evaluation of Synergy of Combination of Compound A & Compound B with Deltamethrin Against Susceptible German Cockroach (Monheim Strain)

The objective of this study was to investigate the synergistic effect of deltamethrin in combination with adjuvant on efficacy against susceptible/normal German cockroach (Monheim), *Blattella germanica*.

MATERIALS AND METHODS: Aqueous solutions of deltamethrin at 1% AI were prepared with and without adjuvant. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm²) for easy, handling. Treatments were allowed to dry overnight. Five male German cockroaches were placed within a Fluon-coated PVC ring (φ7.6 cm×H 5.1 cm) under continuous exposure. Treatments were replicated a minimum of three times. Evaluations for cockroach knockdown/mortality were made at various intervals for 20 minutes after exposure.

RESULTS: Table 32 and FIG. 29: Summary of deltamethrin/adjuvant synergy study against German cockroach (Monheim strain)

| Treatment | Rate (g/m²) | Average % Mortality after | | | |
|---|---|---|---|---|---|
| | | 4 min | 8 min | 12 min | 20 min |
| UTC | | 0 | 0 | 0 | 0 |
| deltamethrin (1%) | 0.62 | 27 | 100 | 100 | 100 |
| deltamethrin (1%) + adjuvant | 0.62 | 13 | 100 | 100 | 100 |
| adjuvant | | 0 | 0 | 0 | 0 |

SUMMARY: Synergy between deltamethrin at 1% AI and adjuvant was not seen against susceptible/normal German cockroaches (Monheim). A lower rate of deltamethrin in combination with adjuvant may produce a positive response.

Example 30

Evaluation of Synergy of Combination of Compound A & Compound B Synergy Thiamethoxam Against *Aedes aegypti* Mosquito The objective of this study was to investigate the synergistic effect of thiamethoxam in combination with adjuvant on efficacy against *Aedes aegypti* mosquitoes.

MATERIALS AND METHODS: A solution of thiamethoxam at 1, 0.1 and 0.01% AI were prepared with and without adjuvant in acetone. The adjuvant is a combination of Compound A at 1% and Compound B at 0.5%. Treatments were applied using a micropipette to dispense 1 ml of test solution evenly on 6"×6" glazed tile. Actual coverage was about 5"×5" (or 161 cm$^2$) for easy handling. Treatments were allowed to dry overnight. USDA Petri Dish Method was used as initial screening protocol. Twenty, 4-6 day old female *Aedes aegypti* mosquitoes were exposed to each treatment for 3 minutes and then moved to a clean untreated white paper index card. Treatments were replicated a minimum of three times. Mosquito knockdown was evaluated at various intervals through 7 hours after exposure. A small cotton ball soaked in sucrose solution was added on the screen top of the petri-dish as a drinking source. Mortality was evaluated at 24 hours after exposure.

RESULTS: Table 33 (no figure): Summary of thiamethoxam/adjuvant synergy study against *Aedes aegypti* mosquito

| Treatment | Rate (g/m$^2$) | Average % Knockdown & Mortality after | | | |
|---|---|---|---|---|---|
| | | 2 hr | 3 hr | 7 hr | 24 hr |
| UTC | | 0 | 0 | 0 | 0 |
| Thiamethoxam (1%) | 0.62 | 2 | 2 | 4 | 4 |
| Thiamethoxam (1%) + adjuvant | 0.62 | 4 | 5 | 5 | 5 |
| Thiamethoxam (0.1%) | 0.06 | 0 | 0 | 0 | 0 |
| Thiamethoxam (0.1%) + adjuvant | 0.06 | 0 | 0 | 0 | 2 |
| Thiamethoxam (0.01%) | 0.006 | 0 | 0 | 0 | 0 |
| Thiamethoxam (0.01%) + adjuvant | 0.006 | 2 | 6 | 13 | 13 |
| adjuvant | | 2 | 2 | 2 | 2 |

SUMMARY: No activity was observed with thiamethoxam and adjuvant against *Aedes aegypti* mosquito.

Example 31

Evaluation of Synergy of Combination of Compound A & Compound B with Thiamethoxam Against Argentine Ant The objective of this study was to investigate the synergistic effect of thiamethoxam in combination with adjuvant on efficacy against Argentine ant, *Linepithema humile*.

MATERIALS AND METHODS: Solutions of thiamethoxam at 1, 0.1 and 0.01% AI were prepared with and without adjuvant in acetone. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm$^2$) for easy handling. Treatments were allowed to dry overnight. Ten Argentine ant workers were placed within a talc-coated PVC ring ($\phi$7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

RESULTS: Table 34 and FIG. 30: Summary of thiamethoxam/adjuvant synergy study against Argentine ant

| Treatment | Rate (g/m$^2$) | Average % Mortality after | | | | |
|---|---|---|---|---|---|---|
| | | 15 min | 60 min | 1 hr | 3 hr | 21 hr |
| UTC | | 0 | 0 | 0 | 0 | 25 |
| Thiamethoxam (1%) | 0.62 | 3 | 6 | 22 | 34 | 100 |
| Thiamethoxam (1%) + adjuvant | 0.62 | 0 | 0 | 73 | 89 | 100 |
| Thiamethoxam (0.1%) | 0.06 | 12 | 21 | 36 | 46 | 100 |
| Thiamethoxam (0.1%) + adjuvant | 0.06 | 3 | 21 | 79 | 97 | 100 |
| Thiamethoxam (0.01%) | 0.006 | 0 | 3 | 13 | 19 | 100 |
| Thiamethoxam (0.01%) + adjuvant | 0.006 | 0 | 0 | 55 | 77 | 100 |
| adjuvant | | 0 | 0 | 12 | 29 | 88 |

SUMMARY: All rates of thiamethoxam in combination with adjuvant showed a synergistic effect against Argentine ant for speed of knockdown (FIG. 30). Overall ant mortality was equivalent against thiamethoxam with or without adjuvant. Synergy was still evident even though adjuvant-only treatment had high ant mortality.

Example 32

Evaluation of Synergy of Combination of Compound A & Compound B with Thiamethoxam Against Odorous House Ant The objective of this study was to investigate the synergistic effect of thiamethoxam in combination with adjuvant on efficacy against Odorous House ant, *Tapinoma sessile*.

MATERIALS AND METHODS: Solutions of thiamethoxam at 1, 0.1 and 0.01% AI were prepared with and without adjuvant in acetone. The adjuvant is a combination of Compound A at 1% and Compound B at 0.5%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Ten odorous house ant workers were placed within a talc-coated PVC ring ($\phi$7.6 cm×H 5.1 cm) under continuous exposure. A small vial cap filled with a cotton ball soaked in water was added as a drinking source after 3 hours. Treatments were replicated minimum three times. Evaluations for ant knockdown/mortality were made at various intervals and at 24 hours after exposure.

RESULTS: Table 35 and FIG. 31: Summary of thiamethoxam/adjuvant synergy study against Odorous House ant

| Treatment | Rate (g/m²) | Average % Knockdown & Mortality after | | | | |
|---|---|---|---|---|---|---|
| | | 15 min | 30 min | 60 min | 2 hr | 20 hr |
| UTC | 0 | 0 | 0 | 0 | 0 | 10 |
| Thiamethoxam (1%) | 0.62 | 0 | 0 | 0 | 21 | 65 |
| Thiamethoxam (1%) + adjuvant | 0.62 | 0 | 0 | 7 | 13 | 70 |
| Thiamethoxam (0.1%) | 0.06 | 0 | 0 | 0 | 3 | 33 |
| Thiamethoxam (0.1%) + adjuvant | 0.06 | 0 | 4 | 11 | 32 | 61 |
| Thiamethoxam (0.01%) | 0.006 | 0 | 0 | 0 | 9 | 71 |
| Thiamethoxam (0.01%) + adjuvant | 0.006 | 3 | 9 | 23 | 31 | 60 |
| adjuvant | 0 | 0 | 0 | 0 | 0 | 22 |

SUMMARY: Thiamethoxam at 0.1% in combination with adjuvant showed an increase in speed of knockdown and efficacy compared to thiamethoxam alone (FIG. 31). No treatment reached 100% control of Odorous House ant.

Example 33

Evaluation of Synergy of Combination of Compound A & Compound B with Thiamethoxam Against Susceptible German Cockroach (Monheim Strain)

The objective of this study was to investigate the synergistic effect of thiamethoxam in combination with adjuvant on efficacy against susceptible/normal German cockroach strain (Monheim strain).

MATERIALS AND METHODS: Solutions of thiamethoxam at 1.0, 0.1 and 0.01% AI were prepared with and without adjuvant in acetone. The adjuvant is a combination of Compound A at 1% and Compound B at 0.5%. Treatments were applied using a micropipette to dispense 1 ml of test solution evenly on a 6"×6" glazed tile. Actual coverage was about 5"×5" (or 161 cm²) for easy handling. Treatments were allowed to dry overnight. Five male German cockroaches were placed within a talc-coated PVC ring (ϕ7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

RESULTS: Table 36 and FIG. 32: Summary of thiamethoxam/adjuvant synergy study against German cockroach (Monheim)

| Treatment | Rate (g/m²) | Average % Knockdown & Mortality after | | | | |
|---|---|---|---|---|---|---|
| | | 30 min | 60 min | 90 min | 3 hr | 24 hr |
| UTC | 0 | 0 | 0 | 0 | 0 | 7 |
| Thiamethoxam (1%) | 0.62 | 13 | 73 | 80 | 93 | 100 |
| Thiamethoxam (1%) + adjuvant | 0.62 | 60 | 100 | 100 | 100 | 100 |
| Thiamethoxam (0.1%) | 0.06 | 7 | 73 | 93 | 100 | 100 |
| Thiamethoxam (0.1%) + adjuvant | 0.06 | 7 | 87 | 100 | 100 | 100 |
| Thiamethoxam (0.01%) | 0.006 | 13 | 67 | 87 | 100 | 100 |
| Thiamethoxam (0.01%) + adjuvant | 0.006 | 7 | 53 | 93 | 100 | 100 |
| adjuvant | 0 | 0 | 0 | 0 | 0 | 7 |

SUMMARY: Thiamethoxam at 1% in combination with adjuvant showed a synergistic effect against susceptible German cockroach for speed of knockdown (FIG. 32). At 3 hours after exposure, cockroach knockdown/mortality was similar with and without adjuvant. The lower rates of thiamethoxam showed no synergy with the adjuvant Example 34

Evaluation of Synergy of Combination of Compound A & Compound B with Resmethrin Against *Aedes aegypti* Mosquito The objective of this study was to investigate the synergistic effect of resmethrin in combination with adjuvant on efficacy against *Aedes aegypti* mosquitoes.

MATERIALS AND METHODS: Solutions of resmethrin at 1 and 0.5% AI were prepared with and without adjuvant in acetone. The adjuvant is a combination of Compound A at 1% and Compound B at 0.5%. Treatments were applied using a micropipette to dispense 1 ml of test solution evenly on 6"×6" glazed tile. Actual coverage was about 5"×5" (or 161 cm²) for easy handling. Due to the extremely short half life of resmethrin exposed to light, treatments were covered with aluminum foil and placed in a dark room to dry (2-3 hours). USDA Petri Dish Method was used as initial screening protocol. Twenty, 4-6 day old female *Aedes aegypti* mosquitoes were exposed to each treatment for 3 minutes and then moved to a clean untreated white paper index card. Treatments were replicated a minimum of three times. Mosquito knockdown was evaluated at 3 minute intervals for the first 15 minutes and then at 5 minute intervals for the remainder of an hour. A small cotton ball soaked in sucrose solution was added on the screen top of the petri-dish as a drinking source. Mortality was evaluated at 24 hours after exposure.

RESULTS: Table 37 and FIG. 33: Summary of resmethrin/adjuvant synergy study against *Aedes aegypti* mosquito

| Treatment | Rate (g/m²) | Average % Knockdown & Mortality after | | | | |
|---|---|---|---|---|---|---|
| | | 3 min | 15 min | 30 min | 60 min | 24 hr |
| UTC | 0 | 0 | 0 | 0 | 0 | 2 |
| Resmethrin (1%) | 0.62 | 66 | 100 | 100 | 100 | 100 |
| Resmethrin (1%) + adjuvant | 0.62 | 26 | 65 | 66 | 71 | 71 |

RESULTS: Table 37 and FIG. 33: Summary of
resmethrin/adjuvant synergy study
against *Aedes aegypti* mosquito

| | | Average % Knockdown & Mortality after | | | | |
|---|---|---|---|---|---|---|
| Treatment | Rate (g/m$^2$) | 3 min | 15 min | 30 min | 60 min | 24 hr |
| Resmethrin (0.5%) | 0.31 | 0 | 0 | 0 | 0 | 8 |
| Resmethrin (0.5%) + adjuvant | 0.31 | 25 | 97 | 100 | 100 | 100 |

SUMMARY: Although an antagonistic effect was seen with resmethrin at 1% in combination with adjuvant, an increase in efficacy was seen with resmethrin at 0.5% AI and adjuvant against *Aedes aegypti* (FIG. 33) Resmethrin at 0.5% AI alone did not provide mosquito knockdown; however, the addition of adjuvant caused a significant increase in efficacy to nearly 100% in 15 minutes.

Example 35

Evaluation of Synergy of Combination of Compound A & Compound B with Resmethrin Against *Culex quinquefasciatus* Mosquito The objective of this study was to investigate the synergistic effect of Resmethrin in combination with adjuvant on efficacy against *Culex quinquefasciatus* mosquitoes.

MATERIALS AND METHODS: Solutions of resmethrin at 1 and 0.5% AI were prepared with and without adjuvant in acetone. The adjuvant is a combination of Compound A at 1% and Compound B at 0.5%. Treatments were applied using a micropipette to dispense 1 ml of test solution evenly on 6"×6" glazed tile. Actual coverage was about 5"×5" (or 161 cm$^2$) for easy handling. Due to the extremely short half life of resmethrin exposed to light, treatments were covered with aluminum foil and placed in a dark room to dry (2-3 hours). USDA Petri Dish Method was used as initial screening protocol. Twenty, 4-6 day old female *Culex quinquefasciatus* mosquitoes were exposed to each treatment for 3 minutes and then moved to a clean untreated white paper index card. Treatments were replicated a minimum of three times. Mosquito knockdown was evaluated at 3 minute intervals for the first 15 minutes and then at 5 minute intervals for the remainder of an hour. A small cotton ball soaked in sucrose solution was added on the screen top of the petri-dish as a drinking source after the 2 hour evaluation. Mortality was evaluated at 24 hours after exposure.

SUMMARY: Although some mosquito recovery occurred with resmethrin at 0.5% AI and adjuvant, synergy was still evident (FIG. 34).

Example 36

Evaluation of Synergy of Combination of Compound A & Compound B with Permethrin Against *Aedes aegypti* Mosquito The objective of this study was to investigate the synergistic effect of permethrin in combination with adjuvant on efficacy against *Aedes aegypti* mosquito.

MATERIALS AND METHODS: Several rates of permethrin without adjuvant were prepared using product sold under the tradename Permanone® 40 to determine an effective rate against *Aedes aegypti* mosquitoes. After determining an effective rate range, aqueous solutions of permethrin at 1.25, 1.0 and 0.05% AI were prepared with and without adjuvant. The adjuvant is a combination of Compound A at 1% and Compound B at 0.5%. Pre-cut fiberglass screens (5"×5" or 161.3 cm$^2$) were dipped in each treatment solution allowing excessive solution to drain completely. Weight of the solution coated on the screen was then determined. The treated screen was then allowed to air-dry overnight. USDA Petri Dish Method was used as initial screening protocol (see photo, right). Twenty, 4-6 day old female *Aedes aegypti* were exposed to treated window screen for 3 minutes and then moved to a clean untreated white paper index card. Treatments were replicated a minimum of three times. Mosquito knockdown was evaluated at 3 minute intervals for the first 15 minutes and then at 5 minute intervals for the remainder of an hour. A small cotton ball with sucrose solution was added on the screen top of the petri-dish as a drinking source. Mortality was evaluated at 24 hours after exposure.

RESULTS: Table 38 and FIG. 34: Summary of Resmethrin/adjuvant
synergy study against *Culex quinquefasciatus* mosquito

| | | Average % Knockdown & Mortality after | | | | | |
|---|---|---|---|---|---|---|---|
| Treatment | Rate (g/m$^2$) | 3 min | 15 min | 30 min | 60 min | 2 hr | 24 hr |
| UTC | | 0 | 0 | 0 | 0 | 0 | 0 |
| Resmethrin (1%) | 0.62 | 0 | 2 | 13 | 11 | 2 | 4 |
| Resmethrin (1%) + adjuvant | 0.62 | 0 | 2 | 2 | 2 | 2 | 0 |
| Resmethrin (0.5%) | 0.31 | 0 | 0 | 0 | 0 | 0 | 0 |
| Resmethrin (0.5%) + adjuvant | 0.31 | 2 | 49 | 53 | 55 | 51 | 34 |

RESULTS: Tables 39 and 40 and FIG. 35: Summary of Permethrin without adjuvant against *Aedes aegypti* mosquito

| Treatment | Rate (g/m²) | Average % Knockdown & Mortality after | | | | | |
|---|---|---|---|---|---|---|---|
| | | 3 min | 9 min | 15 min | 30 min | 60 min | 24 hr |
| UTC | 0 | 0 | 0 | 0 | 0 | 0 | 0 |
| Permethrin (5%) | 2.4 | 75 | 100 | 100 | 100 | 100 | 100 |
| Permethrin (2.5%) | 1.2 | 56 | 100 | 100 | 100 | 100 | 100 |
| Permethrin (1.75%) | 0.84 | 40 | 95 | 100 | 100 | 100 | 100 |
| Permethrin (1.5%)* | 0.72 | 0 | 0 | 2 | 2 | 3 | 16 |
| Permethrin (1.25%)* | 0.60 | 46 | 71 | 71 | 72 | 79 | 82 |
| Permethrin (1.0%) | 0.48 | 0 | 2 | 2 | 5 | 18 | 34 |
| Permethrin (0.5%) | 0.24 | 0 | 0 | 0 | 0 | 0 | 9 |
| Permethrin (0.1%) | 0.05 | 0 | 0 | 0 | 0 | 0 | 5 |

*Possible error with dilution of Permethrin at 1.5% AI and/or 1.25% AI.

TABLE 40

(no figure): Summary of Permethrin/adjuvant study against *Aedes aegypti* mosquito

| Treatment | Rate (g/m²) | Average % Knockdown & Mortality after | | | | | |
|---|---|---|---|---|---|---|---|
| | | 3 min | 9 min | 15 min | 30 min | 60 min | 24 hr |
| UTC | 0 | 0 | 0 | 0 | 0 | 0 | 0 |
| Permethrin (1.25%) | 0.60 | 0 | 0 | 2 | 2 | 3 | 7 |
| Permethrin (1.25%) + adjuvant | 0.60 | 0 | 19 | 31 | 40 | 47 | 50 |
| Permethrin (1.0%) | 0.48 | 2 | 2 | 2 | 4 | 13 | 28 |
| Permethrin (1.0%) + adjuvant | 0.48 | 0 | 3 | 12 | 44 | 64 | 64 |
| Permethrin (0.5%) | 0.24 | 0 | 1 | 1 | 0 | 0 | 6 |
| Permethrin (0.5%) + adjuvant | 0.24 | 3 | 41 | 80 | 95 | 100 | 100 |
| adjuvant | | 0 | 0 | 0 | 0 | 0 | 0 |

SUMMARY: A synergistic effect was seen with permethrin and adjuvant at all three rates tested; however, permethrin at 0.5% AI with adjuvant showed the greatest increase in mosquito knockdown and mortality.

Example 37

Evaluation of Synergy of Combination of Compound A & Compound B with Permethrin Against Argentine Ant The objective of this study was to investigate the synergistic effect of permethrin in combination with adjuvant on efficacy against Argentine ant, *Linepithema humile*.

MATERIALS AND METHODS: Aqueous solutions of permethrin at 0.5% AI were prepared with and without adjuvant. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm²) for easy handling. Treatments were allowed to dry overnight. Ten Argentine ant workers were placed within a fluon or talc-coated PVC ring (φ7.6 cm×H 5.1 cm) under continuous exposure. Treatments were replicated a minimum of three times. Evaluations for ant knockdown/mortality were made at 5 minute intervals for 20 minutes after exposure.

RESULTS: Table 41 and FIG. 36: Summary of permethrin/adjuvant synergy study against Argentine ant

| Treatment | Rate (g/m²) | Average % Mortality after | | | |
|---|---|---|---|---|---|
| | | 5 min | 10 min | 15 min | 20 min |
| UTC | | 0 | 0 | 0 | 0 |
| Permethrin (0.5%) | 0.31 | 58 | 100 | 100 | 100 |
| Permethrin (0.5%) + adjuvant | 0.31 | 78 | 100 | 100 | 100 |
| adjuvant | | 0 | 0 | 0 | 0 |

SUMMARY: Evaluations were terminated at 20 minutes due to 100% ant mortality. No significant difference was seen between permethrin alone and permethrin with adjuvant (FIG. 36). It is believed that lower rates of permethrin can be used synergistically with an adjuvant, likely functioning, in this instance, as free radical stabilizers, and this will show comparable efficacy as higher rates of permethrin in the absence of such free radical stabilizers.

Example 38

Evaluation of Synergy of Combination of Compound A & Compound B with Permethrin Against Bait Averse/Resistant German Cockroach (IHOP Strain)

The objective of this study was to investigate the synergistic effect of permethrin in combination with adjuvant on efficacy against bait averse/resistant German cockroach (IHOP strain), *Blattella germanica*.

MATERIALS AND METHODS: Aqueous solutions of permethrin at 0.5% AI were prepared with and without adjuvant. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm$^2$) for easy handling. Treatments were allowed to dry overnight. Five male German cockroaches were placed within a Fluon-coated PVC ring ($\phi$7.6 cm×H 5.1 cm) under continuous exposure. Evaluations for cockroach knockdown/mortality were made at various intervals and at 60 minutes after exposure.

RESULTS: Table 42 and FIG. 37: Summary of Permethrin/adjuvant synergy study against bait averse German cockroach (IHOP)

| Treatment | Rate (g/m$^2$) | Average % Mortality after | | | |
|---|---|---|---|---|---|
| | | 10 min | 20 min | 40 min | 60 min |
| UTC | | 0 | 0 | 0 | 0 |
| Permethrin (0.5%) | 0.31 | 40 | 87 | 93 | 100 |
| Permethrin (0.5%) + adjuvant | 0.31 | 20 | 87 | 100 | 100 |
| adjuvant | | 0 | 0 | 0 | 0 |

SUMMARY: Permethrin is very fast acting against a bait adverse strain of German cockroaches (IHOP), with or without added adjuvant (see FIG. 37). In situations such as this, where the insecticidal agent works very quickly, presumably by quickly penetrating the insect cuticle even in the absence of an adjuvant (permethrin referred to in Table 1 as fast with a Log P of 6.1), synergism may not be observed readily at all concentrations. It is believed that by using the adjuvant, in this case a free radical stabilizer, one can achieve high mortality with lower rates of permethrin, compared to using permethrin alone, against bait averse/resistant German cockroaches.

Example 39

Evaluation of Synergy of Combination of Compound A & Compound B with Permethrin Against Odorous House Ant The objective of this study was to investigate the synergistic effect of permethrin in combination with adjuvant on efficacy against Odorous House ant, *Tapinoma sessile*.

MATERIALS AND METHODS: Aqueous solutions of permethrin at 0.5% AI were prepared with and without adjuvant. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm$^2$) for easy handling. Treatments were allowed to dry overnight. Ten Odorous House ant workers were placed within a fluon or talc-coated PVC ring ($\phi$7.6 cm×H 5.1 cm) under continuous exposure. Treatments were replicated minimum three times. Evaluations for ant knockdown/mortality were made at 5 minute intervals for 60 minutes after exposure.

RESULTS: Table 43 and FIG. 38: Summary of Permethrin/adjuvant synergy study against Odorous House ant

| Treatment | Rate (g/m$^2$) | Average % Mortality after | | | |
|---|---|---|---|---|---|
| | | 10 min | 20 min | 30 min | 60 min |
| UTC | | 0 | 0 | 0 | 0 |
| Permethrin (0.5%) | 0.31 | 13 | 50 | 93 | 100 |
| Permethrin (0.5%) + adjuvant | 0.31 | 97 | 100 | 100 | 100 |
| adjuvant | | 0 | 0 | 0 | 0 |

SUMMARY: Permethrin at 0.5% AI with adjuvant showed synergy against Odorous House ants (FIG. 38). Evaluations were terminated after 60 minutes due to 100% ant control.

Example 40

Evaluation of Synergy of Combination of Compound A & Compound B with Permethrin Against Red Imported Fire Ant The objective of this study was to investigate the synergistic effect of permethrin in combination with adjuvant on efficacy against Red Imported Fire ant, *Solenopsis invicta*.

MATERIALS AND METHODS: Aqueous solutions of permethrin at 0.5% AI were prepared with and without adjuvant. The adjuvant is a combination of Compound A at 1% and Compound B at 0.5%. Treatments were applied using a micropipette to dispense 1 ml of treatment solution on 6"×6" glazed tile. Actual coverage was about 5"×5" (or161 cm$^2$) for easy handling. Treatments were allowed to dry overnight. Ten Red Imported Fire ant workers were placed within a fluon or talc-coated PVC ring ($\phi$7.6 cm×H 5.1 cm) under continuous exposure. Treatments were replicated a minimum of three times. Evaluations for ant knockdown/mortality were made at various intervals and at 60 minutes after exposure.

RESULTS: Table 44 and FIG. 39: Summary of Permethrin/adjuvant synergy study against RIFA

| Treatment | Rate (g/m$^2$) | Average % Mortality after | | | |
|---|---|---|---|---|---|
| | | 5 min | 15 min | 30 min | 60 min |
| UTC | | 0 | 3 | 3 | 3 |
| Permethrin (0.5%) | 0.31 | 43 | 100 | 100 | 100 |
| Permethrin (0.5%) + adjuvant | 0.31 | 93 | 100 | 100 | 100 |
| adjuvant | | 3 | 3 | 7 | 7 |

SUMMARY: Permethrin is active against Red Imported Fire ants, even in the absence of an adjuvant that works as a free radical stabilizer. Thus, the synergistic effect is minimal (see FIG. 39). One can see that near 100% mortality was achieved in about 6 minutes when the adjuvant was added, versus about 13 minutes in the absence of the adjuvant. Due to 100% ant mortality, evaluations were terminated after 60 minutes. It is believed that lower application rates of permethrin can be used, when combined with free radical stabilizers, to achieve the same results.

Example 41

Evaluation of Synergy of Combination of Compound A & Compound B with Permethrin Against Susceptible German Cockroach (Monheim Strain)

The objective of this study was to investigate the synergistic effect of permethrin in combination with adjuvant on efficacy against susceptible/normal German cockroach (Monheim strain), *Blattella germanica*.

MATERIALS AND METHODS: Aqueous solutions of permethrin at 0.5% AI were prepared with and without adjuvant. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm$^2$) for easy handling. Treatments were allowed to dry overnight. Five male German cockroaches were placed within a Fluon-coated PVC ring ($\phi$7.6 cm×H 5.1 cm) under continuous exposure. Treatments were replicated a minimum of three times. Evaluations for cockroach knockdown/mortality were made at 10 minute intervals for 30 minutes and at 4 hours after exposure.

RESULTS: Table 45 and FIG. 40: Summary of Permethrin/adjuvant synergy study against bait normal German cockroach (Monheim)

| Treatment | Rate (g/m$^2$) | Average % Mortality after | | | |
|---|---|---|---|---|---|
| | | 10 min | 20 min | 30 min | 4 hr |
| UTC | | 0 | 0 | 0 | 0 |
| Permethrin (0.5%) | 0.31 | 100 | 100 | 100 | 100 |
| Permethrin (0.5%) + adjuvant | 0.31 | 100 | 100 | 100 | 100 |
| adjuvant | | 0 | 0 | 0 | 0 |

SUMMARY: As shown in FIG. 40, permethrin was effective against susceptible/normal German cockroach strain (Monheim), even in the absence of the added free radical stabilizers. Although this rate of permethrin appears too high to show synergy with adjuvant against a susceptible/normal German cockroach strain (Monheim), it is believed that lower rates of permethrin can be used, in combination with an adjuvant acting as a free radical stabilizers, than permethrin alone, to achieve a comparable mortality rate in a comparable amount of time.

Example 42

Evaluation of Synergy of Compound A with Fipronil Against Argentine Ant

The objective of this study was to investigate the synergistic effect of fipronil in combination with Compound A on efficacy against Argentine ant, *Linepithema humile*.

MATERIALS AND METHODS: Solutions of fipronil at 0.01 and 0.001% AI were prepared with and without Compound A at 1, 0.1, and 0.01% in acetone. Treatments were applied using a micropipette to dispense 1 ml of treatment solution on 6"×6" glazed tile. Actual coverage was about 5"×5" (or 161 cm$^2$) for easy handling. Treatments were allowed to dry overnight. Ten Argentine ant workers were placed within a talc-coated PVC ring ($\phi$7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

RESULTS: Table 46, Trial 1, see also FIG. 41 Summary of Fipronil/Compound A synergy study against Argentine ant

| Treatment | Rate (g/m$^2$) | Average % Mortality after | | | | | | |
|---|---|---|---|---|---|---|---|---|
| | | 5 min | 15 min | 30 min | 60 min | 2 hr | 4 hr | 24 hr |
| UTC | | 0 | 0 | 0 | 0 | 0 | 0 | 21 |
| Fipronil (.01%) | 0.0062 | 0 | 0 | 0 | 0 | 0 | 47 | 100 |
| Fipronil (.01%) + Compound A (1%) | 0.0062 | 10 | 76 | 100 | 100 | 100 | 100 | 100 |
| Fipronil (.01%) + Compound A (0.1%) | 0.0062 | 0 | 0 | 0 | 0 | 29 | 100 | 100 |
| Fipronil (.01%) + Compound A (0.01%) | 0.0062 | 0 | 0 | 0 | 0 | 0 | 100 | 100 |
| Fipronil (.001%) | 0.00062 | 0 | 0 | 0 | 0 | 0 | 74 | 100 |
| Fipronil (.001%) + Compound A (1%) | 0.00062 | 10 | 81 | 100 | 100 | 100 | 100 | 100 |
| Fipronil (.001%) + Compound A (0.1%) | 0.00062 | 0 | 0 | 0 | 0 | 0 | 61 | 100 |
| Fipronil (.001%) + Compound A (0.01%) | 0.00062 | 0 | 0 | 0 | 0 | 0 | 93 | 100 |
| Compound A (1%) | 0 | 33 | 100 | 100 | 100 | 100 | 100 | 100 |
| Compound A (0.01%) | 0 | 0 | 0 | 0 | 0 | 0 | 0 | 13 |

Trial 2, Table 47, see FIG. 41: Summary of Fipronil/Compound A synergy study against Argentine ant

| Treatment | Rate (g/m$^2$) | Average % Mortality after | | | | | | |
|---|---|---|---|---|---|---|---|---|
| | | 5 min | 15 min | 30 min | 60 min | 2 hr | 4 hr | 24 hr |
| UTC | | 0 | 0 | 0 | 0 | 0 | 0 | 7 |
| Fipronil (.001%) | 0.00062 | 0 | 0 | 0 | 0 | 0 | 28 | 100 |
| Fipronil (.001%) + Compound A (1%) | 0.00062 | 0 | 94 | 100 | 100 | 100 | 100 | 100 |
| Fipronil (.001%) + Compound A (0.1%) | 0.00062 | 0 | 0 | 0 | 0 | 0 | 3 | 100 |
| Fipronil (.001%) + Compound A (0.01%) | 0.00062 | 0 | 0 | 0 | 0 | 0 | 21 | 100 |
| Compound A (1%) | 0 | 0 | 65 | 94 | 100 | 100 | 100 | 100 |
| Compound A (0.1%) | 0 | 0 | 0 | 0 | 0 | 0 | 13 | 19 |
| Compound A (0.01%) | 0 | 0 | 0 | 0 | 0 | 0 | 3 | 26 |
| Combination (Compound A + Compound B) | 0 | 0 | 0 | 0 | 0 | 19 | 52 | 71 |

SUMMARY: Although both rates of fipronil in combination with Compound A (1%) showed increased speed of knockdown and mortality against Argentine ant, Compound A (1%) alone also displayed the same efficacy. A second trial was conducted to repeat Fipronil at 0.001% AI in combination with the three rates of Compound A. Compound A (0.1%) alone and the Combination (Compound A+Compound B) were also added for comparison. The same results were achieved in the second trial as in the first. Argentine ant efficacy with fipronil (0.001%) in combination with Compound A (1%) was very similar to Compound A (1%) alone. This data is summarized in FIG. 41. The single adjuvant (Compound A) had significant ant mortality at 24 hours, as previously seen with Combination (Compound A and Compound B, supra) the Argentine ant; however, Compound A (1%) alone was more toxic to Argentine ant. The addition of only Compound A to fipronil appears to increase the speed of knockdown, but not to provide a synergistic effect.

Example 43

Evaluation of Synergy of Combination of Compound A & Compound B with Fipronil Against *Aedes aegypti* Mosquito The objective of this study was to investigate the synergistic effect of fipronil in combination with adjuvant on efficacy against *Aedes aegypti* mosquitoes.

MATERIALS AND METHODS: Solutions of fipronil at 0.01, 0.001 and 0.0001% AI were prepared with and without adjuvant in acetone. The adjuvant is a combination of Compound A at 1% and Compound B at 0.5%. Treatments were applied using a micropipette to dispense 1 ml of test solution evenly on 6"×6" glazed tile. Actual coverage was about 5"×5" (or 161 cm$^2$) for easy handling. Treatments were allowed to dry overnight. USDA Petri Dish Method was used as initial screening protocol. Twenty, 4-6 day old female *Aedes aegypti* mosquitoes were exposed to each treatment for 3 minutes and then moved to a clean untreated white paper index card. Treatments were replicated a minimum of three times. Mosquito knockdown was evaluated at various intervals through 6 hours after exposure. A small cotton ball soaked in sucrose solution was added on the screen top of the petri-dish as a drinking source. Mortality was evaluated at 24 hours after exposure.

RESULTS: Table 48 and FIG. 42: Summary of Fipronil/adjuvant synergy study against *Aedes aegypti* mosquito

| Treatment | Rate (g/m$^2$) | Average % Knockdown & Mortality after | | | | | |
|---|---|---|---|---|---|---|---|
| | | 15 min | 30 min | 60 min | 4 hr | 6 hr | 24 hr |
| UTC | | 0 | 0 | 0 | 0 | 0 | 2 |
| Fipronil (.01%) | 0.0062 | 5 | 6 | 19 | 42 | 56 | 72 |
| Fipronil (.01%) + adjuvant | 0.0062 | 17 | 28 | 41 | 51 | 62 | 91 |
| Fipronil (.001%) | 0.00062 | 0 | 0 | 0 | 0 | 3 | 3 |
| Fipronil (.001%) + adjuvant | 0.00062 | 4 | 4 | 13 | 7 | 7 | 7 |
| Fipronil (.0001%) | 0.000062 | 0 | 0 | 0 | 3 | 3 | 9 |
| Fipronil (.0001%) + adjuvant | 0.000062 | 0 | 0 | 2 | 1 | 11 | 22 |
| adjuvant | | 0 | 0 | 0 | 0 | 0 | 0 |

SUMMARY: A synergistic effect was seen with fipronil at 0.01% AI in combination with adjuvant against *Aedes aegypti* mosquito (see FIG. 42).

Example 44

Evaluation of Synergy of Combination of Compound A & Compound B with Fipronil Against Argentine Ant The objective of this study was to investigate the synergistic effect of fipronil in combination with adjuvant on efficacy against Argentine ant, *Linepithema humile*.

MATERIALS AND METHODS: Solutions of fipronil at 0.01, 0.001 and 0.0001% AI were prepared with and without adjuvant in acetone. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm$^2$) for easy handling. Treatments were allowed to dry overnight. Ten Argentine ant workers were placed within a fluon or talc-coated PVC ring (φ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

RESULTS: Table 49 and FIG. 43: Summary of Fipronil/adjuvant synergy study against Argentine ant

| Treatment | Rate (g/m$^2$) | Average % Mortality after | | | | |
|---|---|---|---|---|---|---|
| | | 30 min | 60 min | 2 hr | 3 hr | 24 hr |
| UTC | | 0 | 0 | 0 | 0 | 3 |
| Fipronil (.01%) | 0.0062 | 0 | 0 | 0 | 0 | 100 |
| Fipronil (.01%) + adjuvant | 0.0062 | 9 | 56 | 82 | 100 | 100 |
| Fipronil (.001%) | 0.00062 | 0 | 0 | 0 | 3 | 100 |
| Fipronil (.001%) + adjuvant | 0.00062 | 30 | 76 | 91 | 100 | 100 |
| Fipronil (.0001%) | 0.000062 | 0 | 0 | 0 | 0 | 74 |
| Fipronil (.0001%) + adjuvant | 0.000062 | 0 | 3 | 3 | 9 | 71 |
| adjuvant | | 0 | 0 | 3 | 12 | 73 |

SUMMARY: In this trial, fipronil at 0.001% AI in combination with adjuvant showed a increase in efficacy against Argentine ant. Synergy was also seen with adjuvant and fipronil at 0.01%. The results are summarized in FIG. 43. As shown in FIG. 43, 100% mortality was seen in as little as 4 hours when fipronil is combined with the adjuvant, believed acting as a free radical stabilizer, as compared to around 25 hours in the absence of the adjuvant.

Example 45

Evaluation of Synergy of Combination of Compound A & Compound B with Fipronil Against *Culex quinquefasciatus* Mosquito The objective of this study was to investigate the synergistic effect of fipronil in combination with adjuvant on efficacy against *Culex quinquefasciatus* mosquitoes.

MATERIALS AND METHODS: Solutions of Fipronil at 0.01, 0.001 and 0.0001% AI were prepared with and without adjuvant in acetone. The adjuvant is a combination of Compound A at 1% and Compound B at 0.5%. Treatments were applied using a micropipette to dispense 1 ml of test solution evenly on 6"×6" glazed tile. Actual coverage was about 5"×5" (or 161 cm$^2$) for easy handling. Treatments were allowed to dry overnight. USDA Petri Dish Method was used as initial screening protocol. Twenty, 4-6 day old female Culex mosquitoes were exposed to each treatment for 3 minutes and then moved to a clean untreated white paper index card. Treatments were replicated a minimum of three times. Mosquito knockdown was evaluated at various intervals through 3 hours after exposure. A small cotton ball soaked in sucrose solution was added on the screen top of the petri-dish as a drinking source. Mortality was evaluated at 24 hours after exposure.

RESULTS: Table 50 and FIG. 44: Summary of Fipronil/adjuvant synergy study against *Culex quinquefasciatus* mosquito

| Treatment | Rate (g/m$^2$) | Average % Knockdown & Mortality after | | | | |
|---|---|---|---|---|---|---|
| | | 30 min | 60 min | 2 hr | 3 hr | 24 hr |
| UTC | | 0 | 0 | 0 | 0 | 0 |
| Fipronil (.01%) | 0.0062 | 0 | 0 | 0 | 0 | 48 |
| Fipronil (.01%) + adjuvant | 0.0062 | 0 | 0 | 2 | 2 | 95 |
| Fipronil (.001%) | 0.00062 | 0 | 0 | 0 | 0 | 2 |
| Fipronil (.001%) + adjuvant | 0.00062 | 0 | 5 | 5 | 4 | 0 |
| adjuvant | | 0 | 0 | 0 | 0 | 0 |

SUMMARY: Although no initial synergy was seen with fipronil and adjuvant, an increase in efficacy was seen with fipronil at 0.01% AI in combination with adjuvant at 24 hours (FIG. 44). Indeed, mortality approaching 100% was observed when the free radical stabilizer was combined with fipronil, compared to around 50% mortality in the absence of the adjuvant, believed to be acting as a free radical stabilizer.

Example 46

Evaluation of Synergy of Combination of Compound A & Compound B with Fipronil Against Odorous House Ant The objective of this study was to investigate the synergistic effect of fipronil in combination with adjuvant on efficacy against Odorous House ant, *Tapinoma sessile*.

MATERIALS AND METHODS: Solutions of Fipronil at 0.01, 0.001 and 0.0001% AI were prepared with and without adjuvant in acetone. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm$^2$) for easy handling. Treatments were allowed to thy overnight. Ten Odorous House ant workers were placed within a talc-coated PVC ring (φ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

RESULTS: Table 51 and FIG. 45: Summary of Fipronil/adjuvant synergy study against Odorous House ant

| Treatment | Rate (g/m²) | Average % Mortality after | | | |
|---|---|---|---|---|---|
| | | 30 min | 60 min | 2 hr | 24 hr |
| UTC | | 0 | 0 | 0 | 3 |
| Fipronil (.01%) | 0.0062 | 0 | 0 | 6 | 100 |
| Fipronil (.01%) + adjuvant | 0.0062 | 44 | 79 | 97 | 100 |
| Fipronil (.001%) | 0.00062 | 0 | 0 | 0 | 100 |
| Fipronil (.001%) + adjuvant | 0.00062 | 39 | 70 | 97 | 100 |
| Fipronil (.0001%) | 0.000062 | 0 | 3 | 3 | 54 |
| Fipronil (.0001%) + adjuvant | 0.000062 | 0 | 3 | 3 | 45 |
| adjuvant | | 0 | 0 | 0 | 50 |

SUMMARY: In this trial, fipronil at 0.001% AI in combination with adjuvant was the lowest rate that showed the greatest increase in efficacy against Odorous House ant. Synergy was also seen with adjuvant and fipronil at 0.01%. Results are summarized in FIG. 46. As shown in FIG. 45, 100% mortality was observed in around 1 hour in the presence of the adjuvant, believed to be acting as a free radical stabilizer, versus 25 hours in the absence of the adjuvant. This shows a synergistic effect of the adjuvant.

Example 47

Evaluation of Synergy of Combination of Compound A & Compound B with Fipronil Against Red Imported Fire Ant The objective of this study was to investigate the synergistic effect of fipronil in combination with adjuvant on efficacy against Red Imported Fire ant, *Solenopsis invicta*.

MATERIALS AND METHODS: Solutions of Fipronil at 0.01, 0.001 and 0.0001% AI were prepared with and without adjuvant in acetone. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm²) for easy handling. Treatments were allowed to dry overnight. Ten Red Imported Fire ant workers were placed within a talc-coated PVC ring (ϕ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

RESULTS: Table 52 and FIG. 46: Summary of Fipronil/adjuvant synergy study against Red Imported Fire ant

| Treatment | Rate (g/m²) | Average % Mortality after | | | | |
|---|---|---|---|---|---|---|
| | | 30 min | 60 min | 2 hr | 3 hr | 24 hr |
| UTC | | 0 | 0 | 0 | 0 | 11 |
| Fipronil (.01%) | 0.0062 | 0 | 0 | 0 | 0 | 100 |
| Fipronil (.01%) + adjuvant | 0.0062 | 0 | 3 | 38 | 76 | 100 |
| Fipronil (.001%) | 0.00062 | 0 | 0 | 0 | 25 | 100 |
| Fipronil (.001%) + adjuvant | 0.00062 | 3 | 3 | 12 | 18 | 82 |
| Fipronil (.0001%) | 0.000062 | 3 | 3 | 3 | 6 | 47 |
| Fipronil (.0001%) + adjuvant | 0.000062 | 0 | 0 | 0 | 3 | 50 |
| adjuvant | | 0 | 0 | 0 | 3 | 65 |

SUMMARY: A synergistic effect was seen with fipronil at 0.01% AI in combination with adjuvant against Red Imported Fire ant (see FIG. 46). As shown in FIG. 47, a relatively high percentage of mortality (around 80%) was observed in just around 3 hours when the adjuvant, believed to be acting as a free radical stabilizer, is present, versus a comparable level of mortality in around 20 hours in the absence of the adjuvant.

Example 48

Evaluation of Synergy of Combination of Compound A & Compound B with Fipronil Against Susceptible German Cockroach (Monheim Strain)

The objective of this study was to investigate the synergistic effect of fipronil in combination with adjuvant on efficacy against susceptible/normal German cockroach strain (Monheim strain).

MATERIALS AND METHODS: Solutions of fipronil at 0.01, 0.001 and 0.0001% AI were prepared with and without adjuvant in acetone. The UV Blocker is a combination of Compound A at 1% and Compound B at 0.5%. Treatments were applied using a micropipette to dispense 1 ml of test solution evenly on a 6"×6" glazed tile (FIG. 48). Actual coverage was about 5"×5" (or 161 cm²) for easy handling. Treatments were allowed to dry overnight. Five male German cockroaches were placed within a talc-coated PVC ring (ϕ7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

RESULTS: Table 53 and FIG. 48: Summary of Fipronil/adjuvant synergy study against German cockroach (Monheim)

| Treatment | Rate (g/m²) | Average % Knockdown & Mortality after | | | |
|---|---|---|---|---|---|
| | | 60 min | 3 hr | 5 hr | 24 hr |
| UTC | 0 | 0 | 0 | 0 | 7 |
| Fipronil (.01%) | 0.0062 | 0 | 7 | 7 | 100 |
| Fipronil (.01%) + adjuvant | 0.0062 | 0 | 0 | 33 | 100 |
| Fipronil (.001%) | 0.00062 | 0 | 0 | 0 | 40 |
| Fipronil (.001%) + adjuvant | 0.00062 | 0 | 0 | 0 | 100 |
| Fipronil (.0001%) | 0.000062 | 0 | 7 | 7 | 7 |
| Fipronil (.0001%) + adjuvant | 0.000062 | 0 | 7 | 7 | 13 |
| adjuvant | 0 | 0 | 0 | 0 | 7 |

SUMMARY: An increase in overall mortality was seen with fipronil at 0.001% AI and adjuvant against susceptible German cockroach (FIG. 48). As shown in FIG. 48, 100% mortality was observed at 25 hours in the presence of the adjuvant, compared to around 40% mortality at 25 hours in the absence of the adjuvant.

Example 49

Evaluation of Synergy of Compound A with Ethiprole Against Argentine Ant

The objective of this study was to investigate the synergistic effect of ethiprole in combination with Compound A on efficacy against Argentine ant, *Linepithema humile*.

MATERIALS AND METHODS: Solutions of ethiprole at 0.01 and 0.001% AI were prepared with and without Compound A at 1, 0.1, and 0.01% in acetone. Treatments were applied using a micropipette to dispense 1 ml of treatment solution on 6"×6" glazed tile. Actual coverage was about 5"×5" (or 161 cm$^2$) for easy handling. Treatments were allowed to dry overnight. Ten Argentine ant workers were placed within a talc-coated PVC ring ($\phi$7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

nificant ant mortality at 24 hours, as previously seen with adjuvant and Argentine ant; however, Compound A (1%) alone was even more toxic to Argentine ant. In this trial, a synergistic effect was seen with ethiprole (0.01%) in combination with Compound A at 0.1%, neither of which were effective alone at this dosage rate. The results are shown in FIG. 549. Accordingly, a significantly lower amount (i.e., around 90% less) ethiprole can be used, to achieve the same mortality rate, when the adjuvant is present (even at concentrations at which the adjuvant is not active at causing insect mortality.

Example 50

Evaluation of Synergy of Combination of Compound A & Compound B with Ethiprole Against *Aedes aegypti* Mosquito The objective of this study was to investigate the synergistic effect of ethiprole in combination with adjuvant on efficacy against *Aedes aegypti* mosquitoes.

RESULTS: Table 54 (no figure): Trial 1: Summary of Ethiprole/Compound A synergy study against Argentine ant

| Treatment | Rate (g/m$^2$) | Average % Mortality after | | | | | | |
|---|---|---|---|---|---|---|---|---|
| | | 10 min | 30 min | 60 min | 90 min | 2 hr | 4 hr | 24 hr |
| UTC | | 0 | 0 | 0 | 0 | 0 | 0 | 10 |
| Ethiprole (0.01%) | 0.0062 | 0 | 0 | 0 | 0 | 0 | 16 | 100 |
| Ethiprole (0.01%) + Compound A (1%) | 0.0062 | 36 | 91 | 100 | 100 | 100 | 100 | 100 |
| Ethiprole (0.01%) + Compound A (0.1%) | 0.0062 | 0 | 0 | 10 | 42 | 55 | 100 | 100 |
| Ethiprole (0.01%) + Compound A (0.01%) | 0.0062 | 0 | 0 | 0 | 0 | 0 | 10 | 81 |
| Compound A (1%) | 0 | 25 | 91 | 100 | 100 | 100 | 100 | 100 |
| Compound A (0.01%) | 0 | 0 | 0 | 0 | 0 | 0 | 17 | 36 |

Table 55 and FIG. 49: Trial 2: Summary of Ethiprole/Compound A synergy study against Argentine ant

| Treatment | Rate (g/m$^2$) | Average % Mortality after | | | | | | |
|---|---|---|---|---|---|---|---|---|
| | | 10 min | 30 min | 60 min | 90 min | 2 hr | 3 hr | 24 hr |
| UTC | | 0 | 0 | 0 | 0 | 0 | 0 | 0 |
| Ethiprole (0.01%) | 0.00062 | 0 | 0 | 0 | 0 | 0 | 6 | 72 |
| Ethiprole (0.01%) + Compound A (1%) | 0.00062 | 100 | 100 | 100 | 100 | 100 | 100 | 100 |
| Ethiprole (0.01%) + Compound A (0.1%) | 0.00062 | 0 | 0 | 24 | 86 | 100 | 100 | 100 |
| Ethiprole (0.01%) + Compound A (0.01%) | 0.00062 | 0 | 0 | 0 | 0 | 4 | 11 | 89 |
| Compound A (1%) | 0 | 57 | 100 | 100 | 100 | 100 | 100 | 100 |
| Compound A (0.1%) | 0 | 0 | 4 | 4 | 12 | 12 | 16 | 16 |
| Compound A (0.01%) | 0 | 0 | 0 | 0 | 0 | 24 | 31 | 62 |
| UVB (Compound A + Compound B) | 0 | 0 | 0 | 13 | 23 | 40 | 50 | 83 |

SUMMARY: In the first trial, ethiprole (0.01% AI) in combination with Compound A (1%) showed increased speed of knockdown and mortality against Argentine ant; however, Compound A (1%) alone also displayed the same efficacy. A second trial was conducted to repeat the treatments in the first trial, as well as, add Compound A (0.1%) alone and combination (Compound A+Compound B) for comparison. The same results were achieved in the second trial as in the first. Compound A (1%) alone was just as active as in combination with ethiprole at 0.01% AI. The adjuvant treatment had sig- MATERIALS AND METHODS: Solutions of ethiprole at 1, 0.1 and 0.01% AI were prepared with and without adjuvant in acetone. The adjuvant is a combination of Compound A at 1% and Compound B at 0.5%. Treatments were applied using a micropipette to dispense 1 ml of test solution evenly on 6"×6" glazed tile. Actual coverage was about 5"×5" (or 161 cm$^2$) for easy handling. Treatments were allowed to dry overnight. USDA Petri Dish Method was used as initial screening protocol. Twenty, 4-6 day old female *Aedes aegypti* mosquitoes were exposed to each treatment for 3 minutes and then moved to a clean untreated white paper index card. Treatments were replicated a minimum of three times. Mosquito knockdown was evaluated at 5 minute intervals for the first hour and then at 2, 4 and 6 hours. A small cotton ball soaked in sucrose solution was added on the screen top of the petri-dish as a drinking source. Mortality was evaluated at 24 hours after exposure.

RESULTS: Table 56 and FIG. 50: Summary of Ethiprole/adjuvant synergy study against *Aedes aegypti* mosquito

| Treatment | Rate (g/m$^2$) | Average % Knockdown & Mortality after | | | |
|---|---|---|---|---|---|
| | | 2 hr | 4 hr | 6 hr | 24 hr |
| UTC | | 0 | 0 | 0 | 8 |
| Ethiprole (1%) | 0.62 | 2 | 17 | 27 | 46 |
| Ethiprole (1%) + adjuvant | 0.62 | 14 | 24 | 34 | 81 |
| Ethiprole (.1%) | 0.062 | 3 | 3 | 15 | 25 |
| Ethiprole (.1%) + adjuvant | 0.062 | 10 | 21 | 45 | 93 |
| Ethiprole (.01%) | 0.0062 | 0 | 2 | 12 | 17 |
| Ethiprole (.01%) + adjuvant | 0.0062 | 21 | 32 | 71 | 95 |
| adjuvant | | 9 | 13 | 17 | 17 |

SUMMARY: Synergy was observed with ethiprole and adjuvant against *Aedes aegypti* mosquitoes at all rates tested. The greatest synergy was seen with ethiprole at 0.01% AI and adjuvant. The results are shown in FIG. 50. As shown in the Figure, not only was the rate of mortality higher, the mortality rate peaked at around 15-18% in the absence of the adjuvant, believed to be acting as a free radical stabilizer, but increased over time to around 95% in the presence of the adjuvant.

Example 51

Evaluation of Synergy of Combination of Compound A & Compound B with Ethiprole Against Argentine Ant The objective of this study was to investigate the synergistic effect of ethiprole in combination with adjuvant on efficacy against Argentine ant, *Linepithema humile*.

MATERIALS AND METHODS: Solutions of ethiprole at 1, 0.5 and 0.1% AI were prepared with and without adjuvant in acetone. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm$^2$) for easy handling. Treatments were allowed to dry overnight. Ten Argentine ant workers were placed within a fluon or talc-coated PVC ring (φ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

RESULTS: Table 57 and FIG. 51: Summary of Ethiprole/adjuvant synergy study against Argentine ant

| Treatment | Rate (g/m$^2$) | Average % Mortality after | | | |
|---|---|---|---|---|---|
| | | 15 min | 30 min | 45 min | 60 min |
| UTC | | 0 | 0 | 0 | 0 |
| Ethiprole (1%) | 0.62 | 0 | 0 | 0 | 0 |
| Ethiprole (1%) + adjuvant | 0.62 | 0 | 0 | 0 | 0 |
| Ethiprole (0.1%) | 0.062 | 0 | 0 | 0 | 0 |
| Ethiprole (0.1%) + adjuvant | 0.062 | 10 | 60 | 97 | 100 |
| Ethiprole (0.01%) | 0.006 | 0 | 0 | 0 | 0 |
| Ethiprole (0.01%) + adjuvant | 0.006 | 0 | 80 | 97 | 100 |
| adjuvant | | 0 | 41 | 57 | 69 |

SUMMARY: Ethiprole at 0.1 and 0.01% AI in combination with adjuvant showed increased speed of knockdown and mortality compared to ethiprole alone against Argentine ant. The adjuvant only treatment also had high ant mortality. In this example, the adjuvant, believed to be acting as a free radical stabilizer, shows insecticidal activity, unlike other examples where the adjuvant does not show insecticidal activity. The results are summarized in FIG. 51.

Example 52

Evaluation of Synergy of Combination Compound A and Compound B with Ethiprole Against Housefly The objective of this study was to investigate the synergistic effect of ethiprole in combination with adjuvant on efficacy against housefly, *Musca domestica*.

MATERIALS AND METHODS: Solutions of ethiprole at 1.0, 0.1 and 0.01% AI were prepared with and without adjuvant in acetone. The adjuvant is a combination of Compound A at 1% and Compound B at 0.5%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. The housefly testing arena consisted of a 16 oz. paper cup where the bottom of the cup was removed and replaced with a piece of standard window screen. Ten adult houseflies (mixed ratio) were placed in each cup and covered with a 4"×5" index card to prevent escape. Houseflies were continuously exposed to the treatment by inverting the testing arena and sliding the cup from the index card to the treated tile surface. Treatments were replicated a minimum of three times. Evaluations for knockdown/mortality were made at various intervals and at 24 hours after exposure.

RESULTS: Table 58 and FIG. 52: Summary of Ethiprole/adjuvant synergy study against housefly

| Treatment | Rate (g/m$^2$) | Average % Knockdown & Mortality after | | | | |
|---|---|---|---|---|---|---|
| | | 1 hr | 3 hr | 5 hr | 7 hr | 24 hr |
| UTC | 0 | 0 | 0 | 0 | 0 | 0 |
| Ethiprole (1%) | 0.62 | 0 | 0 | 0 | 3 | 97 |
| Ethiprole (1%) + adjuvant | 0.62 | 0 | 3 | 12 | 29 | 91 |
| Ethiprole (0.1%) | 0.06 | 0 | 0 | 3 | 10 | 100 |
| Ethiprole (0.1%) + | 0.06 | 0 | 19 | 66 | 75 | 100 |

-continued

RESULTS: Table 58 and FIG. 52: Summary of
Ethiprole/adjuvant synergy study against housefly

| Treatment | Rate (g/m$^2$) | Average % Knockdown & Mortality after | | | | |
|---|---|---|---|---|---|---|
| | | 1 hr | 3 hr | 5 hr | 7 hr | 24 hr |
| adjuvant Ethiprole (0.01%) | 0.006 | 0 | 0 | 0 | 3 | 100 |
| Ethiprole (0.01%) + adjuvant | 0.006 | 0 | 40 | 63 | 78 | 100 |
| adjuvant | 0 | 0 | 0 | 0 | 0 | 16 |

SUMMARY: All rates of ethiprole in combination with the adjuvant, believed to be acting as a free radical stabilizer showed a synergistic effect against housefly for speed of knockdown. The overall mortality with ethiprole was equivalent at all rates tested with or without the addition of adjuvant. The results are shown in FIG. 52. As shown in the Figure, after about 6 hours, roughly 80% mortality was observed in the presence of the adjuvant, versus only around 6% in the absence of the adjuvant.

Example 53

Evaluation of Synergy of Combination of Compound A and Compound B with Ethiprole Against Odorous House Ant The objective of this study was to investigate the synergistic effect of ethiprole in combination with adjuvant on efficacy against Odorous House ant, *Tapinoma sessile*.

MATERIALS AND METHODS: Solutions of ethiprole at 1, 0.1 and 0.01% AI were prepared with and without adjuvant in acetone. The adjuvant is a combination of Compound A at 1% and Compound B at 0.5%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Ten odorous house ant workers were placed within a talc-coated PVC ring ($\phi$7.6 cm×H 5.1 cm) under continuous exposure. Treatments were replicated minimum three times. Evaluations for ant knockdown/mortality were made at 5 minute intervals for the first hour and then at 2 hours after exposure.

RESULTS: Table 59 and FIG. 53: Summary of
Ethiprole/adjuvant synergy study against Odorous House ant

| Treatment | Rate (g/m$^2$) | Average % Knockdown & Mortality after | | | | |
|---|---|---|---|---|---|---|
| | | 15 min | 30 min | 45 min | 60 min | 2 hr |
| UTC | 0 | 0 | 0 | 0 | 0 | 0 |
| Ethiprole (1%) | 0.62 | 0 | 0 | 0 | 3 | 7 |
| Ethiprole (1%) + adjuvant | 0.62 | 0 | 0 | 3 | 7 | 53 |
| Ethiprole (0.1%) | 0.06 | 0 | 0 | 0 | 0 | 0 |
| Ethiprole (0.1%) + adjuvant | 0.06 | 3 | 13 | 37 | 70 | 100 |
| Ethiprole (0.01%) | 0.006 | 0 | 0 | 0 | 0 | 3 |
| Ethiprole (0.01%) + adjuvant | 0.006 | 10 | 67 | 93 | 100 | 100 |
| adjuvant | 0 | 0 | 0 | 0 | 0 | 0 |

SUMMARY: All rates of ethiprole in combination with adjuvant showed synergistic effect against Odorous House ant. The lowest rate of ethiprole (0.01%) showed the greatest increase in speed of knockdown and efficacy. The results are shown in FIG. 53. As shown in the Figure, 100% mortality was observed in just around 1 hour in the presence of the adjuvant, which is believed to be acting as a free radical stabilizer, versus around 4% mortality in 2 hours in the absence of the adjuvant.

Example 54

Evaluation of Synergy of combination of Compound A and Compound B with Ethiprole against Red Imported Fire Ant The objective of this study was to investigate the synergistic effect of ethiprole in combination with adjuvant on efficacy against Red Imported Fire ant, *Solenopsis invicta*.

MATERIALS AND METHODS: Solutions of ethiprole at 1, 0.1 and 0.01% AI were prepared with and without adjuvant in acetone. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm$^2$) for easy handling. Treatments were allowed to dry overnight. Ten Red Imported Fire ant workers were placed within a talc-coated PVC ring ($\phi$7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure.

RESULTS: Table 60 and FIG. 54: Summary of
Ethiprole/adjuvant synergy study against
Red Imported Fire ant

| Treatment | Rate (g/m$^2$) | Average % Mortality after | | | | |
|---|---|---|---|---|---|---|
| | | 30 min | 1 hr | 1.5 hr | 2 hr | 3 hr |
| UTC | | 0 | 0 | 0 | 0 | 0 |
| Ethiprole (1%) | 0.62 | 0 | 0 | 0 | 0 | 10 |
| Ethiprole (1%) + adjuvant | 0.62 | 0 | 3 | 20 | 63 | 100 |
| Ethiprole (0.1%) | 0.06 | 0 | 0 | 0 | 0 | 10 |
| Ethiprole (0.1%) + adjuvant | 0.06 | 3 | 50 | 80 | 97 | 100 |
| Ethiprole (0.01%) | 0.006 | 0 | 0 | 0 | 0 | 3 |
| Ethiprole (0.01%) + adjuvant | 0.006 | 0 | 13 | 60 | 100 | 100 |
| adjuvant | | 0 | 0 | 0 | 10 | 14 |

SUMMARY: All rates of ethiprole in combination with adjuvant showed a synergistic effect against Red Imported Fire Ant. The results are shown in FIG. 54. As shown in the Figure, 100% mortality was observed in just 2 hours in the presence of the adjuvant, believed acting as a free radical stabilizer, versus less than around 5% mortality in 3 hours in the absence of the adjuvant.

Example 55

Evaluation of Synergy of Combination of Compound A and Compound B with Ethiprole Against Susceptible German Cockroach (Monheim Strain)

The objective of this study was to investigate the synergistic effect of ethiprole in combination with adjuvant on efficacy against susceptible/normal German cockroach strain (Monheim strain).

MATERIALS AND METHODS: Solutions of ethiprole at 1.0, 0.1 and 0.01% AI were prepared with and without adjuvant in acetone. The adjuvant is a combination of Compound A at 1% and Compound B at 0.5%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five male German cockroaches were placed within a talc-coated PVC ring ($\phi$7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure.

RESULTS: Table 61 and FIG. 55: Summary of Ethiprole/adjuvant synergy study against German cockroach (Monheim)

| Treatment | Rate (g/m$^2$) | 1 hr | 3 hr | 5 hr | 24 hr |
|---|---|---|---|---|---|
| UTC | 0 | 0 | 0 | 0 | 0 |
| Ethiprole (1%) | 0.62 | 0 | 13 | 27 | 73 |
| Ethiprole (1%) + adjuvant | 0.62 | 0 | 87 | 93 | 100 |
| Ethiprole (0.1%) | 0.06 | 0 | 27 | 33 | 80 |
| Ethiprole (0.1%) + adjuvant | 0.06 | 0 | 40 | 67 | 100 |
| Ethiprole (0.01%) | 0.006 | 0 | 0 | 7 | 13 |
| Ethiprole (0.01%) + adjuvant | 0.006 | 0 | 27 | 80 | 100 |
| adjuvant | 0 | 0 | 0 | 0 | 0 |

SUMMARY: All rates of ethiprole tested in combination with adjuvant showed a synergistic effect against susceptible German cockroach (Monheim strain) for both speed of knockdown and increased efficacy. The results are shown in FIG. 55. As shown in the Figure, after just 5 hours, around 80% mortality was observed in the presence of the adjuvant, believed to be acting as a free radical stabilizer, and this increased linearly to around 100% mortality in 25 hours, versus a mortality of around 5-15% from 5 to 25 hours in the absence of the adjuvant.

Example 56

Evaluation of Bendiocarb alone and in Combination with Compound A, Derivative 3 and Additional Penetration Enhancers in Acetone on Glazed Tiles and Plywood Against the Tropical House Mosquito *Culex quinquefasciatus*

The objective of this example was to test products identified as penetration enhancers, as previously described, in comparison to Compound A and Derivative 3 as also noted herein as sebacic acid dibenzyl ester.

Method for Determining the Efficacy of Formulations on Surfaces

The surfaces were treated as follows:

The ingredients were diluted in acetone to give a concentration which corresponds to the desired quantity of a.i./m$^2$. A 1 ml quantity of the solution was applied by pipette onto the 15 cm×15 cm surfaces without treating the outer edge of 1 cm.

Ten 3 day old *Culex quinquefasciatus* mosquitoes were exposed to each treatment for 3 minutes under a perforated petri dish, and then a clean untreated white paper index card was moved between treated surface and petri dish. A water-soaked cotton pad was applied immediately after.

Each test consisted of three replicates (three batches of ten mosquitoes were exposed for three minutes to the same surface, each one hour later), of which the mean values are calculated.

The test insects were *Culex quinquefasciatus* (adults, 3 days old). The compositions were evaluated for their ability to provide effective knock down after 3, 9, 15, and 30 minutes, 1, 2, 3, 4 and 24 hours (mortality). The experiments were performed in triplicate on glazed tile, but not repeated on wood. The compositions that were tested are shown in the following table, with results shown in FIGS. 56 and 57.

TABLE 62

Tested mixtures:

| | |
|---|---|
| 0.1% Bendiocarb | |
| 0.1% bendiocarb + | 0.1% bendiocarb + |
| 1% Compound A | 1% L-ascorbic acid* |
| 0.1% bendiocarb + | 0.1% bendiocarb + |
| 1% Derivative 3 | 1% Palmitic acid |
| (Sebacic acid dibenzyl ester) | |
| 0.1% bendiocarb + | 0.1% bendiocarb + |
| 1% Butylhydroxytoluol (BHT) | 1% Palmitic acid-methyl ester |
| 0.1% bendiocarb + | 0.1% bendiocarb + |
| 1% Butylhydroxyanisol (BHA) | 1% Oleic acid |
| 0.1% bendiocarb + | 0.1% bendiocarb + |
| 1% Diethylsebacate | 1% Oleic acid-methyl ester |
| 0.1% bendiocarb + | 0.1% bendiocarb + |
| 1% Bis (2-Ethylhexyl) Sebacate | 1% Linoleic acid |
| 0.1% bendiocarb + | 0.1% bendiocarb + |
| 1% Dibutylsebacate | 1% Linoleic acid-methyl ester |
| 0.1% bendiocarb + | 0.1% bendiocarb + |
| 1% Diphenylmethan | 1% Tetramethylsilane |

Summary

No activity was observed on wood, perhaps due to its porous surface. On glazed tile, the efficacy of 0.1% bendiocarb was strongly enhanced by the following compounds:

TABLE 63

| | |
|---|---|
| 1% Butylhydroxytoluol | 1% Oleic acid |
| 1% Butylhydroxyanisol (BHA) | 1% Oleic acid-methyl ester |
| 1% Diethylsebacate | 1% Linoleic acid |
| 1% Bis (2-Ethylhexyl) Sebacate | 1% Linoleic acid-methyl ester |

The addition of ascorbic acid led to a complete decrease of efficacy.

Example 57

Spider Control with Imidacloprid and Adjuvants

The purpose of this example was to evaluate the efficacy of a combination of imidacloprid and various adjuvant, each believed acting as a free radical stabilizers at effecting spider control.

The general methodology used in this example involved locating one or more structure(s) which possessed a number of established spider webs around windows, in corners, under eaves, etc. Replicated plots (e.g., 1 meter sq. or as site dictates) were defined for treatment and observations. All living spiders in this area were counted, and the trial was begun by sweeping down all webbing, being careful not to harm the resident spiders in the process. The combinations were applied in the very sites formerly occupied by the spiders. The sites were re-visited intermittently, and total number of spiders in treated and untreated plots were counted. The evaluations were continued until the control failed, or as long as was practical. Treatments: All formulations were suspension concentrates, at concentrations as indicated in the tables below. All formulations were diluted in water before treatment. All imidacloprid treatments were applied to the plots at the same rate of ca. 22 mg AI per sq. m. of surface area; deltamethrin was applied at the label rate of ca. 12 mg AI per sq. m. of surface area and served as a positive control. All treatments were replicated in three plots.

TABLE 64

(no figure): Counts of spider numbers

|  | Pre-Treat | 4 days | 9 days | 15 days | 23 days | 30 days | 37 days |
|---|---|---|---|---|---|---|---|
| Untreated | 3.00 | 4.25 | 9.50 | 10.75 | 13.50 | 13.75 | 14.75 |
| deltamethrin (4.75%) | 4.50 | 1.00 | 1.75 | 1.75 | 2.00 | 2.00 | 1.75 |
| imidacloprid (21.4%) | 2.25 | 2.25 | 6.75 | 9.75 | 11.75 | 11.50 | 10.00 |
| imidacloprid (21.4%) + Compound A (10.7%) | 4.50 | 2.75 | 3.50 | 5.00 | 6.25 | 6.25 | 6.75 |
| imidacloprid (21.4%) + Compound A (4.28%) | 3.00 | 2.75 | 4.25 | 5.00 | 5.25 | 6.75 | 6.75 |
| imidacloprid (21.4%) + Compound A (2.14%) | 2.75 | 2.00 | 4.75 | 5.50 | 7.25 | 7.00 | 5.25 |

TABLE 65

(no figure): Reduction (%) in spider numbers, relative to untreated plots

|  | Pre-Treat | 4 days | 9 days | 15 days | 23 days | 30 days | 37 days | X-trial average |
|---|---|---|---|---|---|---|---|---|
| Untreated |  |  |  |  |  |  |  |  |
| deltamethrin (4.75%) |  | 76.5% | 81.6% | 83.7% | 85.2% | 85.5% | 88.1% | 83.4% |
| imidacloprid (21.4%) |  | 47.1% | 28.9% | 9.3% | 13.0% | 16.4% | 32.2% | 24.5% |
| imidacloprid (21.4%) + Compound A (10.7%) |  | 35.3% | 63.2% | 53.5% | 53.7% | 54.5% | 54.2% | 52.4% |
| imidacloprid (21.4%) + Compound A (4.28%) |  | 35.3% | 55.3% | 53.5% | 61.1% | 50.9% | 54.2% | 51.7% |
| imidacloprid (21.4%) + Compound A (2.14%) |  | 52.9% | 50.0% | 48.8% | 46.3% | 49.1% | 64.4% | 51.9% |

Imidacloprid alone was not effective against spiders, as populations after treatment were suppressed at only around 24.5% [cross trial average] relative to the untreated control. However, all three of the imidacloprid +adjuvant treatments were better at suppressing the spider populations, suppressing spider populations at 51.7% to 52.4% relative to the untreated control. The deltamethrin positive control was effective, maintaining spider control at 83.4% relative to the untreated control populations.

Example 58

Ant Control with Imidacloprid and Adjuvants

The purpose of this example was to consider whether combinations of imidacloprid and adjuvant, believed acting as free radical stabilizers, is effective at controlling ant populations. The general methodology used in this analysis first involved locating a site with persistent ant trails; e.g., trails over surfaces of buildings, at structural guidelines (expansion joints, utility lines, and the like), or points where ants emerge from beneath or behind a structural element. A point of observation was fixed along the trail or point of emergence as the individual plot(s) for observations of the effects of treatment on ant activity. The near environment (structural substrate, mulch beds, ground, and the like) was sprayed to form a continuous barrier that intercepts the trailing ants in a barrier ca. 2 ft up and 2 ft out from foundation wall, and extending 2 to 3 feet on either side of the ant trail. After treatment, the observers returned to observe ant activity and count ant traffic at intervals after treatment. The evaluations were continued until the control failed, or as long as was practical.

Treatments: All formulations were suspension concentrates, at concentrations as indicated in the tables. All formulations were diluted in water before treatment. Application rates, in terms of mg AI per sq. m., were as indicated in the tables. deltamethrin served as a positive control. All treatments were replicated in four plots.

TABLE 66

(no figure): Counts of ant numbers per minute of observation

| | mg AI per m² | Pre-Treat | 4 days | 7 days | 14 days | 32 days | 39 days |
|---|---|---|---|---|---|---|---|
| Untreated | NA | 12.00 | 16.25 | 10.00 | 16.25 | 12.00 | 6.75 |
| deltamethrin (4.75%) | 24 | 40.00 | 14.25 | 19.50 | 25.50 | 13.00 | 12.00 |
| imidacloprid (21.4%) | 42 | 24.75 | 16.75 | 16.50 | 22.00 | 14.00 | 12.25 |
| imidacloprid (21.4%) + Compound A (4.28%) | 42 | 30.67 | 11.00 | 0.00 | 0.00 | 0.00 | 0.00 |
| imidacloprid (21.4%) + Compound A (10.7%) | 42 | 31.50 | 13.00 | 0.75 | 0.00 | 0.00 | 0.75 |
| imidacloprid (21.4%) + Compound A (10.7%) | 84 | 59.00 | 0.75 | 0.00 | 0.00 | 0.00 | 1.00 |

TABLE 67

(no figure): Reduction (%) in ant numbers, relative to pretreatment counts

| | mg AI per m² | Pre-Treat | 4 days | 7 days | 14 days | 32 days | 39 days | X-trial average |
|---|---|---|---|---|---|---|---|---|
| Untreated | NA | | −35.4% | 16.7% | −35.4% | 0.0% | 43.8% | 2.1% |
| deltamethrin (4.75%) | 24 | | 64.4% | 51.3% | 36.3% | 67.5% | 70.0% | 57.9% |
| imidacloprid (21.4%) | 42 | | 32.3% | 33.3% | 11.1% | 43.4% | 50.5% | 34.1% |
| imidacloprid (21.4%) + Compound A (4.28%) | 42 | | 64.1% | 100.0% | 100.0% | 100.0% | 100.0% | 92.8% |
| imidacloprid (21.4%) + Compound A (10.7%) | 42 | | 58.7% | 97.6% | 100.0% | 100.0% | 97.6% | 90.8% |
| imidacloprid (21.4%) + Compound A (10.7%) | 84 | | 98.7% | 100.0% | 100.0% | 100.0% | 98.3% | 99.4% |

Population levels in untreated areas did vary over time, but remained largely unchanged over the course of the study (cross trial average). imidacloprid alone was very weak against ants, causing a mere 34.1% reduction in cross-trial average. However, the influence of adjuvant on the imidacloprid led to virtually wiping out the ant activity, with the lower, 42 mg AI rate being somewhat slower than the 84 mg AI rate. All imidacloprid+adjuvant treatments were more effective than deltamethrin, the positive control, which averaged only 57.9% reductions in ant activity.

Example 59

Performance Enhancement of Botanical Oils (Rosemary+Peppermint Oils) with Compound A Against the German Cockroach The objective of this study was to investigate the performance enhancement of botanical oils (sold under the tradename EcoExempt IC²) in combination with a sebacate, Compound A, on knockdown and mortality against German cockroach (*B. germanica*, T-164 strain).

MATERIALS AND METHODS: Compound A was directly added to and mixed in the concentrate of EcoExempt IC² (Rosemary oil 10%+peppermint oil 2%), then the premix was diluted in acetone to make the final treatment solutions (see table below). The botanical oils (EcoExempt IC²) treatments without Compound A were prepared by diluting the concentrate in acetone to the desired concentrations. Treatments were applied using a micropipette to dispense 1 ml of test solution evenly on a 6"×6" glazed tile. Actual coverage was about 5"×5" (or 161 cm²) for easy handling. Treatments were allowed to dry for approximately 3 hours. Five male German cockroaches were placed within a Fluon-coated PVC ring (φ7.6 cm×H 5.1 cm) under continuous exposure. A small vial cap filled with a cotton ball soaked in water was added as a drinking source after 3 hours of exposure. Treatments were replicated a minimum of three times. Evaluations for knockdown/mortality were made at various intervals and at 24 hours after exposure.

The results are shown in the following table, and summarized in FIG. 59.

Table 68 and FIG. 58: Summary of EcoExempt IC² + Compound A combination study against German cockroach (T-164 strain)

| Treatment | Rate (g/m²) | Average % Knockdown & Mortality after | | | | |
|---|---|---|---|---|---|---|
| | | 30 min | 1 hr | 2 hr | 3 hr | 24 hr |
| UTC | 0 | 0 | 0 | 0 | 0 | 27 |
| IC² (1.2%) + Compound A (1.0%) | 0.75 | 7 | 7 | 27 | 53 | 100 |
| IC² (0.6%) + Compound A 0.5%) | 0.37 | 0 | 0 | 7 | 33 | 100 |
| IC² (0.12%) + Compound A (0.1%) | 0.07 | 7 | 7 | 7 | 7 | 33 |
| EcoExempt IC² (1.2%) | 0.75 | 0 | 0 | 0 | 0 | 27 |
| EcoExempt IC² (0.6%) | 0.37 | 0 | 0 | 0 | 0 | 27 |
| EcoExempt IC² (0.12%) | 0.07 | 0 | 0 | 0 | 0 | 60 |

SUMMARY: As shown in FIG. 58, EcoExempt IC² treatments alone rates of 0.6 and 1.2% were ineffective against the German cockroach. A significant performance enhancement (rapid KD and mortality) was observed with combinations of EcoExempt IC² (both 0.6 and 1.2%)+Compound A (0.5 and 1%) against German cockroaches, with both combinations providing 100% mortality in 24 hours.

Example 60

Performance Enhancement of Botanical Oils (Peanut Oil) with Compound A Against Susceptible German Cockroach The objective of this study was to investigate the performance enhancement of botanical oils (sold under the tradename EcoACU PCO) in combination with a sebacate, Compound A, on knockdown and mortality against German cockroach (*B. germanica*, UCR strain).

MATERIALS AND METHODS: The de-gassed concentrate of EcoACU PCO (peanut oil, or 2-phenethyl propionate 0.1%) was mixed with or without Compound A in acetone (1.0%). Compound A in acetone (1.0%) was used as positive check. Treatments were applied using a micropipette to dispense 1 ml of test solution evenly on a 6"×6" glazed tile. Actual coverage was about 5"×5" (or 161 cm$^2$) for easy handling. Treatments were allowed to dry for approximately 3 hours. Five male German cockroaches were placed within a Fluon-coated PVC ring ($\phi$7.6 cm×H 5.1 cm) under continuous exposure. A small vial cap filled with a cotton ball soaked in water was added as a drinking source after 3 hours of exposure. Treatments were replicated a minimum of three times. Evaluations for knockdown/mortality were made at various intervals and at 24 hours after exposure. The results are summarized in Table 69, and also in FIG. 59.

TABLE 69

Summary of EcoACU PCO + Compound A combination study against German cockroach (UCR strain)

| Treatment | Rate (g/m$^2$) | Average % Knockdown & Mortality after | | | |
|---|---|---|---|---|---|
| | | 30 min | 2 hr | 4 hr | 24 hr |
| UTC | 0 | 0 | 0 | 0 | 7 |
| EcoPCO ACU (0.1%) | 0.06 | 0 | 0 | 47 | 73 |
| EcoPCO ACU (0.1%) + Compound A (1.0%) | 0.06 | 87 | 93 | 93 | 100 |
| Compound A (1.0%) | 0 | 13 | 40 | 87 | 87 |

As shown in the Table and FIG. 59, performance enhancement (a very rapid KD and mortality within 30 min) was observed with the combination of EcoACU PCO+Compound A against German cockroaches. EcoACU PCO treatment alone showed no KD/mortality before 4 h after exposure, and Compound A at 1.0% showed delayed toxicity (after 2 h of exposure) against the German cockroach.

Example 61

Performance Enhancement of Pyrethrins with Compound A Against House Crickets The objective of this study was to investigate the performance enhancement of pyrethrins (sold under the tradename Kicker EC) in combination with a sebacate, Compound A, on knockdown and mortality against the house cricket (*Acheta domesticus*).

MATERIALS AND METHODS: Kicker EC (pyrethrins 6%+PBO 60%) was premixed with three concentrations of Compound A in acetone, then diluted in H$_2$O to make the final treatment solutions (see table below), respectively. Kicker EC treatment without Compound A was prepared by diluting with H$_2$O to the desired concentration. Compound A was dissolved in acetone to make the final three treatment concentrations of 0.01, 0.1 and 1.0%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five adult crickets were placed within an inversed 1 quarter Mason jar under continuous exposure. A small slice of potato was added as a food source after 3 hours of exposure. Treatments were replicated four times. Evaluations for knockdown/mortality were made at various intervals and at 24 hours after exposure.

The results are summarized in Table 70, and also in FIG. 60.

TABLE 70

Summary of Kicker + Compound A combination study against house crickets

| Treatment | Rate (mg/m$^2$) | Average % Knockdown & Mortality after | | | | |
|---|---|---|---|---|---|---|
| | | 15 min | 30 min | 1 hr | 2 hr | 24 hr |
| UTC | 0 | 0 | 0 | 0 | 0 | 10 |
| Kicker (0.006%) | 3.73 | 0 | 0 | 0 | 0 | 5 |
| Kicker (0.006%) + Compound A (1.0%) | 3.73 | 50 | 80 | 80 | 80 | 80 |
| Kicker (0.006%) + Compound A (0.1%) | 3.73 | 0 | 20 | 45 | 70 | 70 |
| Kicker (0.006%) + Compound A (0.01%) | 3.73 | 0 | 0 | 0 | 25 | 25 |
| Compound A (1.0%) | 0 | 0 | 0 | 0 | 0 | 45 |
| Compound A (0.1%) | 0 | 0 | 0 | 0 | 0 | 15 |
| Compound A (0.01%) | 0 | 0 | 0 | 0 | 0 | 20 |

As shown in FIG. 60, a performance enhancement (better KD and mortality) was observed with the two higher rates of Compound A in combination with pyrethrins at 0.006% against crickets. Pyrethrins (Kicker) at 0.006% was ineffective against crickets. Except at a 1.0% level, Compound A alone was not toxic to the house cricket.

Example 62

Performance Enhancement of Pyrethrins with Compound A Against Susceptible German Cockroach The objective of this study was to investigate the performance enhancement of pyrethrins (sold under the tradename Kicker EC) in combination with a sebacate, Compound A, on knockdown and mortality against susceptible German cockroach (UCR strain).

MATERIALS AND METHODS: Kicker EC (pyrethrins 6%+PBO 60%) was premixed with three concentrations of Compound A in acetone, then diluted in H$_2$O to make the final treatment solutions (see table below), respectively. Kicker EC treatment without Compound A was prepared by diluting with H$_2$O to the desired concentration. Compound A was dissolved in acetone to make the final three treatment concentrations of 0.01, 0.1 and 1.0%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five male German cockroaches were placed within a Fluon-coated PVC ring ($\phi$7.6 cm×H 5.1 cm) under continuous exposure. A small vial cap filled with a cotton ball soaked in water was added as a drinking source after 3 hours of exposure. Treatments were replicated four times. Evaluations for knockdown/mortality were made at various intervals and at 24 hours after exposure.

RESULTS: Table 71 and FIG. 61: Summary of Kicker + Compound A combination study against German cockroach (UCR strain)

| Treatment | Rate (mg/m$^2$) | Average % Knockdown & Mortality after | | | | |
|---|---|---|---|---|---|---|
| | | 15 min | 30 min | 1 hr | 2 hr | 24 hr |
| UTC | 0 | 0 | 0 | 0 | 0 | 5 |
| Kicker (0.006%) | 3.73 | 20 | 40 | 25 | 25 | 25 |
| Kicker (0.006%) + Compound A (1.0%) | 3.73 | 35 | 50 | 50 | 80 | 100 |
| Kicker (0.006%) + Compound A (0.1%) | 3.73 | 30 | 75 | 75 | 90 | 90 |
| Kicker (0.006%) + Compound A (0.01%) | 3.73 | 10 | 35 | 50 | 85 | 80 |
| Compound A (1.0%) | 0 | 0 | 0 | 0 | 5 | 25 |
| Compound A (0.1%) | 0 | 0 | 0 | 0 | 0 | 10 |
| Compound A (0.01%) | 0 | 0 | 0 | 0 | 0 | 0 |

As seen in FIG. 61, a performance enhancement (rapid KD and mortality) was observed with all the three rates of Compound A in combination with pyrethrins at 0.006% against German cockroaches. Compound A alone was not toxic to the German cockroach at the rates tested.

Example 63

Combination of Compound A and Compound B—Synergy with β-cyfluthrin Against *Aedes aegypti* Mosquito The objective of this study was to investigate the synergistic effect of β-cyfluthrin in combination with adjuvant on efficacy against *Aedes aegypti* mosquitoes.

MATERIALS AND METHODS: Solutions of β-cyfluthrin at 0.1, 0.05, 0.025, 0.01, 0.005 and 0.001% AI were prepared with and without adjuvant in acetone. The adjuvant is a combination of Compound A at 1% and Compound B at 0.5%. Treatments were applied using a micropipette to dispense 1 ml of test solution evenly on 6"×6" glazed tile. Actual coverage was about 5"×5" (or 161 cm$^2$) for easy handling. Treatments were allowed to dry overnight. USDA Petri Dish Method was used as initial screening protocol. Twenty, 4-6 day old female *Aedes aegypti* mosquitoes were exposed to each treatment for 3 minutes and then moved to a clean untreated white paper index card. Treatments were replicated a minimum of three times. Mosquito knockdown was evaluated at 3-5 minute intervals for the first hour. A small cotton ball soaked in sucrose solution was then added on the screen top of the petri-dish as a drinking source. Mortality was evaluated at 24 hours after exposure.

RESULTS: The results showed that at the application rates tested (0.062 g AI/m$^2$ of a 0.1%, 0.05, 0.025, 0.01, 0.005, and 0.001 solutions of (β-cyfluthrin), the compositions were effective in providing 100% knockdown, or nearly 100% knockdown even in the absence of the adjuvant.

SUMMARY: Accordingly, no synergy was observed with β-cyfluthrin and adjuvant against *Aedes aegypti* mosquitoes at the rates tested. It is believed that synergy would be observed if lower rates of β-cyfluthrin were combined with adjuvant. The adjuvant alone was not toxic to *Aedes aegypti*.

Example 64

Combination of Compound A and Compound B—Synergy with β-cyfluthrin Against Argentine Ant The objective of this study was to investigate the synergistic effect of β-cyfluthrin in combination with adjuvant on efficacy against Argentine ant, *Linepithema humile*.

MATERIALS AND METHODS: Solutions of β-cyfluthrin at 0.1, 0.05, 0.025, 0.01, 0.005 and 0.001% AI were prepared with and without adjuvant in acetone. The adjuvant is a combination of Compound A at 1% and Compound B at 0.5%. Treatments were applied using a micropipette to dispense 1 ml of test solution on 6"×6" glazed tile. Actual coverage was about 5"×5" (or 161 cm$^2$) for easy handling. Treatments were allowed to dry overnight. Ten Argentine ant workers were placed within a fluon or talc-coated PVC ring (φ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 6 hours after exposure.

UTC was ineffective at killing the ants, while the β-cyfluthrin was extremely effective at killing the ants, and the adjuvant were effective at killing the ants, albeit at a much slower rate than the β-cyfluthrin. The results are shown in FIG. 62.

SUMMARY: Because β-cyfluthrin was so effective on its own in killing the Argentine ant, it required lower concentrations in order to observe a synergistic effect with the adjuvant. At a concentration of 0.001%, the β-cyfluthrin took a relatively longer time to achieve high mortality rates, and there was a synergistic effect against Argentine ants within the first hour of observation when the β-cyfluthrin was combined with the adjuvant. It is believed that synergy will also be observed at lower rates of β-cyfluthrin with adjuvant. Adjuvant alone was toxic to the Argentine ant.

Example 65

Combination of Compound A and Compound B—Synergy with β-cyfluthrin Against Bait Averse/Resistant German Cockroach (IHOP strain)

The objective of this study was to investigate the synergistic effect of β-cyfluthrin in combination with adjuvant on efficacy against bait averse/resistant German cockroach (IHOP strain), *Blattella germanica*.

MATERIALS AND METHODS: Solutions of β-cyfluthrin at 0.005 and 0.001% AI were prepared with and without adjuvant in acetone. The adjuvant is a combination of Compound A at 1% and Compound B at 0.5%. Treatments were applied using a micropipette to dispense 1 ml of test solution on 6"×6" glazed tile. Actual coverage was about 5"×5" (or 161 cm$^2$) for easy handling. Treatments were allowed to dry overnight. Five male German cockroaches were placed within a Fluon-coated PVC ring (φ7.6 cm×H 5.1 cm) under continuous exposure. A small vial cap filled with a cotton ball soaked in water was added as drinking source after 3 hours. Treatments were replicated a minimum of three times. Evaluations for cockroach knockdown/mortality were made at various intervals and at 24 hours after exposure. The results are shown in FIG. 63.

SUMMARY: No synergy (but some antagonistic effect) was observed with β-cyfluthrin and adjuvant against the resistant German cockroaches at the rates tested. It is believed that synergy will be observed at lower rates of β-cyfluthrin when they are combined with adjuvant. The adjuvant alone was not toxic to the resistant German cockroaches.

Example 66

Combination of Compound A and Compound B—Synergy with β-cyfluthrin Against Susceptible German Cockroach (Monheim strain)

The objective of this study was to investigate the synergistic effect of β-cyfluthrin in combination with adjuvant on efficacy against susceptible German cockroach (Monheim strain), *Blattella germanica*.
MATERIALS AND METHODS: Solutions of β-cyfluthrin at 0.005 and 0.001% AI were prepared with and without adjuvant in acetone. The adjuvant is a combination of Compound A at 1% and Compound B at 0.5%. Treatments were applied using a micropipette to dispense 1 ml of test solution on 6"×6" glazed tile. Actual coverage was about 5"×5" (or 161 cm$^2$) for easy handling. Treatments were allowed to dry overnight. Five male German cockroaches were placed within a fluon-coated PVC ring (φ7.6 cm×H 5.1 cm) under continuous exposure. Treatments were replicated a minimum of three times. Cockroach knockdown/mortality was evaluated at 5 minute intervals for 40 minutes after exposure. The results are shown in FIG. 65. Due to complete cockroach mortality and the inability to differentiate between treatments, evaluations were terminated after 40 minutes.
SUMMARY: As shown in FIG. 64, no synergy (but some antagonistic effect for the initial 10-20 min) was observed with β-cyfluthrin and adjuvant against the susceptible German cockroaches at the rates tested. It is believed that synergy may be exhibited at lower rates of β-cyfluthrin with adjuvant. The adjuvant alone was not toxic to the susceptible German cockroaches.

Example 67

Combination of Compound A and Compound B—Synergy with β-cyfluthrin Against Odorous House Ant The objective of this study was to investigate the synergistic effect of β-cyfluthrin in combination with adjuvant on efficacy against the odorous house ant, *Tapinoma sessile*.
MATERIALS AND METHODS: Solutions of β-cyfluthrin at 0.005% and 0.001% were prepared with and without adjuvant in acetone. The adjuvant is a combination of Compound A at 1% and Compound B at 0.5%. Treatments were applied using a micropipette to dispense 1 ml of test solution on a 6"×6" glazed tile. Actual coverage was about 5"×5" (or 161 cm$^2$) for easy handling. Treatments were allowed to dry overnight. Ten Odorous House ant workers were placed within a fluon or talc-coated PVC ring (φ7.6 cm×H 5.1 cm) under continuous exposure. A small vial cap filled with a cotton ball soaked in water was added as a drinking source after 3 hours. Treatments were replicated a minimum of three times. Evaluations for ant knockdown/mortality were made at various intervals and at 24 hours after exposure.
The results are shown in FIG. 65
SUMMARY: As shown in FIG. 66, β-cyfluthrin at 0.005 and 0.001% AI in combination with adjuvant showed synergy against the odorous house ant. The adjuvant alone had some delayed toxicity to the odorous house ant.

Example 68

Combination Compound A and Compound B—Synergy with β-cyfluthrin Against Red Imported Fire Ant (RIFA)

The objective of this study was to investigate the synergistic effect of β-cyfluthrin in combination with adjuvant on efficacy against the red imported fire ant, *Solenopsis invicta*.
MATERIALS AND METHODS: Solutions of β-cyfluthrin at 0.005% and 0.001% were prepared with and without adjuvant in acetone. The adjuvant is a combination of Compound A at 1% and Compound B at 0.5%. Treatments were applied using a micropipette to dispense 1 ml of test solution on a 6"×6" glazed tile. Actual coverage was about 5"×5" (or 161 cm$^2$) for easy handling. Treatments were allowed to dry overnight. Ten Red Imported Fire ant workers were placed within a talc-coated PVC ring (φ7.6 cm×H 5.1 cm) under continuous exposure. A small vial cap filled with a cotton ball soaked in water was added as a drinking source after 3 hours. Treatments were replicated a minimum of three times. Evaluations for ant knockdown/mortality were made at various intervals and at 24 hours after exposure. The results are shown in the table below.

TABLE 72

(no figure): Summary of β-cyfluthrin/adjuvant synergy study against Red Imported Fire ant

| Treatment | Rate (g/m$^2$) | Average % Mortality after | | | |
|---|---|---|---|---|---|
| | | 15 min | 30 min | 60 min | 24 hr |
| UTC | | 0 | 0 | 0 | 0 |
| β-cyfluthrin (.005%) | 0.0031 | 100 | 100 | 100 | 100 |
| β-cyfluthrin (.005%) + adjuvant | 0.0031 | 100 | 100 | 100 | 100 |
| β-cyfluthrin (.001%) | 0.00062 | 39 | 100 | 100 | 100 |
| β-cyfluthrin (.001%) + adjuvant | 0.00062 | 8 | 41 | 100 | 100 |
| adjuvant | | 0 | 0 | 0 | 53 |

SUMMARY: No synergy was observed against the RIFA at the 0.005% rate tested. However, antagonistic effect was observed at the 0.001% rate tested. Adjuvant alone had a delayed toxicity to the RIFA.

Example 69

Combination of Compound A and Compound B—Synergy with Bendiocarb Against *Aedes aegypti* Mosquito The objective of this study was to investigate the synergistic effect of bendiocarb in combination with adjuvant on efficacy against *Aedes aegypti* mosquitoes.
MATERIALS AND METHODS: Solutions of bendiocarb at 0.1 and 0.01% AI were prepared with and without adjuvant in acetone. The adjuvant is a combination of Compound A at 1% and Compound B at 0.5%. Treatments were applied using a micropipette to dispense 1 ml of test solution evenly on 6"×6" glazed tile. Actual coverage was about 5"×5" (or 161 cm$^2$) for easy handling. Treatments were allowed to dry overnight. USDA Petri Dish Method was used as initial screening protocol. Twenty, 4-6 day old female *Aedes aegypti* mosquitoes were exposed to each treatment for 3 minutes and then moved to a clean untreated white paper index card. Treatments were replicated a minimum of three times. Mosquito knockdown was evaluated at various intervals through 2 hours after exposure. A small cotton ball soaked in sucrose solution was then added on the screen top of the petri-dish as a drinking source. Mortality was evaluated at 24 hours after exposure. The results are shown in FIG. 66.

SUMMARY: A synergistic effect was seen with bendiocarb at 0.1% AI in combination with adjuvant against *Aedes aegypti*. Significant increase in mosquito knockdown/mortality was observed within 15 minutes after exposure versus bendiocarb alone. No synergistic effect was noted with bendiocarb at 0.01% and adjuvant. Adjuvant alone was not toxic to *Aedes aegypti*.

Example 70

Combination of Compound A and Compound B—Synergy with Bendiocarb Against Argentine Ant The objective of this study was to investigate the synergistic effect of bendiocarb in combination with adjuvant on efficacy against *Linepithema humile*, Argentine ant.

MATERIALS AND METHODS: Solutions of bendiocarb at 0.005% and 0.001% were prepared with and without adjuvant in acetone. The adjuvant is a combination of Compound A at 1% and Compound B at 0.5%. Treatments were applied using a micropipette to dispense 1 ml of test solution on a 6"x6" glazed tile. Actual coverage was about 5"×5" (or 161 cm$^2$) for easy handling. Treatments were allowed to dry overnight. Ten Argentine ant workers were placed within a talc-coated PVC ring (ϕ7.6 cm×H 5.1 cm) under continuous exposure. Treatments were replicated a minimum of three times. Evaluations for ant knockdown/mortality were made at 5 minute intervals for 45 minutes and then at 1 and 2 hours after exposure. A small vial filled with a cotton ball soaked in water was added as a drinking source after 2 hours. Mortality was evaluated at 21 hours after exposure. The results are shown in FIG. 67.

SUMMARY: A synergistic effect was seen with bendiocarb at 0.001% AI in combination with adjuvant against the Argentine ant. However, no synergistic effect was noted with bendiocarb at 0.005% AI in combination with adjuvant. Adjuvant treatment alone was toxic to the Argentine ant.

Example 71

Combination of Compound A and Compound B—Synergy with Bendiocarb Against Culex quinquefasciatus Mosquito The objective of this study was to investigate the synergistic effect of bendiocarb in combination with adjuvant on efficacy against Culex quinquefasciatus mosquitoes.

MATERIALS AND METHODS: Solutions of bendiocarb at 0.1 and 0.01% AI were prepared with and without UV adjuvant in acetone. The adjuvant is a combination of Compound A at 1% and Compound B at 0.5%. Treatments were applied using a micropipette to dispense 1 ml of test solution evenly on 6"x6" glazed tile. Actual coverage was about 5"×5" (or 161 cm$^2$) for easy handling. Treatments were allowed to dry overnight. USDA Petri Dish Method was used as initial screening protocol. Twenty, 4-6 day old female *Culex quinquefasciatus* mosquitoes were exposed to each treatment for 3 minutes and then moved to a clean untreated white paper index card. Treatments were replicated a minimum of three times. Mosquito knockdown was evaluated at various intervals through 2 hours after exposure. A small cotton ball soaked in sucrose solution was then added on the screen top of the petri-dish as a drinking source. Mortality was evaluated at 24 hours after exposure. The results are shown in FIG. 68.

TABLE 73

Adjuvant in combination with Bendiocarb (in acetone)
On glazed tiles, *Culex quinquefasciatus*, 20 insects (three replicates) 3' exposure time

| Concentration and quantity on surface | % KD and Mortality | | | | | | | | | |
|---|---|---|---|---|---|---|---|---|---|---|
| | 3' | 9' | 15' | 30' | 1 h | 2 h | 3 h | 4 h | 6 h | 24 h |
| 0.1% = 50 mg Bendiocarb/m$^2$ | 0 | 0 | 0 | 15 | 37 | nt | nt | nt | nt | 81 |
| 0.1% = 50 mg Bendiocarb/m$^2$ + 1% = 500 mg Compound A/m$^2$ + 0.5% = 250 mg Compound B/m$^2$ | 28 | 83 | 88 | 100 | 100 | nt | nt | nt | nt | 100 |
| 0.01% = 5 mg Bendiocarb/m$^2$ | 0 | 0 | 0 | 0 | 0 | nt | nt | nt | nt | 0 |
| 0.01% = 5 mg Bendiocarb/m$^2$ + 1% = 500 mg Compound A/m$^2$ + 0.5% = 250 mg Compound B/m$^2$ | 0 | 0 | 0 | 0 | 21 | nt | nt | nt | nt | 21 |
| 1% = 500 mg Compound A/m$^2$ + 0.5% = 250 mg Compound B/m$^2$ | 0 | 0 | 0 | 0 | 0 | nt | nt | nt | nt | 0 |
| Acetone only | 0 | 0 | 0 | 0 | 0 | nt | nt | nt | nt | 0 |

TABLE 74

Adjuvant in combination with Bendiocarb (in acetone)
On glazed tiles, *Culex quinquefasciatus*, 10 insects (three replicates) 3' exposure time

| Concentration and quantity on surface | 3' | 9' | 15' | 30' | 1 h | 2 h | 3 h |
|---|---|---|---|---|---|---|---|
| 0.1% = 50 mg Bendiocarb/m$^2$ | 0 | 0 | 0 | 7 | 57 | 90 | 97 |
| 0.1% = 50 mg Bendiocarb/m$^2$ + | 70 | 83 | 100 | 100 | 100 | 100 | 100 |

TABLE 74-continued

Adjuvant in combination with Bendiocarb (in acetone)
On glazed tiles, *Culex quinquefasciatus*, 10 insects (three replicates) 3' exposure time

| Concentration and quantity on surface | 3' | 9' | 15' | 30' | 1 h | 2 h | 3 h |
|---|---|---|---|---|---|---|---|
| 1% = 500 mg Compound A/m² + 0.5% = 250 mg Compound B/m² 0.1% = 50 mg Bendiocarb/m² + 1% = 500 mg Compound A/m² | 77 | 97 | 100 | 100 | 100 | 100 | 100 |
| 0.1% = 50 mg Bendiocarb/m² + 0.5% = 250 mg Compound B/m² | 7 | 3 | 7 | 40 | 83 | 100 | 100 |
| 1% = 500 mg Compound A/m² + 0.5% = 250 mg Compound B/m² | 0 | 0 | 0 | 0 | 0 | 0 | 0 |
| 1% = 500 mg Compound A/m² | 0 | 0 | 0 | 0 | 0 | 0 | 0 |
| 0.5% = 250 mg Compound B/m² | 0 | 0 | 0 | 0 | 0 | 0 | 0 |
| Acetone only | 0 | 0 | 0 | 0 | 0 | 0 | 0 |

TABLE 75

On filter paper, *C. quinquefasciatus*, 10 insects (three replicates) 3' exposure time

| Concentration and quantity on surface | 3' | 9' | 15' | 30' | 1 h | 2 h | 3 h |
|---|---|---|---|---|---|---|---|
| 0.1% = 50 mg Bendiocarb/m² | 0 | 0 | 0 | 0 | 3 | 0 | 0 |
| 0.1% = 50 mg Bendiocarb/m² + 1% = 500 mg Compound A/m² + 0.5% = 250 mg Compound B/m² | 0 | 0 | 0 | 0 | 3 | 3 | 3 |
| Acetone only | 0 | 0 | 0 | 0 | 0 | 0 | 0 |

TABLE 76

Adjuvant in combination with Bendiocarb (in EC-formulations)
On glazed tiles, *Culex quinquefasciatus*, 10 insects (one replicate) 3' exposure time

| Concentration and quantity on surface | % KD and Mortality | | | | | | | | | |
|---|---|---|---|---|---|---|---|---|---|---|
| | 3' | 9' | 15' | 30' | 1 h | 2 h | 3 h | 4 h | 6 h | 24 h |
| 0.1% = 50 mg Bendiocarb/m² | nt | nt | 0 | 0 | 80 | 100 | 100 | 100 | 100 | 100 |
| 0.1% = 50 mg Bendiocarb/m² + 1% = 500 mg Compound A/m² | nt | nt | 0 | 0 | 30 | 30 | 90 | 100 | 100 | 100 |
| 0.1% = 50 mg Bendiocarb/m² + 0.2% = 100 mg Compound A/m² | nt | nt | 0 | 0 | 0 | 30 | 70 | 70 | 70 | 90 |
| 0.1% = 50 mg Bendiocarb/m² + 0.04% = 20 mg Compound A/m² | nt | nt | 0 | 0 | 0 | 0 | 70 | 70 | 70 | 90 |

SUMMARY: A synergistic effect was seen with bendiocarb at 0.1% AI in combination with adjuvant against *Culex quinquefasciatus*. Significant increase in mosquito knockdown/mortality was observed within 30 minutes after exposure versus bendiocarb alone. A delayed synergistic effect was noted with bendiocarb at 0.01% and adjuvant. Adjuvant alone was not toxic to *Culex quinquefasciatus*.

Example 72

Combination Compound A and Compound B—Synergy with Bendiocarb Against Odorous House Ant The objective of this study was to investigate the synergistic effect of bendiocarb in combination with adjuvant on efficacy against the odorous house ant, Tapinoma sessile.

MATERIALS AND METHODS: Solutions of bendiocarb at 0.005% and 0.001% were prepared with and without adjuvant in acetone. The adjuvant is a combination of Compound A at 1% and Compound B at 0.5%. Treatments were applied using a micropipette to dispense 1 ml of test solution on a 6"×6" glazed tile. Actual coverage was about 5"×5" (or 161 cm²) for easy handling. Treatments were allowed to dry overnight. Ten Odorous House ant workers were placed within a talc-coated PVC ring ($\phi$7.6 cm×H 5.1 cm) under continuous exposure. Treatments were replicated a minimum of three times. Evaluations for ant knockdown/mortality were made at 5 minute intervals for 1 hour and then at 2 and 4 hours after exposure. The results are shown in FIG. 69.

SUMMARY: A synergistic effect was seen with both rates of bendiocarb in combination with adjuvant against the odorous house ant. The bendiocarb at 0.001%+adjuvant showed the greatest effect in speed of KD and mortality, while no KD/mortality was noted among the treatments with bendiocarb alone. Adjuvant alone was slightly toxic to the odorous house ant.

Example 73

Combination of Compound A and Compound B—Synergy with Carbaryl Against *Aedes aegypti* Mosquito The objective of this study was to investigate the synergistic effect of carbaryl in combination with adjuvant on efficacy against *Aedes aegypti* mosquitoes.

MATERIALS AND METHODS: Solutions of carbaryl at 5, 2.5, 1 and 0.1% AI were prepared with and without adjuvant in acetone. The adjuvant is a combination of Compound A at 1% and Compound B at 0.5%. Treatments were applied using a micropipette to dispense 1 ml of test solution evenly on 6"×6" glazed tile. Actual coverage was about 5"×5" (or 161 cm$^2$) for easy handling. Treatments were allowed to dry overnight. USDA Petri Dish Method was used as initial screening protocol. Twenty, 4-6 day old female Aedes aegypti mosquitoes were exposed to each treatment for 3 minutes and then moved to a clean untreated white paper index card. Treatments were replicated a minimum of three times. Mosquito knockdown was evaluated at various hourly intervals. A small cotton ball soaked in sucrose solution was added on the screen top of the petri-dish as a drinking source after 2 hours. Mortality was evaluated at 24 hours after exposure. The results are shown in FIG. 70. The trial was terminated after 2 hours.

SUMMARY: Carbaryl at 0.1% AI in combination with adjuvant showed some synergistic effect against *A. aegypti* but mortality was less than 60% by 24 hours. All other rates of carbaryl showed no synergistic effect. Adjuvant treatment alone was not toxic to *A. aegypti*.

Example 74

Combination of Compound A and Compound B—Synergy with Carbaryl Against Argentine Ant The objective of this study was to investigate the synergistic effect of carbaryl in combination with adjuvant on efficacy against *Linepithema humile*, Argentine ant.

MATERIALS AND METHODS: Solutions of carbaryl at 0.05% and 0.01% were prepared with and without adjuvant in acetone. The adjuvant is a combination of Compound A at 1% and Compound B at 0.5%. Treatments were applied using a micropipette to dispense 1 ml of test solution on a 6"×6" glazed tile. Actual coverage was about 5"×5" (or161 cm$^2$) for easy handling. Treatments were allowed to dry overnight. Ten Argentine ant workers were placed within a talc-coated PVC ring (φ7.6 cm×H 5.1 cm) under continuous exposure.

Treatments were replicated a minimum of three times. Evaluations for ant knockdown/mortality were made at 5 minute intervals for 65 minutes after exposure. The results are shown in FIG. 71.

SUMMARY: A synergistic effect was observed with both rates of carbaryl in combination with adjuvant against the Argentine ant. Carbaryl at 0.01% AI in combination with adjuvant provided the greatest increase in KD/mortality. Adjuvant alone was toxic to the Argentine ant.

Example 75

Combination of Compound A and Compound B—Synergy with Carbaryl Against *Culex quinquefasciatus* Mosquito The objective of this study was to investigate the synergistic effect of carbaryl in combination with adjuvant on efficacy against *Culex quinquefasciatus* mosquitoes.

MATERIALS AND METHODS: Solutions of carbaryl at 5, 2.5, 1 and 0.1% AI were prepared with and without adjuvant in acetone. The adjuvant is a combination of Compound A at 1% and Compound B at 0.5%. Treatments were applied using a micropipette to dispense 1 ml of test solution evenly on 6"×6" glazed tile. Actual coverage was about 5"×5" (or 161 cm$^2$) for easy handling. Treatments were allowed to dry overnight. USDA Petri Dish Method was used as initial screening protocol. Twenty, 4-6 day old female *Culex quinquefasciatus* mosquitoes were exposed to each treatment for 3 minutes and then moved to a clean untreated white paper index card. Treatments were replicated a minimum of three times. Mosquito knockdown was evaluated at various hourly intervals. A small cotton ball soaked in sucrose solution was added on the screen top of the petri-dish as a drinking source after 2 hours. Mortality was evaluated at 24 hours after exposure. The results are shown in the table below.

TABLE 77

(no figure): Summary of carbaryl/adjuvant synergy study against *Culex quinquefasciatus*

| Treatment | Rate (g/m$^2$) | Average % Mortality after | | | |
|---|---|---|---|---|---|
| | | 1 hr | 3 hr | 5 hr | 24 hr |
| UTC | | 0 | 0 | 0 | 0 |
| carbaryl (5%) | 3.1 | 0 | 0 | 0 | 0 |
| carbaryl (5%) + adjuvant | 3.1 | 0 | 0 | 2 | 11 |
| carbaryl (2.5%) | 1.55 | 0 | 0 | 2 | 5 |
| carbaryl (2.5%) + adjuvant | 1.55 | 0 | 0 | 0 | 0 |
| carbaryl (1%) | 0.62 | 0 | 0 | * | * |
| carbaryl (1%) + adjuvant | 0.62 | 0 | 0 | * | * |
| carbaryl (0.1%) | 0.062 | 0 | 0 | * | * |
| carbaryl (0.1%) + adjuvant | 0.062 | 0 | 0 | * | * |
| adjuvant | | 0 | 0 | 0 | 0 |

*Due to poor efficacy, trial terminated after 3 hours.

SUMMARY: No synergy was seen with carbaryl and adjuvant against *Culex quinquefasciatus* mosquitoes at the rates tested. Adjuvant treatment alone was not toxic to *C. quinquefasciatus*.

Example 76

Combination of Compound A and Compound B—Synergy with Carbaryl Against Odorous House Ant The objective of this study was to investigate the synergistic effect of carbaryl in combination with adjuvant on efficacy against the odorous house ant, *Tapinoma sessile*.

MATERIALS AND METHODS: Solutions of carbaryl at 0.05% and 0.01% were prepared with and without adjuvant in acetone. The adjuvant is a combination of Compound A at 1% and Compound B at 0.5%. Treatments were applied using a micropipette to dispense 1 ml of test solution on a 6"×6" glazed tile. Actual coverage was about 5"×5" (or 161 cm$^2$) for easy handling. Treatments were allowed to dry overnight. Ten Odorous House ant workers were placed within a fluon or talc-coated PVC ring ($\phi$7.6 cm×H 5.1 cm) under continuous exposure. Treatments were replicated a minimum of three times. Evaluations for ant knockdown/mortality were made at 5 minute intervals for 60 minutes and at 2 and 3 hours after exposure. The results are shown in FIG. 72.

SUMMARY: A synergistic effect was observed with both rates of carbaryl in combination with adjuvant against the odorous house ant. Carbaryl at 0.01% AI in combination with adjuvant provided the greatest increase in KD/mortality. The adjuvant alone was not toxic to the odorous house ants.

Example 77

Combination of Compound A and Compound B—Synergy with Carbaryl Against Red Imported Fire Ant (RIFA)

The objective of this study was to investigate the synergistic effect of carbaryl in combination with adjuvant on efficacy against Red Imported Fire ant, *Solenopsis invicta*.

MATERIALS AND METHODS: Solutions of carbaryl at 0.05% and 0.01% were prepared with and without adjuvant in acetone. The adjuvant is a combination of Compound A at 1% and Compound B at 0.5%. Treatments were applied using a micropipette to dispense 1 ml of test solution on a 6"×6" glazed tile. Actual coverage was about 5"×5" (or 161 cm$^2$) for easy handling. Treatments were allowed to dry overnight. Ten Red Imported Fire ant workers were placed within a talc-coated PVC ring ($\phi$7.6cm×H 5.1 cm) under continuous exposure.

Treatments were replicated a minimum of three times. Evaluations for ant knockdown/mortality were made at 5 minute intervals for 60 minutes. The results are shown in FIG. 73.

SUMMARY: No synergy was seen between carbaryl and adjuvant against RIFA at the rates tested. There is a need to investigate further, as there is believed that a synergy may be exhibited at lower rates of carbaryl+adjuvant. Adjuvant alone was moderately toxic to the RIFA.

Example 78

Combination of Compound A and Compound B—Synergy with Carbaryl Against Susceptible German Cockroach (Monheim strain)

The objective of this study was to investigate the synergistic effect of carbaryl in combination with adjuvant on efficacy against susceptible/normal German cockroach (Monheim), *Blattella germanica*.

MATERIALS AND METHODS: Solutions of carbaryl at 0.05 and 0.01% AI were prepared with and without UV adjuvant in acetone. The adjuvant is a combination of Compound A at 1% and Compound B at 0.5%. Treatments were applied using a micropipette to dispense 1 ml of test solution on 6"×6" glazed tile. Actual coverage was about 5"×5" (or 161 cm$^2$) for easy handling. Treatments were allowed to dry overnight. Five male German cockroaches were placed within a talc-coated PVC ring ($\phi$7.6cm×H 5.1cm) under continuous exposure. Treatments were replicated a minimum of three times. Cockroach knockdown/mortality was evaluated at 5 minute intervals for the first 60 minutes after exposure and then at 2, 18 and 24 hours. The results are shown in FIG. 74.

SUMMARY: Both rates of carbaryl showed synergistic effect with adjuvant against susceptible German cockroaches with 0.05% providing the greatest difference with and without adjuvant. However, adjuvant alone was moderately toxic to the German cockroach.

Example 79

Combination of Compound A and Compound B—Synergy with Clothianidin Against *Aedes aegypti* Mosquito The objective of this study was to investigate the synergistic effect of clothianidin in combination with adjuvant on efficacy against *Aedes aegypti* mosquitoes.

MATERIALS AND METHODS: A solution of clothianidin at 1% AI was prepared with and without adjuvant in acetone. The adjuvant is a combination of Compound A at 1% and Compound B at 0.5%. Treatments were applied using a micropipette to dispense 1 ml of test solution evenly on 6"×6" glazed tile. Actual coverage was about 5"×5" (or 161 cm$^2$) for easy handling. Treatments were allowed to dry overnight. USDA Petri Dish Method was used as initial screening protocol. Twenty, 4-6 day old female *Aedes aegypti* mosquitoes were exposed to each treatment for 3 minutes and then moved to a clean untreated white paper index card. Treatments were replicated a minimum of three times. Mosquito knockdown was evaluated at various intervals through 4 hours after exposure. A small cotton ball soaked in sucrose solution was added on the screen top of the petri-dish as a drinking source. Mortality was evaluated at 24 hours after exposure. The results are shown in the table below.

TABLE 78

(no figure): Summary of clothianidin/adjuvant synergy study against *Aedes aegypti* mosquito

| Treatment* | Rate (g/m$^2$) | Average % Knockdown & Mortality after | | | |
| --- | --- | --- | --- | --- | --- |
| | | 1 hr | 2 hr | 4 hr | 24 hr |
| UTC | | 0 | 0 | 0 | 0 |
| Clothianidin (1%) | 0.62 | 0 | 0 | 0 | 0 |
| Clothianidin (1%) + adjuvant | 0.62 | 0 | 0 | 0 | 0 |
| adjuvant | 0 | 0 | 0 | 0 | 0 |

*Only the 1% level was tested due to availability of *Aedes* mosquitoes.

SUMMARY: No synergistic effect was observed with clothianidin at 1.0% and adjuvant against *Aedes aegypti* mosquito. The adjuvant alone was not toxic to *Aedes aegypti*.

Example 80

Combination of Compound A and Compound B—Synergy with Clothianidin against Argentine Ant The objective of this study was to investigate the synergistic effect of clothianidin in combination with adjuvant on efficacy against Argentine ant, *Linepithema humile*.

MATERIALS AND METHODS: Solutions of clothianidin at 1, 0.5 and 0.1% AI were prepared with and without adjuvant in acetone. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm$^2$) for easy handling. Treatments were allowed to dry overnight. Ten Argentine ant workers were placed within a talc-coated PVC ring (φ7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure. The results are shown in FIG. 75.

SUMMARY: All rates of clothianidin in combination with adjuvant showed a synergistic effect against the Argentine ant. The lower clothianidin rate+adjuvant showed more synergistic effect in speed of KD/mortality than the higher rate. Adjuvant treatment alone was moderately toxic to the Argentine ant.

Example 81

Combination of Compound A and Compound B—Synergy with Clothianidin Against Odorous House Ant The objective of this study was to investigate the synergistic effect of clothianidin in combination with adjuvant on efficacy against the odorous house ant, *Tapinoma sessile*.

MATERIALS AND METHODS: Solutions of clothianidin at 1, 0.5 and 0.1% AI were prepared with and without adjuvant in acetone. The adjuvant is a combination of Compound A at 1% and Compound B at 0.5%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Ten odorous house ant workers were placed within a talc-coated PVC ring (φ7.6 cm×H 5.1 cm) under continuous exposure. A small vial cap filled with a cotton ball soaked in water was added as a drinking source after 3 hours. Treatments were replicated minimum three times. Evaluations for ant knockdown/mortality were made at various intervals and at 24 hours after exposure. The results are shown in FIG. 76.

SUMMARY: All rates of clothianidin in combination with adjuvant showed a synergistic effect against the odorous house ant. The lower clothianidin rate+adjuvant showed more synergistic effect in speed of KD/mortality than the higher rate. Adjuvant treatment alone was moderately toxic to the odorous house ant.

Example 82

Combination of Compound A and Compound B—Synergy with Clothianidin against Susceptible German Cockroach (Monheim Strain)

The objective of this study was to investigate the synergistic effect of clothianidin in combination with adjuvant on efficacy against susceptible/normal German cockroach strain (Monheim strain).

MATERIALS AND METHODS: Solutions of clothianidin at 1.0, 0.5 and 0.1% AI were prepared with and without adjuvant in acetone. The adjuvant is a combination of Compound A at 1% and Compound B at 0.5%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five male German cockroaches were placed within a talc-coated PVC ring (φ7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure. The results are shown in FIG. 77.

SUMMARY: The lower rates of clothianidin (0.5 & 0.1%) in combination with adjuvant showed synergistic effect than the high rate (@1.0%) against the susceptible German cockroach. Adjuvant alone was slightly toxic to the German cockroach.

Example 83

Compound A Synergy with Imidacloprid Against Odorous House Ant

The objective of this study was to investigate the synergistic effect of imidacloprid in combination with Compound A on efficacy against the odorous house ant, *Tapinoma sessile*.

MATERIALS AND METHODS: Solutions of imidacloprid at 0.5 and 0.1% AI were prepared with and without Compound A at 1.0, 0.1 and 0.01% in acetone. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Ten odorous house ant workers were placed within a talc-coated PVC ring (φ7.6 cm×H 5.1 cm) under continuous exposure. A small vial cap filled with a cotton ball soaked in water was added as a drinking source after 4 hours. Treatments were replicated a minimum of three times. Evaluations for ant knockdown/mortality were made at various intervals and at 24 hours after exposure. The results are shown in FIGS. 78 and 79.

SUMMARY: Compound A at 1.0% alone or in combination with imidacloprid (both 0.5 & 0.1%) provided very rapid knockdown and mortality against the odorous house ant (OHA). When combined with imidacloprid (1:2 and 1:10 IMI:Compound A ratios), the acute toxicity of Compound A alone became slightly moderated. However, when combined with Compound B, a significant "masking" effect was observed. The lower rates (0.1 & 0.01%) of Compound A were not toxic to the OHA whether in combination with imidacloprid or treated alone. It is believed that the effective concentration of Compound A can be optimized at between 0.1-1.0%, and will prove to be synergistic with imidacloprid. However, at the combination rates tested, there was no clear synergistic effect, but rather a dose-dependent response of Compound A against the Odorous House Ant.

Example 84

Combination of Compound A and Compound B—Synergy with Imidacloprid Against *Aedes aegypti* Mosquito The objective of this study was to investigate the synergistic effect of imidacloprid in combination with adjuvant on efficacy against *Aedes aegypti* mosquitoes.

MATERIALS AND METHODS: Solutions of imidacloprid at 1, 0.5 and 0.1% AI were prepared with and without adjuvant in acetone. The adjuvant is a combination of Compound A at 1% and Compound B at 0.5%. Treatments were applied using a micropipette to dispense 1 ml of test solution evenly on 6"×6" glazed tile. Actual coverage was about 5"×5" (or 161 cm$^2$) for easy handling. Treatments were allowed to dry overnight. USDA Petri Dish Method was used as initial screening protocol. Twenty, 4-6 day old female *Aedes aegypti* mosquitoes were exposed to each treatment for 3 minutes and then moved to a clean untreated white paper index card.

Treatments were replicated a minimum of three times. Mosquito knockdown was evaluated at various intervals through 4 hours after exposure. A small cotton ball soaked in sucrose solution was added on the screen top of the petri-dish as a drinking source. Mortality was evaluated at 24 hours after exposure. The results are shown in FIG. 80.

SUMMARY: A synergistic effect was observed with all the rates of imidacloprid and adjuvant against *Aedes aegypti*, though 24 HAT mosquito mortality was low (around 20%). Adjuvant alone was not toxic to *A. aegypti*.

Example 85

Combination of Compound A and Compound B—Synergy with Imidacloprid Against Argentine Ant The objective of this study was to investigate the synergistic effect of imidacloprid in combination with adjuvant on efficacy against Argentine ant, *Linepithema humile*.

MATERIALS AND METHODS: Solutions of imidacloprid at 1, 0.5 and 0.1% AI were prepared with and without adjuvant in acetone. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm$^2$) for easy handling. Treatments were allowed to dry overnight. Ten Argentine ant workers were placed within a fluon or talc-coated PVC ring ($\phi$7.6 cm×H 5.1 cm) under continuous exposure. A small vial filled with a cotton ball soaked in water was added as a drinking source after 3 hours. Treatments were replicated a minimum of three times. Evaluations for ant knockdown/mortality were made at various intervals and at 24 hours after exposure. The results are shown in in FIG. 81.

SUMMARY: Imidacloprid at both 0.5 and 0.1% in combination with adjuvant showed synergistic effect against Argentine ants, but not at the 1% level. Adjuvant alone had a delayed toxicity to the Argentine ants.

Example 86

Combination of Compound A and Compound B—Synergy with Imidacloprid Against Bait Averse/Resistant German Cockroach (IHOP Strain)

The objective of this study was to investigate the synergistic effect of imidacloprid in combination with adjuvant on efficacy against bait averse/resistant German cockroach (IHOP strain).

MATERIALS AND METHODS: Solutions of imidacloprid at 1.0, 0.5 and 0.1% AI were prepared with and without adjuvant in acetone. The adjuvant is a combination of Compound A at 1% and Compound B at 0.5%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five male German cockroaches were placed within a Fluon-coated PVC ring ($\phi$7.6 cm×H 5.1 cm) under continuous exposure. A small vial cap filled with a cotton ball soaked in water was added as a drinking source after 3 hours. Treatments were replicated a minimum of three times. Evaluations for knockdown/mortality were made at various intervals and at 24 hours after exposure. The results are shown in FIG. 82.

SUMMARY: A synergistic effect was seen with all rates of imidacloprid and adjuvant against the insecticide-resistant German cockroaches (IHOP strain). However, some recovery was observed at all rates of imidacloprid with adjuvant at 24 hours. Adjuvant alone was not toxic to the resistant German cockroach strain.

Example 87

Combination of Compound A and Compound B—Synergy with Imidacloprid Against Susceptible German Cockroach (Monheim Strain)

The objective of this study was to investigate the synergistic effect of imidacloprid in combination with adjuvant on efficacy against susceptible/normal German cockroach strain (Monheim strain).

MATERIALS AND METHODS: Solutions of imidacloprid at 1.0, 0.5 and 0.1% AI were prepared with and without adjuvant in acetone. The adjuvant is a combination of Compound A at 1% and Compound B at 0.5%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five male German cockroaches were placed within a Fluon-coated PVC ring ($\phi$7.6 cm×H 5.1 cm) under continuous exposure. A small vial cap filled with a cotton ball soaked in water was added as a drinking source after 3 hours. Treatments were replicated a minimum of three times.

Evaluations for knockdown/mortality were made at various intervals and at 24 hours after exposure. The results are shown in FIG. 83.

SUMMARY: A synergistic effect was seen with all rates of imidacloprid and adjuvant against the susceptible German cockroaches (Monheim strain). No KD/mortality recovery was observed at all rates of imidacloprid with or without adjuvant at 24 hours.

Example 88

Combination of Compound A and Compound B—Synergy with Imidacloprid Against Odorous House Ant The objective of this study was to investigate the synergistic effect of imidacloprid in combination with adjuvant on efficacy against the odorous house ant, *Tapinoma sessile*.

MATERIALS AND METHODS: Solutions of imidacloprid at 1, 0.5 and 0.1% AI were prepared with and without adjuvant in acetone. The adjuvant is a combination of Compound A at 1% and Compound B at 0.5%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Ten odorous house ant workers were placed within a Fluon-coated PVC ring ($\phi$7.6 cm×H 5.1 cm) under continuous exposure. A small vial cap filled with a cotton ball soaked in water was added as a drinking source after 3 hours. Treatments were replicated minimum of three times. Evaluations for ant knockdown/mortality were made at various intervals and at 24 hours after exposure. The results are shown in FIG. 84 (No adjuvant alone treatment was performed).

SUMMARY: All rates of imidacloprid in combination with adjuvant showed synergistic effect against the odorous house ant. The lower rates of imidacloprid (0.5 & 0.1%) provided better synergistic effect.

Example 89

Combination of Compound A and Compound B—Synergy with Imidacloprid Against Red Imported Fire Ant The objective of this study was to investigate the synergistic effect of imidacloprid in combination with adjuvant on efficacy against the Red Imported Fire Ant, *Solenopsis invicta*.

MATERIALS AND METHODS: Solutions of imidacloprid at 1, 0.5 and 0.1% AI were prepared with and without adjuvant in acetone. The adjuvant is a combination of Compound A at 1% and Compound B at 0.5%. Treatments were applied using a micropipette to dispense 1 ml of treatment solution on 6"×6" glazed tile. Actual coverage was about 5"×5" (or 161 cm$^2$) for easy handling. Treatments were allowed to dry overnight. Ten RIFA workers were placed within a fluon or talc-coated PVC ring ($\phi$7.6 cm×H 5.1 cm) under continuous exposure. A small vial filled with a cotton ball soaked in water was added as a drinking source after 3 hours. Treatments were replicated a minimum of three times.

Evaluations for ant knockdown/mortality were made at various intervals and at 24 hours after exposure. The results are shown in FIG. 85.

SUMMARY: All rates of imidacloprid in combination with adjuvant showed synergistic knockdown effect against the RIFA. The lower rates of imidacloprid (0.5 & 0.1%) with adjuvant provided better synergistic KD effect, but showed no differentiation in 24-h mortality. Adjuvant alone had a delayed toxicity to the Red Imported Fire Ant.

Example 90

Performance Enhancement of Pyrethrins with Compound A Against House Crickets The objective of this study was to investigate the performance enhancement of pyrethrins (sold under the tradename Kicker EC) in combination with a sebacate, Compound A, on knockdown and mortality against the house cricket (*Acheta domesticus*).

MATERIALS AND METHODS: Kicker EC (pyrethrins 6%+PBO 60%) was premixed with three concentrations of Compound A in acetone, then diluted in H$_2$O to make the final treatment solutions (see table below), respectively. Kicker EC treatment without Compound A was prepared by diluting with H$_2$O to the desired concentration. Compound A was dissolved in acetone to make the final three treatment concentrations of 0.01, 0.1 and 1.0%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five adult crickets were placed within an inversed 1 quarter Mason jar under continuous exposure. A small slice of potato was added as a food source after 3 hours of exposure. Treatments were replicated four times. Evaluations for knockdown/mortality were made at various intervals and at 24 hours after exposure. The results are shown in FIG. 60.

SUMMARY: A significant performance enhancement (better KD and mortality) was observed with the two higher rates of Compound A in combination with pyrethrins at 0.006% against crickets. Pyrethrins (Kicker), alone, at 0.006% was totally ineffective against crickets. Except at 1.0% level, Compound A alone was not toxic to the house cricket.

Example 91

Performance Enhancement of Pyrethrins with Compound A Against Susceptible German Cockroach The objective of this study was to investigate the performance enhancement of pyrethrins (sold under the tradename Kicker EC) in combination with a sebacate, Compound A, on knockdown and mortality against susceptible German cockroach (UCR strain).

MATERIALS AND METHODS: Kicker EC (pyrethrins 6%+PBO 60%) was premixed with three concentrations of Compound A in acetone, then diluted in H$_2$O to make the final treatment solutions (see table below), respectively. Kicker EC treatment without Compound A was prepared by diluting with H$_2$O to the desired concentration. Compound A was dissolved in acetone to make the final three treatment concentrations of 0.01, 0.1 and 1.0%. Treatments were applied using a micropipette to dispense 1 ml of test solution evenly on a 6"×6" glazed tile. Actual coverage was about 5"×5" (or 161 cm$^2$) for easy handling. Treatments were allowed to dry overnight. Five male German cockroaches were placed within a Fluon-coated PVC ring ($\phi$7.6 cm×H 5.1 cm) under continuous exposure. A small vial cap filled with a cotton ball soaked in water was added as a drinking source after 3 hours of exposure. Treatments were replicated four times. Evaluations for knockdown/mortality were made at various intervals and at 24 hours after exposure. The results are shown in FIG. 61.

SUMMARY: A significant performance enhancement (rapid KD and mortality) was observed with all the three rates of Compound A in combination with pyrethrins at 0.006% against German cockroaches. Compound A alone was not toxic to the German cockroach at the rates tested.

Example 92

Efficacy of Low Quantities of Bendiocarb and Deltamethrin on Filter Paper with and Without Adjuvant Against the Malaria Mosquito (*Anopheles gambiae*)

The objective of this study was to evaluate the influence of adjuvant on the efficacy of different quantities of deltamethrin and Bendiocarb, respectively Method: Five-minute exposure bioassay The bioassays were carried out using the WHO Adult Mosquito Susceptibility Test Kit, (WHONBC 81.805, 1981) with plastic cylinders (4.5 cm diameter, 12 cm height). All bioassays were done using preferably female sugar fed *Anopheles gambiae* mosquitoes. Knock down was recorded after at 5, 10, 15, 20, 25, 30, 45 and 60 minutes, when the mosquitoes were supplied with a 5% sugar water source for 24 hours. Mortality was recorded 24 hours post exposure. Each test consisted of three replicates from which the mean values were calculated. The insecticides (all technical grades) were applied as 2 ml acetone solutions onto filter papers (12 cm×15 cm).

TABLE 79

Tested combinations
(Adjuvant = 1% Compound A + 0.5% Compound B):

bendiocarb 40 mg, 20 mg, 10 mg and 5 mg a.i./m$^2$, respectively

TABLE 79-continued

Tested combinations
(Adjuvant = 1% Compound A + 0.5% Compound B):

bendiocarb 40 mg, 20 mg, 10 mg and 5 mg a.i./m², respectively + Adjuvant
deltamethrin 40 mg, 20 mg, 10 mg and 5 mg a.i./m², respectively
deltamethrin 40 mg, 20 mg, 10 mg and 5 mg a.i./m², respectively + Adjuvant

TABLE 80

Results

| Sample (technical) on filter paper (mg/m²) | % knock down after | | | | | | | | % mortality | minutes | |
|---|---|---|---|---|---|---|---|---|---|---|---|
| | 5' | 10' | 15' | 20' | 25' | 30' | 45' | 60' | 1 d | KT 50 | KT 95 |
| 40 mg bendiocarb | 16 | 50 | 56 | 68 | 74 | 76 | 81 | 85 | 94 | 12 | >60 |
| 40 mg bendiocarb + adjuvant | 8 | 9 | 14 | 17 | 22 | 22 | 25 | 25 | 28 | >60 | >60 |
| 20 mg Bendiocarb | 3 | 6 | 4 | 6 | 13 | 13 | 20 | 21 | 27 | >60 | >60 |
| 20 mg bendiocarb + adjuvant | 0 | 0 | 0 | 0 | 0 | 0 | 0 | 0 | 0 | >60 | >60 |
| 10 mg Bendiocarb | 2 | 2 | 2 | 27 | 2 | 2 | 2 | 2 | 9 | >60 | >60 |
| 10 mg bendiocarb + adjuvant | 0 | 0 | 0 | 0 | 0 | 0 | 0 | 0 | 0 | >60 | >60 |
| 5 mg Bendiocarb | 6 | 6 | 6 | 6 | 6 | 6 | 6 | 6 | 12 | >60 | >60 |
| 5 mg bendiocarb + adjuvant | 2 | 2 | 2 | 2 | 2 | 2 | 2 | 2 | 5 | >60 | >60 |
| 40 mg DTM | 22 | 53 | 66 | 76 | 92 | 97 | 100 | 100 | 83 | 10 | 40 |
| 40 mg DTM + adjuvant | 6 | 20 | 39 | 67 | 76 | 81 | 91 | 94 | 67 | 17 | 51 |
| 20 mg DTM | 9 | 23 | 39 | 45 | 52 | 66 | 79 | 86 | 75 | 21 | >60 |
| 20 mg DTM + adjuvant | 4 | 7 | 19 | 33 | 33 | 51 | 67 | 70 | 39 | 33 | >60 |
| 10 mg DTM | 0 | 2 | 2 | 2 | 5 | 9 | 18 | 26 | 17 | >60 | >60 |
| 10 mg DTM + adjuvant | 10 | 10 | 12 | 10 | 12 | 13 | 31 | 46 | 17 | >60 | >60 |
| 5 mg DTM | 6 | 6 | 4 | 6 | 6 | 7 | 15 | 19 | 13 | >60 | >60 |
| 5 mg DTM + adjuvant | 0 | 2 | 2 | 2 | 3 | 3 | 8 | 8 | 12 | >60 | >60 |
| UTC (Acetone) | 3 | 3 | 3 | 3 | 3 | 3 | 3 | 3 | 6 | >60 | >60 |
| UTC (Acetone + adjuvant) | 2 | 2 | 2 | 2 | 2 | 2 | 2 | 2 | 7 | >60 | >60 |

SUMMARY: The efficacy for each insecticide quantity in combination with the adjuvant was lower than without adjuvant or equal (10 mg DTM+adjuvant versus 10 mg DTM alone). The cylinder method did not detect any synergistic effects between bendiocarb or deltamethrin and adjuvant. Rather, the addition of the adjuvant appears to cause inhibition effects.

Example 93

Bendiocarb Alone and in Combination with Compound A in Different Solvents and in Combination with Other Potential Efficacy Enhancers in Acetone on Glazed Tiles Against the Tropical House Mosquito *Culex quinquefasciatus*

The objective of this study was to evaluate the influence of different solvents on the efficacy (to select suitable solvents for formulation development) and to check the efficacy of other enhancers. The standard method for determining the efficacy of a formulation on surfaces was used.

Test Insects are *Culex quinquefasciatus* (adults, 3 days old). The Application provides the technical compounds were dissolved in acetone and applied as 1 ml solutions onto glazed tiles (15 cm×15 cm). An evaluation is provided at knock down after 3, 9, 15, and 30 minutes, 1, 2, 3, 4 and 24 hours (mortality). There are 3 replicates. The results are shown in Table 83.

TABLE 81

| Composition | Solvent | Bendiocarb alone | Efficacy enhancement compared to Bendiocarb alone |
|---|---|---|---|
| 0.1% bendiocarb + 1% Compound A | Acetone | + | ++ |
| 0.1% bendiocarb + 1% Compound A | Acetone + 0.05% citric acid | ++ | − |
| 0.1% bendiocarb + 1% Compound A | Methanol | + | +++ |
| 0.1% bendiocarb + 1% Compound A | Ethylacetate | + | +++ |
| 0.1% bendiocarb + 1% Compound A | γ-Butyrolactone | The solutions did not evaporate overnight but constricted to a small puddle. Thus, a test was not possible | |
| 0.1% bendiocarb + 1% Compound A | 2006-009112 | − | − |
| 0.1% bendiocarb + 1% Castor oil | Acetone | + | ++ |
| 0.1% bendiocarb + 1% Genapol X 080 | Acetone | + | ++ |
| 0.1% bendiocarb + 1% Purasolv EHC | Acetone | + | +(+) |

TABLE 82

| Formulation (1 part to be mixed with 9 parts of water) | | |
|---|---|---|
| 1% Bendiocarb | 5% Rhodasurf 860/P | 10% Soprophor 796/P |
| 10% Compound A | 74% γ-Butyrolactone | |

Conclusions: The EC formulation (with bendiocarb alone or combined with Compound A) impaired the efficacy and did not reveal synergistic affects. 0.1% bendiocarb+1% Compound A in acetone did show an efficacy enhancement. Addition of 0.05% citric acid led to a better efficacy of bendiocarb alone, but not to an efficacy enhancement by the addition of Compound A. The use of methanol and ethylacetate led to a strong efficacy enhancement by Compound A. The addition of castor oil or genapol to bendiocarb exhibited effects which were in the range of Compound A, while the efficacy enhancement of the product sold under the tradename Purasolv was lower than that of Compound A. γ-Butyrolactone appeared to not be a suitable solvent.

TABLE 83

| | | Results | | | | | | | | |
|---|---|---|---|---|---|---|---|---|---|---|
| | | % KD and Mortality | | | | | | | | |
| Composition | Solvent | 3' | 9' | 15' | 30' | 1 h | 2 h | 3 h | 4 h | 24 h |
| 0.1% bendiocarb | Acetone | 3 | 3 | 3 | 13 | 77 | 100 | 100 | 100 | 100 |
| 0.1% bendiocarb + 1% Compound A | Acetone | 0 | 47 | 73 | 90 | 93 | 100 | 100 | 100 | 100 |
| 1% Compound A | Acetone | 7 | 10 | 10 | 7 | 7 | 7 | 7 | 7 | 10 |
| UTC (solvent only) | Acetone | 0 | 0 | 0 | 0 | 0 | 0 | 0 | 0 | 7 |
| 0.1% bendiocarb | Acetone + 0.05% citric acid | 13 | 33 | 70 | 97 | 97 | 97 | 100 | 100 | 100 |
| 0.1% bendiocarb + 1% Compound A | Acetone + 0.05% citric acid | 3 | 30 | 53 | 73 | 93 | 83 | 80 | 77 | 90 |
| 1% Compound A | Acetone + 0.05% citric acid | 7 | 3 | 7 | 7 | 3 | 0 | 0 | 3 | 13 |
| UTC (solvent only) | Acetone + 0.05% citric acid | 0 | 0 | 0 | 0 | 0 | 0 | 0 | 0 | 0 |
| 0.1% bendiocarb | Methanol | 0 | 0 | 0 | 13 | 57 | 73 | 73 | 73 | 87 |
| 0.1% bendiocarb + 1% Compound A | Methanol | 20 | 50 | 87 | 93 | 100 | 97 | 93 | 93 | 100 |
| 1% Compound A | Methanol | 7 | 10 | 10 | 7 | 7 | 7 | 7 | 7 | 10 |
| UTC (solvent only) | Methanol | 3 | 3 | 3 | 3 | 0 | 0 | 0 | 0 | 10 |
| 0.1% bendiocarb | Ethylacetate | 0 | 3 | 7 | 27 | 50 | 73 | 70 | 80 | 80 |
| 0.1% bendiocarb + 1% Compound A | Ethylacetate | 40 | 77 | 87 | 100 | 100 | 100 | 100 | 100 | 100 |
| 1% Compound A | Ethylacetate | 10 | 17 | 20 | 23 | 30 | 23 | 23 | 23 | 30 |
| UTC (solvent only) | Ethylacetate | 3 | 3 | 7 | 7 | 7 | 7 | 10 | 10 | 17 |
| 0.1% bendiocarb | γ-Butyrolactone | The solutions did not evaporate overnight but constricted to a small puddle. Thus, a test was not possible | | | | | | | | |
| 0.1% bendiocarb + 1% Compound A | γ-Butyrolactone | | | | | | | | | |
| UTC (solvent only) | γ-Butyrolactone | | | | | | | | | |
| 0.1% bendiocarb | 2006-009114 | 10 | 17 | 23 | 27 | 43 | 87 | 93 | 97 | 97 |
| 0.1% bendiocarb + 1% Compound A | 2006-009112 | 27 | 33 | 33 | 33 | 67 | 77 | 87 | 93 | 93 |
| UTC | Blank formulation | 3 | 7 | 10 | 10 | 10 | 10 | 10 | 10 | 13 |
| 0.1% bendiocarb | Acetone | 3 | 3 | 3 | 13 | 77 | 100 | 100 | 100 | 100 |
| 0.1% bendiocarb + 1% Castor oil | Acetone | 7 | 47 | 90 | 97 | 100 | 100 | 100 | 100 | 100 |
| UTC (1% oil only) | Acetone | 0 | 0 | 0 | 0 | 0 | 0 | 0 | 0 | 10 |
| 0.1% bendiocarb | Acetone | 3 | 3 | 3 | 13 | 77 | 100 | 100 | 100 | 100 |
| 0.1% bendiocarb + 1% Genapol X 080 | Acetone | 20 | 53 | 77 | 100 | 100 | 100 | 100 | 100 | 100 |
| UTC (1% Genapol) | Acetone | 7 | 7 | 7 | 7 | 0 | 0 | 0 | 0 | 40 |
| 0.1% bendiocarb | Acetone | 3 | 3 | 3 | 13 | 77 | 100 | 100 | 100 | 100 |
| 0.1% bendiocarb + 1% Purasolv EHC | Acetone | 0 | 13 | 30 | 47 | 80 | 97 | 97 | 93 | 100 |
| UTC (1 Purasolv EHC) | Acetone | 0 | 0 | 0 | 0 | 0 | 0 | 0 | 0 | 13 |

Example 94

Bendiocarb Alone and in Combination with Compound A and Derivatives in Acetone on Glazed Tiles Against the Tropical House Mosquito *Culex quinquefasciatus*

The objective of this study was to test different derivatives of Compound A for possible structure efficacy relationships. As herein described, compounds may be referred to by Derivative Number for ease of reference. The standard method for determining the efficacy of a formulation on surfaces was used.

Test Insects: *Culex quinquefasciatus* (adults, 3 days old)

Application: The technical compounds were dissolved in acetone and applied as 1 ml solutions onto glazed tiles (15 cm×15 cm).

Evaluation: Knock down after 3, 9, 15, and 30 minutes, 1, 2, 3, 4 and 24 hours (mortality)

Replicates: 3

Conclusions: In general, Compound A acted weaker than in the previous tests. Nevertheless, an efficacy enhancement of the combination with bendiocarb compared to bendiocarb alone was obvious. From nine derivatives, Sebacic acid dibenzyl ester and 4-Hydroxy-2,2,6,6-tetramethylpiperidine appear superior to Compound A. Sebacic acid-bis-(N-succinimidyl)ester was equivalent to Compound A. Dimethyl sebacate, Sebacic acid and 1,2,2,6,6-Pentamethyl-4-piperidinol revealed no efficacy enhancement, while bis(1-octyloxy-2,2,6,6-tetramethyl-4-piperidyl)sebacate, 4-Hydroxy-2,2,6,6 tetramethylpiperidin-1-oxyl (free radical) and especially bis (2,2,6,6-tetramethyl-4-piperidyl)sebacate, inhibited the efficacy of bendiocarb compared to bendiocarb alone. None of the derivatives revealed an efficacy when tested without Bendiocarb. The efficacy enhancement was not due to oily consistency because all three derivatives were solid.

TABLE 84

| Composition | % KD and Mortality | | | | | | | | |
|---|---|---|---|---|---|---|---|---|---|
| | 3' | 9' | 15' | 30' | 1 h | 2 h | 3 h | 4 h | 24 h |
| 0.1% bendiocarb | 0 | 0 | 3 | 17 | 50 | 73 | 80 | 90 | 100 |
| 0.1% bendiocarb + 1% Compound A oily | 0 | 53 | 77 | 80 | 83 | 87 | 83 | 83 | 80 |
| 1% Compound A | 0 | 0 | 3 | 3 | 3 | 3 | 3 | 3 | 13 |
| 0.1% bendiocarb + 1% Dimethyl sebacate | 0 | 0 | 0 | 10 | 40 | 63 | 73 | 73 | 77 |
| 1% Dimethyl sebacate | 0 | 0 | 0 | 0 | 0 | 0 | 0 | 0 | 0 |
| 0.1% bendiocarb + 1% Sebacic acid powder | 3 | 3 | 7 | 10 | 53 | 73 | 80 | 83 | 87 |
| 1% Sebacic acid | 3 | 3 | 3 | 3 | 3 | 3 | 3 | 3 | 13 |
| 0.1% bendiocarb + 1% Sebacic acid dibenzyl ester crystalline | 3 | 50 | 93 | 97 | 100 | 100 | 100 | 100 | 100 |
| 1% Sebacic acid dibenzyl ester | 0 | 0 | 0 | 0 | 0 | 0 | 3 | 3 | 7 |
| 0.1% bendiocarb + 1% Sebacic acid-bis-(N-succinimidyl) ester powder | 0 | 0 | 3 | 40 | 67 | 97 | 100 | 100 | 100 |
| 1% Sebacic acid-bis-(N-succinimidyl) ester | 0 | 0 | 0 | 0 | 0 | 0 | 0 | 0 | 0 |
| 0.1% bendiocarb + 1% Bis(1-octyloxy-2,2,6,6-tetramethyl-4-piperidyl) sebacate oily | 0 | 7 | 10 | 27 | 40 | 43 | 43 | 43 | 47 |
| 1% Bis(1-octyloxy-2,2,6,6-tetramethyl-4-piperidyl) sebacate | 3 | 3 | 3 | 3 | 3 | 3 | 3 | 3 | 7 |
| 0.1% bendiocarb + 1% Bis (2,2,6,6-tetramethyl-4-piperidyl) sebacate powder | 3 | 3 | 3 | 3 | 3 | 7 | 7 | 7 | 7 |
| 1% Bis (2,2,6,6-tetramethyl-4-piperidyl) sebacate | 0 | 0 | 0 | 0 | 3 | 0 | 3 | 3 | 17 |
| 0.1% bendiocarb + 1% 4-Hydroxy-2,2,6,6-tetramethylpiperidine powder | 0 | 7 | 67 | 100 | 100 | 100 | 100 | 100 | 100 |
| 1% 4-Hydroxy-2,2,6,6-tetramethylpiperidine | 0 | 0 | 0 | 0 | 0 | 0 | 0 | 0 | 3 |
| 0.1% bendiocarb + 1% 1,2,2,6,6-Pentamethyl-4-piperidinol crystalline | 3 | 3 | 7 | 30 | 53 | 57 | 60 | 57 | 63 |
| 1% 1,2,2,6,6-Pentamethyl-4-piperidinol | 0 | 0 | 0 | 0 | 0 | 0 | 0 | 0 | 0 |
| 0.1% bendiocarb + 1% 4-Hydroxy-2,2,6,6 tetramethylpiperidin-1-oxyl (free radical) crystalline | 0 | 0 | 0 | 0 | 20 | 27 | 37 | 37 | 40 |
| 1% 4-Hydroxy-2,2,6,6 tetramethylpiperidin-1-oxyl (free radical) | 0 | 0 | 0 | 0 | 0 | 0 | 0 | 0 | 7 |

Example 95

Bendiocarb Alone and in Combination with Compound A and 2 Derivatives in Different Solvents on Glazed Tiles Against the Tropical House Mosquito Culex quinquefasciatus The objective of this study was to evaluate the influence of different solvents on the efficacy and to select suitable solvents for potential for formulation development. The standard method for determining the efficacy of a formulation on surfaces was used.

Test Insects: Culex quinquefasciatus (adults, 3 days old)

Application: The technical compounds were dissolved in the solvent and applied as 1 ml solutions onto glazed tiles (15 cm×15 cm) one day before test start.

Evaluation: Knock down after 3, 9, 15, and 30 minutes, 1, 2, 3, 4 and 24 hours (mortality)

Replicates: 3

The results are shown in FIG. 86.

Conclusions:

Compounds in ethylacetate: Both Compound A and Sebacic acid dibenzyl ester improved markedly the efficacy of bendiocarb compared to bendiocarb without additive. Compound A acted slightly better than Sebacic acid dibenzyl ester. The efficacy enhancement of 4-Hydroxy-2,2,6,6-tetramethylpiperidine was weaker, which may be due to its insolubility in ethylacetate.

Compounds in other solvents: When dissolved in cyclohexanone, no efficacy enhancement was observed with bendiocarb+Compound A compared to bendiocarb alone. In contrary, even the efficacy of bendiocarb alone was weaker than that of bendiocarb in ethylacetate. The compounds had not been tested in benzylacohol and propylenecarbamate because they collected in one patch or several patches one day after application.

Example 96

Bendiocarb Alone and in Combination with Compound A and Derivatives in Acetone on Glazed Tiles as well as Genapol and Purasolv Against the Tropical House Mosquito Culex quinquefasciatus The objective of this study was to test different derivatives of Compound A and possible structure efficacy relationships. The standard method for determining the efficacy of a formulation on surfaces was used.

Test Insects: Culex quinquefasciatus (adults, 3 days old)

Application: The technical compounds were dissolved in acetone and applied as 1 ml solutions onto glazed tiles (15 cm×15 cm).

Evaluation: Knock down after 3, 9, 15, and 30 minutes, 1, 2, 3, 4 and 24 hours (mortality)

Replicates: 3

TABLE 85

Tested compounds
For ease of reference, the compounds may be referred to herein as Derivative Number, namely Derivative 2 refers to sebacic acid as referenced in Table 85.

| | |
|---|---|
| 1) Dimethyl sebacate crystalline | 2) Sebacic acid powder |
| 3) Sebacic acid dibenzyl ester crystalline | 4) Sebacic acid-bis-(N-succinimidyl) ester Powder |
| 5) Bis(1-octyloxy-2,2,6,6-tetramethyl-4-piperidyl) sebacate oily | 6) Bis (2,2,6,6-tetramethyl-4-piperidyl) sebacate powder |
| 7) 4-Hydroxy-2,2,6,6-tetramethylpiperidine powder | 8) 1,2,2,6,6-Pentamethyl-4-piperidinol crystalline |
| 9) 4-Hydroxy-2,2,6,6 tetramethylpiperidin-1-oxyl (free radical) crystalline | Compound A oily |
| Genapol X080 $CH_3(CH_2)_{12}$—O—$(CH_2CH_2O)_8$—H | |

The results are shown in FIGS. 87-94. As shown in the Figures, the only derivative that was equal or superior to Compound A, was Sebacic acid dibenzyl ester. The Derivatives 1, 2, 4, 5, 8 and 9 acted weaker. Derivative 7 was superior to Compound A (first test) or weaker (second test). Derivative 6 inhibited the efficacy in both tests. Among the both tensides, Genapol X 080 was in the same range as Derivative 3. Purasolv EHC acted weaker. Derivative 1 (Dimethyl sebacate) and derivative 2 (Sebacic acid) acted weaker in both tests. Derivative 3 (Sebacic acid dibenzyl ester) was superior to Compound A (first test) or equal (second test). Derivative 4 (Sebacic acid-bis-(N-succinimidyl)ester) and Derivative 5 (Bis(1-octyloxy-2,2,6,6-tetramethyl-4-piperidyl)sebacate) were weaker as Compound A in both tests. Derivative 6 (Bis(2,2,6,6-tetramethyl-4-piperidyl)sebacate) inhibited the efficacy of bendiocarb in both tests. Derivative 7 (4-Hydroxy-2,2,6,6-tetramethylpiperidine) was superior to Compound A in the first test and inferior in the second test. Derivative 8 (1,2,2,6,6-Pentamethyl-4-piperidinol) and derivative 9 (4-Hydroxy-2,2,6,6 tetramethylpiperidin-1-oxyl) acted weaker in both tests. Genapol X 080 was superior to Compound A (first test) or equal (second test). Purasolv EHC was inferior to Compound A in both tests.

Example 97

Compound A in Acetone in Combination with Imidacloprid and Deltamethrin (as SC Formulations) on Two Surfaces Against Mosquitoes (Culex quinquefasciatus)

The objective of this study was to evaluate the influence of acetone solutions of Compound A on the efficacy of available SC formulations. The standard method for determining the efficacy of a formulation on surfaces was used.

Test Insects: Tropical house mosquito Culex quinquefasciatus (adults, susceptible strain)

TABLE 86

Formulations:

imidacloprid 350 SC (lab code 3554/583) to be dissolved in water
deltamethrin 10 SC (Pt. OP240153) to be dissolved in water
Compound A in acetone Application:

Aqueous solutions of imidacloprid 350 SC or deltamethrin 10 SC were applied by pipette onto glazed tiles (15×15 cm). 1% Compound A in acetone was applied immediately afterwards or one day later.

Evaluation: Knock down after 3, 9, 15, and 30 minutes, 1, 2, 4 and 24 hours (mortality)

Replicates: 1

The results are shown in FIG. 95 (imidacloprid 350 SC) and FIG. 96 (deltamethrin 10 SC). The few dead mosquitoes in some cases were due to biological variations. The acetone application influenced the efficacy of deltamethrin alone. On glazed tiles, the acetone application immediately after the deltamethrin 10 SC application, diminished the efficacy (with or without Compound A), whereas it was increased when the acetone was applied 1 day later (with or without Compound A). This efficacy enhancement was higher with Compound A than without Compound A. On unglazed tiles an efficacy inhibition by both acetone applications was observed and no synergistic effects were seen. It is believed that the acetone transports the deltamethrin into deeper zones of the tile, so it is no longer bioavailable. Compound A in acetone with imidacloprid 350 SC or deltamethrin 10 SC Culex quinquefasciatus.

TABLE 87

Table 87: Compound A in acetone with Imidacloprid 350 SC or Deltamethrin 10 SC
(*Culex quinquefasciatus*)
10 mosquitoes, 3' exposure time, 1 replicate

| | | | % Mortality | | | | | | | |
|---|---|---|---|---|---|---|---|---|---|---|
| Concentration | Formulation | Tile | 3' | 9' | 15' | 30' | 1 h | 2 h | 4 h | 24 h |
| 1 0.1% imidacloprid | Imidacloprid 350 SC | glazed | 0 | 0 | 0 | 0 | 0 | 0 | 0 | 0 |
| | | unglazed | 0 | 0 | 0 | 0 | 0 | 0 | 0 | 0 |
| 2 0.1% imidacloprid actone directly afterward | | glazed | 0 | 0 | 0 | 0 | 0 | 0 | 0 | 0 |
| | | unglazed | 0 | 0 | 0 | 0 | 0 | 0 | 0 | 0 |
| 3 0.1% imidacloprid 1% BLS292 in acetone directly afterward | | glazed | 0 | 0 | 0 | 0 | 0 | 0 | 0 | 20 |
| | | unglazed | 0 | 0 | 0 | 0 | 0 | 0 | 0 | 10 |
| 4 0.1% imidacloprid acetone one day later | | glazed | 0 | 0 | 0 | 0 | 0 | 0 | 0 | 20 |
| | | unglazed | 0 | 0 | 0 | 0 | 0 | 0 | 0 | 10 |
| 5 0.1% imidacloprid 1% BLS292 in acetone one day later | | glazed | 0 | 0 | 0 | 0 | 0 | 0 | 0 | 20 |
| | | unglazed | 0 | 0 | 0 | 0 | 0 | 0 | 0 | 0 |
| 6 0.002% deltamethrin | Deltamethrin SC | glazed | 0 | 0 | 0 | 0 | 0 | 0 | 0 | 50 |
| | | unglazed | 0 | 0 | 0 | 0 | 0 | 10 | 10 | 80 |
| 7 0.002% deltamethrin acetone directly afterward | | glazed | 0 | 0 | 0 | 0 | 0 | 0 | 10 | 10 |
| | | unglazed | 0 | 0 | 0 | 0 | 0 | 0 | 0 | 30 |
| 8 0.002% deltamethrin 1% BLS292 in acetone directly afterward | | glazed | 10 | 10 | 10 | 10 | 10 | 10 | 10 | 10 |
| | | unglazed | 0 | 0 | 0 | 0 | 0 | 0 | 0 | 0 |
| 9 0.002% deltamethrin acetone one day later | | glazed | 10 | 10 | 10 | 10 | 10 | 40 | 40 | 100 |
| | | unglazed | 0 | 0 | 0 | 0 | 0 | 0 | 0 | 0 |
| 10 0.002% deltamethrin 1% BLS292 in acetone one day later | | glazed | 0 | 10 | 20 | 20 | 30 | 60 | 90 | 90 |
| | | unglazed | 0 | 0 | 0 | 0 | 0 | 0 | 0 | 10 |
| 11 UTC | acetone | glazed | 0 | 0 | 0 | 0 | 0 | 0 | 0 | 0 |
| | | unglazed | 0 | 0 | 0 | 0 | 0 | 0 | 0 | 10 |

Evaluation: Mortality was evaluated cumulatively at different times.

Replicates: 3

TABLE 88

| Tested formulations: | |
|---|---|
| SUSCEPTIBLE FLIES: | 0.001% DELTAMETHRIN IN 1.1 ML ACETONE |
| Susceptible flies: | 0.001% deltamethrin + 1% Compound A + 0.5% Compound B in 1.1 ml acetone |
| Resistant flies: | 0.02% deltamethrin in 1.1 ml acetone |
| Resistant flies: | 0.02% deltamethrin + 1% Compound A + 0.5% Compound B in 1.1 ml acetone |

Example 98

Deltamethrin Technical, Alone and in Combination with Adjuvant (1% Compound A+0.5% Compound B) (Acetone Solutions): Efficacy Against the House Fly (*Musca domestica*), Susceptible Strain WHO(N) and Resistant Strain Reichswald, on Glazed Tiles The objective of this study was to verify the efficacy enhancement by the addition of adjuvant to deltamethrin, found in Clayton, N.C., USA (window screens against *Aedes aegypti*).

The standard method for determining the efficacy of a formulation on surfaces was used.

Test Insects: House flies (Musca domestica) of both sexes, susceptible strain WHO(N) and resistant strain Reichswald Summary:

Susceptible strain: The deltamethrin solution with adjuvant had killed 48% of the flies after 15', 80% after 30', 97% after 1 h, 98% after 2 h and 3 h and 100% after 24 h. The corresponding values for deltamethrin alone were 2%, 18%, 58%, 80%, 88% and 92% respectively. Resistant strain: The deltamethrin solution with adjuvant had killed 45% of the flies after 24h, deltamethrin alone 7%.

The addition of the adjuvant to an acetone solution of deltamethrin enhances the efficacy, especially against susceptible flies. The results obtained with window screens against *Aedes aegypti* were verified.

TABLE 89

RESULTS:
Mean of three replicates

| | | % Mortality after | | | | | |
|---|---|---|---|---|---|---|---|
| Strain | Formulation | 15' | 30' | 1 h | 2 h | 3 h | 24 h |
| WHO(N) | 0.001% DTM | 2 | 18 | 58 | 80 | 88 | 92 |
| | 0.001% DTM + 1.000% Compound A + 0.500% Compound B | 48 | 80 | 97 | 98 | 98 | 100 |
| RW | 0.020% DTM | 0 | 0 | 0 | 0 | 0 | 7 |
| | 0.020% DTM + 1.000% Compound A + 0.500% Compound B | 0 | 0 | 2 | 2 | 2 | 45 |
| WHO(N) | Control | 0 | 0 | 0 | 7 | 8 | 10 |
| RW | Control | 0 | 0 | 0 | 0 | 0 | 0 |

WHO(N) = susceptible strain,
RW = resistant strain

Example 99

Imidacloprid GR 0.5 and Imidacloprid WG 10 with and Without Adjuvant: Efficacy Against the House Fly (*Musca domestica*), Susceptible Strain WHO(N)

The objective of this study was to evaluate the efficacy enhancement by the addition of adjuvant to fly control products. The method used to evaluate baits and traps against flies in chambers that was used is described below: The trials are conducted in 0.5 m³ chambers (72 cm wide, 71 cm deep and 100 cm high). Paint on baits are prepared according to the label and the amount of 3 g is painted in three horizontal stripes (five cm width each) (total of 3 g) on cardboard (20×20 cm) which is hung on the upper part of the back wall of the chamber two hours later. Spray on baits are prepared according to the label and the amount of 5 g is sprayed onto fake board (50×50 cm) which is placed against the back wall of the chamber two hours later. Two hours before starting the trial, 100 flies (3 days old) are anaesthetized with $CO_2$ and introduced into gauze covered beakers. These are placed in the chambers at the beginning of the trial. The flies are released and the beakers are removed. The % knockdown is determined at 10 minutes, 30 minutes and 60 minutes. After that a drinking station (beaker with cotton soaked with 10% sugar water) is placed in the center of the floor. At 4 hours the knockdown effect is recorded again and at 20 hours the mortality and the "optical effect" is registered. That is the number of dead flies, which can be found around the glass plates within the 20×20 cm quadrate and below the cardboard and flake boards within the last ten cm in front of the back wall, respectively. All the above figures are expressed in cumulative %.

The formulations are tested at one day and three replicates are made at following days (four replicates in total).

TABLE 90

Tested formulations:

imidacloprid WG 0.5 (0.5% imidacloprid) + adjuvant as paint on ready to use
imidacloprid WG 0.5 (0.5% imidacloprid) as paint on ready to use
imidacloprid WG 10 (10% imidacloprid) + adjuvant as spray on ready to use
imidacloprid WG 10 (10% imidacloprid) as spray on ready to use
imidacloprid WG 0.5 (0.5% imidacloprid) product of trade: paint on, 3 g mixture in 3 horizontal stripes on cardboard (20 × 20 cm) (mixture = 12.5 g product + 10 ml water)
imidacloprid WG 10 (10% imidacloprid) product of trade: sprayed, 5 ml mixture auf flake board (mixture = 2.5 g product + 20 ml water)

Adjuvant = 1% Compound A + 0.5% Compound B

The experimental products were made as ready to use mixtures for paint on and spray on, respectively, because of the addition of Paraffin and products sold under the tradenames Arlatone T and Rhodasurf 860P. These additional excipients were necessary to formulate the adjuvant and were added also to the experimental formulations without adjuvant.

Summary:

The efficacy of the trade products were in the range of previous tests (fast action, final mortality between 71% and 78%. The experimental formulations (with and without UV blocker revealed a slow action and a final mortality between 16 and 27%. Compared to the trade products, the number of fly contacts with the experimental formulations was strongly decreased.

Conclusion:

The addition of the excipients resulted in a strong repellent effect, which makes them unsuitable to formulate the adjuvant.

TABLE 91

RESULTS:

| | % knock down after | | | | % Mortality | OE (%) | KT 50 |
|---|---|---|---|---|---|---|---|
| Product | 10' | 30' | 60' | 4 h | after 20 h | 20 h | hours |
| imidacloprid WG 0.5 (0.5% imidacloprid) + adjuvant as paint on, ready to use | 0 | 1 | 2 | 5 | 16 | 2 | 162.0 |
| imidacloprid WG 0.5 (0.5% imidacloprid) as paint on, ready to use | 3 | 9 | 15 | 17 | 27 | 3 | 297.1 |
| imidacloprid WG 10 (10% imidacloprid) + adjuvant as spray on, ready to use | 1 | 3 | 4 | 5 | 16 | 2 | 334.0 |
| imidacloprid WG 10 (10% imidacloprid) as spray on, ready to use | 4 | 9 | 12 | 11 | 19 | 1 | 5245.0 |
| imidacloprid WG 0.5 (0.5% imidacloprid) product of trade: paint on | 25 | 51 | 55 | 68 | 78 | 12 | 0.8 |

TABLE 91-continued

RESULTS:

| Product | % knock down after | | | | % Mortality after 20 h | OE (%) 20 h | KT 50 hours |
|---|---|---|---|---|---|---|---|
| | 10' | 30' | 60' | 4 h | | | |
| imidacloprid WG 10 (10% imidacloprid) product of trade: sprayed | 18 | 48 | 59 | 72 | 71 | 14 | 0.9 |
| Control | 0 | 2 | 3 | 4 | 8 | — | — | adjuvant = 1% Compound A + 0.5% Compound B

Example 100

Imidacloprid GR 0.5 with and Without Combination of Compound A and Compound B—(Applied as Acetone Solution Onto the Bait): Efficacy Against the House Fly (*Musca domestica*), Susceptible Strain WHO(N)

The objective of the study was to evaluate the efficacy enhancement by the addition of adjuvant to fly control products. The trials were conducted in 0.5 m³ chambers (72 cm wide, 71 cm deep and 100 cm high).

Granular baits are scattered into a petri dish at 1 g and tested without (dry testing) or with 1 ml water (wet testing). Paint on baits are prepared according to the label and the amount of 3 g is painted in three horizontal stripes (five cm width each) (total of 3 g) on cardboard (20×20 cm) which is hung on the upper part of the back wall of the chamber two hours later. Two hours before starting the trial, 100 flies (3 days old) are anaesthetized with $CO_2$ and introduced into gauze covered beakers. These are placed in the chambers at the beginning of the trial. The flies are released and the beakers are removed. The % knockdown is determined at 10 minutes, 30 minutes and 60 minutes. After that a drinking station (beaker with cotton soaked with 10% sugar water) is placed in the center of the floor. At 4 hours the knockdown effect is recorded again and at 20 hours the mortality and the "optical effect" is registered. That is the number of dead flies, which can be found around the glass plates within the 20×20 cm quadrate and below the cardboard and flake boards within the last ten cm in front of the back wall, respectively. All the above figures are expressed in cumulative %.

The formulations are tested at one day and three replicates are made at following days (four replicates in total).

TABLE 92

Tested formulations:

imidacloprid WG 0.5 (0.5% imidacloprid) without and with adjuvant as dry granule
imidacloprid WG 0.5 (0.5% imidacloprid) without and with adjuvant as wet granule
imidacloprid WG 0.5 (0.5% imidacloprid) without and with adjuvant as paint on adjuvant = 1% Compound A + 0.5% Compound B Summary:

The efficacy of the product without adjuvant (with or without acetone) was in the range of previous tests (fast action, final mortality between 72% and 80 ° A)). The experimental formulation with adjuvant in acetone revealed a slow action and a final mortality between 8 and 30%. The experimental formulations were visited by the flies in the same frequency as the product without adjuvant.

The efficacy of the formulations with adjuvant declined significantly, although no repellent effects were observed. One possible hypothesis is that the adjuvant decreases the bioavailability of imidacloprid. The same effects had been observed in the case of formulations with 0.01% deltamethrin mixed with each individual adjuvant. With Compound B alone, a synergistic effect had been found.

TABLE 93

| imidacloprid WG 0.5 | % knock down after | | | | % Mortality after 20 h | OE (%) 20 h | KT 50 hours |
|---|---|---|---|---|---|---|---|
| | 10' | 30' | 60' | 4 h | | | |
| as dry granule | 7 | 19 | 25 | 41 | 72 | 27 | 5.6 |
| + acetone as dry granule | 9 | 21 | 30 | 59 | 80 | 27 | 2.8 |
| + adjuvant in acetone as dry granule | 0 | 0 | 1 | 4 | 11 | 1 | >20 |
| as wet granule | 19 | 38 | 48 | 55 | 72 | 20 | 2.0 |
| + acetone as wet granule | 16 | 38 | 44 | 58 | 75 | 19 | 2.0 |
| + adjuvant in acetone as wet granule | 0 | 1 | 1 | 6 | 30 | 8 | >20 |
| as paint on | 28 | 57 | 66 | 75 | 79 | 14 | 0.5 |
| + acetone as paint on | 27 | 49 | 52 | 64 | 77 | 13 | 0.9 |
| + adjuvant in acetone as paint on | 0 | 0 | 1 | 2 | 8 | 2 | >20 |
| Control | 0 | 0 | 0 | 0 | 2 | — | — | adjuvant = 1% Compound A + 0.5% COMPOUND B

No repellent effects were observed.

Example 101

Deltamethrin with and Without Compound A and Compound B—(all in Acetone Solutions): Efficacy Against the Housefly (*Musca domestica*), Susceptible Strain WHO(N), After Topical Application The objective of this study was to evaluate an alternative application technique to detect differences between deltamethrin with and without adjuvant Method: Topical insecticide application to houseflies Male *Musca domestica*, susceptible strain WHO(N), or other strains were used.

The flies were anaesthetized with $CO_2$, and ten individuals were positioned (on their back) on a filter paper which was on the top of a carbon dioxide emitting device.

In this position, 0.5 µl of a formulation dissolved in water, were applied on the ventral thorax of each fly with a micro liter syringe.

Afterwards the insects were transferred into a beaker closed by a gauze lid with a water saturated cotton pad on the top.

At regular intervals, mortality was recorded (cumulatively).

TABLE 94

Tested formulations:

deltamethrin (0.00064%, 0.000128% and 0.0000256%) in acetone
deltamethrin (0.00064%, 0.000128% and 0.0000256%) in acetone + 1% Compound A + 0.5% Compound B
deltamethrin (0.00064%, 0.000128% and 0.0000256%) in acetone + 1% Compound A
deltamethrin (0.00064%, 0.000128% and 0.0000256%) in acetone + 0.5% Compound B
1% Compound A + 0.5% COMPOUND B
1% Compound A
0.5% Compound B
all without deltamethrin Summary:

The mortality rates were in the same range for each deltamethrin concentration, either for deltamethrin alone and with both the combination of Compound A and Compound B or with the single compounds. The combination or each compound alone (without insecticide) revealed moderate mortality rates about 50% after 1 day (end of test), but no efficacy within the first 4 hours. The topical application method has not detected any synergistic effects between deltamethrin and adjuvant.

TABLE 95

| % a.i. conc. In acetone (0.5 µl per fly) | % Mortality after | | | | | |
|---|---|---|---|---|---|---|
| | 15' | 30' | 1 h | 2 h | 4 h | 1 d |
| 0.00064% DTM | 100 | 100 | 100 | 100 | 100 | 80 |
| 0.00064% DTM + 1% Compound A + 0.5% Compound B | 70 | 80 | 100 | 100 | 100 | 100 |
| 0.00064% DTM + 1% Compound A | 60 | 90 | 100 | 100 | 100 | 90 |
| 0.00064% DTM + 0.5% Compound B | 90 | 90 | 100 | 100 | 100 | 100 |
| 0.000128% DTM | 20 | 50 | 70 | 70 | 80 | 50 |
| 0.000128% DTM + 1% Compound A + 0.5% Compound B | 0 | 10 | 70 | 100 | 70 | 90 |
| 0.000128% DTM + 1% Compound A | 30 | 60 | 60 | 80 | 80 | 70 |
| 0.000128% DTM + 0.5% Compound B | 80 | 80 | 80 | 90 | 90 | 90 |
| 0.0000256% DTM | 10 | 20 | 30 | 20 | 20 | 60 |
| 0.0000256% DTM + 1% Compound A + 0.5% Compound B | 10 | 10 | 10 | 10 | 10 | 60 |
| 0.0000256% DTM + 1% Compound A | 0 | 10 | 20 | 30 | 20 | 50 |
| 0.0000256% DTM + 0.5% Compound B | 0 | 10 | 10 | 20 | 10 | 60 |
| 1% Compound A + 0.5% Compound B | 0 | 10 | 10 | 10 | 10 | 60 |
| 1% Compound A | 0 | 0 | 0 | 0 | 0 | 40 |
| 0.5% Compound B | 0 | 0 | 0 | 0 | 0 | 60 |
| Acetone only | 0 | 0 | 0 | 0 | 0 | 10 |

Example 102

Deltamethrin with and Without Compound A and Compound B—(all in Acetone Solutions): Efficacy Against the Housefly (*Musca domestica*), Susceptible Strain WHO(N), on Filter Papers in Glass Dishes The objective of this study was to evaluate an alternative application technique to detect differences between deltamethrin with and without adjuvant, alone and in combination.

Method: Contact efficacy against houseflies

Male *Musca domestica*, susceptible strain WHO(N), were used.

A solution of the active ingredient in acetone was prepared. A concentration row was made. After evaporation of the acetone (30'), the dishes were closed by a glass lid and transferred into the test room. One day later twenty flies, anaesthetized with $CO_2$, are counted into each dish. At regular intervals, knock down was recorded (cumulatively). Each test consisted of one replicate.

TABLE 96

Tested formulations:

deltamethrin (0.0016%, 0.00032%, 0.000064% and 0.0000128%) in acetone
deltamethrin (0.0016%, 0.00032%, 0.000064% and 0.0000128) in acetone + 1% Compound A + 0.5% Compound B
deltamethrin (0.0016%, 0.00032%, 0.000064% and 0.000012)8 in acetone + 1% Compound A
deltamethrin (0.0016%, 0.00032%, 0.000064% and 0.0000128) in acetone + 0.5% Compound B
1% Compound A + 0.5% Compound B in acetone
1% Compound A in acetone
0.5% Compound B in acetone
all without deltamethrin Summary:

The formulations 0.00032% deltamethrin+1% Compound A as well as 0.000064% deltamethrin+1% Compound A revealed higher knock down rates than the same concentrations of deltamethrin alone.

In all other cases the knock down rates were in the same range for each deltamethrin concentration, either for deltamethrin alone and with both Compound A and Compound B or with the single compounds. In contrary, the combination with both Compound A and Compound B caused some inhibiting effects.

The combination or each compound alone (all without insecticide) revealed moderate mortality rates from 50% to 70% after 1 day (end of test) but no efficacy within the first 6 hours.

The contact efficacy method has detected a synergistic effect of 0.00032% and 0.000064% deltamethrin, each with 1% Compound A compared to the same concentrations of deltamethrin alone.

TABLE 97

| % a.i. conc. in acetone | % knock down after | | | | | | | | |
|---|---|---|---|---|---|---|---|---|---|
| | 15' | 30' | 1 h | 1.5 h | 2 h | 3 h | 4 h | 6 h | 1 d |
| 0.0016% DTM | 0 | 5 | 70 | 90 | 100 | 100 | 100 | 100 | 95 |
| 0.0016% DTM + 1% Compound A + 0.5% Compound B | 0 | 0 | 10 | 30 | 55 | 100 | 100 | 90 | 95 |
| 0.0016% DTM + 1% Compound A | 0 | 0 | 65 | 80 | 100 | 100 | 100 | 100 | 100 |
| 0.0016% DTM + 0.5% Compound B | 0 | 0 | 20 | 60 | 90 | 95 | 100 | 70 | 100 |
| 0.00032% DTM | 0 | 0 | 5 | 30 | 50 | 65 | 65 | 60 | 95 |
| 0.00032% DTM + 1% Compound A + 0.5% Compound B | 0 | 0 | 0 | 0 | 0 | 15 | 30 | 80 | 90 |
| 0.00032% DTM + 1% Compound A | 0 | 0 | 20 | 50 | 100 | 100 | 100 | 90 | 90 |
| 0.00032% DTM + 0.5% Compound B | 0 | 0 | 10 | 50 | 75 | 80 | 80 | 30 | 80 |
| 0.000064% DTM | 0 | 0 | 0 | 0 | 0 | 0 | 0 | 15 | 80 |
| 0.000064% DTM + 1% Compound A + 0.5% Compound B | 0 | 0 | 0 | 0 | 0 | 0 | 0 | 0 | 85 |
| 0.000064% DTM + 1% Compound A | 0 | 0 | 45 | 60 | 75 | 80 | 60 | 40 | 90 |
| 0.000064% DTM + 0.5% Compound B | 0 | 0 | 0 | 0 | 0 | 0 | 10 | 25 | 45 |
| 0.0000128% DTM | 0 | 0 | 0 | 0 | 0 | 0 | 0 | 15 | 70 |
| 0.0000128% DTM + 1% Compound A + 0.5% Compound B | 0 | 0 | 0 | 0 | 0 | 0 | 0 | 0 | 50 |
| 0.0000128% DTM + 1% Compound A | 0 | 0 | 0 | 0 | 5 | 35 | 60 | 50 | 60 |
| 0.0000128% DTM + 0.5% Compound B | 0 | 0 | 0 | 0 | 0 | 0 | 0 | 0 | 45 |
| 1% Compound A + 0.5% Compound B | 0 | 0 | 0 | 0 | 0 | 0 | 0 | 0 | 60 |
| 1% Compound A | 0 | 0 | 0 | 0 | 0 | 0 | 0 | 0 | 50 |
| 0.5% Compound B | 0 | 0 | 0 | 0 | 0 | 0 | 0 | 0 | 70 |
| Acetone only | 0 | 0 | 0 | 0 | 0 | 0 | 0 | 0 | 10 |

Replicates: 1

TABLE 98

Tested formulations

Susceptible strain: 0.0016%, 0.00032%, 0.000064% and 0.0000128% in water
Susceptible strain: 0.0016%, 0.00032%, 0.000064% and 0.0000128% in EW formulation
Resistant strain: 5%, 1%, 0.2% and 0.04% in water
Resistant strain: 5%, 1%, 0.2% and 0.04% in EW formulation EW formulation without deltamethrin Summary:

Against susceptible flies, the knock down rates were higher for all deltamethrin concentrations on the filter papers treated with K-Othrine WG 250 dissolved in water than for all corresponding deltamethrin concentrations on the filter papers treated with K-Othrine WG 250 dissolved in the EW formulation.

Against resistant flies even the final mortality rates were low for all treatments. There was no difference between the two solvents.

The EW formulation alone (without insecticide) revealed mortality rates of 50% (susceptible flies) and 75% (resistant flies) after 1 day (end of test) but no efficacy within the first 6 hours.

The contact efficacy method has detected no enhancing effects by the use of the EW formulation. In contrary, the EW formulation with K-Othrine WG 250 seems to cause some inhibition effects against susceptible flies compared to water with K-Othrine WG 250.

Example 103

K-Othrine WG 250 (250 g Deltamethrin/kg)
Dissolved in Water or in an EW Formulation
Efficacy Against the Housefly (*Musca domestica*),
Susceptible Strain WHO(N) and Resistant Strain
Reichswald, on Filter Papers in Glass Dishes The objective of this study was to evaluate the influence of the EW formulation on the efficacy of deltamethrin against houseflies. The same methodology was used as in Example 102.

Test Insects: Male and female houseflies (*Musca domestica*), susceptible strain WHO(N) and resistant strain Reichswald Evaluation: Knock down is evaluated after 15', 30', 1 h, 1.5 h, 3 h, 4 h, 6 h and 1 d.

RESULTS:

TABLE 99

| | Susceptible Flies | | | | | | | | |
|---|---|---|---|---|---|---|---|---|---|
| % a.i. | % knock down after | | | | | | | | |
| concentration | 15' | 30' | 1 h | 1.5 h | 2 h | 3 h | 4 h | 6 h | 1 d |
| 0.0016% DTM in water | 0 | 0 | 50 | 60 | 90 | 100 | 100 | 100 | 100 |
| 0.0016% DTM in EW formulation | 0 | 0 | 45 | 45 | 60 | 80 | 30 | 35 | 80 |
| 0.00032% DTM in water | 0 | 0 | 25 | 45 | 55 | 60 | 30 | 30 | 80 |
| 0.00032% DTM in EW formulation | 0 | 0 | 0 | 0 | 0 | 5 | 0 | 0 | 40 |
| 0.000064% DTM in water | 0 | 0 | 0 | 0 | 5 | 20 | 0 | 5 | 55 |
| 0.000064% DTM in EW formulation | 0 | 0 | 0 | 0 | 0 | 0 | 0 | 0 | 45 |
| 0.0000128% DTM in water | 0 | 0 | 0 | 0 | 0 | 0 | 0 | 0 | 25 |
| 0.0000128% DTM in EW formulation | 0 | 0 | 0 | 0 | 0 | 0 | 0 | 0 | 30 |
| EW formulation | 0 | 0 | 0 | 0 | 0 | 0 | 0 | 0 | 50 |
| Water | 0 | 0 | 0 | 0 | 0 | 0 | 0 | 0 | 30 |

TABLE 100

| | Resistant Flies | | | | | | | | |
|---|---|---|---|---|---|---|---|---|---|
| | % knock down after | | | | | | | | |
| % a.i. concentration | 15' | 30' | 1 h | 1.5 h | 2 h | 3 h | 4 h | 6 h | 1 d |
| 0.0016% DTM in water | 0 | 0 | 5 | 5 | 5 | 5 | 5 | 10 | 45 |
| 0.0016% DTM in EW formulation | 0 | 0 | 0 | 0 | 0 | 5 | 10 | 15 | 50 |
| 0.00032% DTM in water | 0 | 0 | 0 | 0 | 0 | 0 | 0 | 0 | 40 |
| 0.00032% DTM in EW formulation | 0 | 0 | 0 | 0 | 0 | 0 | 0 | 0 | 40 |
| 0.000064% DTM in water | 0 | 0 | 0 | 0 | 0 | 0 | 0 | 0 | 30 |
| 0.000064% DTM in EW formulation | 0 | 0 | 0 | 0 | 0 | 0 | 0 | 0 | 30 |
| 0.0000128% DTM in water | 0 | 0 | 0 | 0 | 0 | 0 | 0 | 0 | 35 |
| 0.0000128% DTM in EW formulation | 0 | 0 | 0 | 0 | 0 | 0 | 0 | 0 | 10 |
| EW formulation | 0 | 0 | 0 | 0 | 0 | 0 | 0 | 0 | 75 |
| Water | 0 | 0 | 0 | 0 | 0 | 0 | 0 | 0 | 35 |

Example 104

Compound A in Combination with Cyfluthrin (all as EW Formulations) on Two Surfaces Susceptible and Resistant Flies The objective of this study was to evaluate formulations in comparison to acetone solutions. The standard method for determining the efficacy of a formulation on surfaces was used.

Test Insects: *Musca domestica* (adults, susceptible strain WHO-N and resistant strain Reichswald)

Formulations: Insecticide with or without 10%, 2% or 0.4% Compound A (as EW), to be diluted with water (1 part formulation+9 parts water)

Application: 1 ml of the diluted formulations was applied by pipette onto glazed tiles (15×15 cm)

Evaluation: Knock down 15, and 30 minutes, 1, 2, 4 and 24 hours (mortality)

Replicates: 1

The results are shown in FIG. 97 (*Musca domestica*, susceptible strain WHO(N)) and FIG. 98 (*Musca domestica*, resistant strain Reichswald). As shown in FIG. 97, in general, the efficacy was higher with the acetone solution than with the EW formulations. On glazed tiles an enhancement of the efficacy by addition of 1% or 0.2% Compound A was observed but not on unglazed tiles. As shown in FIG. 98, no effects were observed, which corresponds to the results obtained with deltamethrin with and without Compound A in a previous test.

In all trials with resistant flies, no efficacy enhancement was observed, with the exception of Compound A+imidacloprid. The same ineffectiveness (imidacloprid+adjuvant) was observed against resistant bed bugs.

These findings suggest that Compound A does not help the pesticide overcome metabolic resistance, but rather functions to effect cuticular penetration.

Example 105

Deltamethrin or Imidacloprid with and Without Combination of Compound A and Compound B (all in Acetone Solutions): Efficacy Against the Bedbug (*Cimex lectularius*) on Filter Papers in Glass Dishes The objective of this study was to evaluate differences between deltamethrin and imidacloprid with and without adjuvant against bedbugs.

Method for Determining Contact Efficacy against Bedbugs:

Adult *Cimex lectularius*, susceptible strain, were used. A solution of the active ingredient in acetone was prepared. In the same mode a complete complete row of was made. All these works were done under drawing off conditions. After evaporation of the acetone (30') the dishes were closed by a glass lid and transferred into the test room.

One day later ten bedbugs, anaesthetized with $CO_2$, were counted into each dish. At regular intervals, knock down was recorded (cumulatively).

TABLE 101

Tested formulations:

deltamethrin (0.000064% and 0.0000128%) in acetone
deltamethrin (0.000064% and 0.0000128%) + 1% Compound A + 0.5% Compound B in acetone
imidacloprid (0.008% and 0.0016%) in acetone
imidacloprid (0.008% and 0.0016%) + 1% Compound A + 0.5% Compound B in acetone
1% Compound A + 0.5% Compound B in acetone without active ingredient Summary:

The efficacy was in the same range for each deltamethrin concentration, either for deltamethrin alone or with both adjuvant. The combination of both imidacloprid concentrations with both Compound A and Compound B revealed a synergistic effect (100% efficacy after one hour) compared to 40% to 80% efficacy after 6 days (first test) and 0% to 10% efficacy after 6 days (second test) for both imidacloprid concentrations alone. Compound A or Compound B alone revealed a rate of moribund bedbugs of 40% (first test) and 0% (second test).

The contact efficacy method has detected a synergistic effect of 0.008% and 0.0016% imidacloprid, each with 1% Compound A+0.5% Compound B compared to the same concentrations of imidacloprid alone.

RESULTS:

TABLE 102

First test

| | \% knock down or moribund after | | | | | | |
|---|---|---|---|---|---|---|---|
| % a.i. conc. In acetone | 1 h | 2 h | 4 h | 6 h | 1 d | 2 d | 6 d |
| 0.000064% Deltamethrin | 20 | 20 | 70 | 70 | 70 | 80 | 100 |
| 0.000064% Deltamethrin + 1% Compound A + 0.5% Compound B | 0 | 0 | 0 | 0 | 50 | 50 | 80 |
| 0.0000128% Deltamethrin | 0 | 0 | 0 | 0 | 20 | 20 | 20 |
| 0.0000128% Deltamethrin + 1% Compound A + 0.5% Compound B | 0 | 0 | 0 | 0 | 0 | 0 | 20 |
| 0.008% Imidacloprid | 0 | 0 | 0 | 20 | 30 | 40 | 80 |
| 0.008% Imidacloprid + 1% Compound A + 0.5% Compound B | 100 | 100 | 100 | 100 | 100 | 100 | 100 |
| 0.0016% Imidacloprid | 0 | 0 | 0 | 10 | 20 | 20 | 40 |
| 0.0016% Imidacloprid + 1% Compound A + 0.5% Compound B | 100 | 100 | 100 | 100 | 100 | 100 | 100 |
| 1% Compound A + 0.5% Compound B | 0 | 0 | 0 | 0 | 0 | 0 | 40 |
| Acetone only | 0 | 0 | 0 | 0 | 0 | 0 | 0 |

TABLE 103

Second test

| | \% knock down or moribund after | | | | | | |
|---|---|---|---|---|---|---|---|
| % a.i. conc. in acetone | 1 h | 2 h | 4 h | 6 h | 1 d | 2 d | 6 d |
| 0.000064% Deltamethrin | 0 | 40 | 40 | 40 | 40 | 60 | 60 |
| 0.000064% Deltamethrin + 1% Compound A + 0.5% Compound B | 0 | 0 | 0 | 0 | 70 | 80 | 80 |
| 0.0000128% Deltamethrin | 0 | 0 | 0 | 0 | 10 | 10 | 40 |
| 0.0000128% Deltamethrin + 1% Compound A + 0.5% Compound B | 0 | 0 | 0 | 0 | 10 | 10 | 30 |
| 0.008% Imidacloprid | 0 | 0 | 0 | 0 | 0 | 0 | 10 |
| 0.008% Imidacloprid + 1% Compound A + 0.5% Compound B | 100 | 100 | 100 | 100 | 100 | 100 | 100 |
| 0.0016% Imidacloprid | 0 | 0 | 0 | 0 | 0 | 0 | 0 |
| 0.0016% Imidacloprid + 1% Compound A + 0.5% Compound B | 100 | 100 | 100 | 100 | 100 | 100 | 100 |
| 1% Compound A + 0.5% Compound B | 0 | 0 | 0 | 0 | 0 | 0 | 0 |
| Acetone only | 0 | 0 | 0 | 0 | 0 | 0 | 0 |

Example 106

Imidacloprid with and Without Combination of Compound A and Compound B—(all in Acetone Solutions): Efficacy Against the Bedbug (*Cimex lectularius*) on Filter Papers and on Various Surfaces The objective of this study was to evaluate differences between imidacloprid without and with adjuvant (both a combination of Compound A and Compound B together and as single compounds) on filter paper and on five different surfaces (imidacloprid without and with adjuvant) against bedbugs.

The same methodology was used as was used in Example 105.

TABLE 104

Tested formulations:

Imidacloprid (0.0016% and 0.00032%) in acetone on filter paper
Imidacloprid (0.0016% and 0.00032%) + 1% Compound TABLE 104-continued Tested formulations:

A + 0.5% Compound B and 0.2%
Compound A + 0.1% COMPOUND B in acetone on filter paper
Imidacloprid (0.0016% and 0.00032%) + 1% Compound A and 0.2% Compound A in acetone on filter paper
Imidacloprid (0.0016% and 0.00032%) + 0.5% Compound B and 0.1% Compound B in acetone on filter paper
Imidacloprid (0.008% and 0.0016%) in acetone on wood, PVC, wallpaper, mattress and glass
Imidacloprid (0.008% and 0.0016%) + 1% Compound A + 0.5% Compound B in acetone on wood, PVC, wallpaper, mattress and glass
1% Compound A + 0.5% Compound B in acetone without active ingredient on filter paper, wood, PVC, wallpaper, mattress and glass Summary:

Filter Paper

The formulation of 0.0016% imidacloprid (6 mg a.i./m$^2$) with 1% Compound A+0.5% Compound B revealed a synergistic effect (100% efficacy after four hours) compared to 0 efficacy after 6 days for 0.0016% imidacloprid alone.

The formulation of 0.0016% imidacloprid with 1% Compound A alone revealed the same mortality rates as the combination of both, whereas the formulation with 0.5% Compound B was ineffective.

The reduction of the adjuvant concentration to a fifth reduced the fastness of action (90% efficacy after 6 days for 0.2% Compound A+0.1% Compound B, 100% efficacy for 0.2% Compound A).

A lower quantity of imidacloprid (0.00032%=1 mg a.i./m$^2$) was not sufficient. Only the combination with 1% Compound A+0.5% Compound B revealed a certain efficacy (70% efficacy after 6 days).

Other Surfaces

No efficacy was found on wood, PVC, wallpaper and mattress with 0.008% or 0.0016% imidacloprid (30 and 6 mg a.i./m$^2$) without or with 1% Compound A+0.5% Compound B. On glass, 0.008% imidacloprid alone acted relatively fast and had killed all bed bugs within one day. The combination had killed all insects within one hour. The adjuvants alone had no effects on the insects.

The synergistic effect of the combination with 0.0016% imidacloprid on filter paper was confirmed. The synergistic principle seems to adhere in Compound A alone.

TABLE 105

RESULTS: imidacloprid without and with Combination of Compound A and Compound B -- (both together and as single compounds): efficacy against the bedbug (*Cimex lectularius*) on filter papers in glass dishes

| % a.i. conc. in acetone | % knock down or moribund after | | | | | | |
|---|---|---|---|---|---|---|---|
| | 1 h | 2 h | 4 h | 6 h | 1 d | 2 d | 6 d |
| 0.0016% imidacloprid (6 mg/m$^2$) | 0 | 0 | 0 | 0 | 0 | 0 | 0 |
| 0.0016% imidacloprid (6 mg/m$^2$) + 1% Compound A + 0.5% Compound B | 60 | 80 | 100 | 100 | 100 | 100 | 100 |
| 0.0016% imidacloprid (6 mg/m$^2$) + 1% Compound A | 60 | 80 | 100 | 100 | 100 | 100 | 100 |
| 0.0016% imidacloprid (6 mg/m$^2$) + 0.5% Compound B | 0 | 0 | 0 | 0 | 0 | 0 | 0 |
| 0.0016% imidacloprid (6 mg/m$^2$) + 0.2% Compound A + 0.1% Compound B | 0 | 20 | 40 | 40 | 50 | 70 | 90 |
| 0.0016% imidacloprid (6 mg/m$^2$) + 0.2% Compound A | 20 | 50 | 60 | 70 | 80 | 80 | 100 |
| 0.0016% imidacloprid (6 mg/m$^2$) + 0.1% Compound B | 0 | 0 | 0 | 0 | 0 | 0 | 0 |
| 0.00032% imidacloprid (1 mg/m$^2$) | 0 | 0 | 0 | 0 | 0 | 0 | 0 |
| 0.00032% imidacloprid (1 mg/m$^2$) + 1% Compound A + 0.5% Compound B | 0 | 20 | 30 | 50 | 60 | 70 | 70 |
| 0.00032% imidacloprid (1 mg/m$^2$) + 1% Compound A | 0 | 0 | 0 | 0 | 0 | 0 | 30 |
| 0.00032% imidacloprid (1 mg/m$^2$) + 0.5% Compound B | 0 | 0 | 0 | 0 | 0 | 0 | 0 |
| 0.00032% imidacloprid (1 mg/m$^2$) + 0.2% Compound A + 0.1% Compound B | 0 | 0 | 0 | 0 | 0 | 0 | 0 |
| 0.00032% imidacloprid (1 mg/m$^2$) + 0.2% Compound A | 0 | 0 | 0 | 0 | 0 | 0 | 0 |
| 0.00032% imidacloprid (1 mg/m$^2$) + 0.1% Compound B | 0 | 0 | 0 | 0 | 0 | 0 | 10 |
| 1% Compound A + 0.5% Compound B | 0 | 0 | 0 | 0 | 0 | 0 | 0 |
| Acetone only | 0 | 0 | 0 | 0 | 0 | 0 | 0 |

TABLE 106 imidacloprid with and without Combination of Compound A and Compound B -- (all in acetone solutions): efficacy against the bedbug (*Cimex lectularius*) on various surfaces (One replicate)

| | % a.i. conc. in acetone | % knock down or moribund after | | | | | | |
|---|---|---|---|---|---|---|---|---|
| | | 1 h | 2 h | 4 h | 6 h | 1 d | 2 d | 6 d |
| Wood | 0.008% imidacloprid (30 mg/m$^2$) | 0 | 0 | 0 | 0 | 0 | 0 | 0 |
| | 0.008% imidacloprid (30 mg/m$^2$) + 1% Compound A + 0.5% Compound B | 0 | 0 | 0 | 0 | 0 | 0 | 0 |
| | 0.0016% imidacloprid (6 mg/m$^2$) | 0 | 0 | 0 | 0 | 0 | 0 | 10 |
| | 0.0016% imidacloprid (6 mg/m$^2$) + 1% Compound A + 0.5% Compound B | 0 | 0 | 0 | 0 | 0 | 0 | 0 |
| | 1% Compound A + 0.5% Compound B | 0 | 0 | 0 | 0 | 0 | 0 | 0 |
| | Acetone only | 0 | 0 | 0 | 0 | 0 | 0 | 0 |
| PVC | 0.008% imidacloprid (30 mg/m$^2$) | 0 | 0 | 0 | 0 | 0 | 0 | 40 |
| | 0.008% imidacloprid (30 mg/m$^2$) + | 0 | 0 | 0 | 0 | 0 | 0 | 20 |

TABLE 106-continued imidacloprid with and without Combination of Compound A and Compound B -- (all in acetone solutions): efficacy against the bedbug (*Cimex lectularius*) on various surfaces
(One replicate)

| | | % knock down or moribund after | | | | | | |
|---|---|---|---|---|---|---|---|---|
| | % a.i. conc. in acetone | 1 h | 2 h | 4 h | 6 h | 1 d | 2 d | 6 d |
| | 1% Compound A + 0.5% Compound B | | | | | | | |
| | 0.0016% imidacloprid (6 mg/m$^2$) | 0 | 0 | 0 | 0 | 0 | 0 | 20 |
| | 0.0016% imidacloprid (6 mg/m$^2$) + 1% Compound A + 0.5% Compound B | 0 | 0 | 0 | 0 | 0 | 0 | 0 |
| | 1% Compound A + 0.5% Compound B | 0 | 0 | 0 | 0 | 0 | 0 | 0 |
| | Acetone only | 0 | 0 | 0 | 0 | 0 | 0 | 0 |
| Wallpaper | 0.008% imidacloprid (30 mg/m$^2$) + | 0 | 0 | 0 | 0 | 0 | 0 | 0 |
| | 0.008% imidacloprid (30 mg/m$^2$) + 1% Compound A + 0.5% Compound B | 0 | 0 | 0 | 0 | 0 | 0 | 0 |
| | 0.0016% imidacloprid (6 mg/m$^2$) | 0 | 0 | 0 | 0 | 0 | 0 | 0 |
| | 0.0016% imidacloprid (6 mg/m$^2$) + 1% Compound A + 0.5% Compound B | 0 | 0 | 0 | 0 | 0 | 0 | 0 |
| | 1% Compound A + 0.5% Compound B | 0 | 0 | 0 | 0 | 0 | 0 | 0 |
| | Acetone only | 0 | 0 | 0 | 0 | 0 | 0 | 0 |
| Mattress | 0.008% imidacloprid (30 mg/m$^2$) | 0 | 0 | 0 | 0 | 0 | 0 | 0 |
| | 0.008% imidacloprid (30 mg/m$^2$) + 1% Compound A + 0.5% Compound B | 0 | 0 | 0 | 0 | 0 | 0 | 0 |
| | 0.0016% imidacloprid (6 mg/m$^2$) | 0 | 0 | 0 | 0 | 0 | 0 | 0 |
| | 0.0016% imidacloprid (6 mg/m$^2$) + 1% Compound A + 0.5% Compound B | 0 | 0 | 0 | 0 | 0 | 0 | 0 |
| | 1% Compound A + 0.5% Compound B | 0 | 0 | 0 | 0 | 0 | 0 | 0 |
| | Acetone only | 0 | 0 | 0 | 0 | 0 | 0 | 0 |
| Glass | 0.008% imidacloprid (30 mg/m$^2$) | 0 | 100* | 85 | 90 | 100 | 100 | 100 |
| | 0.008% imidacloprid (30 mg/m$^2$) + 1% Compound A + 0.5% Compound B | 100 | 100 | 100 | 100 | 100 | 100 | 100 |
| | 1% Compound A + 0.5% Compound B | 0 | 0 | 0 | 20 | 80 | 100 | 100 |
| | Acetone only | 0 | 0 | 0 | 0 | 20 | 20 | 30 |

*knocked down

Example 107

Imidacloprid Technical, with and Without Combination of Compound A and Compound B—on Glazed Tiles: Efficacy Against the German Cockroach (*Blattella germanica*)

The objective of this study was to validate the results of an equivalent trial.

Method For Determining Contact Efficacy against Cockroaches

Male *Blattella germanica*, susceptible strain, were used. A solution of the active ingredient in acetone pipetted onto the corresponding tile on an area of 12.5 cm×12.5 cm.

One day later, a glass ring (diameter 9.5 cm, height 5.5 cm) inner wall treated with talcum was placed on the tile and five male German cockroaches were introduced. Knock down and mortality, respectively, were evaluated after 30', 1 h, 3 h and 1 d. A water soaked cotton pad was added after 3 hours.

Each trial consisted of three replicates of which the mean values are calculated.

TABLE 107

Tested formulations:

imidacloprid (1%, 0.5% and 0.1%) in acetone imidacloprid (1%, 0.5% and 0.1%) in acetone + 1% Compound A + 0.5% Compound B (UVB)

1% Compound A + 0.5% Compound B in acetone without imidacloprid

Summary:

The combination 0.5% imidacloprid+adjuvant as well as 0.1% imidacloprid+adjuvant revealed higher knock down and mortality rates than the same concentrations of imidacloprid alone. The combination 1% imidacloprid+adjuvant revealed no higher efficacy than imidacloprid alone. The adjuvant combination alone (all without insecticide) revealed no knock down and mortality over the whole testing period. The contact efficacy method has detected a synergistic effect of 0.5% and 0.1 imidacloprid, each with 1% Compound A+0.5% Compound B, compared to the same concentrations of imidacloprid alone.

TABLE 108

RESULTS:

| Treatment | (mg/m$^2$) | Average % knockdown & mortality after | | | |
|---|---|---|---|---|---|
| | | 30 min | 60 min | 3 hr | 24 hr |
| imidacloprid (1%) | 620 | 0 | 0 | 13 | 40 |
| imidacloprid (1%) + adjuvant | 620 | 0 | 0 | 0 | 20 |
| imidacloprid (0.5%) | 310 | 0 | 0 | 0 | 0 |
| imidacloprid (0.5%) + adjuvant | 310 | 0 | 0 | 47 | 47 |
| imidacloprid (0.1%) | 60 | 0 | 0 | 20 | 40 |
| imidacloprid (0.1%) + adjuvant | 60 | 0 | 0 | 80 | 60 |
| adjuvant | 0 | 0 | 0 | 0 | 0 |
| UTC | 0 | 0 | 0 | 0 | 0 |

UV: 1% Compound A + 0.5% Compound B

Example 108

Deltamethrin or Imidacloprid with and Without Combination of Compound A and Compound B (all in Acetone Solutions): Efficacy Against the German Cockroach (*Blattella germanica*) on Filter Papers in Glass Dishes The objective of this study was to evaluate differences between deltamethrin and imidacloprid with and without adjuvant against cockroaches. The method for determining contact efficacy against cockroaches was the same as that in Example 107.

TABLE 109

Tested formulations:

Deltamethrin (0.0016% and 0.00032%) in acetone
deltamethrin (0.0016% and 0.00032%) + 1% Compound A + 0.5% Compound B in acetone
imidacloprid (0.2% and 0.4%) in acetone
imidacloprid (0.2% and 0.4%) + 1% Compound A + 0.5% Compound B in acetone
1% Compound A + 0.5% Compound B in acetone without active ingredient Summary:

The efficacy of 0.0016% deltamethrin concentration with adjuvant was inhibited compared to the corresponding concentration of deltamethrin alone. At 0.00032% deltamethrin no differences were observed. In the case of imidacloprid no mortality was observed, with or without adjuvant. The adjuvant alone revealed a mortality rate of 0%.

The contact efficacy method has detected no synergistic effect either of deltamethrin or imidacloprid, each with 1% Compound A+0.5% Compound B compared to the same concentrations of deltamethrin or imidacloprid alone.

TABLE 110

RESULTS:

| % a.i. conc. in acetone | % Mortality after | | | | | | |
|---|---|---|---|---|---|---|---|
| | 15' | 30' | 1 h | 2 h | 4 h | 6 h | 1 d |
| 0.0016% Deltamethrin | 40 | 60 | 80 | 100 | 100 | 100 | 100 |
| 0.0016% Deltamethrin + 1% Compound A + 0.5% Compound B | 20 | 20 | 40 | 80 | 100 | 100 | 100 |
| 0.00032% Deltamethrin | 0 | 0 | 0 | 20 | 20 | 20 | 100 |
| 0.00032% Deltamethrin + 1% Compound A + 0.5% Compound B | 0 | 0 | 0 | 20 | 20 | 20 | 100 |
| 0.2% Imidacloprid | 0 | 0 | 0 | 0 | 0 | 0 | 0 |
| 0.2% Imidacloprid + 1% Compound A + 0.5% Compound B | 0 | 0 | 0 | 0 | 0 | 0 | 0 |
| 0.04% Imidacloprid | 0 | 0 | 0 | 0 | 0 | 0 | 0 |
| 0.04% Imidacloprid + 1% Compound A + 0.5% Compound B | 0 | 0 | 0 | 0 | 0 | 0 | 0 |
| 1% Compound A + 0.5% Compound B | 0 | 0 | 0 | 0 | 0 | 0 | 0 |
| Acetone only | 0 | 0 | 0 | 0 | 0 | 0 | 0 |

Example 109

Imidacloprid, Fipronil, and Ethiprole (all in Lutrol) with and Without Compound A: Efficacy Against the American Cockroach (*Periplaneta americana*) After Oral Application The objective of this study was to evaluate the influence of Compound A on the efficacy if insecticides after oral application.

Method: Oral insecticide application to cockroaches (*Periplaneta americana*)

The insects were kept without food and water 24 hours before trial started.

Each cockroach was treated orally with a micro liter syringe (2.5 µl=maximum of applicable amount). The cockroach was introduced into a plastic container (17.5 cm×12.5 cm, 6 cm high) with a folded filter paper. Per compound and concentration, 15 cockroaches were treated, which were kept as five insects per beaker (=three replicates).

After 24 hours the insects received' a drinking station (water soaked cotton pad in petri dish of 3,5 cm Ø and 1 cm height) and a piece of rusk.

At regular intervals the percentage of mortality was recorded cumulatively and at the end of the test (6 days) the mean values were calculated.

The results are shown in FIG. 99. As shown in this figure, the efficacy of the insecticides was not increased by the addition of Compound A. Rather, a slight inhibition seemed to occur when Compound A was added to Fipronil and Ethiprole.

TABLE 111

| Formulation | ConCentration | % Mortality after | | | | | | | |
|---|---|---|---|---|---|---|---|---|---|
| | | 1d | 2d | 3d | 6d | 9d | 14d | 21d | 28d |
| Imidacloprid | 0.25% | 100 | 40 | 40 | 20 | 20 | 20 | | |
| | 0.05% | 0 | 0 | 0 | 0 | 0 | 0 | | |
| | 0.01% | 0 | 0 | 0 | 0 | 0 | 0 | | |
| Fipronil | 0.5% | 100 | 100 | | | | | | |
| | 0.1% | 100 | 100 | | | | | | |
| | 0.02% | 0 | 40 | 60 | 100 | | | | |
| Ethiprole | 1% | 100 | 100 | | | | | | |
| | 0.1% | 40 | 40 | 40 | 40 | 40 | 40 | | |
| | 0.02% | 0 | 0 | 0 | 20 | 20 | 20 | | |
| UTC | | 0 | 0 | 0 | 0 | 0 | 0 | | |
| | | 0 | 0 | 0 | 0 | 0 | 0 | | |

| Formulation | Concentration Compound A | % Mortality after | | | | | | | |
|---|---|---|---|---|---|---|---|---|---|
| | | 1d | 2d | 3d | 6d | 9d | 14d | 21d | 28d |
| Imidacloprid 0.25% | w/o Compound A | 80 | 40 | 0 | 0 | | | | |
| | | 100 | 20 | 20 | 0 | | | | |
| | | 100 | 100 | 40 | 0 | | | | |
| | | 93 | 53 | 20 | 0 | | | | |
| | 1% | 100 | 20 | 20 | 0 | | | | |
| | | 100 | 60 | 60 | 20 | | | | |
| | | 80 | 40 | 40 | 0 | | | | |
| | | 93 | 40 | 40 | 7 | | | | |
| | 0.2% | 100 | 60 | 40 | 20 | | | | |
| | | 100 | 40 | 40 | 0 | | | | |
| | | 100 | 60 | 20 | 20 | | | | |
| | | 100 | 53 | 33 | 13 | | | | |
| | 0.04% | 100 | 40 | 20 | 0 | | | | |
| | | 80 | 40 | 20 | 0 | | | | |
| | | 100 | 60 | 40 | 20 | | | | |
| | | 93 | 47 | 27 | 7 | | | | |
| Fipronil 0.02% | w/o Compound A | 20 | 80 | 100 | 100 | | | | |
| | | 0 | 60 | 80 | 100 | | | | |
| | | 0 | 80 | 100 | 100 | | | | |
| | | 7 | 73 | 93 | 100 | | | | |
| | 1% | 0 | 100 | 100 | 100 | | | | |
| | | 0 | 20 | 40 | 80 | | | | |
| | | 20 | 40 | 60 | 100 | | | | |
| | | 7 | 53 | 67 | 93 | | | | |
| | 0.2% | 0 | 60 | 80 | 100 | | | | |
| | | 0 | 40 | 80 | 100 | | | | |
| | | 0 | 40 | 40 | 100 | | | | |
| | | 0 | 47 | 67 | 100 | | | | |
| | 0.04% | 20 | 40 | 60 | 100 | | | | |
| | | 40 | 60 | 80 | 80 | | | | |
| | | 0 | 20 | 60 | 100 | | | | |
| | | 20 | 40 | 67 | 93 | | | | |

TABLE 111-continued

| Ethiprole 0.1% | w/o Compound A | 80 | 80 | 80 | 80 | | | | |
|---|---|---|---|---|---|---|---|---|---|
| | | 100 | 100 | 100 | 100 | | | | |
| | | 60 | 60 | 60 | 60 | | | | |
| | | 80 | 80 | 80 | 80 | | | | |
| | 1% | 80 | 80 | 80 | 80 | | | | |
| | | 60 | 40 | 40 | 20 | | | | |
| | | 60 | 60 | 60 | 40 | | | | |
| | | 67 | 60 | 60 | 47 | | | | |
| | 0.2% | 40 | 40 | 40 | 40 | | | | |
| | | 20 | 20 | 20 | 20 | | | | |
| | | 100 | 100 | 100 | 100 | | | | |
| | | 53 | 53 | 53 | 53 | | | | |
| | 0.04% | 80 | 80 | 80 | 80 | | | | |
| | | 40 | 60 | 60 | 40 | | | | |
| | | 60 | 60 | 60 | 60 | | | | |
| | | 60 | 67 | 67 | 60 | | | | |
| UTC | w/o Compound A | 0 | 0 | 0 | 0 | | | | |
| | 1% Compound A | 0 | 0 | 0 | 0 | | | | |
| | 0.2% Compound A | 0 | 0 | 0 | 0 | | | | |
| | 0.04% Compound A | 0 | 0 | 0 | 0 | | | | |

Concentration for the main test

Example 110

Compound A in Different Concentrations in Combination with Different Insecticides (in EC-Formulations) Against Different Insects The objective of this study was to evaluate the influence of Compound A (without Compound B) on the efficacy of insecticides, when applied not in acetone but in EC formulations.

The standard method for determining the efficacy of a formulation on surfaces was used.

Test Insects: *Culex quinquefasciatus* (adults) (3 minutes exposure time according to USDA Petri Dish Method), *Musca domestica* (adults), susceptible and resistant strain, *Blattella germanica* (males), *Cimex lectularius* (adults) (all: continuous exposure time)

Application: The EC formulation (diluted with water 1:9) were applied as 0.85 ml solutions onto glazed tiles (15 cm×15 cm)

Evaluation: Knock down after 15, and 30 minutes, 1, 2, 3, 4, 6 and 24 hours (mortality)

Replicates: 1

TABLE 112

| Tested combinations: | |
|---|---|
| Concentration in EC | Concentration and quantity on tiles |
| 1% imidacloprid | 0.1% = 50 mg imidacloprid/m² |
| 1% imidacloprid + 10% Compound A | 0.1% = 50 mg imidacloprid/m² + 1% = 500 mg Compound A/m² |
| 1% imidacloprid + 2% Compound A | 0.1% = 50 mg imidacloprid/m² + 0.2% = 100 mg Compound A/m² |
| 1% imidacloprid + 0.4% Compound A | 0.1% = 50 mg imidacloprid/m² + 0.04% = 20 mg Compound A/m² |
| 1% bendiocarb | 0.1% = 50 mg Bendiocarb/m² |
| 1% bendiocarb + 10% Compound A | 0.1% = 50 mg Bendiocarb/m² + 1% = 500 mg Compound A/m² |
| 1% bendiocarb + 2% Compound A | 0.1% = 50 mg Bendiocarb/m² + 0.2% = 100 mg Compound A/m² |
| 1% bendiocarb + 0.4% Compound A | 0.1% = 50 mg Bendiocarb/m² + 0.04% = 20 mg Compound A/m² |
| 0.2% Ethiprole | 0.02% = 10 mg Ethiprole/m² |
| 0.2% Ethiprole + 10% Compound A | 0.02% = 10 mg Ethiprole/m² + 1% = 500 mg Compound A/m² |
| 0.2% Ethiprole + 2% Compound A | 0.02% = 10 mg Ethiprole/m² + 0.2% = 100 mg Compound A/m² |
| 0.2% Ethiprole + 0.4% Compound A | 0.02% = 10 mg Ethiprole/m² + 0.04% = 20 mg Compound A/m² |
| 0.02% DTM | 0.002% = 1 mg DTM/m² |
| 0.02% DTM + 10% Compound A | 0.002% = 1 mg DTM/m² + 1% = 500 mg Compound A/m² |
| 0.02% DTM + 2% Compound A | 0.002% = 1 mg DTM/m² + 0.2% = 100 mg Compound A/m² |
| 0.02% DTM + 0.4% Compound A | 0.002% = 1 mg DTM/m² + 0.04% = 20 mg Compound A/m² |
| Blank formulation + 10% Compound A | Blank formulation + 1% = 500 mg Compound A/m² |
| Blank formulation + 2% Compound A | Blank formulation + 0.2% = 100 mg Compound A/m² |
| Blank formulation + 0.4% Compound A | Blank formulation + 0.04% = 20 mg Compound A/m² |
| Blank formulation | — |

Summary:

Independent from the active ingredient used in the EC and the % Compound A there was not observed any difference in efficacy between formulation with or without Compound A. Efficacy increase could only be observed in very few experiments.

The reasons for the poor results are not known (Compound A alone without Compound B, or the use of the EC formulations instead of acetone solutions), a test with acetone solutions of bendiocarb with and without UV blocker against *Culex quinquefasciatus* on tiles was initiated.

TABLE 113

*Culex quinquefasciatus*

| Concentration and quantity on tiles | % KD and Mortality | | | | | | | |
|---|---|---|---|---|---|---|---|---|
| | 15' | 30' | 1 h | 2 h | 3 h | 4 h | 6 h | 24 h |
| 0.1% = 50 mg imidacloprid/m$^2$ | 0 | 0 | 0 | 10 | 20 | 20 | 20 | 100 |
| 0.1% = 50 mg imidacloprid/m$^2$ + 1% = 500 mg Compound A/m$^2$ | 0 | 0 | 20 | 20 | 40 | 50 | 60 | 90 |
| 0.1% = 50 mg imidacloprid/m$^2$ + 0.2% = 100 mg Compound A/m$^2$ | 0 | 0 | 10 | 10 | 10 | 10 | 10 | 90 |
| 0.1% = 50 mg imidacloprid/m$^2$ + 0.04% = 20 mg Compound A/m$^2$ | 0 | 0 | 0 | 0 | 0 | 0 | 0 | 100 |
| 0.1% = 50 mg Bendiocarb/m$^2$ | 0 | 0 | 80 | 100 | 100 | 100 | 100 | 100 |
| 0.1% = 50 mg Bendiocarb/m$^2$ + 1% = 500 mg Compound A/m$^2$ | 0 | 0 | 30 | 30 | 90 | 100 | 100 | 100 |
| 0.1% = 50 mg Bendiocarb/m$^2$ + 0.2% = 100 mg Compound A/m$^2$ | 0 | 0 | 0 | 30 | 70 | 70 | 70 | 90 |
| 0.1% = 50 mg Bendiocarb/m$^2$ + 0.04% = 20 mg Compound A/m$^2$ | 0 | 0 | 0 | 0 | 70 | 70 | 70 | 90 |
| 0.02% = 10 mg Ethiprole/m$^2$ | 0 | 0 | 0 | 10 | 10 | 10 | 10 | 60 |
| 0.02% = 10 mg Ethiprole/m$^2$ + 1% = 500 mg Compound A/m$^2$ | 0 | 0 | 0 | 0 | 10 | 10 | 10 | 70 |
| 0.02% = 10 mg Ethiprole/m$^2$ + 0.2% = 100 mg Compound A/m$^2$ | 0 | 0 | 0 | 0 | 20 | 20 | 20 | 100 |
| 0.02% = 10 mg Ethiprole/m$^2$ + 0.04% = 20 mg Compound A/m$^2$ | 0 | 0 | 0 | 0 | 0 | 0 | 0 | 100 |
| 0.002% = 1 mg DTM/m$^2$ | 0 | 0 | 10 | 10 | 10 | 10 | 20 | 80 |
| 0.002% = 1 mg DTM/m$^2$ + 1% = 500 mg Compound A/m$^2$ | 0 | 0 | 0 | 0 | 0 | 0 | 10 | 100 |
| 0.002% = 1 mg DTM/m$^2$ + 0.2% = 100 mg Compound A/m$^2$ | 0 | 0 | 0 | 0 | 10 | 10 | 10 | 80 |
| 0.002% = 1 mg DTM/m$^2$ + 0.04% = 20 mg Compound A/m$^2$ | 0 | 0 | 0 | 0 | 0 | 0 | 0 | 80 |
| Blank formulation + 1% = 500 mg Compound A/m$^2$ | 0 | 0 | 0 | 0 | 0 | 0 | 0 | 20 |
| Blank formulation + 0.2% = 100 mg Compound A/m$^2$ | 0 | 0 | 0 | 0 | 0 | 0 | 0 | 50 |
| Blank formulation + 0.04% = 20 mg Compound A/m$^2$ | 0 | 0 | 0 | 0 | 0 | 0 | 0 | 60 |
| Blank formulation | 0 | 0 | 0 | 0 | 0 | 0 | 0 | 20 |
| UTC | 0 | 0 | 0 | 0 | 0 | 0 | 0 | 30 |

TABLE 114

*Musca domestica*

| Concentration and quantity on tiles | % KD and Mortality | | | | | | | |
|---|---|---|---|---|---|---|---|---|
| | 15' | 30' | 1 h | 2 h | 3 h | 4 h | 6 h | 24 h |
| 0.1% = 50 mg imidacloprid/m$^2$ | 25 | 55 | 40 | 95 | 95 | 95 | 95 | 100 |
| 0.1% = 50 mg imidacloprid/m$^2$ + 1% = 500 mg Compound A/m$^2$ | 35 | 65 | 90 | 95 | 95 | 100 | 100 | 100 |
| 0.1% = 50 mg imidacloprid/m$^2$ + 0.2% = 100 mg Compound A/m$^2$ | 5 | 40 | 65 | 70 | 75 | 75 | 75 | 95 |
| 0.1% = 50 mg imidacloprid/m$^2$ + 0.04% = 20 mg Compound A/m$^2$ | 5 | 40 | 45 | 65 | 70 | 75 | 75 | 95 |
| 0.1% = 50 mg Bendiocarb/m$^2$ | 25 | 65 | 85 | 85 | 85 | 85 | 85 | 95 |
| 0.1% = 50 mg Bendiocarb/m$^2$ + 1% = 500 mg Compound A/m$^2$ | 20 | 75 | 95 | 95 | 95 | 95 | 95 | 95 |
| 0.1% = 50 mg Bendiocarb/m$^2$ + 0.2% = 100 mg Compound A/m$^2$ | 30 | 75 | 80 | 85 | 85 | 85 | 85 | 85 |
| 0.1% = 50 mg Bendiocarb/m$^2$ + 0.04% = 20 mg Compound A/m$^2$ | 15 | 55 | 80 | 90 | 90 | 90 | 90 | 90 |
| 0.02% = 10 mg Ethiprole/m$^2$ | 0 | 0 | 0 | 5 | 15 | 15 | 25 | 95 |
| 0.02% = 10 mg Ethiprole/m$^2$ + 1% = 500 mg Compound A/m$^2$ | 0 | 0 | 0 | 0 | 0 | 10 | 40 | 95 |
| 0.02% = 10 mg Ethiprole/m$^2$ + 0.2% = 100 mg Compound A/m$^2$ | 0 | 0 | 0 | 0 | 0 | 5 | 20 | 85 |
| 0.02% = 10 mg Ethiprole/m$^2$ + 0.04% = 20 mg Compound A/m$^2$ | 0 | 0 | 0 | 30 | 30 | 30 | 70 | 90 |
| 0.002% = 1 mg DTM/m$^2$ | 10 | 85 | 95 | 100 | 100 | 100 | 100 | 100 |
| 0.002% = 1 mg DTM/m$^2$ + 1% = 500 mg Compound A/m$^2$ | 40 | 90 | 95 | 95 | 100 | 100 | 100 | 100 |
| 0.002% = 1 mg DTM/m$^2$ + | 25 | 85 | 95 | 95 | 95 | 95 | 95 | 100 |

TABLE 114-continued

*Musca domestica*

| Concentration and quantity on tiles | % KD and Mortality | | | | | | | |
|---|---|---|---|---|---|---|---|---|
| | 15' | 30' | 1 h | 2 h | 3 h | 4 h | 6 h | 24 h |
| 0.2% = 100 mg Compound A/m$^2$ | | | | | | | | |
| 0.002% = 1 mg DTM/m$^2$ + 0.04% = 20 mg Compound A/m$^2$ | 10 | 60 | 90 | 90 | 95 | 95 | 95 | 100 |
| Blanc formulation + 1% = 500 mg Compound A/m$^2$ | 0 | 0 | 0 | 0 | 0 | 20 | 25 | 60 |
| Blanc formulation + 0.2% = 100 mg Compound A/m$^2$ | 0 | 0 | 0 | 0 | 15 | 20 | 20 | 25 |
| Blanc formulation + 0.04% = 20 mg Compound A/m$^2$ | 0 | 0 | 0 | 0 | 0 | 0 | 0 | 0 |
| Blank formulation | 0 | 0 | 0 | 0 | 0 | 0 | 0 | 5 |
| UTC | 0 | 0 | 0 | 0 | 0 | 0 | 0 | 0 |

TABLE 115

*Musca domestica*

| Concentration and quantity on tiles | % KD and Mortality | | | | | | | |
|---|---|---|---|---|---|---|---|---|
| | 15' | 30' | 1 h | 2 h | 3 h | 4 h | 6 h | 24 h |
| 0.1% = 50 mg imidacloprid/m$^2$ | 5 | 5 | 5 | 5 | 5 | 5 | 5 | 20 |
| 0.1% = 50 mg imidacloprid/m$^2$ + 1% = 500 mg Compound A/m$^2$ | 5 | 5 | 5 | 15 | 15 | 15 | 15 | 60 |
| 0.1% = 50 mg imidacloprid/m$^2$ + 0.2% = 100 mg Compound A/m$^2$ | 5 | 5 | 5 | 5 | 5 | 10 | 10 | 50 |
| 0.1% = 50 mg imidacloprid/m$^2$ + 0.04% = 20 mg Compound A/m$^2$ | 5 | 5 | 5 | 5 | 5 | 5 | 5 | 5 |
| 0.1% = 50 mg Bendiocarb/m$^2$ | 0 | 0 | 0 | 0 | 0 | 0 | 0 | 5 |
| 0.1% = 50 mg Bendiocarb/m$^2$ + 1% = 500 mg Compound A/m$^2$ | 0 | 0 | 0 | 0 | 0 | 0 | 0 | 10 |
| 0.1% = 50 mg Bendiocarb/m$^2$ + 0.2% = 100 mg Compound A/m$^2$ | 0 | 0 | 0 | 0 | 5 | 5 | 10 | 10 |
| 0.1% = 50 mg Bendiocarb/m$^2$ + 0.04% = 20 mg Compound A/m$^2$ | 0 | 0 | 0 | 0 | 0 | 0 | 0 | 5 |
| 0.02% = 10 mg Ethiprole/m$^2$ | 0 | 0 | 0 | 0 | 0 | 10 | 15 | 60 |
| 0.02% = 10 mg Ethiprole/m$^2$ + 1% = 500 mg Compound A/m$^2$ | 0 | 0 | 0 | 0 | 0 | 0 | 0 | 20 |
| 0.02% = 10 mg Ethiprole/m$^2$ + 0.2% = 100 mg Compound A/m$^2$ | 0 | 0 | 0 | 0 | 0 | 0 | 0 | 30 |
| 0.02% = 10 mg Ethiprole/m$^2$ + 0.04% = 20 mg Compound A/m$^2$ | 0 | 0 | 0 | 0 | 0 | 0 | 0 | 35 |
| 0.002% = 1 mg DTM/m$^2$ | 0 | 0 | 0 | 0 | 0 | 0 | 0 | 5 |
| 0.002% = 1 mg DTM/m$^2$ + 1% = 500 mg Compound A/m$^2$ | 0 | 0 | 0 | 0 | 0 | 0 | 0 | 25 |
| 0.002% = 1 mg DTM/m$^2$ + 0.2% = 100 mg Compound A/m$^2$ | 5 | 5 | 5 | 5 | 5 | 5 | 5 | 10 |
| 0.002% = 1 mg DTM/m$^2$ + 0.04% = 20 mg Compound A/m$^2$ | 5 | 5 | 5 | 5 | 5 | 5 | 5 | 10 |
| Blanc formulation + 1% = 500 mg Compound A/m$^2$ | 0 | 0 | 0 | 0 | 0 | 0 | 0 | 15 |
| Blanc formulation + 0.2% = 100 mg Compound A/m$^2$ | 0 | 0 | 0 | 0 | 0 | 0 | 0 | 15 |
| Blanc formulation + 0.04% = 20 mg Compound A/m$^2$ | 0 | 0 | 0 | 0 | 0 | 0 | 0 | 5 |
| Blank formulation | 0 | 0 | 0 | 0 | 0 | 0 | 0 | 5 |
| UTC | 0 | 0 | 0 | 0 | 0 | 0 | 0 | 0 |

TABLE 116

*Blattella germanica*

| Concentration and quantity on tiles | % KD and Mortality | | | | | | | |
|---|---|---|---|---|---|---|---|---|
| | 15' | 30' | 1 h | 2 h | 3 h | 4 h | 6 h | 24 h |
| 0.1% = 50 mg imidacloprid/m$^2$ | 0 | 0 | 20 | 80 | 100 | 100 | 100 | 100 |
| 0.1% = 50 mg imidacloprid/m$^2$ + 1% = 500 mg Compound A/m$^2$ | 0 | 20 | 40 | 80 | 80 | 80 | 80 | 80 |
| 0.1% = 50 mg imidacloprid/m$^2$ + 0.2% = 100 mg Compound A/m$^2$ | 0 | 20 | 60 | 80 | 100 | 100 | 100 | 100 |
| 0.1% = 50 mg imidacloprid/m$^2$ + 0.04% = 20 mg Compound A/m$^2$ | 0 | 0 | 20 | 60 | 80 | 80 | 100 | 100 |
| 0.1% = 50 mg Bendiocarb/m$^2$ | 0 | 40 | 60 | 60 | 80 | 80 | 80 | 80 |
| 0.1% = 50 mg Bendiocarb/m$^2$ + 1% = 500 mg Compound A/m$^2$ | 0 | 20 | 80 | 100 | 100 | 100 | 100 | 100 |
| 0.1% = 50 mg Bendiocarb/m$^2$ + 0.2% = 100 mg Compound A/m$^2$ | 0 | 20 | 80 | 100 | 100 | 100 | 100 | 100 |
| 0.1% = 50 mg Bendiocarb/m$^2$ + 0.04% = 20 mg Compound A/m$^2$ | 0 | 0 | 60 | 80 | 100 | 100 | 100 | 100 |
| 0.02% = 10 mg Ethiprole/m$^2$ | 0 | 0 | 0 | 80 | 100 | 100 | 100 | 100 |

TABLE 116-continued

| | *Blattella germanica* | | | | | | | |
|---|---|---|---|---|---|---|---|---|
| | % KD and Mortality | | | | | | | |
| Concentration and quantity on tiles | 15' | 30' | 1 h | 2 h | 3 h | 4 h | 6 h | 24 h |
| 0.02% = 10 mg Ethiprole/m² + 1% = 500 mg Compound A/m² | 0 | 0 | 0 | 60 | 80 | 80 | 80 | 100 |
| 0.02% = 10 mg Ethiprole/m² + 0.2% = 100 mg Compound A/m² | 0 | 0 | 0 | 60 | 80 | 100 | 100 | 100 |
| 0.02% = 10 mg Ethiprole/m² + 0.04% = 20 mg Compound A/m² | 0 | 0 | 0 | 60 | 80 | 100 | 100 | 100 |
| 0.002% = 1 mg DTM/m² | 0 | 40 | 100 | 100 | 100 | 100 | 100 | 100 |
| 0.002% = 1 mg DTM/m² + 1% = 500 mg Compound A/m² | 0 | 0 | 60 | 60 | 60 | 60 | 80 | 100 |
| 0.002% = 1 mg DTM/m² + 0.2% = 100 mg Compound A/m² | 0 | 0 | 60 | 60 | 80 | 80 | 80 | 100 |
| 0.002% = 1 mg DTM/m² + 0.04% = 20 mg Compound A/m² | 0 | 0 | 40 | 60 | 60 | 60 | 60 | 100 |
| Blanc formulation + 1% = 500 mg Compound A/m² | 0 | 0 | 0 | 0 | 0 | 0 | 0 | 0 |
| Blanc formulation + 0.2% = 100 mg Compound A/m² | 0 | 0 | 0 | 0 | 0 | 0 | 0 | 0 |
| Blanc formulation + 0.04% = 20 mg Compound A/m² | 0 | 0 | 0 | 0 | 0 | 0 | 0 | 0 |
| Blank formulation | 0 | 0 | 0 | 0 | 0 | 0 | 0 | 0 |
| UTC | 0 | 0 | 0 | 0 | 0 | 0 | 0 | 0 |

TABLE 117

| | *Cimex lectularius* | | | | | | | |
|---|---|---|---|---|---|---|---|---|
| | % KD and Mortality | | | | | | | |
| Concentration and quantity on tiles | 15' | 30' | 1 h | 2 h | 3 h | 4 h | 6 h | 24 h |
| 0.1% = 50 mg imidacloprid/m² | 100 | 100 | 100 | 100 | 100 | 100 | 100 | 100 |
| 0.1% = 50 mg imidacloprid/m² + 1% = 500 mg Compound A/m² | 100 | 100 | 100 | 100 | 100 | 100 | 100 | 100 |
| 0.1% = 50 mg imidacloprid/m² + 0.2% = 100 mg Compound A/m² | 100 | 100 | 100 | 100 | 100 | 100 | 100 | 100 |
| 0.1% = 50 mg imidacloprid/m² + 0.04% = 20 mg Compound A/m² | 100 | 100 | 100 | 100 | 100 | 100 | 100 | 100 |
| 0.1% = 50 mg Bendiocarb/m² | 100 | 100 | 100 | 100 | 100 | 100 | 100 | 100 |
| 0.1% = 50 mg Bendiocarb/m² + 1% = 500 mg Compound A/m² | 100 | 100 | 100 | 100 | 100 | 100 | 100 | 100 |
| 0.1% = 50 mg Bendiocarb/m² + 0.2% = 100 mg Compound A/m² | 50 | 70 | 100 | 100 | 100 | 100 | 100 | 100 |
| 0.1% = 50 mg Bendiocarb/m² + 0.04% = 20 mg Compound A/m² | 50 | 80 | 100 | 100 | 100 | 100 | 100 | 100 |
| 0.02% = 10 mg Ethiprole/m² | 0 | 0 | 0 | 10 | 10 | 10 | 70 | 100 |
| 0.02% = 10 mg Ethiprole/m² + 1% = 500 mg Compound A/m² | 0 | 0 | 0 | 0 | 0 | 0 | 40 | 100 |
| 0.02% = 10 mg Ethiprole/m² + 0.2% = 100 mg Compound A/m² | 0 | 0 | 0 | 0 | 0 | 0 | 0 | 100 |
| 0.02% = 10 mg Ethiprole/m² + 0.04% = 20 mg Compound A/m² | 0 | 0 | 0 | 0 | 0 | 0 | 0 | 100 |
| 0.002% = 1 mg DTM/m² | 0 | 0 | 0 | 10 | 80 | 100 | 100 | 100 |
| 0.002% = 1 mg DTM/m² + 1% = 500 mg Compound A/m² | 0 | 0 | 0 | 30 | 60 | 80 | 100 | 100 |
| 0.002% = 1 mg DTM/m² + 0.2% = 100 mg Compound A/m² | 0 | 0 | 0 | 20 | 70 | 90 | 100 | 100 |
| 0.002% = 1 mg DTM/m² + 0.04% = 20 mg Compound A/m² | 0 | 0 | 0 | 10 | 60 | 90 | 100 | 100 |
| Blank formulation + 1% = 500 mg Compound A/m² | 0 | 0 | 0 | 0 | 0 | 0 | 90 | 100 |
| Blank formulation + 0.2% = 100 mg Compound A/m² | 0 | 0 | 0 | 0 | 0 | 0 | 100 | 100 |
| Blank formulation + 0.04% = 20 mg Compound A/m² | 0 | 0 | 0 | 0 | 0 | 0 | 0 | 10 |
| Blank formulation | 0 | 0 | 0 | 0 | 0 | 0 | 0 | 20 |
| UTC | 0 | 0 | 0 | 0 | 0 | 0 | 0 | 0 |

Example 111

Compound A in Different Concentrations in Combination with Different Insecticides (all in Acetone) Against Different Insects The objective of this study was to evaluate the influence of Compound A on the efficacy of insecticides, in acetone solutions on glazed tiles.

The standard method for determining the efficacy of a formulation on surfaces was used.

Test Insects: *Culex quinquefasciatus* (adults) (3 minutes exposure time according to USDA Petri Dish Method), *Cimex lectularius* (adults), *Acheta domesticus* (middle nymphs) (both: continuous exposure time)

Application: The active ingredients were applied as 1 ml acetone solutions onto glazed tiles (15 cm×15 cm)

Evaluation: Knock down after 3, 9 (mosquitoes only), 15, and 30 minutes, 1, 2, 3, 4 and 24 hours (mortality)

Replicates: 1

The results are shown in FIG. 100 (*Culex quinquefasciatus*), FIG. 101 (*Culex lectularius*), and FIG. 102 (*Acheta domesticus*). As shown, the addition of Compound A to bendiocarb led to an efficacy enhancement, especially at 1% and 0.2%. There was no efficacy enhancement of imidacloprid by addition of Compound A, independent of the concentration. As shown, there was efficacy enhancement of bendiocarb by addition of 1% or 0.2% Compound A. An efficacy enhancement was achieved even by adding 0.04% Compound A. Similar effects were observed with imidacloprid, although imidacloprid alone revealed already a high efficacy. The efficacy of Ethiprole was enhanced by addition of 1% Compound A, whereas the lower concentrations revealed no marked effects. As shown, there was an efficacy inhibition by addition of Compound A, which was concentration dependent.

For the mosquitoes, the USDA Petri Dish Method is used. Ten 3 day old *Culex quinquefasciatus* mosquitoes are exposed to each treatment for 3 minutes under a perforated petri dish and then a clean untreated white paper index card is moved between treated surface and petri dish. A water-soaked cotton pad is applied immediately after.

Example 112

Compound A in Combination with Different Insecticides (all as EC Formulations) on Two Surfaces Against Mosquitoes, Flies, and Cockroaches The objective of this study was to evaluate formulations instead of acetone solutions.

The standard method for determining the efficacy of a formulation on surfaces was used.

Test Insects: *Culex quinquefasciatus* (adults, susceptible) (3 minutes exposure time according to USDA Petri Dish Method), *Musca domestica* (adults, susceptible and resistant), *Blattella germanica* (males, susceptible) (both: continuous exposure time)

Formulations: Insecticide with or without 10% Compound A (as EC), to be diluted with water (1 part formulation+9 parts water)

Application: 1 ml of the diluted formulations was applied by pipette onto glazed tiles (15×15 cm)

Evaluation: Knock down after 3, 9 (mosquitoes only), 15, and 30 minutes, 1, 2, 3, 4 and 24 hours (mortality)

Replicates: 1

The results are shown in FIG. 103 (*Culex quinquefasciatus*, susceptible), FIG. 104 (*Musca domestica*, susceptible strain WHO(N)), FIG. 105 (*Musca domestica*, resistant strain Reichswald), and FIG. 106 (*Blattella germanica*). As shown in FIG. 103, in general, the efficacy was higher on glazed tiles than on unglazed tiles. On glazed tiles an inhibition of the insecticidal efficacy by addition of Compound A was observed; on unglazed tiles the efficacy was weak. As shown in FIG. 104, in general, the efficacy was higher on glazed tiles than on unglazed tiles. No synergistic effects were observed on glazed tiles, whereas a certain efficacy enhancement by the addition of Compound A occurred on unglazed tiles with exception of ethiprole). As shown in FIG. 105, in general, the efficacy was weak, either on glazed tiles or unglazed tiles. Only with imidacloprid, an efficacy enhancement occurred on glazed tiles when combined with Compound A. As shown in FIG. 106, no synergistic effect was observed on glazed tiles. On unglazed the addition of Compound A to the insecticides inhibited the efficacy compared to the insecticide alone.

Conclusion: Problems may arise where surfaces other than glazed tiles are used, or other formulations than acetone solutions are applied.

Example 113

Compound A in Different Concentrations in Combination with two Organophosphates (all in Acetone on Glazed Tiles) Against the Tropical House Mosquito (*Culex quinquefasciatus*) and the Bed Bug (*Cimex lectularius*)

The objective of this study was to evaluate the influence of Compound A on the efficacy of organophosphates in acetone solutions on glazed tiles.

The standard method for determining the efficacy of a formulation on surfaces was used.

Test Insects: *Culex quinquefasciatus* (adults) (3 minutes exposure time according to USDA Petri Dish Method), *Cimex lectularius* (adults), (continuous exposure time)

Application: The active ingredients were applied as 1 ml acetone solutions onto glazed tiles (15 cm×15 cm)

Evaluation: Knock down after 3, 9 (mosquitoes only), 15, and 30 minutes, 1, 2, 3, 4 and 24 hours (mortality)

Replicates: 1

The results are shown in FIG. 107 (Culex quinquefasciatus) and FIG. 108 (*Cimex lectularius*).

As shown in FIG. 107, efficacy was inhibited by adding Compound A either to fenithrothion or Fenthion, independent of the concentration of Compound A.

As shown in FIG. 108, efficacy was slightly enhanced by adding 0.04% Compound A to fenithrothion. In the case of fenthion, the effects were a little more distinct, especially with 0.04% Compound A.

Example 114

Compound A in Different Concentrations in Combination with One Phthalic Acid-Diamide, One Ketoenole and One Butenolide (all in Acetone on Glazed tiles) Against the Bed Bug (*Cimex lectularius*), the Tropical House Mosquito (*Culex quinquefasciatus*) and the House Fly (*Musca domestica*), Susceptible Strains The objective of this study was to evaluate the influence of Compound A on the efficacy of several chemical classes in acetone solutions on glazed tiles.

The standard test method for evaluating the performance of compositions on surfaces was used.

Test Insects: *Cimex lectularius, Culex quinquefasciatus, Musca domestica* (all adults, susceptible strains)

Application: The active ingredients were applied as 1 ml acetone solutions onto glazed tiles (15 cm×15 cm), continuous exposure time Evaluation: Knock down after 3, 9 (mosquitoes only), 15, and 30 minutes, 1, 2, 3, 4 and 24 hours (mortality)

Replicates: 3

TABLE 118

Chemical structure references as used herein:

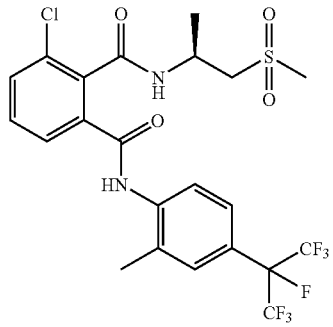

A phthalic acid diamide derivative sometimes referred to as Compound D

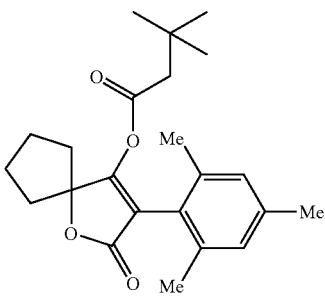

A ketoenole referred to as spiromesifen

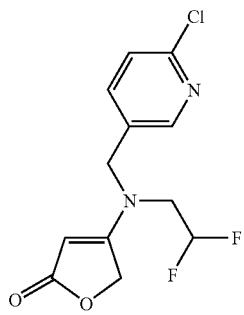

A butenolide, referred to as Compound E

The results are shown in FIG. 109 (*Cimex lectularius*), FIG. 110 (*Culex quinquefasciatus*), and FIG. 111 (*Musca domestica* (susceptible strain)).

As shown in FIG. 109, no efficacy enhancement was observed by adding Compound A to a phthalic acid diamide derivative or spiromesifen. The mortality rate of 1% Compound A alone was masked by these insecticides. The addition of 1% or 0.2% Compound A to a butenolide enhanced its efficacy, whereas the addition of 0.04% Compound A had no effect on the efficacy of a butenolide alone.

As shown in FIG. 110, no efficacy enhancement was observed by adding Compound A to a phthalic acid diamide derivative or spiromesifen. The mortality rate of 1% alone was partly masked by these insecticides. The addition of 1% or 0.2% Compound A to a butenolide enhanced slightly its efficacy, whereas the addition of 0.04% Compound A had no effect on the efficacy of a butenolide alone.

As shown in FIG. 111, no efficacy enhancement was observed by adding Compound A to a phthalic acid diamide derivative or spiromesifen. The high mortality rate of 1% alone was partly masked by these insecticides. The addition of 1% to a butenolide did not enhance really the efficacy because the efficacy of this combination was in the range of 1% Compound A alone. The addition of 0.2% or 0.04% Compound A inhibited the efficacy of a butenolide alone and masked the high mortality rate of 1% alone.

An efficacy enhancement was only observed with a butenolide in combination with 1% or 0.2% Compound A against bed bugs.

Adjuvants, such as free radical stabilizers, can enhance the activity of a broad spectrum of pesticides, including but not limited to insecticides and agricultural chemicals. Free radical stabilizers appear to increase the penetration of pesticides, such as insecticides, across pest cuticles, where the pests include both insects and arachnids. Free radical stabilizers also increase the penetration of insecticides, fungicides, herbicides, plant growth regulators, and other chemicals used in the agricultural industry, across plant cuticles.

While the foregoing description teaches the principles of the present invention, with examples provided for the purpose of illustration, it will be understood that the practice of the invention encompasses all variations, adaptations, or modifications considered by those skilled in the art and encompassed by the following claims.

The invention claimed is:

1. A composition comprising imidacloprid and dibutyl sebacate.

2. A composition comprising imidacloprid and oleic acid.

3. A composition comprising imidacloprid and benzenepropanoic acid.

4. A composition consisting of imidacloprid and methyl oleate.

5. A composition comprising imidacloprid and methyl linoleate.

6. A composition comprising 0.5% imidacloprid and 5% butylated hydroxyanisole (BHA).

7. A composition comprising imidacloprid and two or more sebacates wherein the sebacates are hindered amine light stabilizers and wherein said composition does not include an attractant.

8. The composition of claim 7, wherein the sebacates are bis (1,2,2,6,6-pentamethyl-4-piperidinyl) sebacate and methyl (1,2,2,6,6-pentamethyl-4-piperidinyl) sebacate.

9. A method for controlling or preventing a pest infestation comprising administering the composition of any one of claims 1-7 to a place in need thereof.

* * * * *